(12) United States Patent
Cochran et al.

(10) Patent No.: US 10,350,266 B2
(45) Date of Patent: Jul. 16, 2019

(54) METHOD OF TREATING CANCER WITH A MULTIPLE INTEGRIN BINDING FC FUSION PROTEIN

(71) Applicant: Nodus Therapeutics, Menlo Park, CA (US)

(72) Inventors: Jennifer R. Cochran, Stanford, CA (US); Karl Dane Wittrup, Menlo Park, CA (US)

(73) Assignee: NODUS THERAPEUTICS, INC., Menlo Park, CA (US)

(*) Notice: Subject to any disclaimer, the term of this patent is extended or adjusted under 35 U.S.C. 154(b) by 0 days.

(21) Appl. No.: 15/608,715

(22) Filed: May 30, 2017

(65) Prior Publication Data

US 2017/0368138 A1 Dec. 28, 2017

Related U.S. Application Data

(60) Provisional application No. 62/444,660, filed on Jan. 10, 2017, provisional application No. 62/466,298, filed on Mar. 2, 2017.

(51) Int. Cl.

| | | |
|---|---|---|
| *A61K 38/17* | (2006.01) | |
| *A61P 35/00* | (2006.01) | |
| *A61K 38/20* | (2006.01) | |
| *A61K 39/00* | (2006.01) | |
| *C07K 14/00* | (2006.01) | |
| *C07K 14/47* | (2006.01) | |
| *C07K 14/55* | (2006.01) | |
| *C07K 16/28* | (2006.01) | |
| *A61K 39/395* | (2006.01) | |

(52) U.S. Cl.
CPC ...... *A61K 38/1709* (2013.01); *A61K 38/2013* (2013.01); *A61K 39/39541* (2013.01); *A61P 35/00* (2018.01); *C07K 14/00* (2013.01); *C07K 14/47* (2013.01); *C07K 14/55* (2013.01); *C07K 16/2818* (2013.01); *C07K 16/2839* (2013.01); *A61K 2039/505* (2013.01); *C07K 2318/20* (2013.01); *C07K 2319/30* (2013.01); *C07K 2319/74* (2013.01)

(58) Field of Classification Search
None
See application file for complete search history.

(56) References Cited

U.S. PATENT DOCUMENTS

| | | |
|---|---|---|
| 4,399,216 A | 8/1983 | Axel |
| 4,634,665 A | 1/1987 | Axel |
| 5,179,017 A | 1/1993 | Axel |
| 5,281,698 A | 1/1994 | Nitecki |
| 5,382,657 A | 1/1995 | Karasiewcz et al. |
| 5,876,969 A | 3/1999 | Fleer et al. |
| 5,932,462 A | 8/1999 | Harris et al. |
| 6,054,297 A | 4/2000 | Carter et al. |
| 6,455,043 B1 * | 9/2002 | Grillo-Lopez ... A61K 39/39541 424/155.1 |
| 6,582,959 B2 | 6/2003 | Kim |
| 6,682,736 B1 | 1/2004 | Hanson et al. |
| 6,703,030 B2 | 3/2004 | Klein |
| 6,884,879 B1 | 4/2005 | Baca et al. |
| 6,984,720 B1 | 1/2006 | Korman et al. |
| 7,060,269 B1 | 6/2006 | Baca et al. |
| 7,176,278 B2 | 2/2007 | Prior |
| 7,610,156 B2 | 10/2009 | Desjarlais et al. |
| 7,847,062 B2 | 12/2010 | Chen et al. |
| 8,158,579 B2 | 4/2012 | Balance et al. |
| 8,536,301 B2 * | 9/2013 | Cochran ............... C07K 14/47 530/324 |
| 8,741,839 B2 | 6/2014 | Cochran et al. |
| 2002/0018780 A1 | 2/2002 | Koenig et al. |
| 2002/0039581 A1 | 4/2002 | Carreno et al. |
| 2002/0086014 A1 | 7/2002 | Korman et al. |
| 2003/0190317 A1 | 10/2003 | Baca et al. |
| 2003/0203409 A1 | 10/2003 | Kim |
| 2003/0206899 A1 | 11/2003 | Ferrara et al. |
| 2004/0132659 A1 | 7/2004 | Markland et al. |
| 2005/0075323 A1 | 4/2005 | Day et al. |
| 2005/0112126 A1 | 5/2005 | Baca et al. |
| 2005/0186208 A1 | 8/2005 | Fyfe et al. |
| 2005/0196427 A1 | 9/2005 | Tirrell et al. |
| 2005/0201994 A1 | 9/2005 | Korman et al. |
| 2005/0287153 A1 | 12/2005 | Dennis |
| 2006/0009360 A1 | 1/2006 | Pifer et al. |
| 2006/0029544 A1 | 2/2006 | Sutcliffe-Goulder et al. |
| 2007/0003549 A1 | 1/2007 | Ignatovich et al. |
| 2007/0048282 A1 | 3/2007 | Rosen et al. |

(Continued)

FOREIGN PATENT DOCUMENTS

| | | |
|---|---|---|
| EP | 0058481 | 8/1982 |
| EP | 0133988 | 3/1985 |

(Continued)

OTHER PUBLICATIONS

Fernando et al., Principles of cancer treatment by immunotherapy Surgery 33, 117-121, 2015. (Year: 2015).*
Attwood, T., Science, 290: pp. 471-473 (2000).
Brooks et al., Science, 264: 5158, pp. 569-571 (1994).
Charych et al., Clin Cancer Res., 22: 3, pp. 680-690 (2016).

(Continued)

*Primary Examiner* — Elly-Gerald Stoica

(74) *Attorney, Agent, or Firm* — Morgan, Lewis & Bockius LLP; Jeffry S. Mann; Christina A. MacDougall

(57) ABSTRACT

The present invention provides a method of treating cancer with an integrin-binding-Fc fusion protein alone or in combination with IL-2 and/or an immune checkpoint inhibitor. The invention also provides composition for use in such methods.

17 Claims, 31 Drawing Sheets

Specification includes a Sequence Listing.

(56) References Cited

U.S. PATENT DOCUMENTS

| | | | |
|---|---|---|---|
| 2007/0111281 | A1 | 5/2007 | Sondermann et al. |
| 2007/0178082 | A1 | 8/2007 | Silence et al. |
| 2007/0269422 | A1 | 11/2007 | Beirnaert et al. |
| 2010/0113339 | A1 | 5/2010 | Beirnaert et al. |
| 2010/0144599 | A1 | 6/2010 | Mendlein et al. |
| 2010/0179094 | A1 | 7/2010 | Emanuel et al. |
| 2010/0210511 | A1 | 8/2010 | Carvajal |
| 2011/0020345 | A1 | 1/2011 | Herring et al. |
| 2011/0150892 | A1 | 6/2011 | Thudium et al. |
| 2012/0094909 | A1 | 4/2012 | Camphausen et al. |
| 2013/0149236 | A1 | 6/2013 | Johnson et al. |
| 2014/0057851 | A1 | 2/2014 | Yla-Herttuala |
| 2014/0073518 | A1 | 3/2014 | Cochran et al. |

FOREIGN PATENT DOCUMENTS

| | | | | |
|---|---|---|---|---|
| EP | | 0338841 | 10/1989 | |
| WO | WO 1987/004462 | | 7/1987 | |
| WO | WO 1989/001036 | | 2/1989 | |
| WO | WO 1993/0015722 | | 8/1993 | |
| WO | WO 1994/001451 | | 1/1994 | |
| WO | WO 1994/010202 | | 5/1994 | |
| WO | WO 1994/020069 | | 9/1994 | |
| WO | WO 1996/030046 | | 10/1996 | |
| WO | WO 1997/044453 | | 11/1997 | |
| WO | WO 1998/045332 | | 10/1998 | |
| WO | WO 2002/060955 | | 8/2002 | |
| WO | WO 2002/096948 | | 12/2002 | |
| WO | WO 2005/000895 | | 1/2005 | |
| WO | WO 2005/018572 | | 3/2005 | |
| WO | WO 2005/044853 | | 5/2005 | |
| WO | WO 2008/045252 | | 4/2008 | |
| WO | WO 2009/083804 | | 7/2009 | |
| WO | WO 2009/133208 | | 11/2009 | |
| WO | WO 2011/051478 | | 5/2011 | |
| WO | WO 2011/124718 | | 10/2011 | |
| WO | WO 2012/064658 | | 5/2012 | |
| WO | WO-2012064658 A1 * | | 5/2012 | ....... C07K 14/43518 |
| WO | WO 2012/120125 | | 9/2012 | |
| WO | WO 2013/075066 | | 5/2013 | |
| WO | WO 2013/177187 | | 11/2013 | |
| WO | WO 2013/181452 | | 12/2013 | |
| WO | WO 2014/063012 | | 4/2014 | |
| WO | WO2015112900 | * | 7/2015 | ............ C07K 16/28 |
| WO | WO 2016/025642 | | 2/2016 | |

OTHER PUBLICATIONS

Copie et al., JMB, 277: pp. 663-682 (1998).
Cristmann et al., Protein Engineering, 12: 9, pp. 797-806 (1999).
Daly et al., The Journal of Biol. Chem., 278: 4, pp. 6314-6322 (2003).
Elangbam et al., Vet Pathol., 34: pp. 61-73 (1997).
Favel et al., Int. J. Peptide Protein Res., 33: pp. 202-208 (1989).
Garsky et al., PNAS, 86: pp. 4022-4026 (1989).
Gelly et al., Nucleic Acids Res., 32: pp. D156-D159 (2004).
Hautanen et al., The Journal of Biol. Chem., 264: 3, pp. 1437-1442 (1989).
Herzenberg et al., Nature Immunology, 7: 7, pp. 681-685 (2006).
Hla et al., PNAS, 89: pp. 7384-7388 (1992).
Hosse et al., Protein Science, 15: pp. 14-27 (2006).
Kandalaft et al., Cancer Immunology and Immunotherapy, 344: pp. 129-148 (2010).
Kimura et al., Cancer Res., 69: 6, pp. 2435-2442 (2009).
Koivunen et al., Bio/Technology, 13: pp. 265-270 (1995).
Koivunen et al., The Journal of Nuclear Medicine, 40: 5, pp. 883-888 (1999).
Konrad et al., Cancer Research, 50: pp. 2009-2017 (1990).
Kontermann, R., Curr. Opin. In Biotech., 22: pp. 868-876 (2011).
Kunick et al., The Journal of Biol. Chem., 270: 28, pp. 16660-16665 (1995).
Kuntz, I., Science, 257: pp. 1078-1082 (1992).
Li et al., Protein Engineering, 16: 1, pp. 66-72 (2003).
Liang et al., The Journal of Biol. Chem., 281: 2, pp. 951-961 (2006).
Liu, S., Molecular Pharmaceutics, 3: 5, pp. 472-487 (2006).
Lu et al., Biochem. J., 304: pp. 929-936 (1994).
McNulty et al., Biochemistry, NMR Structure of AGRP, pp. 87-132 (2001).
Miller and Dill, Protein Science, 6: pp. 2166-2179 (1997).
Millhauser et al., Ann. N.Y. Acad. Sci., 994: pp. 27-35 (2003).
Moore et al., PNAS, 110: 36, pp. 14598-14603 (2013).
Reiss et al., Platelets, 17:3, pp. 153-157 (2006).
Scarborough et al., The Journal of Bio. Chem., 268: 2, pp. 1058-1065 (1993).
Segura et al., MPMI, 12: 1, pp. 16-23 (1999).
Skerra, A., Journal of Mol. Recognit. 13: pp. 167-187 (2000).
Skolnick and Fetrow, Tibtech, 18: pp. 34-39 (2000).
Smith et al., JMB, 277: pp. 317-332 (1998).
Terme et al., Clin. and Dev. Immun., 8 pages, (2012).
Treister and Roederer, FlowJo—Data Analysis Software for Flow Cytometry User Documentation Tutuorial, Trustees of the Leland Stanford Jr. University and Tree Star, Inc., Version 3.4 (2001).
Voron et al., Frontiers in Oncology, 4: 70, pp. 1-9 (2014).
Wattam et al., Biochem. J., 356: pp. 11-17 (2001).
Wentzel et al., The Journal of Bio. Chem., 274: 30, pp. 21037-21043 (1999).
Wu et all, PNAS, 95: pp. 6037-6042 (1998).

* cited by examiner

Drugs and Treatment:

| Gr. | N | Regimen 1 | | | | Regimen 2 | | | | Regimen 3 | | | |
|---|---|---|---|---|---|---|---|---|---|---|---|---|---|
| | | Agent | μg/animal | Route | Schedule | Agent | μg/animal | Route | Schedule | Agent | μg/animal | Route | Schedule |
| 1[#] | 10 | vehicle | - | iv | days 1,7,13,19 | - | - | - | - | - | - | - | - |
| 2 | 10 | NOD201M | 500 | iv | days 1,7,13,19 | - | - | - | - | - | - | - | - |
| 3 | 10 | Proleukin | 40 | iv | days 2-4,8-10,14-16,20-22 | - | - | - | - | - | - | - | - |
| 4 | 10 | Proleukin | 4 | sc | days 2-4,8-10,14-16,20-22 | - | - | - | - | - | - | - | - |
| 5 | 10 | NOD201M | 500 | iv | days 1,7,13,19 | Proleukin | 40 | iv | days 2-4,8-10,14-16,20-22 | - | - | - | - |
| 6 | 10 | NOD201M | 500 | iv | days 1,7,13,19 | Proleukin | 4 | sc | days 2-4,8-10,14-16,20-22 | - | - | - | - |
| 7 | 10 | anti-PD-1 RMP1-14 | 200 | iv | days 1,7,13,19 | - | - | - | - | - | - | - | - |
| 8 | 10 | NOD201M | 500 | iv | days 1,7,13,19 | anti-PD-1 RMP1-14 | 200 | iv | days 1,7,13,19 | - | - | - | - |
| 9 | 10 | NOD201M | 500 | iv | days 1,7,13,19 | anti-PD-1 RMP1-14 | 200 | iv | days 1,7,13,19 | Proleukin | 4 | Sc | days 2-4,8-10,14-16,20-22 |
| 10 | 10 | NOD201M | 1000 | iv | days 1,7,13,19 | anti-PD-1 RMP1-14 | 200 | iv | days 1,7,13,19 | Proleukin | 4 | Sc | days 2-4,8-10,14-16,20-22 |
| 11 | 10 | NOD20M | 1000 | iv | days 1,7,13,19 | Proleukin | 4 | sc | days 2-4,8-10,14-16,20-22 | - | - | - | - |

- Control Group
*- mg/kg

FIG. 22A – FIG. 22B

SEQUENCE LISTING

```
<160> NUMBER OF SEQ ID NOS: 143

<210> SEQ ID NO 1
<211> LENGTH: 330
<212> TYPE: PRT
<213> ORGANISM: Artificial Sequence
<220> FEATURE:
<223> OTHER INFORMATION: Synthetic Human IgG1 constant region

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80
```

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 232
<212> TYPE: PRT
<213> ORGANISM: Artificial Sequence
<220> FEATURE:
<223> OTHER INFORMATION: Synthetic Human IgG1 Fc domain

<400> SEQUENCE: 2

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110
```

```
Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 3
<211> LENGTH: 227
<212> TYPE: PRT
<213> ORGANISM: Artificial Sequence
<220> FEATURE:
<223> OTHER INFORMATION: Synthetic Human IgG1 Fc domain

<400> SEQUENCE: 3

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 4
<211> LENGTH: 447
<212> TYPE: DNA
<213> ORGANISM: Artificial Sequence
<220> FEATURE:
<223> OTHER INFORMATION: Synthetic Mouse IL-2

<400> SEQUENCE: 4

```
gcacccactt caagctccac ttcaagctct acagcggaag cacagcagca gcagcagcag      60
cagcagcagc agcagcagca cctggagcag ctgttgatgg acctacagga gctcctgagc     120
aggatggaga attacaggaa cctgaaactc cccaggatgc tcaccttcaa attttacttg     180
cccaagcagg ccacagaatt gaaagatctt cagtgcctag aagatgaact tggacctctg     240
cggcatgttc tggatttgac tcaaagcaaa agctttcaat ggaagatgc tgagaatttc      300
atcagcaata tcagagtaac tgttgtaaaa ctaaagggct ctgacaacac atttgagtgc     360
caattcgatg atgagtcagc aactgtggtg gactttctga ggagatggat agccttctgt     420
caaagcatca tctcaacaag ccctcaa                                         447
```

<210> SEQ ID NO 5
<211> LENGTH: 149
<212> TYPE: PRT
<213> ORGANISM: Artificial Sequence
<220> FEATURE:
<223> OTHER INFORMATION: Synthetic Mouse IL-2

<400> SEQUENCE: 5

```
Ala Pro Thr Ser Ser Thr Ser Ser Ser Thr Ala Glu Ala Gln Gln
1               5                   10                  15
Gln Gln Gln Gln Gln Gln Gln Gln Gln His Leu Glu Gln Leu Leu
                20                  25                  30
Met Asp Leu Gln Glu Leu Leu Ser Arg Met Glu Asn Tyr Arg Asn Leu
            35                  40                  45
Lys Leu Pro Arg Met Leu Thr Phe Lys Phe Tyr Leu Pro Lys Gln Ala
        50                  55                  60
Thr Glu Leu Lys Asp Leu Gln Cys Leu Glu Asp Glu Leu Gly Pro Leu
65                  70                  75                  80
Arg His Val Leu Asp Leu Thr Gln Ser Lys Ser Phe Gln Leu Glu Asp
                85                  90                  95
Ala Glu Asn Phe Ile Ser Asn Ile Arg Val Thr Val Val Lys Leu Lys
            100                 105                 110
Gly Ser Asp Asn Thr Phe Glu Cys Gln Phe Asp Asp Glu Ser Ala Thr
        115                 120                 125
Val Val Asp Phe Leu Arg Arg Trp Ile Ala Phe Cys Gln Ser Ile Ile
    130                 135                 140
Ser Thr Ser Pro Gln
145
```

<210> SEQ ID NO 6
<211> LENGTH: 447
<212> TYPE: DNA
<213> ORGANISM: Artificial Sequence
<220> FEATURE:
<223> OTHER INFORMATION: Synthetic QQ6210

<400> SEQUENCE: 6

```
gcacccactt caagctccac ttcaagctct acagcggaag cacaacagca gcagcagcag      60
cagcagcagc agcagcagca cctggagcag ctgttgatgg acctacagga actcctgagt     120
```

```
aggatggagg atcacaggaa cctgagactc cccaggatgc tcaccttcaa attttacttg      180
cccgagcagg ccacagaatt ggaagatctt cagtgcctag aagatgaact tgaaccactg      240
cggcaagttc tggatttgac tcaaagcaaa agctttcaat tggaagatgc tgagaatttc      300
atcagcaata tcagagtaac tgttgtaaaa ctaaagggct ctgacaacac atttgagtgc      360
caattcgacg atgagccagc aactgtggtg gactttctga ggagatggat agccttctgt      420
caaagcatca tctcaacaag ccctcaa                                          447
```

<210> SEQ ID NO 7
<211> LENGTH: 149
<212> TYPE: PRT
<213> ORGANISM: Artificial Sequence
<220> FEATURE:
<223> OTHER INFORMATION: Synthetic QQ6210

<400> SEQUENCE: 7

```
Ala Pro Thr Ser Ser Thr Ser Ser Ser Thr Ala Glu Ala Gln Gln
1               5                   10                  15

Gln Gln Gln Gln Gln Gln Gln Gln Gln His Leu Glu Gln Leu Leu
                20                  25                  30

Met Asp Leu Gln Glu Leu Leu Ser Arg Met Glu Asp His Arg Asn Leu
            35                  40                  45

Arg Leu Pro Arg Met Leu Thr Phe Lys Phe Tyr Leu Pro Glu Gln Ala
    50                  55                  60

Thr Glu Leu Glu Asp Leu Gln Cys Leu Glu Asp Glu Leu Glu Pro Leu
65                  70                  75                  80

Arg Gln Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Glu Pro Ala Thr
        115                 120                 125

Val Val Asp Phe Leu Arg Arg Trp Ile Ala Phe Cys Gln Ser Ile Ile
    130                 135                 140

Ser Thr Ser Pro Gln
145
```

<210> SEQ ID NO 8
<211> LENGTH: 447
<212> TYPE: DNA
<213> ORGANISM: Artificial Sequence
<220> FEATURE:
<223> OTHER INFORMATION: Synthetic E76A

<400> SEQUENCE: 8

```
gcacccactt caagctccac ttcaagctct acagcggaag cacagcagca gcagcagcag      60
cagcagcagc agcagcagca cctggagcag ctgttgatgg acctacagga gctcctgagc      120
aggatggaga attacaggaa cctgaaactc cccaggatgc tcaccttcaa attttacttg      180
cccaagcagg ccacagaatt gaaagatctt cagtgcctag aagatgctct tggacctctg      240
cggcatgttc tggatttgac tcaaagcaaa agctttcaat tggaagatgc tgagaatttc      300
atcagcaata tcagagtaac tgttgtaaaa ctaaagggct ctgacaacac atttgagtgc      360
caattcgatg atgagtcagc aactgtggtg gactttctga ggagatggat agccttctgt      420
caaagcatca tctcaacaag ccctcaa                                          447
```

<210> SEQ ID NO 9
<211> LENGTH: 149
<212> TYPE: PRT
<213> ORGANISM: Artificial Sequence
<220> FEATURE:
<223> OTHER INFORMATION: Synthetic E76A

<400> SEQUENCE: 9

```
Ala Pro Thr Ser Ser Ser Thr Ser Ser Thr Ala Glu Ala Gln Gln
1               5                   10                  15

Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
            35                  40                  45

Lys Leu Pro Arg Met Leu Thr Phe Lys Phe Tyr Leu Pro Lys Gln Ala
        50                  55                  60

Thr Glu Leu Lys Asp Leu Gln Cys Leu Glu Asp Ala Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
                100                 105                 110

Gly Ser Asp Asn Thr Phe Glu Cys Gln Phe Asp Asp Glu Ser Ala Thr
            115                 120                 125

Val Val Asp Phe Leu Arg Arg Trp Ile Ala Phe Cys Gln Ser Ile Ile
        130                 135                 140

Ser Thr Ser Pro Gln
145
```

<210> SEQ ID NO 10
<211> LENGTH: 447
<212> TYPE: DNA
<213> ORGANISM: Artificial Sequence
<220> FEATURE:
<223> OTHER INFORMATION: Synthetic E76G

<400> SEQUENCE: 10

```
gcacccactt caagctccac ttcaagctct acagcggaag cacagcagca gcagcagcag    60
cagcagcagc agcagcagca cctggagcag ctgttgatgg acctacagga gctcctgagc   120
aggatggaga attacaggaa cctgaaactc cccaggatgc tcaccttcaa attttacttg   180
cccaagcagg ccacagaatt gaaagatctt cagtgcctag aagatggtct tggacctctg   240
cggcatgttc tggatttgac tcaaagcaaa agctttcaat tggaagatgc tgagaatttc   300
atcagcaata tcagagtaac tgttgtaaaa ctaaagggct ctgacaacac atttgagtgc   360
caattcgatg atgagtcagc aactgtggtg gactttctga ggagatggat agccttctgt   420
caaagcatca tctcaacaag ccctcaa                                       447
```

<210> SEQ ID NO 11
<211> LENGTH: 149
<212> TYPE: PRT
<213> ORGANISM: Artificial Sequence
<220> FEATURE:
<223> OTHER INFORMATION: Synthetic E76G

<400> SEQUENCE: 11

```
Ala Pro Thr Ser Ser Ser Thr Ser Ser Thr Ala Glu Ala Gln Gln
1               5                   10                  15
```

```
Gln Gln Gln Gln Gln Gln Gln Gln Gln His Leu Glu Gln Leu Leu
         20                  25                  30

Met Asp Leu Gln Glu Leu Leu Ser Arg Met Glu Asn Tyr Arg Asn Leu
         35                  40                  45

Lys Leu Pro Arg Met Leu Thr Phe Lys Phe Tyr Leu Pro Lys Gln Ala
    50                  55                  60

Thr Glu Leu Lys Asp Leu Gln Cys Leu Glu Asp Gly Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Ser Ala Thr
        115                 120                 125

Val Val Asp Phe Leu Arg Arg Trp Ile Ala Phe Cys Gln Ser Ile Ile
    130                 135                 140

Ser Thr Ser Pro Gln
145
```

```
<210> SEQ ID NO 12
<211> LENGTH: 816
<212> TYPE: DNA
<213> ORGANISM: Artificial Sequence
<220> FEATURE:
<223> OTHER INFORMATION: Synthetic D265A Fc/Flag

<400> SEQUENCE: 12
atgagggtcc cgctcagct cctggggctc ctgctgctct ggctcccagg tgcacgatgt      60
gagcccagag tgcccataac acagaacccc tgtcctccac tcaaagagtg tccccccatgc   120 gcagctccag acctcttggg tggaccatcc gtcttcatct tccctccaaa gatcaaggat    180
gtactcatga tctccctgag ccccatggtc acatgtgtgg tggtggccgt gagcgaggat    240
gacccagacg tccagatcag ctggtttgtg aacaacgtgg aagtacacac agctcagaca    300
caaacccata gagaggatta caacagtact ctccgggtgg tcagtgccct ccccatccag    360
caccaggact ggatgagtgg caaggagttc aaatgcaagg tcaacaacag agccctccca    420
tcccccatcg agaaaaccat ctcaaaaccc agagggccag taagagctcc acaggtatat    480
gtcttgcctc caccagcaga agatgactaag aagaaagagt cagtctgac ctgcatgatc    540 acaggcttct acctgccga aattgctgtg gactggacca gcaatgggcg tacagagcaa     600
aactacaaga caccgcaac agtcctggac tctgatggtt cttacttcat gtacagcaag     660
ctcagagtac aaaagagcac ttgggaaaga ggaagtcttt tcgcctgctc agtggtccac    720
gagggtctgc acaatcacct tacgactaag accatctccc ggtctctggg taaaggtggc    780
ggatctgact acaaggacga cgatgacaag tgataa                              816
```

```
<210> SEQ ID NO 13
<211> LENGTH: 270
<212> TYPE: PRT
<213> ORGANISM: Artificial Sequence
<220> FEATURE:
<223> OTHER INFORMATION: Synthetic D265A Fc/Flag

<400> SEQUENCE: 13

Met Arg Val Pro Ala Gln Leu Leu Gly Leu Leu Leu Leu Trp Leu Pro
1               5                   10                  15

Gly Ala Arg Cys Glu Pro Arg Val Pro Ile Thr Gln Asn Pro Cys Pro
```

```
            20                  25                  30
Pro Leu Lys Glu Cys Pro Pro Cys Ala Ala Pro Asp Leu Leu Gly Gly
            35                  40                  45

Pro Ser Val Phe Ile Phe Pro Lys Ile Lys Asp Val Leu Met Ile
        50                  55                  60

Ser Leu Ser Pro Met Val Thr Cys Val Val Val Ala Val Ser Glu Asp
65                  70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
            100                 105                 110

Val Val Ser Ala Leu Pro Ile Gln His Gln Asp Trp Met Ser Gly Lys
            115                 120                 125

Glu Phe Lys Cys Lys Val Asn Asn Arg Ala Leu Pro Ser Pro Ile Glu
            130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
            195                 200                 205

Leu Asp Ser Asp Gly Ser Tyr Phe Met Tyr Ser Lys Leu Arg Val Gln
        210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys Gly Gly Gly Ser Asp Tyr Lys Asp Asp Asp Asp Lys
            260                 265                 270

<210> SEQ ID NO 14
<211> LENGTH: 1257
<212> TYPE: DNA
<213> ORGANISM: Artificial Sequence
<220> FEATURE:
<223> OTHER INFORMATION: Synthetic D265A Fc/wt mIL-2

<400> SEQUENCE: 14
atgagggtcc ccgctcagct cctggggctc ctgctgctct ggctcccagg tgcacgatgt      60
gagcccagag tgcccataac acagaacccc tgtcctccac tcaaagagtg tccccccatgc   120 gcagctccag acctcttggg tggaccatcc gtcttcatct ccctccaaa gatcaaggat     180 gtactcatga tctccctgag ccccatggtc acatgtgtgg tggtggccgt gagcgaggat    240
gacccagacg tccagatcag ctggtttgtg aacaacgtgg aagtacacac agctcagaca    300
caaacccata gagaggatta caacagtact ctccgggtgg tcagtgccct ccccatccag    360
caccaggact ggatgagtgg caaggagttc aaatgcaagg tcaacaacag agccctccca    420
tcccccatcg agaaaaccat ctcaaaaccc agagggccag taagagctcc acaggtatat    480
gtcttgcctc caccagcaga agagatgact aagaaagagt tcagtctgac ctgcatgatc    540
acaggcttct acctgccga aattgctgtg gactggacca gcaatgggcg tacagagcaa    600
aactacaaga caccgcaac agtcctggac tctgatggtt cttacttcat gtacagcaag    660
```

```
ctcagagtac aaaagagcac ttgggaaaga ggaagtcttt tcgcctgctc agtggtccac    720
gagggtctgc acaatcacct tacgactaag accatctccc ggtctctggg taaaggaggg    780
ggctccgcac ccacttcaag ctccacttca agctctacag cggaagcaca gcagcagcag    840
cagcagcagc agcagcagca gcagcacctg gagcagctgt tgatggacct acaggagctc    900
ctgagcagga tggagaatta caggaacctg aaactcccca ggatgctcac cttcaaattt    960
tacttgccca agcaggccac agaattgaaa gatcttcagt gcctagaaga tgaacttgga   1020
cctctgcggc atgttctgga tttgactcaa agcaaaagct ttcaattgga agatgctgag   1080
aatttcatca gcaatatcag agtaactgtt gtaaaactaa agggctctga caacacattt   1140
gagtgccaat tcgatgatga gtcagcaact gtggtggact ttctgaggag atggatagcc   1200
ttctgtcaaa gcatcatctc aacaagccct caacaccatc accaccatca ctgataa     1257
```

<210> SEQ ID NO 15
<211> LENGTH: 417
<212> TYPE: PRT
<213> ORGANISM: Artificial Sequence
<220> FEATURE:
<223> OTHER INFORMATION: Synthetic D265A Fc/wt mIL-2

<400> SEQUENCE: 15

```
Met Arg Val Pro Ala Gln Leu Leu Gly Leu Leu Leu Leu Trp Leu Pro
1               5                   10                  15

Gly Ala Arg Cys Glu Pro Arg Val Pro Ile Thr Gln Asn Pro Cys Pro
            20                  25                  30

Pro Leu Lys Glu Cys Pro Pro Cys Ala Ala Pro Asp Leu Leu Gly Gly
        35                  40                  45

Pro Ser Val Phe Ile Phe Pro Pro Lys Ile Lys Asp Val Leu Met Ile
    50                  55                  60

Ser Leu Ser Pro Met Val Thr Cys Val Val Val Ala Val Ser Glu Asp
65                  70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
            100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
    130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
    210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys Gly Gly Gly Ser Ala Pro Thr Ser Ser Ser Thr Ser Ser Ser
```

```
                    260                 265                 270
Thr Ala Glu Ala Gln Gln Gln Gln Gln Gln Gln Gln Gln Gln
        275                 280                 285
His Leu Glu Gln Leu Leu Met Asp Leu Gln Glu Leu Leu Ser Arg Met
        290                 295                 300
Glu Asn Tyr Arg Asn Leu Lys Leu Pro Arg Met Leu Thr Phe Lys Phe
305                 310                 315                 320
Tyr Leu Pro Lys Gln Ala Thr Glu Leu Lys Asp Leu Gln Cys Leu Glu
                325                 330                 335
Asp Glu Leu Gly Pro Leu Arg His Val Leu Asp Leu Thr Gln Ser Lys
                340                 345                 350
Ser Phe Gln Leu Glu Asp Ala Glu Asn Phe Ile Ser Asn Ile Arg Val
                355                 360                 365
Thr Val Val Lys Leu Lys Gly Ser Asp Asn Thr Phe Glu Cys Gln Phe
        370                 375                 380
Asp Asp Glu Ser Ala Thr Val Val Asp Phe Leu Arg Arg Trp Ile Ala
385                 390                 395                 400
Phe Cys Gln Ser Ile Ile Ser Thr Ser Pro Gln His His His His
                405                 410                 415
His
```

<210> SEQ ID NO 16
<211> LENGTH: 1257
<212> TYPE: DNA
<213> ORGANISM: Artificial Sequence
<220> FEATURE:
<223> OTHER INFORMATION: Synthetic D265A Fc /QQ6210

<400> SEQUENCE: 16

```
atgagggtcc ccgctcagct cctggggctc ctgctgctct ggctcccagg tgcacgatgt      60
gagcccagag tgcccataac acagaacccc tgtcctccac tcaaagagtg tccccccatgc    120
gcagctccag acctcttggg tggaccatcc gtcttcatct tccctccaaa gatcaaggat     180
gtactcatga tctccctgag ccccatggtc acatgtgtgg tggtggccgt gagcgaggat     240
gacccagacg tccagatcag ctggtttgtg aacaacgtgg aagtacacac agctcagaca     300
caaacccata gagaggatta caacagtact ctccgggtgg tcagtgccct ccccatccag     360
caccaggact ggatgagtgg caaggagttc aaatgcaagg tcaacaacag agccctccca     420
tcccccatcg agaaaaccat ctcaaaaccc agagggccag taagagctcc acaggtatat     480
gtcttgcctc caccagcaga agagatgact aagaaagagt tcagtctgac ctgcatgatc     540
acaggcttct acctgccgga aattgctgtg actggaccag caatgggcg tacagagcaa      600
aactacaaga caccgcaac agtcctggac tctgatggtt cttacttcat gtacagcaag     660
ctcagagtac aaaagagcac ttgggaaaga ggaagtcttt tcgcctgctc agtggtccac     720
gagggtctgc acaatcacct tacgactaag accatctccc ggtctctggg taaaggaggg     780
ggctccgcac ccacttcaag ctccacttca agctctacag cggaagcaca acagcagcag    840
cagcagcagc agcagcagca gcagcacctg gagcagctgt tgatggacct acaggaactc     900
ctgagtagga tggaggatca caggaacctg agactcccca ggatgctcac cttcaaattt     960
tacttgcccg agcaggccac agaattggaa gatcttcagt gcctagaaga tgaacttgaa    1020
ccactgcggc aagttctgga tttgactcaa gcaaaagct ttcaattgga agatgctgag     1080
aatttcatca gcaatatcag agtaactgtt gtaaaactaa agggctctga caacacattt    1140
```

```
gagtgccaat tcgacgatga gccagcaact gtggtggact tctgaggag atggatagcc    1200 ttctgtcaaa gcatcatctc aacaagccct caacaccatc accaccatca ctgataa     1257
```

<210> SEQ ID NO 17
<211> LENGTH: 417
<212> TYPE: PRT
<213> ORGANISM: Artificial Sequence
<220> FEATURE:
<223> OTHER INFORMATION: Synthetic D265A Fc /QQ6210

<400> SEQUENCE: 17

```
Met Arg Val Pro Ala Gln Leu Leu Gly Leu Leu Leu Trp Leu Pro
1               5                   10                  15

Gly Ala Arg Cys Glu Pro Arg Val Pro Ile Thr Gln Asn Pro Cys Pro
            20                  25                  30

Pro Leu Lys Glu Cys Pro Pro Cys Ala Ala Pro Asp Leu Leu Gly Gly
        35                  40                  45

Pro Ser Val Phe Ile Phe Pro Pro Lys Ile Lys Asp Val Leu Met Ile
    50                  55                  60

Ser Leu Ser Pro Met Val Thr Cys Val Val Val Ala Val Ser Glu Asp
65                  70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
            100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
    130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
    210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys Gly Gly Gly Ser Ala Pro Thr Ser Ser Ser Thr Ser Ser Ser
            260                 265                 270

Thr Ala Glu Ala Gln Gln Gln Gln Gln Gln Gln Gln Gln Gln Gln Gln
        275                 280                 285

His Leu Glu Gln Leu Leu Met Asp Leu Gln Glu Leu Leu Ser Arg Met
    290                 295                 300

Glu Asp His Arg Asn Leu Arg Leu Pro Arg Met Leu Thr Phe Lys Phe
305                 310                 315                 320

Tyr Leu Pro Glu Gln Ala Thr Glu Leu Glu Asp Leu Gln Cys Leu Glu
                325                 330                 335

Asp Glu Leu Glu Pro Leu Arg Gln Val Leu Asp Leu Thr Gln Ser Lys
            340                 345                 350
```

Ser Phe Gln Leu Glu Asp Ala Glu Asn Phe Ile Ser Asn Ile Arg Val
        355                 360                 365

Thr Val Val Lys Leu Lys Gly Ser Asp Asn Thr Phe Glu Cys Gln Phe
    370                 375                 380

Asp Asp Glu Pro Ala Thr Val Val Asp Phe Leu Arg Arg Trp Ile Ala
385                 390                 395                 400

Phe Cys Gln Ser Ile Ile Ser Thr Ser Pro Gln His His His His
                405                 410                 415

His

<210> SEQ ID NO 18
<211> LENGTH: 1257
<212> TYPE: DNA
<213> ORGANISM: Artificial Sequence
<220> FEATURE:
<223> OTHER INFORMATION: Synthetic D265A Fc / E76A

<400> SEQUENCE: 18

```
atgagggtcc ccgctcagct cctggggctc ctgctgctct ggctcccagg tgcacgatgt      60
gagcccagag tgcccataac acagaacccc tgtcctccac tcaaagagtg tccccccatgc    120
gcagctccag acctcttggg tggaccatcc gtcttcatct ccctccaaa gatcaaggat      180
gtactcatga tctccctgag ccccatggtc acatgtgtgg tggtggccgt gagcgaggat    240
gacccagacg tccagatcag ctggtttgtg aacaacgtgg aagtacacac agctcagaca    300
caaacccata gagaggatta caacagtact ctccgggtgg tcagtgccct ccccatccag    360
caccaggact ggatgagtgg caaggagttc aaatgcaagg tcaacaacag agccctccca    420
tcccccatcg agaaaaccat ctcaaaaccc agagggccag taagagctcc acaggtatat    480
gtcttgcctc caccagcaga agagatgact aagaaagagt tcagtctgac ctgcatgatc    540
acaggcttct tacctgccga aattgctgtg gactggacca gcaatgggcg tacagagcaa    600
aactacaaga acaccgcaac agtcctggac tctgatggtt cttacttcat gtacagcaag    660
ctcagagtac aaaagagcac ttgggaaaga ggaagtcttt tcgcctgctc agtggtccac    720
gagggtctgc acaatcacct tacgactaag accatctccc ggtctctggg taaaggaggg    780
ggctccgcac ccacttcaag ctccacttca agctctacag cggaagcaca gcagcagcag    840
cagcagcagc agcagcagca gcagcacctg gagcagctgt tgatggacct acaggagctc    900
ctgagcagga tggagaatta caggaacctg aaactcccca ggatgctcac cttcaaattt    960
tacttgccca gcaggccac agaattgaaa gatcttcagt gcctagaaga tgctcttgga   1020
cctctgcggc atgttctgga tttgactcaa agcaaaagct ttcaattgga agatgctgag   1080
aatttcatca gcaatatcag agtaactgtt gtaaaactaa agggctctga caacacattt   1140
gagtgccaat tcgatgatga gtcagcaact gtggtggact ttctgaggag atggatagcc   1200
ttctgtcaaa gcatcatctc aacaagccct caacaccatc accaccatca ctgataa     1257
```

<210> SEQ ID NO 19
<211> LENGTH: 417
<212> TYPE: PRT
<213> ORGANISM: Artificial Sequence
<220> FEATURE:
<223> OTHER INFORMATION: Synthetic D265A Fc / E76A

<400> SEQUENCE: 19

Met Arg Val Pro Ala Gln Leu Leu Gly Leu Leu Leu Leu Trp Leu Pro
1               5                   10                  15

```
Gly Ala Arg Cys Glu Pro Arg Val Pro Ile Thr Gln Asn Pro Cys Pro
            20                  25                  30

Pro Leu Lys Glu Cys Pro Pro Cys Ala Ala Pro Asp Leu Leu Gly Gly
        35                  40                  45

Pro Ser Val Phe Ile Phe Pro Pro Lys Ile Lys Asp Val Leu Met Ile
    50                  55                  60

Ser Leu Ser Pro Met Val Thr Cys Val Val Ala Val Ser Glu Asp
65                  70                  75                  80

Asp Pro Asp Val Gln Ile Ser Trp Phe Val Asn Asn Val Glu Val His
                85                  90                  95

Thr Ala Gln Thr Gln Thr His Arg Glu Asp Tyr Asn Ser Thr Leu Arg
            100                 105                 110

Val Val Ser Ala Leu Pro Ile Gln His Gln Asp Trp Met Ser Gly Lys
        115                 120                 125

Glu Phe Lys Cys Lys Val Asn Asn Arg Ala Leu Pro Ser Pro Ile Glu
    130                 135                 140

Lys Thr Ile Ser Lys Pro Arg Gly Pro Val Arg Ala Pro Gln Val Tyr
145                 150                 155                 160

Val Leu Pro Pro Pro Ala Glu Glu Met Thr Lys Lys Glu Phe Ser Leu
                165                 170                 175

Thr Cys Met Ile Thr Gly Phe Leu Pro Ala Glu Ile Ala Val Asp Trp
            180                 185                 190

Thr Ser Asn Gly Arg Thr Glu Gln Asn Tyr Lys Asn Thr Ala Thr Val
        195                 200                 205

Leu Asp Ser Asp Gly Ser Tyr Phe Met Tyr Ser Lys Leu Arg Val Gln
    210                 215                 220

Lys Ser Thr Trp Glu Arg Gly Ser Leu Phe Ala Cys Ser Val Val His
225                 230                 235                 240

Glu Gly Leu His Asn His Leu Thr Thr Lys Thr Ile Ser Arg Ser Leu
                245                 250                 255

Gly Lys Gly Gly Gly Ser Ala Pro Thr Ser Ser Ser Thr Ser Ser Ser
            260                 265                 270

Thr Ala Glu Ala Gln Gln Gln Gln Gln Gln Gln Gln Gln Gln Gln Gln
        275                 280                 285

His Leu Glu Gln Leu Leu Met Asp Leu Gln Glu Leu Leu Ser Arg Met
    290                 295                 300

Glu Asn Tyr Arg Asn Leu Lys Leu Pro Arg Met Leu Thr Phe Lys Phe
305                 310                 315                 320

Tyr Leu Pro Lys Gln Ala Thr Glu Leu Lys Asp Leu Gln Cys Leu Glu
                325                 330                 335

Asp Ala Leu Gly Pro Leu Arg His Val Leu Asp Leu Thr Gln Ser Lys
            340                 345                 350

Ser Phe Gln Leu Glu Asp Ala Glu Asn Phe Ile Ser Asn Ile Arg Val
        355                 360                 365

Thr Val Val Lys Leu Lys Gly Ser Asp Asn Thr Phe Glu Cys Gln Phe
    370                 375                 380

Asp Asp Glu Ser Ala Thr Val Val Asp Phe Leu Arg Arg Trp Ile Ala
385                 390                 395                 400

Phe Cys Gln Ser Ile Ile Ser Thr Ser Pro Gln His His His His
                405                 410                 415

His
```

```
<210> SEQ ID NO 20
<211> LENGTH: 1257
<212> TYPE: DNA
<213> ORGANISM: Artificial Sequence
<220> FEATURE:
<223> OTHER INFORMATION: Synthetic D265A Fc / E76G

<400> SEQUENCE: 20
atgagggtcc ccgctcagct cctggggctc ctgctgctct ggctcccagg tgcacgatgt      60
gagcccagag tgcccataac acagaacccc tgtcctccac tcaaagagtg tccccccatgc   120
gcagctccag acctcttggg tggaccatcc gtcttcatct ccctccaaa gatcaaggat     180
gtactcatga tctccctgag ccccatggtc acatgtgtgg tggtggccgt gagcgaggat    240
gacccagacg tccagatcag ctggtttgtg aacaacgtgg aagtacacac agctcagaca   300
caaacccata gagaggatta caacagtact ctccgggtgg tcagtgccct ccccatccag    360
caccaggact ggatgagtgg caaggagttc aaatgcaagg tcaacaacag agccctccca   420
tcccccatcg agaaaaccat ctcaaaaccc agagggccag taagagctcc acaggtatat   480
gtcttgcctc caccagcaga gagatgact aagaaagagt tcagtctgac ctgcatgatc     540
acaggcttct tacctgccga aattgctgtg gactggacca gcaatgggcg tacagagcaa   600
aactacaaga acaccgcaac agtcctggac tctgatggtt cttacttcat gtacagcaag   660
ctcagagtac aaaagagcac ttgggaaaga ggaagtcttt tcgcctgctc agtggtccac   720
gagggtctgc acaatcacct tacgactaag accatctccc ggtctctggg taaggagggg   780
ggctccgcac ccacttcaag ctccacttca agctctacag cggaagcaca gcagcagcag   840
cagcagcagc agcagcagca gcagcacctg gagcagctgt tgatggacct acaggagctc   900
ctgagcagga tggagaatta caggaacctg aaactcccca ggatgctcac cttcaaattt   960
tacttgccca gcaggccac agaattgaaa gatcttcagt gcctagaaga tggtcttgga   1020
cctctgcggc atgttctgga tttgactcaa agcaaaagct ttcaattgga agatgctgag  1080
aatttcatca gcaatatcag agtaactgtt gtaaaactaa agggctctga acacacattt  1140
gagtgccaat tcgatgatga gtcagcaact gtggtggact ttctgaggag atggatagcc  1200
ttctgtcaaa gcatcatctc aacaagccct caacaccatc accaccatca ctgataa     1257

<210> SEQ ID NO 21
<211> LENGTH: 417
<212> TYPE: PRT
<213> ORGANISM: Artificial Sequence
<220> FEATURE:
<223> OTHER INFORMATION: Synthetic D265A Fc / E76G

<400> SEQUENCE: 21

Met Arg Val Pro Ala Gln Leu Leu Gly Leu Leu Leu Leu Trp Leu Pro
1               5                   10                  15

Gly Ala Arg Cys Glu Pro Arg Val Pro Ile Thr Gln Asn Pro Cys Pro
            20                  25                  30

Pro Leu Lys Glu Cys Pro Pro Cys Ala Ala Pro Asp Leu Leu Gly Gly
        35                  40                  45

Pro Ser Val Phe Ile Phe Pro Pro Lys Ile Lys Asp Val Leu Met Ile
    50                  55                  60

Ser Leu Ser Pro Met Val Thr Cys Val Val Val Ala Val Ser Glu Asp
65                  70                  75                  80

Asp Pro Asp Val Gln Ile Ser Trp Phe Val Asn Asn Val Glu Val His
                85                  90                  95
```

```
Thr Ala Gln Thr Gln Thr His Arg Glu Asp Tyr Asn Ser Thr Leu Arg
            100                 105                 110
Val Val Ser Ala Leu Pro Ile Gln His Gln Asp Trp Met Ser Gly Lys
        115                 120                 125
Glu Phe Lys Cys Lys Val Asn Asn Arg Ala Leu Pro Ser Pro Ile Glu
    130                 135                 140
Lys Thr Ile Ser Lys Pro Arg Gly Pro Val Arg Ala Pro Gln Val Tyr
145                 150                 155                 160
Val Leu Pro Pro Pro Ala Glu Glu Met Thr Lys Lys Glu Phe Ser Leu
                165                 170                 175
Thr Cys Met Ile Thr Gly Phe Leu Pro Ala Glu Ile Ala Val Asp Trp
            180                 185                 190
Thr Ser Asn Gly Arg Thr Glu Gln Asn Tyr Lys Asn Thr Ala Thr Val
        195                 200                 205
Leu Asp Ser Asp Gly Ser Tyr Phe Met Tyr Ser Lys Leu Arg Val Gln
    210                 215                 220
Lys Ser Thr Trp Glu Arg Gly Ser Leu Phe Ala Cys Ser Val Val His
225                 230                 235                 240
Glu Gly Leu His Asn His Leu Thr Thr Lys Thr Ile Ser Arg Ser Leu
                245                 250                 255
Gly Lys Gly Gly Gly Ser Ala Pro Thr Ser Ser Ser Thr Ser Ser Ser
            260                 265                 270
Thr Ala Glu Ala Gln Gln Gln Gln Gln Gln Gln Gln Gln Gln Gln Gln
            275                 280                 285
His Leu Glu Gln Leu Leu Met Asp Leu Gln Glu Leu Leu Ser Arg Met
        290                 295                 300
Glu Asn Tyr Arg Asn Leu Lys Leu Pro Arg Met Leu Thr Phe Lys Phe
305                 310                 315                 320
Tyr Leu Pro Lys Gln Ala Thr Glu Leu Lys Asp Leu Gln Cys Leu Glu
                325                 330                 335
Asp Gly Leu Gly Pro Leu Arg His Val Leu Asp Leu Thr Gln Ser Lys
            340                 345                 350
Ser Phe Gln Leu Glu Asp Ala Glu Asn Phe Ile Ser Asn Ile Arg Val
        355                 360                 365
Thr Val Val Lys Leu Lys Gly Ser Asp Asn Thr Phe Glu Cys Gln Phe
    370                 375                 380
Asp Asp Glu Ser Ala Thr Val Val Asp Phe Leu Arg Arg Trp Ile Ala
385                 390                 395                 400
Phe Cys Gln Ser Ile Ile Ser Thr Ser Pro Gln His His His His
                405                 410                 415
His
```

<210> SEQ ID NO 22
<211> LENGTH: 447
<212> TYPE: DNA
<213> ORGANISM: Artificial Sequence
<220> FEATURE:
<223> OTHER INFORMATION: Synthetic mIL-2 QQ 6.2-4

<400> SEQUENCE: 22

```
gcacccacct caagctccac ttcaagctct acagcggaag cacaacagca gcagcagcag    60
cagcagcagc agcagcagca cctggagcag ctgttgatgg acctacagga gctcctgagc   120
aggatggagg attccaggaa cctgagactc cccaggatgc tcaccttcaa atttacttg    180
cccaagcagg ccacagaatt ggaagatctt cagtgcctag aagatgaact tgaacctctg   240
```

```
cggcaagttc tggatttgac tcaaagcaaa agctttcaat tggaagatgc tgagaatttc    300
atcagcaata tcagagtaac tgttgtaaaa ctaaagggct ctgacaacac atttgagtgc    360
caattcgatg atgagccagc aactgtggtg ggctttctga ggagatggat agccttctgt    420
caaagcatca tctcaacgag ccctcaa                                        447
```

<210> SEQ ID NO 23
<211> LENGTH: 149
<212> TYPE: PRT
<213> ORGANISM: Artificial Sequence
<220> FEATURE:
<223> OTHER INFORMATION: Synthetic mIL-2 QQ 6.2-4

<400> SEQUENCE: 23

```
Ala Pro Thr Ser Ser Ser Thr Ser Ser Ser Thr Ala Glu Ala Gln Gln
1               5                   10                  15

Gln Gln Gln Gln Gln Gln Gln Gln Gln His Leu Glu Gln Leu Leu
            20                  25                  30

Met Asp Leu Gln Glu Leu Leu Ser Arg Met Glu Asp Ser Arg Asn Leu
        35                  40                  45

Arg Leu Pro Arg Met Leu Thr Phe Lys Phe Tyr Leu Pro Lys Gln Ala
    50                  55                  60

Thr Glu Leu Glu Asp Leu Gln Cys Leu Glu Asp Glu Leu Glu Pro Leu
65                  70                  75                  80

Arg Gln Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Pro Ala Thr
        115                 120                 125

Val Val Gly Phe Leu Arg Arg Trp Ile Ala Phe Cys Gln Ser Ile Ile
    130                 135                 140

Ser Thr Ser Pro Gln
145
```

<210> SEQ ID NO 24
<211> LENGTH: 435
<212> TYPE: DNA
<213> ORGANISM: Artificial Sequence
<220> FEATURE:
<223> OTHER INFORMATION: Synthetic mIL-2 QQ 6.2-8

<400> SEQUENCE: 24

```
gcacccacct caagctccac ttcaagctct acagcggaag cacaacagca gcagcagcag    60
cagcagcacc tggagcagct gttgatggac tacaggagc tcctgagtag gatggaggat    120
cacaggaacc tgagactccc caggatgctc accttcaaat tttacttgcc caagcaggcc    180
acagaattgg aagatcttca gtgcctagaa gatgaacttg aacctctgcg gcaagttctg    240
gatttgactc aaagcaaaag ctttcaattg gaagatgctg agaatttcat cagcaatatc    300
agagtaactg ttgtaaaact aaagggctct gacaacacat ttgagtgcca attcgatgat    360
gagccagcaa ctgtggtgga ctttctgagg agatggatag ccttctgtca aagcatcatc    420
tcaacaagcc ctcga                                                    435
```

<210> SEQ ID NO 25
<211> LENGTH: 145
<212> TYPE: PRT

<213> ORGANISM: Artificial Sequence
<220> FEATURE:
<223> OTHER INFORMATION: Synthetic mIL-2 QQ 6.2-8

<400> SEQUENCE: 25

```
Ala Pro Thr Ser Ser Ser Thr Ser Ser Ser Thr Ala Glu Ala Gln Gln
1               5                   10                  15

Gln Gln Gln Gln Gln Gln His Leu Glu Gln Leu Leu Met Asp Leu Gln
            20                  25                  30

Glu Leu Leu Ser Arg Met Glu Asp His Arg Asn Leu Arg Leu Pro Arg
        35                  40                  45

Met Leu Thr Phe Lys Phe Tyr Leu Pro Lys Gln Ala Thr Glu Leu Glu
    50                  55                  60

Asp Leu Gln Cys Leu Glu Asp Glu Leu Glu Pro Leu Arg Gln Val Leu
65                  70                  75                  80

Asp Leu Thr Gln Ser Lys Ser Phe Gln Leu Glu Asp Ala Glu Asn Phe
                85                  90                  95

Ile Ser Asn Ile Arg Val Thr Val Val Lys Leu Lys Gly Ser Asp Asn
            100                 105                 110

Thr Phe Glu Cys Gln Phe Asp Asp Glu Pro Ala Thr Val Val Asp Phe
        115                 120                 125

Leu Arg Arg Trp Ile Ala Phe Cys Gln Ser Ile Ile Ser Thr Ser Pro
    130                 135                 140

Arg
145
```

<210> SEQ ID NO 26
<211> LENGTH: 447
<212> TYPE: DNA
<213> ORGANISM: Artificial Sequence
<220> FEATURE:
<223> OTHER INFORMATION: Synthetic mIL-2 QQ 6.2-10

<400> SEQUENCE: 26

```
gcacccacct caagctccac ttcaagctct acagcggaag cacaacagca gcagcagcag    60
cagcagcagc agcagcagca cctggagcag ctgttgatgg acctacagga actcctgagt   120
aggatggagg atcacaggaa cctgagactc cccaggatgc tcaccttcaa attttacttg   180
cccgagcagg ccacagaatt ggaagatctt cagtgcctag aagatgaact tgaaccactg   240
cggcaagttc tggatttgac tcaaagcaaa agctttcaat tggaagatgc tgagaatttc   300
atcagcaata tcagagtaac tgttgtaaaa ctaaagggct ctgacaacac atttgagtgc   360
caattcgacg atgagccagc aactgtggtg gactttctga ggagatggat agccttctgt   420
caaagcatca tctcaacaag ccctcag                                      447
```

<210> SEQ ID NO 27
<211> LENGTH: 149
<212> TYPE: PRT
<213> ORGANISM: Artificial Sequence
<220> FEATURE:
<223> OTHER INFORMATION: Synthetic mIL-2 QQ 6.2-10

<400> SEQUENCE: 27

```
Ala Pro Thr Ser Ser Ser Thr Ser Ser Ser Thr Ala Glu Ala Gln Gln
1               5                   10                  15

Gln Gln Gln Gln Gln Gln Gln Gln Gln Gln His Leu Glu Gln Leu Leu
            20                  25                  30

Met Asp Leu Gln Glu Leu Leu Ser Arg Met Glu Asp His Arg Asn Leu
```

```
              35                  40                  45
Arg Leu Pro Arg Met Leu Thr Phe Lys Phe Tyr Leu Pro Glu Gln Ala
 50                  55                  60

Thr Glu Leu Glu Asp Leu Gln Cys Leu Glu Asp Glu Leu Pro Leu
65                  70                  75                  80

Arg Gln Val Leu Asp Leu Thr Gln Ser Lys Ser Phe Gln Leu Glu Asp
                 85                  90                  95

Ala Glu Asn Phe Ile Ser Asn Ile Arg Val Thr Val Val Lys Leu Lys
                100                 105                 110

Gly Ser Asp Asn Thr Phe Glu Cys Gln Phe Asp Asp Glu Pro Ala Thr
                115                 120                 125

Val Val Asp Phe Leu Arg Arg Trp Ile Ala Phe Cys Gln Ser Ile Ile
130                 135                 140

Ser Thr Ser Pro Gln
145
```

<210> SEQ ID NO 28
<211> LENGTH: 438
<212> TYPE: DNA
<213> ORGANISM: Artificial Sequence
<220> FEATURE:
<223> OTHER INFORMATION: Synthetic mIL-2 QQ 6.2-11

<400> SEQUENCE: 28

```
gcacccacct caagctccac ttcaagctct acagcggaag cacaacagca gcagcagcag    60
cagcagcagc acctggagca gctgttgatg gacctacagg agctcctgag caggatggag   120
gattccagga acctgagact ccccagaatg ctcaccttca aattttactt gcccgagcag   180
gccacagaat tgaaagatct ccagtgccta gaagatgaac ttgaacctct gcggcaagtt   240
ctggatttga ctcaaagcaa aagctttcaa ttggaagatg ctgagaattt catcagcaat   300
atcagagtaa ctgttgtaaa actaaagggc tctgacaaca catttgagtg ccaattcgac   360
gatgagccag caactgtggt ggactttctg aggagatgga tagccttctg tcaaagcatc   420
atctcaacaa gccctcag                                                 438
```

<210> SEQ ID NO 29
<211> LENGTH: 146
<212> TYPE: PRT
<213> ORGANISM: Artificial Sequence
<220> FEATURE:
<223> OTHER INFORMATION: Synthetic mIL-2 QQ 6.2-11

<400> SEQUENCE: 29

```
Ala Pro Thr Ser Ser Thr Ser Ser Thr Ala Glu Ala Gln Gln
1               5                  10                  15

Gln Gln Gln Gln Gln Gln His Leu Glu Gln Leu Leu Met Asp Leu
                20                  25                  30

Gln Glu Leu Leu Ser Arg Met Glu Asp Ser Arg Asn Leu Arg Leu Pro
                35                  40                  45

Arg Met Leu Thr Phe Lys Phe Tyr Leu Pro Glu Gln Ala Thr Glu Leu
 50                  55                  60

Lys Asp Leu Gln Cys Leu Glu Asp Glu Leu Pro Leu Arg Gln Val
65                  70                  75                  80

Leu Asp Leu Thr Gln Ser Lys Ser Phe Gln Leu Glu Asp Ala Glu Asn
                 85                  90                  95

Phe Ile Ser Asn Ile Arg Val Thr Val Val Lys Leu Lys Gly Ser Asp
                100                 105                 110
```

```
Asn Thr Phe Glu Cys Gln Phe Asp Asp Glu Pro Ala Thr Val Val Asp
            115                 120                 125

Phe Leu Arg Arg Trp Ile Ala Phe Cys Gln Ser Ile Ile Ser Thr Ser
        130                 135                 140

Pro Gln
145

<210> SEQ ID NO 30
<211> LENGTH: 447
<212> TYPE: DNA
<213> ORGANISM: Artificial Sequence
<220> FEATURE:
<223> OTHER INFORMATION: Synthetic mIL-2 QQ 6.2-13

<400> SEQUENCE: 30
gcacccacct caagctccac ttcaagctct acagcggaag cacaacagca gcagcagcag    60
cagcagcagc agcagcagca cctggagcag ctgttgatgg acctacagga gctcctgagt   120
aggatggagg atcacaggaa cctgagactc cccaggatgc tcaccttcaa attttacttg   180
cccgagcagg ccacagaatt gaaagatctc cagtgcctag aagatgaact gaacctctg    240 cggcaggttc tggatttgac tcaaagcaaa agctttcaat ggaagatgc tgagaatttc    300 atcagcaata tcagagtaac tgttgtaaaa ctaaagggct ctgacaacac atttgagtgc   360
caattcgatg atgagccagc aactgtggtg gactttctga ggagatggat agccttctgt   420
caaagcatca tctcaacaag ccctcag                                       447

<210> SEQ ID NO 31
<211> LENGTH: 149
<212> TYPE: PRT
<213> ORGANISM: Artificial Sequence
<220> FEATURE:
<223> OTHER INFORMATION: Synthetic mIL-2 QQ 6.2-13

<400> SEQUENCE: 31

Ala Pro Thr Ser Ser Thr Ser Ser Ser Thr Ala Glu Ala Gln Gln
1               5                   10                  15

Gln Gln Gln Gln Gln Gln Gln Gln Gln His Leu Glu Gln Leu Leu
            20                  25                  30

Met Asp Leu Gln Glu Leu Leu Ser Arg Met Glu Asp His Arg Asn Leu
        35                  40                  45

Arg Leu Pro Arg Met Leu Thr Phe Lys Phe Tyr Leu Pro Glu Gln Ala
    50                  55                  60

Thr Glu Leu Lys Asp Leu Gln Cys Leu Glu Asp Glu Leu Glu Pro Leu
65                  70                  75                  80

Arg Gln Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Pro Ala Thr
        115                 120                 125

Val Val Asp Phe Leu Arg Arg Trp Ile Ala Phe Cys Gln Ser Ile Ile
    130                 135                 140

Ser Thr Ser Pro Gln
145

<210> SEQ ID NO 32
<211> LENGTH: 461
```

<212> TYPE: DNA
<213> ORGANISM: Artificial Sequence
<220> FEATURE:
<223> OTHER INFORMATION: Synthetic Full length human IL-2

<400> SEQUENCE: 32

```
atgtacagga tgcaactcct gtcttgcatt gcactaagtc ttgcacttgt cacaaacagt      60
gcacctactt caagttctac aaagaaaaca cagctacaac tggagcattt actgctggat     120
ttacagatga ttttgaatgg aattaataat tacaagaatc ccaaactcac caggatgctc     180
acatttaagt tttacatgcc caagaaggcc acagaactga acatcttca gtgtctagaa      240
gaagaactca aacctctgga ggaagtgcta aatttagctc aaagcaaaaa ctttcactta     300
agacccaggg acttaatcag caatatcaac gtaatagttc tggaactaaa gggatctgaa     360
acaacattca tgtgtaatat gctgatgaga cagcaaccat gtagaatttt ctgaacagat     420
ggattacctt ttgtcaaagc atcatctcaa cactgacttg a                         461
```

<210> SEQ ID NO 33
<211> LENGTH: 153
<212> TYPE: PRT
<213> ORGANISM: Artificial Sequence
<220> FEATURE:
<223> OTHER INFORMATION: Synthetic Full length human IL-2

<400> SEQUENCE: 33

```
Met Tyr Arg Met Gln Leu Leu Ser Cys Ile Ala Leu Ser Leu Ala Leu
1               5                   10                  15
Val Thr Asn Ser Ala Pro Thr Ser Ser Ser Thr Lys Lys Thr Gln Leu
            20                  25                  30
Gln Leu Glu His Leu Leu Leu Asp Leu Gln Met Ile Leu Asn Gly Ile
        35                  40                  45
Asn Asn Tyr Lys Asn Pro Lys Leu Thr Arg Met Leu Thr Phe Lys Phe
    50                  55                  60
Tyr Met Pro Lys Lys Ala Thr Glu Leu Lys His Leu Gln Cys Leu Glu
65                  70                  75                  80
Glu Glu Leu Lys Pro Leu Glu Glu Val Leu Asn Leu Ala Gln Ser Lys
                85                  90                  95
Asn Phe His Leu Arg Pro Arg Asp Leu Ile Ser Asn Ile Asn Val Ile
            100                 105                 110
Val Leu Glu Leu Lys Gly Ser Glu Thr Thr Phe Met Cys Glu Tyr Ala
        115                 120                 125
Asp Glu Thr Ala Thr Ile Val Glu Phe Leu Asn Arg Trp Ile Thr Phe
    130                 135                 140
Cys Gln Ser Ile Ile Ser Thr Leu Thr
145                 150
```

<210> SEQ ID NO 34
<211> LENGTH: 401
<212> TYPE: DNA
<213> ORGANISM: Artificial Sequence
<220> FEATURE:
<223> OTHER INFORMATION: Synthetic Human IL-2 without signal peptide

<400> SEQUENCE: 34

```
gcacctactt caagttctac aaagaaaaca cagctacaac tggagcattt actgctggat      60
ttacagatga ttttgaatgg aattaataat tacaagaatc ccaaactcac caggatgctc     120
acatttaagt tttacatgcc caagaaggcc acagaactga acatcttca gtgtctagaa      180
```

```
gaagaactca aacctctgga ggaagtgcta aatttagctc aaagcaaaaa ctttcactta      240
agacccaggg acttaatcag caatatcaac gtaatagttc tggaactaaa gggatctgaa      300
acaacattca tgtgtaatat gctgatgaga cagcaaccat gtagaatttt ctgaacagat      360
ggattacctt tgtcaaagc atcatctcaa cactgacttg a                          401
```

```
<210> SEQ ID NO 35
<211> LENGTH: 133
<212> TYPE: PRT
<213> ORGANISM: Artificial Sequence
<220> FEATURE:
<223> OTHER INFORMATION: Synthetic Human IL-2 without signal peptide

<400> SEQUENCE: 35
```

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

```
<210> SEQ ID NO 36
<211> LENGTH: 749
<212> TYPE: PRT
<213> ORGANISM: Artificial Sequence
<220> FEATURE:
<223> OTHER INFORMATION: Synthetic Human serum albumin

<400> SEQUENCE: 36
```

Met Asp Met Arg Val Pro Ala Gln Leu Leu Gly Leu Leu Leu Leu Trp
1               5                   10                  15

Leu Pro Gly Ala Arg Cys Ala Asp Ala His Lys Ser Glu Val Ala His
            20                  25                  30

Arg Phe Lys Asp Leu Gly Glu Glu Asn Phe Lys Ala Leu Val Leu Ile
        35                  40                  45

Ala Phe Ala Gln Tyr Leu Gln Gln Cys Pro Phe Glu Asp His Val Lys
    50                  55                  60

Leu Val Asn Glu Val Thr Glu Phe Ala Lys Thr Cys Val Ala Asp Glu
65                  70                  75                  80

Ser Ala Glu Asn Cys Asp Lys Ser Leu His Thr Leu Phe Gly Asp Lys
                85                  90                  95

Leu Cys Thr Val Ala Thr Leu Arg Glu Thr Tyr Gly Glu Met Ala Asp
            100                 105                 110

Cys Cys Ala Lys Gln Glu Pro Glu Arg Asn Glu Cys Phe Leu Gln His
        115                 120                 125

```
Lys Asp Asp Asn Pro Asn Leu Pro Arg Leu Val Arg Pro Glu Val Asp
    130                 135                 140

Val Met Cys Thr Ala Phe His Asp Asn Glu Glu Thr Phe Leu Lys Lys
145                 150                 155                 160

Tyr Leu Tyr Glu Ile Ala Arg Arg His Pro Tyr Phe Tyr Ala Pro Glu
                165                 170                 175

Leu Leu Phe Phe Ala Lys Arg Tyr Lys Ala Ala Phe Thr Glu Cys Cys
            180                 185                 190

Gln Ala Ala Asp Lys Ala Ala Cys Leu Leu Pro Lys Leu Asp Glu Leu
        195                 200                 205

Arg Asp Glu Gly Lys Ala Ser Ser Ala Lys Gln Arg Leu Lys Cys Ala
    210                 215                 220

Ser Leu Gln Lys Phe Gly Glu Arg Ala Phe Lys Ala Trp Ala Val Ala
225                 230                 235                 240

Arg Leu Ser Gln Arg Phe Pro Lys Ala Glu Phe Ala Glu Val Ser Lys
                245                 250                 255

Leu Val Thr Asp Leu Thr Lys Val His Thr Glu Cys Cys His Gly Asp
            260                 265                 270

Leu Leu Glu Cys Ala Asp Asp Arg Ala Asp Leu Ala Lys Tyr Ile Cys
        275                 280                 285

Glu Asn Gln Asp Ser Ile Ser Ser Lys Leu Lys Glu Cys Cys Glu Lys
    290                 295                 300

Pro Leu Leu Glu Lys Ser His Cys Ile Ala Glu Val Glu Asn Asp Glu
305                 310                 315                 320

Met Pro Ala Asp Leu Pro Ser Leu Ala Ala Asp Phe Val Glu Ser Lys
                325                 330                 335

Asp Val Cys Lys Asn Tyr Ala Glu Ala Lys Asp Val Phe Leu Gly Met
            340                 345                 350

Phe Leu Tyr Glu Tyr Ala Arg Arg His Pro Asp Tyr Ser Val Val Leu
        355                 360                 365

Leu Leu Arg Leu Ala Lys Thr Tyr Glu Thr Thr Leu Glu Lys Cys Cys
    370                 375                 380

Ala Ala Ala Asp Pro His Glu Cys Tyr Ala Lys Val Phe Asp Glu Phe
385                 390                 395                 400

Lys Pro Leu Val Glu Glu Pro Gln Asn Leu Ile Lys Gln Asn Cys Glu
                405                 410                 415

Leu Phe Glu Gln Leu Gly Glu Tyr Lys Phe Gln Asn Ala Leu Leu Val
            420                 425                 430

Arg Tyr Thr Lys Lys Val Pro Gln Val Ser Thr Pro Thr Leu Val Glu
        435                 440                 445

Val Ser Arg Asn Leu Gly Lys Val Gly Ser Lys Cys Cys Lys His Pro
    450                 455                 460

Glu Ala Lys Arg Met Pro Cys Ala Glu Asp Tyr Leu Ser Val Val Leu
465                 470                 475                 480

Asn Gln Leu Cys Val Leu His Glu Lys Thr Pro Val Ser Asp Arg Val
                485                 490                 495

Thr Lys Cys Cys Thr Glu Ser Leu Val Asn Arg Arg Pro Cys Phe Ser
            500                 505                 510

Ala Leu Glu Val Asp Glu Thr Tyr Val Pro Lys Glu Phe Asn Ala Glu
        515                 520                 525

Thr Phe Thr Phe His Ala Asp Ile Cys Thr Leu Ser Glu Lys Glu Arg
    530                 535                 540

Gln Ile Lys Lys Gln Thr Ala Leu Val Glu Leu Val Lys His Lys Pro
```

```
                545                 550                 555                 560
Lys Ala Thr Lys Glu Gln Leu Lys Ala Val Met Asp Asp Phe Ala Ala
                    565                 570                 575
Phe Val Glu Lys Cys Cys Lys Ala Asp Asp Lys Glu Thr Cys Phe Ala
                    580                 585                 590
Glu Glu Gly Lys Lys Leu Val Ala Ala Ser Gln Ala Ala Leu Gly Leu
                    595                 600                 605
Gly Gly Gly Ser Ala Pro Thr Ser Ser Ser Thr Lys Lys Thr Gln Leu
                    610                 615                 620
Gln Leu Glu His Leu Leu Leu Asp Leu Gln Met Ile Leu Asn Gly Ile
625                 630                 635                 640
Asn Asn Tyr Lys Asn Pro Lys Leu Thr Arg Met Leu Thr Phe Lys Phe
                    645                 650                 655
Tyr Met Pro Lys Lys Ala Thr Glu Leu Lys His Leu Gln Cys Leu Glu
                    660                 665                 670
Glu Glu Leu Lys Pro Leu Glu Glu Val Leu Asn Leu Ala Gln Ser Lys
                    675                 680                 685
Asn Phe His Leu Arg Pro Arg Asp Leu Ile Ser Asn Ile Asn Val Ile
                    690                 695                 700
Val Leu Glu Leu Lys Gly Ser Glu Thr Thr Phe Met Cys Glu Tyr Ala
705                 710                 715                 720
Asp Glu Thr Ala Thr Ile Val Glu Phe Leu Asn Arg Trp Ile Thr Phe
                    725                 730                 735
Cys Gln Ser Ile Ile Ser Thr Leu Thr Gly Gly Gly Ser
                    740                 745

<210> SEQ ID NO 37
<211> LENGTH: 726
<212> TYPE: PRT
<213> ORGANISM: Artificial Sequence
<220> FEATURE:
<223> OTHER INFORMATION: Synthetic Mature HSA

<400> SEQUENCE: 37

Asp Ala His Lys Ser Glu Val Ala His Arg Phe Lys Asp Leu Gly Glu
1               5                   10                  15
Glu Asn Phe Lys Ala Leu Val Leu Ile Ala Phe Ala Gln Tyr Leu Gln
                    20                  25                  30
Gln Cys Pro Phe Glu Asp His Val Lys Leu Val Asn Glu Val Thr Glu
                35                  40                  45
Phe Ala Lys Thr Cys Val Ala Asp Glu Ser Ala Glu Asn Cys Asp Lys
            50                  55                  60
Ser Leu His Thr Leu Phe Gly Asp Lys Leu Cys Thr Val Ala Thr Leu
65                  70                  75                  80
Arg Glu Thr Tyr Gly Glu Met Ala Asp Cys Cys Ala Lys Gln Glu Pro
                    85                  90                  95
Glu Arg Asn Glu Cys Phe Leu Gln His Lys Asp Asp Asn Pro Asn Leu
                100                 105                 110
Pro Arg Leu Val Arg Pro Glu Val Asp Val Met Cys Thr Ala Phe His
                115                 120                 125
Asp Asn Glu Glu Thr Phe Leu Lys Lys Tyr Leu Tyr Glu Ile Ala Arg
            130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
```

```
              165                 170                 175
Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Gly Gly Ser Ala Pro Thr
            580                 585                 590
```

```
Ser Ser Ser Thr Lys Lys Thr Gln Leu Gln Leu Glu His Leu Leu Leu
            595                 600                 605
Asp Leu Gln Met Ile Leu Asn Gly Ile Asn Asn Tyr Lys Asn Pro Lys
    610                 615                 620
Leu Thr Arg Met Leu Thr Phe Lys Phe Tyr Met Pro Lys Lys Ala Thr
625                 630                 635                 640
Glu Leu Lys His Leu Gln Cys Leu Glu Glu Glu Leu Lys Pro Leu Glu
                645                 650                 655
Glu Val Leu Asn Leu Ala Gln Ser Lys Asn Phe His Leu Arg Pro Arg
            660                 665                 670
Asp Leu Ile Ser Asn Ile Asn Val Ile Val Leu Glu Leu Lys Gly Ser
        675                 680                 685
Glu Thr Thr Phe Met Cys Glu Tyr Ala Asp Glu Thr Ala Thr Ile Val
            690                 695                 700
Glu Phe Leu Asn Arg Trp Ile Thr Phe Cys Gln Ser Ile Ile Ser Thr
705                 710                 715                 720
Leu Thr Gly Gly Gly Ser
                725
```

<210> SEQ ID NO 38
<211> LENGTH: 2247
<212> TYPE: DNA
<213> ORGANISM: Artificial Sequence
<220> FEATURE:
<223> OTHER INFORMATION: Synthetic Human serum albumin

<400> SEQUENCE: 38

```
atggatatgc gggtgcctgc tcagctgctg ggactgctgc tgctgtggct gcctggggct     60
agatgcgccg atgctcacaa aagcgaagtc gcacacaggt tcaaagatct gggggaggaa    120
aactttaagg ctctggtgct gattgcattc gcccagtacc tgcagcagtg cccctttgag    180
gaccacgtga aactggtcaa cgaagtgact gagttcgcca agacctgcgt ggccgacgaa    240
tctgctgaga attgtgataa aagtctgcat actctgtttg gggataagct gtgtacagtg    300
gccactctgc gagaaaccta tggagagatg gcagactgct gtgccaaaca ggaacccgag    360
cggaacgaat gcttcctgca gcataaggac gataaccccc atctgcctcg cctggtgcga    420
cctgaggtgg acgtcatgtg tacagccttc acgataatga ggaaactttt ctgaagaaa     480
tacctgtacg aaatcgctcg gagacatcct tacttttatg caccagagct gctgttcttt    540
gccaaacgct acaaggccgc tttcaccgag tgctgtcagg cagccgataa agctgcatgc    600
ctgctgccta agctggacga actgagggat gagggcaagg ccagctccgc taaacagcgc    660
ctgaagtgtg ctagcctgca gaaattcggg gagcgagcct tcaaggcttg gcagtggca    720
cggctgagtc agagattccc aaaggcagaa tttgccgagg tctcaaaact ggtgaccgac    780
ctgacaaagg tgcacaccga tgctgtcat ggcgacctgc tggagtgcgc cgacgatcga    840
gctgatctgg caaagtatat ttgtgagaac caggactcca tctctagtaa gctgaaagaa    900
tgctgtgaga aaccactgct ggaaaagtct cactgcattg ccgaagtgga aacgacgag     960
atgccagctg atctgccctc actggccgct gacttcgtcg aaagcaaaga tgtgtgtaag   1020
aattacgctg aggcaaagga tgtgttcctg ggaatgtttc tgtacgagta tgccaggcgc   1080
cacccagact actccgtggt cctgctgctg aggctggcta aaacatatga aaccacactg   1140
gagaagtgct gtgcagccgc tgatcccca tgaatgctatg ccaaagtctt cgacgagttt   1200
aagccctgg tggaggaacc tcagaacctg atcaaacaga attgtgaact gtttgagcag   1260
```

```
ctgggcgagt acaagttcca gaacgccctg ctggtgcgct ataccaagaa agtcccacag    1320
gtgtccacac ccactctggt ggaggtgagc cggaatctgg gcaaagtggg gagtaaatgc    1380
tgtaagcacc ctgaagccaa gaggatgcca tgcgctgagg attacctgag tgtggtcctg    1440
aatcagctgt gtgtcctgca tgaaaaaaca cctgtcagcg accgggtgac aaagtgctgt    1500
actgagtcac tggtgaaccg acggccctgc tttagcgccc tggaagtcga tgagacttat    1560
gtgcctaaag agttcaacgc tgagaccttc acatttcacg cagacatttg taccctgagc    1620
gaaaaggaga gacagatcaa gaaacagaca gccctggtcg aactggtgaa gcataaaccc    1680
aaggccacaa aagagcagct gaaggctgtc atggacgatt tcgcagcctt tgtggaaaaa    1740
tgctgtaagg cagacgataa ggagacttgc tttgccgagg aaggaaagaa actggtggct    1800
gcatcccagg cagctctggg actgggagga ggatctgccc ctacctcaag ctccactaag    1860
aaaacccagc tgcagctgga gcacctgctg ctggacctgc agatgattct gaacgggatc    1920
aacaattaca aaaatccaaa gctgacccgg atgctgacat tcaagttta tatgcccaag    1980 aaagccacag agctgaaaca cctgcagtgc ctggaggaag agctgaagcc tctggaagag    2040
gtgctgaacc tggcccagag caagaatttc catctgagac aagggatct gatctccaac    2100 attaatgtga tcgtcctgga actgaaggga tctgagacta cctttatgtg cgaatacgct    2160
gacgagactg caaccattgt ggagttcctg aacagatgga tcaccttctg ccagtccatc    2220
atttctactc tgacaggcgg ggggagc                                        2247
```

<210> SEQ ID NO 39
<211> LENGTH: 28
<212> TYPE: PRT
<213> ORGANISM: Artificial Sequence
<220> FEATURE:
<223> OTHER INFORMATION: Synthetic EETI-II from Knottin Database

<400> SEQUENCE: 39

Gly Cys Pro Arg Ile Leu Met Arg Cys Lys Gln Asp Ser Asp Cys Leu
1               5                   10                  15

Ala Gly Cys Val Cys Gly Pro Asn Gly Phe Cys Gly
            20                  25

<210> SEQ ID NO 40
<211> LENGTH: 47
<212> TYPE: PRT
<213> ORGANISM: Artificial Sequence
<220> FEATURE:
<223> OTHER INFORMATION: Synthetic AgRP from Knottin Database

<400> SEQUENCE: 40

Gly Cys Val Arg Leu His Glu Ser Cys Leu Gly Gln Gln Val Pro Cys
1               5                   10                  15

Cys Asp Pro Cys Ala Thr Cys Tyr Cys Arg Phe Phe Asn Ala Phe Cys
            20                  25                  30

Tyr Cys Arg Lys Leu Gly Thr Ala Met Asn Pro Cys Ser Arg Thr
        35                  40                  45

<210> SEQ ID NO 41
<211> LENGTH: 48
<212> TYPE: PRT
<213> ORGANISM: Artificial Sequence
<220> FEATURE:
<223> OTHER INFORMATION: Synthetic Omega agatoxin from Knottin Database

<400> SEQUENCE: 41

Glu Asp Asn Cys Ile Ala Glu Asp Tyr Gly Lys Cys Thr Trp Gly Gly
1               5                   10                  15

Thr Lys Cys Cys Arg Gly Arg Pro Cys Arg Cys Ser Met Ile Gly Thr
            20                  25                  30

Asn Cys Glu Cys Thr Pro Arg Leu Ile Met Glu Gly Leu Ser Phe Ala
        35                  40                  45

<210> SEQ ID NO 42
<211> LENGTH: 33
<212> TYPE: PRT
<213> ORGANISM: Artificial Sequence
<220> FEATURE:
<223> OTHER INFORMATION: Synthetic EETI-II Library
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (9)..(13)
<223> OTHER INFORMATION: Xaa can be any naturally occurring amino acid

<400> SEQUENCE: 42

Gly Cys Xaa Xaa Xaa Arg Gly Asp Xaa Xaa Xaa Xaa Xaa Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 43
<211> LENGTH: 33
<212> TYPE: PRT
<213> ORGANISM: Artificial Sequence
<220> FEATURE:
<223> OTHER INFORMATION: Synthetic EETI-II K15S Mutation Library
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (9)..(13)
<223> OTHER INFORMATION: Xaa can be any naturally occurring amino acid

<400> SEQUENCE: 43

Gly Cys Xaa Xaa Xaa Arg Gly Asp Xaa Xaa Xaa Xaa Xaa Cys Ser Gln
1               5                   10                  15

Asp Ser Asp Cys Leu Ala Gly Cys Val Cys Gly Pro Asn Gly Phe Cys
            20                  25                  30

Gly

<210> SEQ ID NO 44
<211> LENGTH: 822
<212> TYPE: DNA
<213> ORGANISM: Artificial Sequence
<220> FEATURE:
<223> OTHER INFORMATION: Synthetic 2.5F-(K15S) mIgG2aFc

<400> SEQUENCE: 44
ggttgtccaa gaccaagagg tgataatcca ccattgactt gttctcaaga ttctgattgt      60
ttggctggtt gtgtttgtgg tccaaatggt ttttgtggtg gtcgactaga gcccagagtg     120
cccataacac agaaccctg tcctccactc aaagagtgtc ccccatgcgc agctccagac     180
ctcttgggtg gaccatccgt cttcatcttc cctccaaaga tcaaggatgt actcatgatc     240

```
tccctgagcc ccatggtcac atgtgtggtg gtggatgtga gcgaggatga cccagacgtc    300
cagatcagct ggtttgtgaa caacgtggaa gtacacacag ctcagacaca aacccataga    360
gaggattaca acagtactct ccgggtggtc agtgccctcc ccatccagca ccaggactgg    420
atgagtggca aggagttcaa atgcaaggtc aacaacagag ccctcccatc ccccatcgag    480
aaaaccatct caaacccag agggccagta agagctccac aggtatatgt cttgcctcca    540
ccagcagaag agatgactaa gaaagagttc agtctgacct gcatgatcac aggcttctta    600
cctgccgaaa ttgctgtgga ctggaccagc aatgggcgta cagagcaaaa ctacaagaac    660
accgcaacag tcctggactc tgatggttct tacttcatgt acagcaagct cagagtacaa    720
aagagcactt gggaaagagg aagtctttc gcctgctcag tggtccacga gggtctgcac    780
aatcacctta cgactaagac catctcccgg tctctgggta aa                       822
```

```
<210> SEQ ID NO 45
<211> LENGTH: 271
<212> TYPE: PRT
<213> ORGANISM: Artificial Sequence
<220> FEATURE:
<223> OTHER INFORMATION: Synthetic 2.5F-(K15S) mIgG2aFc

<400> SEQUENCE: 45

Gly Cys Pro Arg Pro Arg Gly Asp Asn Pro Leu Thr Cys Ser Gln
1               5                   10                  15

Asp Ser Asp Cys Leu Ala Gly Cys Val Cys Gly Pro Asn Gly Phe Cys
            20                  25                  30

Gly Glu Pro Arg Val Pro Ile Thr Gln Asn Pro Cys Pro Pro Leu Lys
            35                  40                  45

Glu Cys Pro Pro Cys Ala Ala Pro Asp Leu Leu Gly Gly Pro Ser Val
        50                  55                  60

Phe Ile Phe Pro Pro Lys Ile Lys Asp Val Leu Met Ile Ser Leu Ser
65                  70                  75                  80

Pro Met Val Thr Cys Val Val Asp Val Ser Glu Asp Asp Pro Asp
                85                  90                  95

Val Gln Ile Ser Trp Phe Val Asn Asn Val Glu Val His Thr Ala Gln
            100                 105                 110

Thr Gln Thr His Arg Glu Asp Tyr Asn Ser Thr Leu Arg Val Val Ser
            115                 120                 125

Ala Leu Pro Ile Gln His Gln Asp Trp Met Ser Gly Lys Glu Phe Lys
        130                 135                 140

Cys Lys Val Asn Asn Arg Ala Leu Pro Ser Pro Ile Glu Lys Thr Ile
145                 150                 155                 160

Ser Lys Pro Arg Gly Pro Val Arg Ala Pro Gln Val Tyr Val Leu Pro
                165                 170                 175

Pro Pro Ala Glu Glu Met Thr Lys Lys Glu Phe Ser Leu Thr Cys Met
            180                 185                 190

Ile Thr Gly Phe Leu Pro Ala Glu Ile Ala Val Asp Trp Thr Ser Asn
            195                 200                 205

Gly Arg Thr Glu Gln Asn Tyr Lys Asn Thr Ala Thr Val Leu Asp Ser
        210                 215                 220

Asp Gly Ser Tyr Phe Met Tyr Ser Lys Leu Arg Val Gln Lys Ser Thr
225                 230                 235                 240

Trp Glu Arg Gly Ser Leu Phe Ala Cys Ser Val Val His Glu Gly Leu
                245                 250                 255
```

His Asn His Leu Thr Thr Lys Thr Ile Ser Arg Ser Leu Gly Lys
            260                 265                 270

<210> SEQ ID NO 46
<211> LENGTH: 822
<212> TYPE: DNA
<213> ORGANISM: Artificial Sequence
<220> FEATURE:
<223> OTHER INFORMATION: Synthetic 2.5D-(K15S) mIgG2aFc

<400> SEQUENCE: 46

```
ggttgtccac aaggcagagg tgattgggct ccaacttctt gttctcaaga ttctgattgt    60
ttggctggtt gtgtttgtgg tccaaatggt ttttgtggtg gtcgactaga gcccagagtg   120
cccataacac agaacccctg tcctccactc aaagagtgtc ccccatgcgc agctccagac   180
ctcttgggtg gaccatccgt cttcatcttc cctccaaaga tcaaggatgt actcatgatc   240
tccctgagcc ccatggtcac atgtgtggtg gtggatgtga gcgaggatga cccagacgtc   300
cagatcagct ggtttgtgaa caacgtggaa gtacacacag ctcagacaca aacccataga   360
gaggattaca acagtactct ccgggtggtc agtgccctcc catccagca ccaggactgg   420
atgagtggca aggagttcaa atgcaaggtc aacaacagag ccctcccatc ccccatcgag   480
aaaaccatct caaacccag agggccagta agagctccac aggtatatgt cttgcctcca   540
ccagcagaag atgactaa gaaagagttc agtctgacct gcatgatcac aggcttctta   600
cctgccgaaa ttgctgtgga ctggaccagc aatgggcgta cagagcaaaa ctacaagaac   660
accgcaacag tcctggactc tgatggttct tacttcatgt acagcaagct cagagtacaa   720
aagagcactt gggaaagagg aagtcttttc gcctgctcag tggtccacga gggtctgcac   780
aatcacctta cgactaagac catctcccgg tctctgggta aa                     822
```

<210> SEQ ID NO 47
<211> LENGTH: 271
<212> TYPE: PRT
<213> ORGANISM: Artificial Sequence
<220> FEATURE:
<223> OTHER INFORMATION: Synthetic 2.5D-(K15S) mIgG2aFc

<400> SEQUENCE: 47

Gly Cys Pro Gln Gly Arg Gly Asp Trp Ala Pro Thr Ser Cys Ser Gln
1               5                   10                  15

Asp Ser Asp Cys Leu Ala Gly Cys Val Cys Gly Pro Asn Gly Phe Cys
            20                  25                  30

Gly Glu Pro Arg Val Pro Ile Thr Gln Asn Pro Cys Pro Pro Leu Lys
        35                  40                  45

Glu Cys Pro Pro Cys Ala Ala Pro Asp Leu Leu Gly Gly Pro Ser Val
    50                  55                  60

Phe Ile Phe Pro Pro Lys Ile Lys Asp Val Leu Met Ile Ser Leu Ser
65                  70                  75                  80

Pro Met Val Thr Cys Val Val Val Asp Val Ser Glu Asp Asp Pro Asp
            85                  90                  95

Val Gln Ile Ser Trp Phe Val Asn Asn Val Glu Val His Thr Ala Gln
        100                 105                 110

Thr Gln Thr His Arg Glu Asp Tyr Asn Ser Thr Leu Arg Val Val Ser
    115                 120                 125

Ala Leu Pro Ile Gln His Gln Asp Trp Met Ser Gly Lys Glu Phe Lys
130                 135                 140

Cys Lys Val Asn Asn Arg Ala Leu Pro Ser Pro Ile Glu Lys Thr Ile

```
145                 150                 155                 160
Ser Lys Pro Arg Gly Pro Val Arg Ala Pro Gln Val Tyr Val Leu Pro
                165                 170                 175

Pro Pro Ala Glu Glu Met Thr Lys Lys Glu Phe Ser Leu Thr Cys Met
                180                 185                 190

Ile Thr Gly Phe Leu Pro Ala Glu Ile Ala Val Asp Trp Thr Ser Asn
                195                 200                 205

Gly Arg Thr Glu Gln Asn Tyr Lys Asn Thr Ala Thr Val Leu Asp Ser
            210                 215                 220

Asp Gly Ser Tyr Phe Met Tyr Ser Lys Leu Arg Val Gln Lys Ser Thr
225                 230                 235                 240

Trp Glu Arg Gly Ser Leu Phe Ala Cys Ser Val Val His Glu Gly Leu
                245                 250                 255

His Asn His Leu Thr Thr Lys Thr Ile Ser Arg Ser Leu Gly Lys
            260                 265                 270

<210> SEQ ID NO 48
<211> LENGTH: 265
<212> TYPE: PRT
<213> ORGANISM: Artificial Sequence
<220> FEATURE:
<223> OTHER INFORMATION: Synthetic 2.5F-(K15S) hIgG1Fc

<400> SEQUENCE: 48

Gly Cys Pro Arg Pro Arg Gly Asp Asn Pro Leu Thr Cys Ser Gln
1               5                   10                  15

Asp Ser Asp Cys Leu Ala Gly Cys Val Cys Gly Pro Asn Gly Phe Cys
                20                  25                  30

Gly Glu Pro Lys Ser Cys Asp Lys Thr His Thr Cys Pro Pro Cys Pro
            35                  40                  45

Ala Pro Glu Leu Leu Gly Gly Pro Ser Val Phe Leu Phe Pro Pro Lys
50                  55                  60

Pro Lys Asp Thr Leu Met Ile Ser Arg Thr Pro Glu Val Thr Cys Val
65                  70                  75                  80

Val Val Asp Val Ser His Glu Asp Pro Glu Val Lys Phe Asn Trp Tyr
                85                  90                  95

Val Asp Gly Val Glu Val His Asn Ala Lys Thr Lys Pro Arg Glu Glu
            100                 105                 110

Gln Tyr Asn Ser Thr Tyr Arg Val Val Ser Val Leu Thr Val Leu His
        115                 120                 125

Gln Asp Trp Leu Asn Gly Lys Glu Tyr Lys Cys Lys Val Ser Asn Lys
    130                 135                 140

Ala Leu Pro Ala Pro Ile Glu Lys Thr Ile Ser Lys Ala Lys Gly Gln
145                 150                 155                 160

Pro Arg Glu Pro Gln Val Tyr Thr Leu Pro Pro Ser Arg Glu Glu Met
                165                 170                 175

Thr Lys Asn Gln Val Ser Leu Thr Cys Leu Val Lys Gly Phe Tyr Pro
                180                 185                 190

Ser Asp Ile Ala Val Glu Trp Glu Ser Asn Gly Gln Pro Glu Asn Asn
            195                 200                 205

Tyr Lys Thr Thr Pro Pro Val Leu Asp Ser Asp Gly Ser Phe Phe Leu
        210                 215                 220

Tyr Ser Lys Leu Thr Val Asp Lys Ser Arg Trp Gln Gln Gly Asn Val
225                 230                 235                 240

Phe Ser Cys Ser Val Met His Glu Ala Leu His Asn His Tyr Thr Gln
```

<210> SEQ ID NO 49
<211> LENGTH: 260
<212> TYPE: PRT
<213> ORGANISM: Artificial Sequence
<220> FEATURE:
<223> OTHER INFORMATION: Synthetic 2.5F-(K15S) hIgG1Fc Fc Upper Hinge
      Deletion (Delta-EPKSC)

<400> SEQUENCE: 49

Gly Cys Pro Arg Pro Arg Gly Asp Asn Pro Leu Thr Cys Ser Gln
1               5                   10                  15

Asp Ser Asp Cys Leu Ala Gly Cys Val Cys Gly Pro Asn Gly Phe Cys
            20                  25                  30

Gly Asp Lys Thr His Thr Cys Pro Pro Cys Pro Ala Pro Glu Leu Leu
        35                  40                  45

Gly Gly Pro Ser Val Phe Leu Phe Pro Pro Lys Pro Lys Asp Thr Leu
    50                  55                  60

Met Ile Ser Arg Thr Pro Glu Val Thr Cys Val Val Val Asp Val Ser
65                  70                  75                  80

His Glu Asp Pro Glu Val Lys Phe Asn Trp Tyr Val Asp Gly Val Glu
                85                  90                  95

Val His Asn Ala Lys Thr Lys Pro Arg Glu Glu Gln Tyr Asn Ser Thr
            100                 105                 110

Tyr Arg Val Val Ser Val Leu Thr Val Leu His Gln Asp Trp Leu Asn
        115                 120                 125

Gly Lys Glu Tyr Lys Cys Lys Val Ser Asn Lys Ala Leu Pro Ala Pro
    130                 135                 140

Ile Glu Lys Thr Ile Ser Lys Ala Lys Gly Gln Pro Arg Glu Pro Gln
145                 150                 155                 160

Val Tyr Thr Leu Pro Pro Ser Arg Glu Glu Met Thr Lys Asn Gln Val
                165                 170                 175

Ser Leu Thr Cys Leu Val Lys Gly Phe Tyr Pro Ser Asp Ile Ala Val
            180                 185                 190

Glu Trp Glu Ser Asn Gly Gln Pro Glu Asn Asn Tyr Lys Thr Thr Pro
        195                 200                 205

Pro Val Leu Asp Ser Asp Gly Ser Phe Phe Leu Tyr Ser Lys Leu Thr
    210                 215                 220

Val Asp Lys Ser Arg Trp Gln Gln Gly Asn Val Phe Ser Cys Ser Val
225                 230                 235                 240

Met His Glu Ala Leu His Asn His Tyr Thr Gln Lys Ser Leu Ser Leu
                245                 250                 255

Ser Pro Gly Lys
            260

<210> SEQ ID NO 50
<211> LENGTH: 265
<212> TYPE: PRT
<213> ORGANISM: Artificial Sequence
<220> FEATURE:
<223> OTHER INFORMATION: Synthetic 2.5D-(K15S) hIgG1Fc

<400> SEQUENCE: 50

Gly Cys Pro Gln Gly Arg Gly Asp Trp Ala Pro Thr Ser Cys Ser Gln
1               5                   10                  15

Asp Ser Asp Cys Leu Ala Gly Cys Val Cys Gly Pro Asn Gly Phe Cys
           20                  25                  30

Gly Glu Pro Lys Ser Cys Asp Lys Thr His Thr Cys Pro Pro Cys Pro
           35                  40                  45

Ala Pro Glu Leu Leu Gly Gly Pro Ser Val Phe Leu Phe Pro Pro Lys
 50                  55                  60

Pro Lys Asp Thr Leu Met Ile Ser Arg Thr Pro Glu Val Thr Cys Val
 65                  70                  75                  80

Val Val Asp Val Ser His Glu Asp Pro Glu Val Lys Phe Asn Trp Tyr
               85                  90                  95

Val Asp Gly Val Glu Val His Asn Ala Lys Thr Lys Pro Arg Glu Glu
              100                 105                 110

Gln Tyr Asn Ser Thr Tyr Arg Val Val Ser Val Leu Thr Val Leu His
          115                 120                 125

Gln Asp Trp Leu Asn Gly Lys Glu Tyr Lys Cys Lys Val Ser Asn Lys
130                 135                 140

Ala Leu Pro Ala Pro Ile Glu Lys Thr Ile Ser Lys Ala Lys Gly Gln
145                 150                 155                 160

Pro Arg Glu Pro Gln Val Tyr Thr Leu Pro Pro Ser Arg Glu Glu Met
              165                 170                 175

Thr Lys Asn Gln Val Ser Leu Thr Cys Leu Val Lys Gly Phe Tyr Pro
          180                 185                 190

Ser Asp Ile Ala Val Glu Trp Glu Ser Asn Gly Gln Pro Glu Asn Asn
      195                 200                 205

Tyr Lys Thr Thr Pro Pro Val Leu Asp Ser Asp Gly Ser Phe Phe Leu
  210                 215                 220

Tyr Ser Lys Leu Thr Val Asp Lys Ser Arg Trp Gln Gln Gly Asn Val
225                 230                 235                 240

Phe Ser Cys Ser Val Met His Glu Ala Leu His Asn His Tyr Thr Gln
              245                 250                 255

Lys Ser Leu Ser Leu Ser Pro Gly Lys
              260                 265

<210> SEQ ID NO 51
<211> LENGTH: 260
<212> TYPE: PRT
<213> ORGANISM: Artificial Sequence
<220> FEATURE:
<223> OTHER INFORMATION: Synthetic 2.5D-(K15S) hIgG1Fc Fc Upper Hinge
      Deletion (Delta-EPKSC)

<400> SEQUENCE: 51

Gly Cys Pro Gln Gly Arg Gly Asp Trp Ala Pro Thr Ser Cys Ser Gln
 1               5                  10                  15

Asp Ser Asp Cys Leu Ala Gly Cys Val Cys Gly Pro Asn Gly Phe Cys
           20                  25                  30

Gly Asp Lys Thr His Thr Cys Pro Pro Cys Pro Ala Pro Glu Leu Leu
           35                  40                  45

Gly Gly Pro Ser Val Phe Leu Phe Pro Pro Lys Pro Lys Asp Thr Leu
 50                  55                  60

Met Ile Ser Arg Thr Pro Glu Val Thr Cys Val Val Val Asp Val Ser
 65                  70                  75                  80

His Glu Asp Pro Glu Val Lys Phe Asn Trp Tyr Val Asp Gly Val Glu
               85                  90                  95

Val His Asn Ala Lys Thr Lys Pro Arg Glu Glu Gln Tyr Asn Ser Thr

```
                    100                 105                 110
Tyr Arg Val Val Ser Val Leu Thr Val Leu His Gln Asp Trp Leu Asn
            115                 120                 125
Gly Lys Glu Tyr Lys Cys Lys Val Ser Asn Lys Ala Leu Pro Ala Pro
        130                 135                 140
Ile Glu Lys Thr Ile Ser Lys Ala Lys Gly Gln Pro Arg Glu Pro Gln
145                 150                 155                 160
Val Tyr Thr Leu Pro Pro Ser Arg Glu Met Thr Lys Asn Gln Val
                165                 170                 175
Ser Leu Thr Cys Leu Val Lys Gly Phe Tyr Pro Ser Asp Ile Ala Val
            180                 185                 190
Glu Trp Glu Ser Asn Gly Gln Pro Glu Asn Asn Tyr Lys Thr Thr Pro
        195                 200                 205
Pro Val Leu Asp Ser Asp Gly Ser Phe Phe Leu Tyr Ser Lys Leu Thr
        210                 215                 220
Val Asp Lys Ser Arg Trp Gln Gln Gly Asn Val Phe Ser Cys Ser Val
225                 230                 235                 240
Met His Glu Ala Leu His Asn His Tyr Thr Gln Lys Ser Leu Ser Leu
                245                 250                 255
Ser Pro Gly Lys
            260

<210> SEQ ID NO 52
<211> LENGTH: 287
<212> TYPE: PRT
<213> ORGANISM: Artificial Sequence
<220> FEATURE:
<223> OTHER INFORMATION: Synthetic hPD-1

<400> SEQUENCE: 52

Met Gln Ile Pro Gln Ala Pro Trp Pro Val Val Trp Ala Val Leu Gln
1               5                   10                  15
Leu Gly Trp Arg Pro Gly Trp Phe Leu Asp Ser Pro Asp Pro Trp Asn
            20                  25                  30
Pro Pro Thr Phe Phe Pro Ala Leu Leu Val Val Thr Glu Gly Asp Asn
        35                  40                  45
Ala Thr Phe Thr Cys Ser Phe Ser Asn Thr Ser Glu Ser Phe Val Leu
    50                  55                  60
Asn Trp Tyr Arg Met Ser Pro Ser Asn Gln Thr Asp Lys Leu Ala Ala
65                  70                  75                  80
Phe Pro Glu Asp Arg Ser Gln Pro Gly Gln Asp Cys Arg Phe Arg Val
                85                  90                  95
Thr Gln Leu Pro Asn Gly Arg Asp Phe His Met Ser Val Val Arg Ala
            100                 105                 110
Arg Arg Asn Asp Ser Gly Thr Tyr Leu Cys Gly Ala Ile Ser Leu Ala
        115                 120                 125
Pro Lys Ala Gln Ile Lys Glu Ser Leu Arg Ala Glu Leu Arg Val Thr
    130                 135                 140
Glu Arg Arg Ala Glu Val Pro Thr Ala His Pro Ser Pro Ser Pro Arg
145                 150                 155                 160
Pro Ala Gly Gln Phe Gln Thr Leu Val Val Gly Val Val Gly Gly Leu
                165                 170                 175
Leu Gly Ser Leu Val Leu Leu Val Trp Val Leu Ala Val Ile Cys Ser
            180                 185                 190
Arg Ala Ala Arg Gly Thr Ile Gly Ala Arg Arg Thr Gly Gln Pro Leu
```

```
            195                 200                 205
Lys Glu Asp Pro Ser Ala Val Pro Val Phe Ser Val Asp Tyr Gly Glu
        210                 215                 220

Leu Asp Phe Gln Trp Arg Glu Lys Thr Pro Glu Pro Pro Val Pro Cys
225                 230                 235                 240

Val Pro Glu Gln Thr Glu Tyr Ala Thr Ile Val Phe Pro Ser Gly Met
                245                 250                 255

Gly Thr Ser Ser Pro Ala Arg Arg Gly Ser Ala Asp Gly Pro Arg Ser
            260                 265                 270

Ala Gln Pro Leu Arg Pro Glu Asp Gly His Cys Ser Trp Pro Leu
            275                 280                 285

<210> SEQ ID NO 53
<211> LENGTH: 290
<212> TYPE: PRT
<213> ORGANISM: Artificial Sequence
<220> FEATURE:
<223> OTHER INFORMATION: Synthetic hPD-L1

<400> SEQUENCE: 53

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
```

```
                         275                 280                 285

Glu Thr
    290

<210> SEQ ID NO 54
<211> LENGTH: 223
<212> TYPE: PRT
<213> ORGANISM: Artificial Sequence
<220> FEATURE:
<223> OTHER INFORMATION: Synthetic hCTLA-4

<400> SEQUENCE: 54

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220

<210> SEQ ID NO 55
<211> LENGTH: 525
<212> TYPE: PRT
<213> ORGANISM: Artificial Sequence
<220> FEATURE:
<223> OTHER INFORMATION: Synthetic hLAG-3

<400> SEQUENCE: 55

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60
```

-continued

His Gln Pro Asp Ser Gly Pro Pro Ala Ala Ala Pro Gly His Pro Leu
 65                  70                  75                  80

Ala Pro Gly Pro His Pro Ala Ala Pro Ser Ser Trp Gly Pro Arg Pro
                 85                  90                  95

Arg Arg Tyr Thr Val Leu Ser Val Gly Pro Gly Leu Arg Ser Gly
            100                 105                 110

Arg Leu Pro Leu Gln Pro Arg Val Gln Leu Asp Glu Arg Gly Arg Gln
            115                 120                 125

Arg Gly Asp Phe Ser Leu Trp Leu Arg Pro Ala Arg Ala Asp Ala
        130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
        290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Leu Leu Phe Leu Ile Leu Gly Val Leu Ser Leu Leu Leu Leu
        450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln

```
                    485                 490                 495
Ser Lys Ile Glu Glu Leu Glu Gln Glu Pro Glu Pro Glu Pro
                500                 505                 510

Glu Pro Glu Pro Glu Pro Glu Pro Glu Pro Glu Gln Leu
            515                 520                 525

<210> SEQ ID NO 56
<211> LENGTH: 300
<212> TYPE: PRT
<213> ORGANISM: Artificial Sequence
<220> FEATURE:
<223> OTHER INFORMATION: Synthetic hTIM-3

<400> SEQUENCE: 56

Met Phe Ser His Leu Pro Phe Asp Cys Val Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65              70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Gly Ile Tyr Ile Gly Ala Gly Ile
        195                 200                 205

Cys Ala Gly Leu Ala Leu Ala Leu Ile Phe Gly Ala Leu Ile Phe Lys
    210                 215                 220

Trp Tyr Ser His Ser Lys Glu Lys Ile Gln Asn Leu Ser Leu Ile Ser
225                 230                 235                 240

Leu Ala Asn Leu Pro Pro Ser Gly Leu Ala Asn Ala Val Ala Glu Gly
                245                 250                 255

Ile Arg Ser Glu Glu Asn Ile Tyr Thr Ile Glu Glu Asn Val Tyr Glu
            260                 265                 270

Val Glu Glu Pro Asn Glu Tyr Tyr Cys Tyr Val Ser Ser Arg Gln Gln
        275                 280                 285

Pro Ser Gln Pro Leu Gly Cys Arg Phe Ala Met Pro
    290                 295                 300

<210> SEQ ID NO 57
<211> LENGTH: 532
<212> TYPE: PRT
```

<213> ORGANISM: Artificial Sequence
<220> FEATURE:
<223> OTHER INFORMATION: Synthetic hB7-H3

<400> SEQUENCE: 57

```
Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Cys Cys Ser Phe Ser Pro Glu Pro Gly Phe Ser Leu Gln Leu Asn Leu
    50                  55                  60

Ile Trp Gln Leu Thr Asp Thr Lys Gln Leu Val His Ser Phe Ala Glu
65                  70                  75                  80

Gly Gln Asp Gln Gly Ser Ala Tyr Ala Asn Arg Thr Ala Leu Phe Pro
                85                  90                  95

Asp Leu Leu Ala Gln Gly Asn Ala Ser Leu Arg Leu Gln Arg Val Arg
            100                 105                 110

Val Ala Asp Glu Gly Ser Phe Cys Phe Val Ser Ile Arg Asp Phe Gly
        115                 120                 125

Ser Ala Ala Val Ser Leu Gln Val Ala Ala Pro Tyr Ser Lys Pro Ser
    130                 135                 140

Met Thr Leu Glu Pro Asn Lys Asp Leu Arg Pro Gly Asp Thr Val Thr
145                 150                 155                 160

Ile Thr Cys Ser Ser Tyr Gln Gly Tyr Pro Glu Ala Glu Val Phe Trp
                165                 170                 175

Gln Asp Gly Gln Gly Val Pro Leu Thr Gly Asn Val Thr Thr Ser Gln
            180                 185                 190

Met Ala Asn Glu Gln Gly Leu Phe Asp Val His Ser Ile Leu Arg Val
        195                 200                 205

Val Leu Gly Ala Asn Gly Thr Tyr Ser Cys Leu Val Arg Asn Pro Val
    210                 215                 220

Leu Gln Gln Asp Ala His Ser Ser Val Thr Ile Thr Pro Gln Arg Ser
225                 230                 235                 240

Pro Thr Gly Ala Val Glu Val Gln Val Pro Glu Asp Pro Val Val Ala
                245                 250                 255

Leu Val Gly Thr Asp Ala Thr Leu Arg Cys Ser Phe Ser Pro Glu Pro
            260                 265                 270

Gly Phe Ser Leu Ala Gln Leu Asn Leu Ile Trp Gln Leu Thr Asp Thr
        275                 280                 285

Lys Gln Leu Val His Ser Phe Thr Glu Gly Arg Asp Gln Gly Ser Ala
    290                 295                 300

Tyr Ala Asn Arg Thr Ala Leu Phe Pro Asp Leu Leu Ala Gln Gly Asn
305                 310                 315                 320

Ala Ser Leu Arg Leu Gln Arg Val Arg Val Ala Asp Glu Gly Ser Phe
                325                 330                 335

Thr Cys Phe Val Ser Ile Arg Asp Phe Gly Ser Ala Ala Val Ser Leu
            340                 345                 350

Gln Val Ala Ala Pro Tyr Ser Lys Pro Ser Met Thr Leu Glu Pro Asn
        355                 360                 365

Lys Asp Leu Arg Pro Gly Asp Thr Val Thr Ile Thr Cys Ser Ser Tyr
    370                 375                 380

Arg Gly Tyr Pro Glu Ala Glu Val Phe Trp Gln Asp Gly Gln Gly Val
```

```
                385                 390                 395                 400
Pro Leu Thr Gly Asn Val Thr Thr Ser Gln Met Ala Asn Glu Gln Gly
                    405                 410                 415

Leu Phe Asp Val His Ser Val Leu Arg Val Val Leu Gly Ala Asn Gly
                    420                 425                 430

Thr Tyr Ser Cys Leu Val Arg Asn Pro Val Leu Gln Gln Asp Ala His
                    435                 440                 445

Gly Ser Val Thr Ile Thr Gly Gln Pro Met Thr Phe Pro Pro Glu Ala
                    450                 455                 460

Leu Trp Val Thr Val Gly Leu Ser Val Cys Leu Ile Ala Leu Leu Val
465                 470                 475                 480

Ala Leu Ala Phe Val Cys Trp Arg Lys Ile Lys Gln Ser Cys Glu Glu
                    485                 490                 495

Glu Asn Ala Gly Ala Glu Asp Gln Asp Gly Glu Gly Glu Gly Ser Lys
                    500                 505                 510

Thr Ala Leu Gln Pro Leu Lys His Ser Asp Ser Lys Glu Asp Asp Gly
                    515                 520                 525

Gln Glu Ile Ala
            530

<210> SEQ ID NO 58
<211> LENGTH: 166
<212> TYPE: PRT
<213> ORGANISM: Artificial Sequence
<220> FEATURE:
<223> OTHER INFORMATION: Synthetic hB7-H4

<400> SEQUENCE: 58

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
                20                  25                  30

Ala Phe Ser Met Pro Glu Val Asn Val Asp Tyr Asn Ala Ser Ser Glu
                35                  40                  45

Thr Leu Arg Cys Glu Ala Pro Arg Trp Phe Pro Gln Pro Thr Val Val
            50                  55                  60

Trp Ala Ser Gln Val Asp Gln Gly Ala Asn Phe Ser Glu Val Ser Asn
65                  70                  75                  80

Thr Ser Phe Glu Leu Asn Ser Glu Asn Val Thr Met Lys Val Val Ser
                85                  90                  95

Val Leu Tyr Asn Val Thr Ile Asn Asn Thr Tyr Ser Cys Met Ile Glu
                100                 105                 110

Asn Asp Ile Ala Lys Ala Thr Gly Asp Ile Lys Val Thr Glu Ser Glu
                115                 120                 125

Ile Lys Arg Arg Ser His Leu Gln Leu Leu Asn Ser Lys Ala Ser Leu
            130                 135                 140

Cys Val Ser Ser Phe Phe Ala Ile Ser Trp Ala Leu Leu Pro Leu Ser
145                 150                 155                 160

Pro Tyr Leu Met Leu Lys
                165

<210> SEQ ID NO 59
<211> LENGTH: 33
<212> TYPE: PRT
<213> ORGANISM: Artificial Sequence
<220> FEATURE:
<223> OTHER INFORMATION: Synthetic Integrin Binding Kn Peptide Identifier 1.4A, Scaffold EETI-II

<400> SEQUENCE: 59

Gly Cys Ala Glu Pro Arg Gly Asp Met Pro Trp Thr Trp Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 60
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 1.4B, Scaffold EETI-II

<400> SEQUENCE: 60

Gly Cys Val Gly Gly Arg Gly Asp Trp Ser Pro Lys Trp Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 61
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 1.4C, Scaffold EETI-II

<400> SEQUENCE: 61

Gly Cys Ala Glu Leu Arg Gly Asp Arg Ser Tyr Pro Glu Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 62
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 1.4E, Scaffold EETI-II

<400> SEQUENCE: 62

Gly Cys Arg Leu Pro Arg Gly Asp Val Pro Arg Pro His Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 63
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 1.4H, Scaffold EEIT-II

<400> SEQUENCE: 63

```
Gly Cys Tyr Pro Leu Arg Gly Asp Asn Pro Tyr Ala Ala Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 64
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 1.5B, Saffold EETI-II

<400> SEQUENCE: 64

Gly Cys Thr Ile Gly Arg Gly Asp Trp Ala Pro Ser Glu Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 65
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Indentifier 1.5F, Scaffold EETI-II

<400> SEQUENCE: 65

Gly Cys His Pro Pro Arg Gly Asp Asn Pro Pro Val Thr Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 66
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 2.3A, Scaffold EETI-II

<400> SEQUENCE: 66

Gly Cys Pro Glu Pro Arg Gly Asp Asn Pro Pro Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 67
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 2.3B, Scaffold EETI-II

<400> SEQUENCE: 67

Gly Cys Leu Pro Pro Arg Gly Asp Asn Pro Pro Ser Cys Lys Gln
1               5                   10                  15
```

```
Asp Ser Asp Cys Gln Ala Gly Cys Val Cys Gly Pro Asn Gly Phe Cys
            20                  25                  30

Gly

<210> SEQ ID NO 68
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 2.3C, Scaffold EETI-II

<400> SEQUENCE: 68

Gly Cys His Leu Gly Arg Gly Asp Trp Ala Pro Val Gly Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 69
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 2.3D, Scaffold EETI-II

<400> SEQUENCE: 69

Gly Cys Asn Val Gly Arg Gly Asp Trp Ala Pro Ser Glu Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 70
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 2.3E, Scaffold EETI-II

<400> SEQUENCE: 70

Gly Cys Phe Pro Gly Arg Gly Asp Trp Ala Pro Ser Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 71
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 2.3F, Scaffold EETI-II

<400> SEQUENCE: 71

Gly Cys Pro Leu Pro Arg Gly Asp Asn Pro Pro Thr Glu Cys Lys Gln
1               5                   10                  15

Asp Ser Asp Cys Gln Ala Gly Cys Val Cys Gly Pro Asn Gly Phe Cys
            20                  25                  30
```

```
<210> SEQ ID NO 72
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 2.3G, Scaffold EETI-II

<400> SEQUENCE: 72

Gly Cys Ser Glu Ala Arg Gly Asp Asn Pro Arg Leu Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 73
<211> LENGTH: 32
<212> TYPE: PRT
<213> ORGANISM: Artificial Sequence
<220> FEATURE:
<223> OTHER INFORMATION: Synthetic Integrin Binding Knottin Sequence
      Peptide Identifier 2.3H, Scaffold EETI-II

<400> SEQUENCE: 73

Gly Cys Leu Leu Gly Arg Gly Asp Trp Ala Pro Glu Ala Cys Lys Gln
1               5                   10                  15

Asp Ser Asp Cys Arg Ala Gly Cys Val Cys Pro Asn Gly Phe Cys Gly
            20                  25                  30

<210> SEQ ID NO 74
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 2.3I, Scaffold EETI-II

<400> SEQUENCE: 74

Gly Cys His Val Gly Arg Gly Asp Trp Ala Pro Leu Lys Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 75
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 2.3J, Scaffold EETI-II

<400> SEQUENCE: 75

Gly Cys Val Arg Gly Arg Gly Asp Trp Ala Pro Pro Ser Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 76
```

```
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 2.4A, Scaffold EETI-II

<400> SEQUENCE: 76

Gly Cys Leu Gly Gly Arg Gly Asp Trp Ala Pro Pro Ala Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 77
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 2.4C, Scaffold EETI-II

<400> SEQUENCE: 77

Gly Cys Phe Val Gly Arg Gly Asp Trp Ala Pro Leu Thr Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 78
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 2.4D, Scaffold EETI-II

<400> SEQUENCE: 78

Gly Cys Pro Val Gly Arg Gly Asp Trp Ser Pro Ala Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 79
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 2.4E, Scaffold EETI-II

<400> SEQUENCE: 79

Gly Cys Pro Arg Pro Arg Gly Asp Asn Pro Pro Leu Thr Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 80
<211> LENGTH: 33
<212> TYPE: PRT
<213> ORGANISM: Artificial Sequence
```

```
<220> FEATURE:
<223> OTHER INFORMATION: Synthetic Integrin Binding Knottin Sequence
      Peptide Identifier 2.4F, Scaffold EETI-II

<400> SEQUENCE: 80

Gly Cys Tyr Gln Gly Arg Gly Asp Trp Ser Pro Ser Ser Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 81
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 2.4G, Scaffold EETI-II

<400> SEQUENCE: 81

Gly Cys Ala Pro Gly Arg Gly Asp Trp Ala Pro Ser Glu Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 82
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 2.4J, Scaffold EETI-II

<400> SEQUENCE: 82

Gly Cys Val Gln Gly Arg Gly Asp Trp Ser Pro Pro Ser Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 83
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 2.5A, Scaffold EETI-II

<400> SEQUENCE: 83

Gly Cys His Val Gly Arg Gly Asp Trp Ala Pro Glu Glu Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 84
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 2.5C, Scaffold EETI-II
```

```
<400> SEQUENCE: 84

Gly Cys Asp Gly Gly Arg Gly Asp Trp Ala Pro Pro Ala Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 85
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 2.5D, Scaffold EETI-II

<400> SEQUENCE: 85

Gly Cys Pro Gln Gly Arg Gly Asp Trp Ala Pro Thr Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 86
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 2.5F, Scaffold EETI-II

<400> SEQUENCE: 86

Gly Cys Pro Arg Pro Arg Gly Asp Asn Pro Pro Leu Thr Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 87
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 2.5D K15S Mutant, Scaffold EETI-II

<400> SEQUENCE: 87

Gly Cys Pro Gln Gly Arg Gly Asp Trp Ala Pro Thr Ser Cys Ser Gln
1               5                   10                  15

Asp Ser Asp Cys Leu Ala Gly Cys Val Cys Gly Pro Asn Gly Phe Cys
            20                  25                  30

Gly

<210> SEQ ID NO 88
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 2.5F K15S Mutant, Scaffold EETI-II

<400> SEQUENCE: 88
```

-continued

```
Gly Cys Pro Arg Pro Arg Gly Asp Asn Pro Leu Thr Cys Ser Gln
1               5                   10                  15

Asp Ser Asp Cys Leu Ala Gly Cys Val Cys Gly Pro Asn Gly Phe Cys
            20                  25                  30

Gly

<210> SEQ ID NO 89
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 2.5H K15S Mutant, Scaffold EETI-II

<400> SEQUENCE: 89

Gly Cys Pro Gln Gly Arg Gly Asp Trp Ala Pro Glu Trp Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 90
<211> LENGTH: 33
<212> TYPE: PRT
<213> ORGANISM: Artificial Sequence
<220> FEATURE:
<223> OTHER INFORMATION: Synthetic Integrin Binding Knottin Sequence
      Peptide Identifier 2.5J K15S Mutant, Scaffold EETI-II

<400> SEQUENCE: 90

Gly Cys Pro Arg Gly Arg Gly Asp Trp Ser Pro Pro Ala Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 91
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 3A, Scaffold AgRp

<400> SEQUENCE: 91

Gly Cys Val Arg Leu His Glu Ser Cys Leu Gly Gln Gln Val Pro Cys
1               5                   10                  15

Cys Asp Pro Ala Ala Thr Cys Tyr Cys Val Val Arg Gly Asp Trp Arg
            20                  25                  30

Lys Arg Cys Tyr Cys Arg
        35

<210> SEQ ID NO 92
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 3B, Scaffold AgRp

<400> SEQUENCE: 92

Gly Cys Val Arg Leu His Glu Ser Cys Leu Gly Gln Gln Val Pro Cys
1               5                   10                  15
```

Cys Asp Pro Ala Ala Thr Cys Tyr Cys Glu Glu Arg Gly Asp Met Leu
            20                  25                  30

Glu Lys Cys Tyr Cys Arg
        35

<210> SEQ ID NO 93
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 3C, Scaffold AgRp

<400> SEQUENCE: 93

Gly Cys Val Arg Leu His Glu Ser Cys Leu Gly Gln Gln Val Pro Cys
1               5                   10                  15

Cys Asp Pro Ala Ala Thr Cys Tyr Cys Glu Thr Arg Gly Asp Gly Lys
            20                  25                  30

Glu Lys Cys Tyr Cys Arg
        35

<210> SEQ ID NO 94
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 3D, Scaffold AgRp

<400> SEQUENCE: 94

Gly Cys Val Arg Leu His Glu Ser Cys Leu Gly Gln Gln Val Pro Cys
1               5                   10                  15

Cys Asp Pro Ala Ala Thr Cys Tyr Cys Gln Trp Arg Gly Asp Gly Asp
            20                  25                  30

Val Lys Cys Tyr Cys Arg
        35

<210> SEQ ID NO 95
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 3E, Scaffold AgRp

<400> SEQUENCE: 95

Gly Cys Val Arg Leu His Glu Ser Cys Leu Gly Gln Gln Val Pro Cys
1               5                   10                  15

Cys Asp Pro Ala Ala Thr Cys Tyr Cys Ser Arg Arg Gly Asp Met Arg
            20                  25                  30

Glu Arg Cys Tyr Cys Arg
        35

<210> SEQ ID NO 96
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 3F, Scaffold AgRp

<400> SEQUENCE: 96

Gly Cys Val Arg Leu His Glu Ser Cys Leu Gly Gln Gln Val Pro Cys

```
                1               5                  10                 15
Cys Asp Pro Ala Ala Thr Cys Tyr Cys Gln Tyr Arg Gly Asp Gly Met
            20                  25                 30

Lys His Cys Tyr Cys Arg
            35

<210> SEQ ID NO 97
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 3G, Scaffold AgRp

<400> SEQUENCE: 97

Gly Cys Val Arg Leu His Glu Ser Cys Leu Gly Gln Gln Val Pro Cys
1               5                  10                 15

Cys Asp Pro Ala Ala Thr Cys Tyr Cys Thr Gly Arg Gly Asp Thr Lys
            20                  25                 30

Val Leu Cys Tyr Cys Arg
            35

<210> SEQ ID NO 98
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 3H, Scaffold AgRp

<400> SEQUENCE: 98

Gly Cys Val Arg Leu His Glu Ser Cys Leu Gly Gln Gln Val Pro Cys
1               5                  10                 15

Cys Asp Pro Ala Ala Thr Cys Tyr Cys Val Glu Arg Gly Asp Met Lys
            20                  25                 30

Arg Arg Cys Tyr Cys Arg
            35

<210> SEQ ID NO 99
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 3I, Scaffold AgRp

<400> SEQUENCE: 99

Gly Cys Val Arg Leu His Glu Ser Cys Leu Gly Gln Gln Val Pro Cys
1               5                  10                 15

Cys Asp Pro Ala Ala Thr Cys Tyr Cys Thr Gly Arg Gly Asp Val Arg
            20                  25                 30

Met Asn Cys Tyr Cys Arg
            35

<210> SEQ ID NO 100
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 3J, Scaffold AgRp

<400> SEQUENCE: 100
```

Gly Cys Val Arg Leu His Glu Ser Cys Leu Gly Gln Gln Val Pro Cys
1               5                   10                  15

Cys Asp Pro Ala Ala Thr Cys Tyr Cys Val Glu Arg Gly Asp Gly Met
            20                  25                  30

Ser Lys Cys Tyr Cys Arg
        35

<210> SEQ ID NO 101
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 4A, Scaffold AgRp

<400> SEQUENCE: 101

Gly Cys Val Arg Leu His Glu Ser Cys Leu Gly Gln Gln Val Pro Cys
1               5                   10                  15

Cys Asp Pro Ala Ala Thr Cys Tyr Cys Arg Gly Arg Gly Asp Met Arg
            20                  25                  30

Arg Glu Cys Tyr Cys Arg
        35

<210> SEQ ID NO 102
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 4B, Scaffold AgRp

<400> SEQUENCE: 102

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Val Lys
            20                  25                  30

Val Asn Cys Tyr Cys Arg
        35

<210> SEQ ID NO 103
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 4C, Scaffold AgRp

<400> SEQUENCE: 103

Gly Cys Val Arg Leu His Glu Ser Cys Leu Gly Gln Gln Val Pro Cys
1               5                   10                  15

Cys Asp Pro Ala Ala Thr Cys Tyr Cys Val Gly Arg Gly Asp Glu Lys
            20                  25                  30

Met Ser Cys Tyr Cys Arg
        35

<210> SEQ ID NO 104
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 4D, Scaffold AgRp

<400> SEQUENCE: 104

```
Gly Cys Val Arg Leu His Glu Ser Cys Leu Gly Gln Gln Val Pro Cys
1               5                   10                  15

Cys Asp Pro Ala Ala Thr Cys Tyr Cys Val Ser Arg Gly Asp Met Arg
            20                  25                  30

Lys Arg Cys Tyr Cys Arg
        35

<210> SEQ ID NO 105
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 4E, Scaffold AgRp

<400> SEQUENCE: 105

Gly Cys Val Arg Leu His Glu Ser Cys Leu Gly Gln Gln Val Pro Cys
1               5                   10                  15

Cys Asp Pro Ala Ala Thr Cys Tyr Cys Glu Arg Arg Gly Asp Ser Val
            20                  25                  30

Lys Lys Cys Tyr Cys Arg
        35

<210> SEQ ID NO 106
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 4F, Scaffold AgRp

<400> SEQUENCE: 106

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Thr Arg
            20                  25                  30

Arg Arg Cys Tyr Cys Arg
        35

<210> SEQ ID NO 107
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 4G, Scaffold AgRp

<400> SEQUENCE: 107

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Val Val
            20                  25                  30

Arg Arg Cys Tyr Cys Arg
        35

<210> SEQ ID NO 108
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 4H, Scaffold AgRp
```

-continued

```
<400> SEQUENCE: 108

Gly Cys Val Arg Leu His Glu Ser Cys Leu Gly Gln Gln Val Pro Cys
1               5                   10                  15

Cys Asp Pro Ala Ala Thr Cys Tyr Cys Lys Gly Arg Gly Asp Asn Lys
            20                  25                  30

Arg Lys Cys Tyr Cys Arg
        35

<210> SEQ ID NO 109
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 4I, Scaffold AgRp
<220> FEATURE:
<221> NAME/KEY: misc_feature
<222> LOCATION: (21)..(21)
<223> OTHER INFORMATION: Xaa can be any naturally occurring amino acid

<400> SEQUENCE: 109

Gly Cys Val Arg Leu His Glu Ser Cys Leu Gly Gln Gln Val Pro Cys
1               5                   10                  15

Cys Asp Pro Ala Xaa Thr Cys Tyr Cys Lys Gly Arg Gly Asp Val Arg
            20                  25                  30

Arg Val Cys Tyr Cys Arg
        35

<210> SEQ ID NO 110
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 4J, Scaffold AgRp

<400> SEQUENCE: 110

Gly Cys Val Arg Leu His Glu Ser Cys Leu Gly Gln Gln Val Pro Cys
1               5                   10                  15

Cys Asp Pro Ala Ala Thr Cys Tyr Cys Val Gly Arg Gly Asp Asn Lys
            20                  25                  30

Val Lys Cys Tyr Cys Arg
        35

<210> SEQ ID NO 111
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 5A, Scaffold AgRp

<400> SEQUENCE: 111

Gly Cys Val Arg Leu His Glu Ser Cys Leu Gly Gln Gln Val Pro Cys
1               5                   10                  15

Cys Asp Pro Ala Ala Thr Cys Tyr Cys Val Gly Arg Gly Asp Asn Arg
            20                  25                  30

Leu Lys Cys Tyr Cys Arg
        35

<210> SEQ ID NO 112
<211> LENGTH: 38
<212> TYPE: PRT
```

<213> ORGANISM: Artificial Sequence
<220> FEATURE:
<223> OTHER INFORMATION: Synthetic Integrin Binding Knottin Sequence
      Peptide Identifier 5B, Scaffold AgRp

<400> SEQUENCE: 112

Gly Cys Val Arg Leu His Glu Ser Cys Leu Gly Gln Gln Val Pro Cys
1               5                   10                  15

Cys Asp Pro Ala Ala Thr Cys Tyr Cys Val Glu Arg Gly Asp Gly Met
            20                  25                  30

Lys Lys Cys Tyr Cys Arg
        35

<210> SEQ ID NO 113
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 5C, Scaffold AgRp

<400> SEQUENCE: 113

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Met Arg
            20                  25                  30

Arg Arg Cys Tyr Cys Arg
        35

<210> SEQ ID NO 114
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 5D, Scaffold AgRp

<400> SEQUENCE: 114

Gly Cys Val Arg Leu His Glu Ser Cys Leu Gly Gln Gln Val Pro Cys
1               5                   10                  15

Cys Asp Pro Ala Ala Thr Cys Tyr Cys Gln Gly Arg Gly Asp Gly Asp
            20                  25                  30

Val Lys Cys Tyr Cys Arg
        35

<210> SEQ ID NO 115
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 5E, Scaffold AgRp

<400> SEQUENCE: 115

Gly Cys Val Arg Leu His Glu Ser Cys Leu Gly Gln Gln Val Pro Cys
1               5                   10                  15

Cys Asp Pro Ala Ala Thr Cys Tyr Cys Ser Gly Arg Gly Asp Asn Asp
            20                  25                  30

Leu Val Cys Tyr Cys Arg
        35

<210> SEQ ID NO 116
<211> LENGTH: 38

```
<212> TYPE: PRT
<213> ORGANISM: Artificial Sequence
<220> FEATURE:
<223> OTHER INFORMATION: Synthetic Integrin Binding Knottin Sequence
      Peptide Identifier 5F, Scaffold AgRp

<400> SEQUENCE: 116

Gly Cys Val Arg Leu His Glu Ser Cys Leu Gly Gln Gln Val Pro Cys
1               5                   10                  15

Cys Asp Pro Ala Ala Thr Cys Tyr Cys Val Glu Arg Gly Asp Gly Met
            20                  25                  30

Ile Arg Cys Tyr Cys Arg
        35

<210> SEQ ID NO 117
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 5G, Scaffold AgRp

<400> SEQUENCE: 117

Gly Cys Val Arg Leu His Glu Ser Cys Leu Gly Gln Gln Val Pro Cys
1               5                   10                  15

Cys Asp Pro Ala Ala Thr Cys Tyr Cys Ser Gly Arg Gly Asp Asn Asp
            20                  25                  30

Leu Val Cys Tyr Cys Arg
        35

<210> SEQ ID NO 118
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 5H, Scaffold AgRp

<400> SEQUENCE: 118

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Met Lys
            20                  25                  30

Met Lys Cys Tyr Cys Arg
        35

<210> SEQ ID NO 119
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 5I, Scaffold AgRp

<400> SEQUENCE: 119

Gly Cys Val Arg Leu His Glu Ser Cys Leu Gly Gln Gln Val Pro Cys
1               5                   10                  15

Cys Asp Pro Ala Ala Thr Cys Tyr Cys Ile Gly Arg Gly Asp Val Arg
            20                  25                  30

Arg Arg Cys Tyr Cys Arg
        35

<210> SEQ ID NO 120
```

```
<211> LENGTH: 38
<212> TYPE: PRT
<213> ORGANISM: Artificial Sequence
<220> FEATURE:
<223> OTHER INFORMATION: Synthetic Integrin Binding Knottin Sequence
      Peptide Identifier 5J, Scaffold AgRp

<400> SEQUENCE: 120

Gly Cys Val Arg Leu His Glu Ser Cys Leu Gly Gln Gln Val Pro Cys
1               5                  10                  15

Cys Asp Pro Ala Ala Thr Cys Tyr Cys Glu Glu Arg Gly As

<210> SEQ ID NO 124
<211> LENGTH: 38
<212> TYPE: PRT
<213> ORGANISM: Artificial Sequence
<220> FEATURE:
<223> OTHER INFORMATION: Synthetic Integrin Binding Knottin Sequence Peptide Identifier 6F, Scaffold AgRp

<400> SEQUENCE: 124

```
Gly Cys Val Arg Leu His Glu Ser Cys Leu Gly Gln Gln Val Pro Cys
 1               5                  10                  15

Cys Asp Pro Ala Ala Thr Cys Tyr Cys Glu Ser Arg Gly Asp Val Val
                20                  25                  30

Arg Lys Cys Tyr Cys Arg
                35
```

<210> SEQ ID NO 125
<211> LENGTH: 38
<212> TYPE: PRT
<213> ORGANISM: Artificial Sequence
<220> FEATURE:
<223> OTHER INFORMATION: Synthetic Integrin Binding Knottin Sequence Peptide Identifier 7C, Scaffold AgRp

<400> SEQUENCE: 125

```
Gly Cys Val Arg Leu His Glu Ser Cys Leu Gly Gln Gln Val Pro Cys
 1               5                  10                  15

Cys Asp Pro Ala Ala Thr Cys Tyr Cys Tyr Gly Arg Gly Asp Asn Asp
                20                  25                  30

Leu Arg Cys Tyr Cys Arg
                35
```

<210> SEQ ID NO 126
<211> LENGTH: 330
<212> TYPE: PRT
<213> ORGANISM: Artificial Sequence
<220> FEATURE:
<223> OTHER INFORMATION: Synthetic Human IgG1 constant region

<400> SEQUENCE: 126

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

Tyr Val Asp Gly Val Glu His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 127
<211> LENGTH: 326
<212> TYPE: PRT
<213> ORGANISM: Artificial Sequence
<220> FEATURE:
<223> OTHER INFORMATION: Synthetic Human IgG2 constant region

<400> SEQUENCE: 127

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 128
<211> LENGTH: 377
<212> TYPE: PRT
<213> ORGANISM: Artificial Sequence
<220> FEATURE:
<223> OTHER INFORMATION: Synthetic Human IgG3 constant region

<400> SEQUENCE: 128

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

```
Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 129
<211> LENGTH: 327
<212> TYPE: PRT
<213> ORGANISM: Artificial Sequence
<220> FEATURE:
<223> OTHER INFORMATION: Synthetic Human IgG4 constant region

<400> SEQUENCE: 129

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205
```

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 130
<211> LENGTH: 33
<212> TYPE: PRT
<213> ORGANISM: Artificial Sequence
<220> FEATURE:
<223> OTHER INFORMATION: Synthetic Peptide Identifier Scaffold
      NOD201 - 2.5F

<400> SEQUENCE: 130

Gly Cys Pro Arg Pro Arg Gly Asp Asn Pro Pro Leu Thr Cys Ser Gln
1               5                   10                  15

Asp Ser Asp Cys Leu Ala Gly Cys Val Cys Gly Pro Asn Gly Phe Cys
            20                  25                  30

Gly

<210> SEQ ID NO 131
<211> LENGTH: 33
<212> TYPE: PRT
<213> ORGANISM: Artificial Sequence
<220> FEATURE:
<223> OTHER INFORMATION: Synthetic Peptide Identifier Scaffold
      NOD201modK - 2.5FmodK

<400> SEQUENCE: 131

Gly Cys Pro Arg Pro Arg Gly Asp Asn Pro Pro Leu Thr Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 132
<211> LENGTH: 38
<212> TYPE: PRT
<213> ORGANISM: Artificial Sequence
<220> FEATURE:
<223> OTHER INFORMATION: Synthetic Peptide Identifier Scaffold
      NOD203 - 2.5F w/GGGGS

<400> SEQUENCE: 132

Gly Cys Pro Arg Pro Arg Gly Asp Asn Pro Pro Leu Thr Cys Ser Gln
1               5                   10                  15

Asp Ser Asp Cys Leu Ala Gly Cys Val Cys Gly Pro Asn Gly Phe Cys
            20                  25                  30

```
Gly Gly Gly Gly Gly Ser
            35

<210> SEQ ID NO 133
<211> LENGTH: 38
<212> TYPE: PRT
<213> ORGANISM: Artificial Sequence
<220> FEATURE:
<223> OTHER INFORMATION: Synthetic Peptide Identifier Scaffold
      NOD203modK - 2.5FmodK w/GGGGS

<400> SEQUENCE: 133

Gly Cys Pro Arg Pro Arg Gly Asp Asn Pro Pro Leu Thr Cys Lys Gln
1               5                   10                  15

Asp Ser Asp Cys Leu Ala Gly Cys Val Cys Gly Pro Asn Gly Phe Cys
            20                  25                  30

Gly Gly Gly Gly Gly Ser
            35

<210> SEQ ID NO 134
<211> LENGTH: 48
<212> TYPE: PRT
<213> ORGANISM: Artificial Sequence
<220> FEATURE:
<223> OTHER INFORMATION: Synthetic Peptide Identifier Scaffold
      NOD204 - 2.5F w/GGGGSGGGGSGGGGS

<400> SEQUENCE: 134

Gly Cys Pro Arg Pro Arg Gly Asp Asn Pro Pro Leu Thr Cys Ser Gln
1               5                   10                  15

Asp Ser Asp Cys Leu Ala Gly Cys Val Cys Gly Pro Asn Gly Phe Cys
            20                  25                  30

Gly Gly Gly Gly Gly Ser Gly Gly Gly Gly Ser Gly Gly Gly Gly Ser
            35                  40                  45

<210> SEQ ID NO 135
<211> LENGTH: 48
<212> TYPE: PRT
<213> ORGANISM: Artificial Sequence
<220> FEATURE:
<223> OTHER INFORMATION: Synthetic Peptide Identifier Scaffold
      NOD204modK - 2.5FmodK w/GGGGSGGGGSGGGGS

<400> SEQUENCE: 135

Gly Cys Pro Arg Pro Arg Gly Asp Asn Pro Pro Leu Thr Cys Lys Gln
1               5                   10                  15

Asp Ser Asp Cys Leu Ala Gly Cys Val Cys Gly Pro Asn Gly Phe Cys
            20                  25                  30

Gly Gly Gly Gly Gly Ser Gly Gly Gly Gly Ser Gly Gly Gly Gly Ser
            35                  40                  45

<210> SEQ ID NO 136
<211> LENGTH: 5
<212> TYPE: PRT
<213> ORGANISM: Artificial Sequence
<220> FEATURE:
<223> OTHER INFORMATION: Synthetic Peptide Identifier Scaffold Linker
      (short)

<400> SEQUENCE: 136

Gly Gly Gly Gly Ser
1               5

<210> SEQ ID NO 137
```

```
<211> LENGTH: 15
<212> TYPE: PRT
<213> ORGANISM: Artificial Sequence
<220> FEATURE:
<223> OTHER INFORMATION: Synthetic Peptide Identifier Scaffold Linker
      (long)

<400> SEQUENCE: 137

Gly Gly Gly Gly Ser Gly Gly Gly Ser Gly Gly Gly Gly Ser
1               5                   10                  15

<210> SEQ ID NO 138
<211> LENGTH: 18
<212> TYPE: PRT
<213> ORGANISM: Artificial Sequence
<220> FEATURE:
<223> OTHER INFORMATION: Synthetic Peptide Identifier Scaffold Signal
      sequence (signal peptide A)

<400> SEQUENCE: 138

Met Thr Arg Leu Thr Val Leu Ala Leu Leu Ala Gly Leu Leu Ala Ser
1               5                   10                  15

Ser Arg

<210> SEQ ID NO 139
<211> LENGTH: 264
<212> TYPE: PRT
<213> ORGANISM: Artificial Sequence
<220> FEATURE:
<223> OTHER INFORMATION: Synthetic Peptide Identifier Scaffold NOD201
      (human Fc; no linker)

<400> SEQUENCE: 139

Gly Cys Pro Arg Pro Arg Gly Asp Asn Pro Leu Thr Cys Ser Gln
1               5                   10                  15

Asp Ser Asp Cys Leu Ala Gly Cys Val Cys Gly Pro Asn Gly Phe Cys
                20                  25                  30

Gly Glu Pro Lys Ser Ser Asp Lys Thr His Thr Cys Pro Pro Cys Pro
            35                  40                  45

Ala Pro Glu Leu Leu Gly Gly Pro Ser Val Phe Leu Phe Pro Pro Lys
        50                  55                  60

Pro Lys Asp Thr Leu Met Ile Ser Arg Thr Pro Glu Val Thr Cys Val
65                  70                  75                  80

Val Val Asp Val Ser His Glu Asp Pro Glu Val Lys Phe Asn Trp Tyr
                85                  90                  95

Val Asp Gly Val Glu Val His Asn Ala Lys Thr Lys Pro Arg Glu Glu
            100                 105                 110

Gln Tyr Asn Ser Thr Tyr Arg Val Val Ser Val Leu Thr Val Leu His
        115                 120                 125

Gln Asp Trp Leu Asn Gly Lys Glu Tyr Lys Cys Lys Val Ser Asn Lys
    130                 135                 140

Ala Leu Pro Ala Pro Ile Glu Lys Thr Ile Ser Lys Ala Lys Gly Gln
145                 150                 155                 160

Pro Arg Glu Pro Gln Val Tyr Thr Leu Pro Pro Ser Arg Asp Glu Leu
                165                 170                 175

Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
        195                 200                 205

Tyr Lys Thr Thr Pro Pro Val Leu Asp Ser Asp Gly Ser Phe Phe Leu
```

210                 215                 220

Tyr Ser Lys Leu Thr Val Asp Lys Ser Arg Trp Gln Gln Gly Asn Val
225                 230                 235                 240

Phe Ser Cys Ser Val Met His Glu Ala Leu His Asn His Tyr Thr Gln
                245                 250                 255

Lys Ser Leu Ser Leu Ser Pro Gly
            260

<210> SEQ ID NO 140
<211> LENGTH: 264
<212> TYPE: PRT
<213> ORGANISM: Artificial Sequence
<220> FEATURE:
<223> OTHER INFORMATION: Synthetic Peptide Identifier Scaffold NOD201X
      (control sequence - NOD201 with scrambled seq, human Fc; no
      linker)

<400> SEQUENCE: 140

Gly Cys Val Thr Gly Arg Asp Gly Ser Pro Ala Ser Ser Cys Ser Gln
1               5                   10                  15

Asp Ser Asp Cys Leu Ala Gly Cys Val Cys Gly Pro Asn Gly Phe Cys
            20                  25                  30

Gly Glu Pro Lys Ser Ser Asp Lys Thr His Thr Cys Pro Pro Cys Pro
        35                  40                  45

Ala Pro Glu Leu Leu Gly Gly Pro Ser Val Phe Leu Phe Pro Pro Lys
50                  55                  60

Pro Lys Asp Thr Leu Met Ile Ser Arg Thr Pro Glu Val Thr Cys Val
65                  70                  75                  80

Val Val Asp Val Ser His Glu Asp Pro Glu Val Lys Phe Asn Trp Tyr
                85                  90                  95

Val Asp Gly Val Glu Val His Asn Ala Lys Thr Lys Pro Arg Glu Glu
            100                 105                 110

Gln Tyr Asn Ser Thr Tyr Arg Val Val Ser Val Leu Thr Val Leu His
        115                 120                 125

Gln Asp Trp Leu Asn Gly Lys Glu Tyr Lys Cys Lys Val Ser Asn Lys
130                 135                 140

Ala Leu Pro Ala Pro Ile Glu Lys Thr Ile Ser Lys Ala Lys Gly Gln
145                 150                 155                 160

Pro Arg Glu Pro Gln Val Tyr Thr Leu Pro Pro Ser Arg Asp Glu Leu
                165                 170                 175

Thr Lys Asn Gln Val Ser Leu Thr Cys Leu Val Lys Gly Phe Tyr Pro
            180                 185                 190

Ser Asp Ile Ala Val Glu Trp Glu Ser Asn Gly Gln Pro Glu Asn Asn
        195                 200                 205

Tyr Lys Thr Thr Pro Pro Val Leu Asp Ser Asp Gly Ser Phe Phe Leu
210                 215                 220

Tyr Ser Lys Leu Thr Val Asp Lys Ser Arg Trp Gln Gln Gly Asn Val
225                 230                 235                 240

Phe Ser Cys Ser Val Met His Glu Ala Leu His Asn His Tyr Thr Gln
                245                 250                 255

Lys Ser Leu Ser Leu Ser Pro Gly
            260

<210> SEQ ID NO 141
<211> LENGTH: 270
<212> TYPE: PRT
<213> ORGANISM: Artificial Sequence
<220> FEATURE:
<223> OTHER INFORMATION: Synthetic Peptide Identifier Scaffold NOD201M
(NOD201 with murine Fc domain; no linker)

<400> SEQUENCE: 141

Gly Cys Pro Arg Pro Arg Gly Asp Asn Pro Pro Leu Thr Cys Ser Gln
1               5                   10                  15

Asp Ser Asp Cys Leu Ala Gly Cys Val Cys Gly Pro Asn Gly Phe Cys
            20                  25                  30

Gly Glu Pro Arg Val Pro Ile Thr Gln Asn Pro Cys Pro Pro Leu Lys
        35                  40                  45

Glu Cys Pro Pro Cys Ala Ala Pro Asp Leu Leu Gly Gly Pro Ser Val
    50                  55                  60

Phe Ile Phe Pro Pro Lys Ile Lys Asp Val Leu Met Ile Ser Leu Ser
65                  70                  75                  80

Pro Met Val Thr Cys Val Val Asp Val Ser Glu Asp Asp Pro Asp
            85                  90                  95

Val Gln Ile Ser Trp Phe Val Asn Asn Val Glu Val His Thr Ala Gln
                100                 105                 110

Thr Gln Thr His Arg Glu Asp Tyr Asn Ser Thr Leu Arg Val Val Ser
            115                 120                 125

Ala Leu Pro Ile Gln His Gln Asp Trp Met Ser Gly Lys Glu Phe Lys
        130                 135                 140

Cys Lys Val Asn Asn Arg Ala Leu Pro Ser Pro Ile Glu Lys Thr Ile
145                 150                 155                 160

Ser Lys Pro Arg Gly Pro Val Arg Ala Pro Gln Val Tyr Val Leu Pro
                165                 170                 175

Pro Pro Ala Glu Glu Met Thr Lys Lys Glu Phe Ser Leu Thr Cys Met
            180                 185                 190

Ile Thr Gly Phe Leu Pro Ala Glu Ile Ala Val Asp Trp Thr Ser Asn
        195                 200                 205

Gly Arg Thr Glu Gln Asn Tyr Lys Asn Thr Ala Thr Val Leu Asp Ser
    210                 215                 220

Asp Gly Ser Tyr Phe Met Tyr Ser Lys Leu Arg Val Gln Lys Ser Thr
225                 230                 235                 240

Trp Glu Arg Gly Ser Leu Phe Ala Cys Ser Val Val His Glu Gly Leu
                245                 250                 255

His Asn His Leu Thr Thr Lys Thr Ile Ser Arg Ser Leu Gly
            260                 265                 270

<210> SEQ ID NO 142
<211> LENGTH: 269
<212> TYPE: PRT
<213> ORGANISM: Artificial Sequence
<220> FEATURE:
<223> OTHER INFORMATION: Synthetic Peptide Identifier Scaffold NOD203
complete (Gly4Ser linker)

<400> SEQUENCE: 142

Gly Cys Pro Arg Pro Arg Gly Asp Asn Pro Pro Leu Thr Cys Ser Gln
1               5                   10                  15

Asp Ser Asp Cys Leu Ala Gly Cys Val Cys Gly Pro Asn Gly Phe Cys
            20                  25                  30

Gly Gly Gly Gly Ser Glu Pro Lys Ser Ser Asp Lys Thr His Thr
        35                  40                  45

Cys Pro Pro Cys Pro Ala Pro Glu Leu Leu Gly Gly Pro Ser Val Phe
    50                  55                  60

```
Leu Phe Pro Pro Lys Pro Lys Asp Thr Leu Met Ile Ser Arg Thr Pro
 65                  70                  75                  80

Glu Val Thr Cys Val Val Asp Val Ser His Glu Asp Pro Glu Val
             85                  90                  95

Lys Phe Asn Trp Tyr Val Asp Gly Val Glu Val His Asn Ala Lys Thr
            100                 105                 110

Lys Pro Arg Glu Glu Gln Tyr Asn Ser Thr Tyr Arg Val Val Ser Val
            115                 120                 125

Leu Thr Val Leu His Gln Asp Trp Leu Asn Gly Lys Glu Tyr Lys Cys
        130                 135                 140

Lys Val Ser Asn Lys Ala Leu Pro Ala Pro Ile Glu Lys Thr Ile Ser
145                 150                 155                 160

Lys Ala Lys Gly Gln Pro Arg Glu Pro Gln Val Tyr Thr Leu Pro Pro
                165                 170                 175

Ser Arg Asp Glu Leu Thr Lys Asn Gln Val Ser Leu Thr Cys Leu Val
            180                 185                 190

Lys Gly Phe Tyr Pro Ser Asp Ile Ala Val Glu Trp Glu Ser Asn Gly
        195                 200                 205

Gln Pro Glu Asn Asn Tyr Lys Thr Thr Pro Pro Val Leu Asp Ser Asp
    210                 215                 220

Gly Ser Phe Phe Leu Tyr Ser Lys Leu Thr Val Asp Lys Ser Arg Trp
225                 230                 235                 240

Gln Gln Gly Asn Val Phe Ser Cys Ser Val Met His Glu Ala Leu His
                245                 250                 255

Asn His Tyr Thr Gln Lys Ser Leu Ser Leu Ser Pro Gly
            260                 265

<210> SEQ ID NO 143
<211> LENGTH: 279
<212> TYPE: PRT
<213> ORGANISM: Artificial Sequence
<220> FEATURE:
<223> OTHER INFORMATION: Synthetic Peptide Identifier Scaffold NOD204
      complete ([Gly4Ser]3 linker)

<400> SEQUENCE: 143

Gly Cys Pro Arg Pro Arg Gly Asp Asn Pro Pro Leu Thr Cys Ser Gln
1               5                   10                  15

Asp Ser Asp Cys Leu Ala Gly Cys Val Cys Gly Pro Asn Gly Phe Cys
            20                  25                  30

Gly Gly Gly Gly Ser Gly Gly Gly Ser Gly Gly Gly Ser
        35                  40                  45

Glu Pro Lys Ser Ser Asp Lys Thr His Thr Cys Pro Pro Cys Pro Ala
    50                  55                  60

Pro Glu Leu Leu Gly Gly Pro Ser Val Phe Leu Phe Pro Pro Lys Pro
65                  70                  75                  80

Lys Asp Thr Leu Met Ile Ser Arg Thr Pro Glu Val Thr Cys Val Val
                85                  90                  95

Val Asp Val Ser His Glu Asp Pro Glu Val Lys Phe Asn Trp Tyr Val
            100                 105                 110

Asp Gly Val Glu Val His Asn Ala Lys Thr Lys Pro Arg Glu Glu Gln
        115                 120                 125

Tyr Asn Ser Thr Tyr Arg Val Val Ser Val Leu Thr Val Leu His Gln
    130                 135                 140

Asp Trp Leu Asn Gly Lys Glu Tyr Lys Cys Lys Val Ser Asn Lys Ala
```

-continued

```
        145                 150                 155                 160

Leu Pro Ala Pro Ile Glu Lys Thr Ile Ser Lys Ala Lys Gly Gln Pro
                165                 170                 175

Arg Glu Pro Gln Val Tyr Thr Leu Pro Pro Ser Arg Asp Glu Leu Thr
            180                 185                 190

Lys Asn Gln Val Ser Leu Thr Cys Leu Val Lys Gly Phe Tyr Pro Ser
        195                 200                 205

Asp Ile Ala Val Glu Trp Glu Ser Asn Gly Gln Pro Glu Asn Asn Tyr
    210                 215                 220

Lys Thr Thr Pro Pro Val Leu Asp Ser Asp Gly Ser Phe Phe Leu Tyr
225                 230                 235                 240

Ser Lys Leu Thr Val Asp Lys Ser Arg Trp Gln Gln Gly Asn Val Phe
                245                 250                 255

Ser Cys Ser Val Met His Glu Ala Leu His Asn His Tyr Thr Gln Lys
            260                 265                 270

Ser Leu Ser Leu Ser Pro Gly
        275
```

METHOD OF TREATING CANCER WITH A MULTIPLE INTEGRIN BINDING FC FUSION PROTEIN

CROSS-REFERENCE TO RELATED APPLICATIONS

The present application claims priority to U.S. Provisional Application No. 62/444,660, filed Jan. 10, 2017 and U.S. Provisional Application No. 62/466,298, filed Mar. 2, 2017, the disclosures of which are hereby incorporated by reference in their entireties for all purposes.

BACKGROUND OF THE INVENTION

Interleukin-2 (IL-2) is a pleiotropic cytokine that activates and induces the proliferation of T cells and NK cells. Although IL-2 is an FDA approved therapy, systemic IL-2 treatment has significant toxicity and the response rate of patients is less than 25%. Combining IL-2 and/or extended half-life IL-2 and an antibody against a tumor-specific antigen to invoke the adaptive and innate arms of the immune system shows promising results for treatment. However, antibody-based therapies often suffer from the fact that many tumors lack known tumor-associated antigens.

Integrins are a family of extracellular matrix adhesion receptors that regulate a diverse array of cellular functions crucial to the initiation, progression and metastasis of solid tumors. The importance of integrins in tumor progression has made them an appealing target for cancer therapy and allows for the treatment of a variety of cancer types. The integrins present on cancerous cells include $\alpha_v\beta_3$, $\alpha_v\beta_5$, and $\alpha_5\beta_1$. A variety of therapeutics have been developed to target individual integrins associated with cancer, including antibodies, linear peptides, cyclic peptides, and peptidomimetics. However, none have utilized small, structured peptide scaffolds or targeted more than two integrins simultaneously. Additionally, current integrin targeting drugs are given as a monotherapy. Novel monotherapies as well as combination therapies are needed to more effectively combat various cancers.

The present invention meets this need and provides novel monotherapies for use in cancer treatment.

BRIEF SUMMARY OF THE INVENTION

The present invention is based, in part, on the discovery that administration of an integrin-binding polypeptide-Fc fusions described herein can be useful in the treatment of cancer.

The present invention provides methods for treating cancer in a subject comprising administering to the subject an effective amount of an integrin-binding polypeptide-Fc fusion wherein said integrin-binding polypeptide-Fc fusion is administered in a therapeutically effective amount, wherein said integrin-binding polypeptide comprises a sequence selected from the group consisting of SEQ ID NO:130 (GCPRPRGDNPPLTCSQDSDCLAGCVCGPNGFCG) and SEQ ID NO:131 (GCPRPRGDNPPLTCKQDSDCLAGCVCGPNGFCG) and wherein said integrin-binding polypeptide is conjugated to an Fc domain.

In some embodiments, the Fc domain is selected from the group consisting of IgG1, IgG2, IgG3, and IgG4.

In some embodiments, the said Fc domain is a human Fc domain.

In some embodiments, the integrin-binding polypeptide is conjugated directly to said Fc domain.

In some embodiments, the integrin-binding polypeptide is conjugated to said Fc domain through a linker polypeptide.

In some embodiments, the linker polypeptide is selected from the group consisting of GGGGS (SEQ ID NO:136) and GGGGSGGGGSGGGGS (SEQ ID NO:137).

In some embodiments, the method further comprises administering an immune checkpoint inhibitor.

In some embodiments, the immune checkpoint inhibitor is a PD-1 inhibitor.

In some embodiments, the PD-1 inhibitor is an anti-PD-1 antibody.

In some embodiments, the integrin-binding polypeptide-Fc fusion comprises an integrin-binding polypeptide sequence in the presence or absence of a linker, wherein said sequence is selected from the group consisting of GCPRPRGDNPPLTCSQDSDCLAGCVCGPNGFCG (SEQ ID NO:130), GCPRPRGDNPPLTCKQDSDCLAGCVCGPNGFCG (SEQ ID NO:131), GCPRPRGDNPPLTCSQDSDCLAGCVCGPNGFCGGGGGS (SEQ ID NO:132), GCPRPRGDNPPLTCKQDSDCLAGCVCGPNGFCGGGGGS (SEQ ID NO:133), GCPRPRGDNPPLTCSQDSDCLAGCVCGPNGFCGGGGGSGGGGSGGGGS (SEQ ID NO:134), and GCPRPRGDNPPLTCKQDSDCLAGCVCGPNGFCGGGGGSGGGGSGGGGS (SEQ ID NO:135), wherein said integrin-binding polypeptide sequence is directly linked to an Fc domain, wherein said Fc domain is selected from the group consisting of IgG1, IgG2, IgG3, and IgG4.

In some embodiments, the method further comprises administering an interleukin-2 (IL-2).

In some embodiments, the IL-2 is Proleukin.

In some embodiments, the IL-2 is administered before, after or simultaneously with administration of said integrin-binding polypeptide-Fc fusion.

In some embodiments, the IL-2 is administered after administration of said integrin-binding Polypeptide-Fc fusion.

In some embodiments, the IL-2 is administered at a 12 MIU/m2 or lower daily dose.

In some embodiments, the IL-2 is administered subcutaneously.

In some embodiments, the method further comprises administering either IL-2 or an immune checkpoint inhibitor.

In some embodiments, the method further comprises administering IL-2 and an immune checkpoint inhibitor.

In some embodiments, the immune checkpoint inhibitor is an anti-PD-1 antibody.

In some embodiments, the said integrin-binding polypeptide-Fc fusion binds to at least two integrins.

In some embodiments, the integrin-binding polypeptide-Fc fusion binds to at least three integrins.

In some embodiments, the integrin-binding polypeptide-Fc fusion binds to at least two integrins selected from the group consisting of $\alpha_v\beta_1$, $\alpha_v\beta_3$, $\alpha_v\beta_5$, $\alpha_v\beta_6$, and $\alpha_5\beta_1$.

In some embodiments, the further administration of IL-2 or an immune checkpoint inhibitor induces tumor infiltration of CD8+ T-cells as compared to non-administration. In some embodiments, the further administration of IL-2 or an anti-PD-1 antibody induces tumor infiltration of CD8+ T-cells as compared to non-administration.

In some embodiments, the further administration of IL-2 or an immune checkpoint inhibitor induces a decrease in myeloid-derived suppressor cells (MDSC) as compared to non-administration. In some embodiments, the further administration of IL-2 or an anti-PD-1 antibody induces a decrease in myeloid-derived suppressor cells (MDSC) as compared to non-administration.

In some embodiments, the further administration of both IL-2 and an immune checkpoint inhibitor induces increased tumor infiltration of CD8+ T-cells as compared to administration of an IL-2 and/or an immune checkpoint inhibitor individually. In some embodiments, the further administration of both IL-2 and an anti-PD-1 antibody induces increased tumor infiltration of CD8+ T-cells as compared to administration of an IL-2 and/or an anti-PD-1 antibody individually.

In some embodiments, the further administration of both IL-2 and an immune checkpoint inhibitor induces a greater decrease in myeloid-derived suppressor cells (MDSC) cells as compared to administration of an IL-2 and/or an immune checkpoint inhibitor individually. In some embodiments, the further administration of both IL-2 and an anti-PD-1 antibody induces a greater decrease in myeloid-derived suppressor cells (MDSC) cells as compared to administration of an IL-2 and/or an anti-PD-1 antibody individually.

The present invention also provides polypeptides comprising an integrin-binding polypeptide sequence in the presence or absence of a linker, wherein said sequence is selected from the group consisting of GCPRPRGDNPPLTCSQDSDCLAGCVCGPNGFCG (SEQ ID NO:130), GCPRPRGDNPPLTCKQDSDCLAGCVCGPNGFCG (SEQ ID NO:131), GCPRPRGDNPPLTCSQDSDCLAGCVCGPNGFCGGGGGS (SEQ ID NO:132), GCPRPRGDNPPLTCKQDSDCLAGCVCGPNGFCGGGGGS (SEQ ID NO:133), GCPRPRGDNPPLTCSQDSDCLAGCVCGPNGFCGGGGGSGGGGSGGGGS (SEQ ID NO:134), and GCPRPRGDNPPLTCKQDSDCLAGCVCGPNGFCGGGGGSGGGGSGGGGS (SEQ ID NO:135), wherein said integrin-binding polypeptide sequence is directly linked to an Fc domain, wherein said Fc domain is selected from the group consisting of IgG1, IgG2, IgG3, and IgG4.

The present invention also provides compositions comprising an integrin-binding polypeptide sequence in the presence or absence of a linker, wherein said sequence is selected from the group consisting of GCPRPRGDNPPLTCSQDSDCLAGCVCGPNGFCG (SEQ ID NO:130), GCPRPRGDNPPLTCKQDSDCLAGCVCGPNGFCG (SEQ ID NO:131), GCPRPRGDNPPLTCSQDSDCLAGCVCGPNGFCGGGGGS (SEQ ID NO:132), GCPRPRGDNPPLTCKQDSDCLAGCVCGPNGFCGGGGGS (SEQ ID NO:133), GCPRPRGDNPPLTCSQDSDCLAGCVCGPNGFCGGGGGSGGGGSGGGGS (SEQ ID NO:134), and GCPRPRGDNPPLTCKQDSDCLAGCVCGPNGFCGGGGGSGGGGSGGGGS (SEQ ID NO:135), wherein said integrin-binding polypeptide sequence is directly linked to an Fc domain, wherein said Fc domain is selected from the group consisting of IgG1, IgG2, IgG3, and IgG4.

The present invention also provides pharmaceutical compositions comprising an integrin-binding polypeptide sequence in the presence or absence of a linker, wherein said sequence is selected from the group consisting of GCPRPRGDNPPLTCSQDSDCLAGCVCGPNGFCG (SEQ ID NO:130), GCPRPRGDNPPLTCKQDSDCLAGCVCGPNGFCG (SEQ ID NO:131), GCPRPRGDNPPLTCSQDSDCLAGCVCGPNGFCGGGGGS (SEQ ID NO:132), GCPRPRGDNPPLTCKQDSDCLAGCVCGPNGFCGGGGGS (SEQ ID NO:133), GCPRPRGDNPPLTCSQDSDCLAGCVCGPNGFCGGGGGSGGGGSGGGGS (SEQ ID NO:134), and GCPRPRGDNPPLTCKQDSDCLAGCVCGPNGFCGGGGGSGGGGSGGGGS (SEQ ID NO:135), wherein said integrin-binding polypeptide sequence is directly linked to an Fc domain, wherein said Fc domain is selected from the group consisting of IgG1, IgG2, IgG3, and IgG4.

The present invention also provides nucleic acids encoding an integrin-binding polypeptide-Fc fusion as described herein.

The present invention also provides expression vectors comprising a nucleic acid encoding an integrin-binding polypeptide-Fc fusion as described herein.

The present invention also provides host cells comprising the expression vector as described herein.

The present invention further provides for a method of making an integrin-binding polypeptide-Fc fusion as described herein comprising
 a) culturing the host cell as described herein under conditions wherein said integrin-binding polypeptide-Fc fusion is expressed; and
 b) recovering said integrin-binding polypeptide-Fc fusion.

The present invention provides methods for activating the immune system in order to treat cancer in a subject comprising administering to the subject an effective amount of an integrin-binding polypeptide-Fc fusion, wherein said integrin-binding polypeptide-Fc fusion is administered in a therapeutically effective amount, wherein said integrin-binding polypeptide comprises a sequence selected from the group consisting of SEQ ID NO:130 (GCPRPRGDNPPLTCSQDSDCLAGCVCGPNGFCG) and SEQ ID NO:131 (GCPRPRGDNPPLTCKQDSDCLAGCVCGPNGFCG), and wherein said integrin-binding polypeptide is conjugated to an Fc domain.

In some embodiments, the Fc domain is selected from the group consisting of IgG1, IgG2, IgG3, and IgG4.

In some embodiments, the Fc domain is a human Fc domain.

In some embodiments, the integrin-binding polypeptide is conjugated directly to said Fc domain.

In some embodiments, the integrin-binding polypeptide is conjugated to said Fc domain through a linker polypeptide.

In some embodiments, the linker polypeptide is selected from the group consisting of GGGGS (SEQ ID NO:136) and GGGGSGGGGSGGGGS (SEQ ID NO:137).

BRIEF DESCRIPTION OF THE DRAWINGS

These and other features, aspects, and advantages of the present invention will become better understood with regard to the following description, and accompanying drawings.

FIG. 1A-FIG. 1B provides examples of IgG1, IgG2, IgG3, and IgG4 sequences.

IL-2 (4 µg; Proleukin) was administered subcutaneously on days 2-4, 8-10, 14-16, 20-22 (days +1, +2, +3). Vehicle: phosphate buffered saline. MC38 colon tumor model.

Figures 5A, 5B:
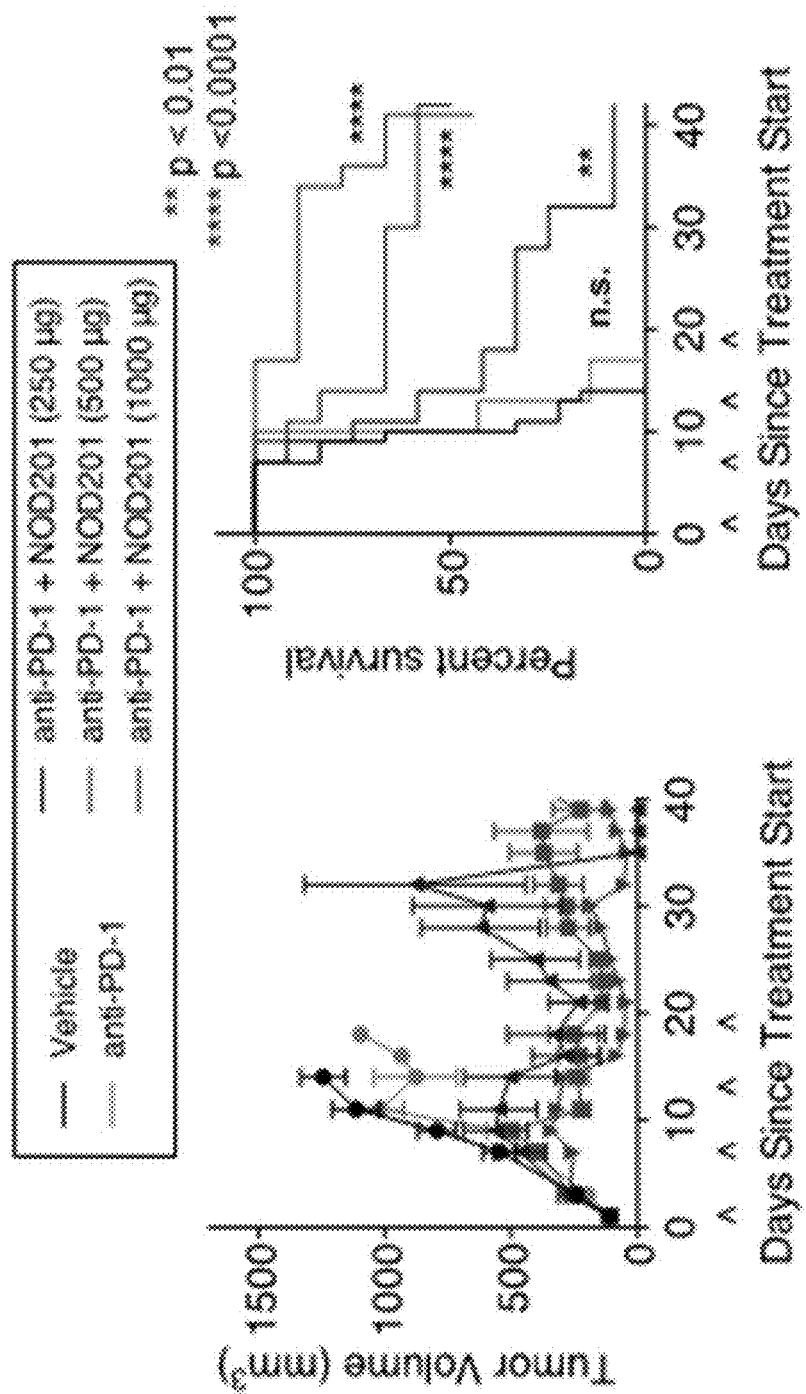
Figures 6A, 6B:
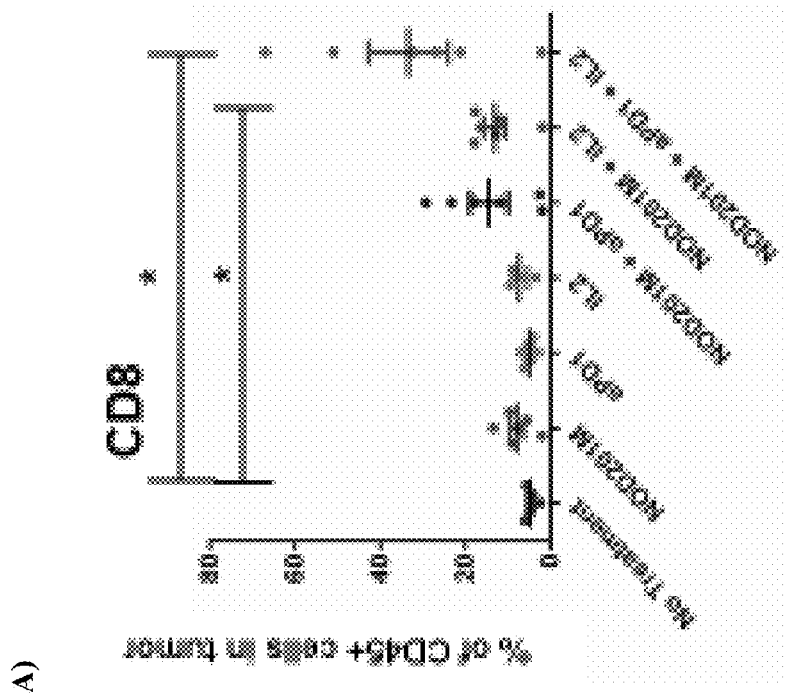
Figures 6C, 6D, 6E:
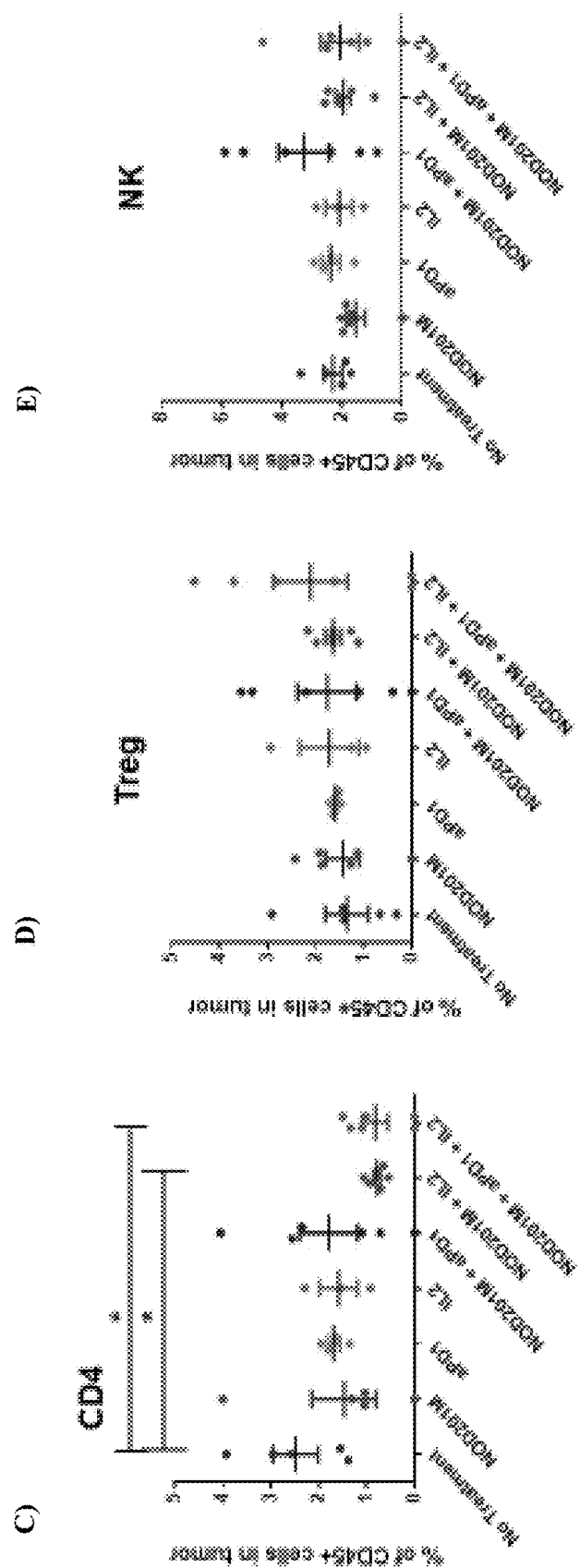
Figures 7A, 7B, 7C, 7D, 7E, 7F:
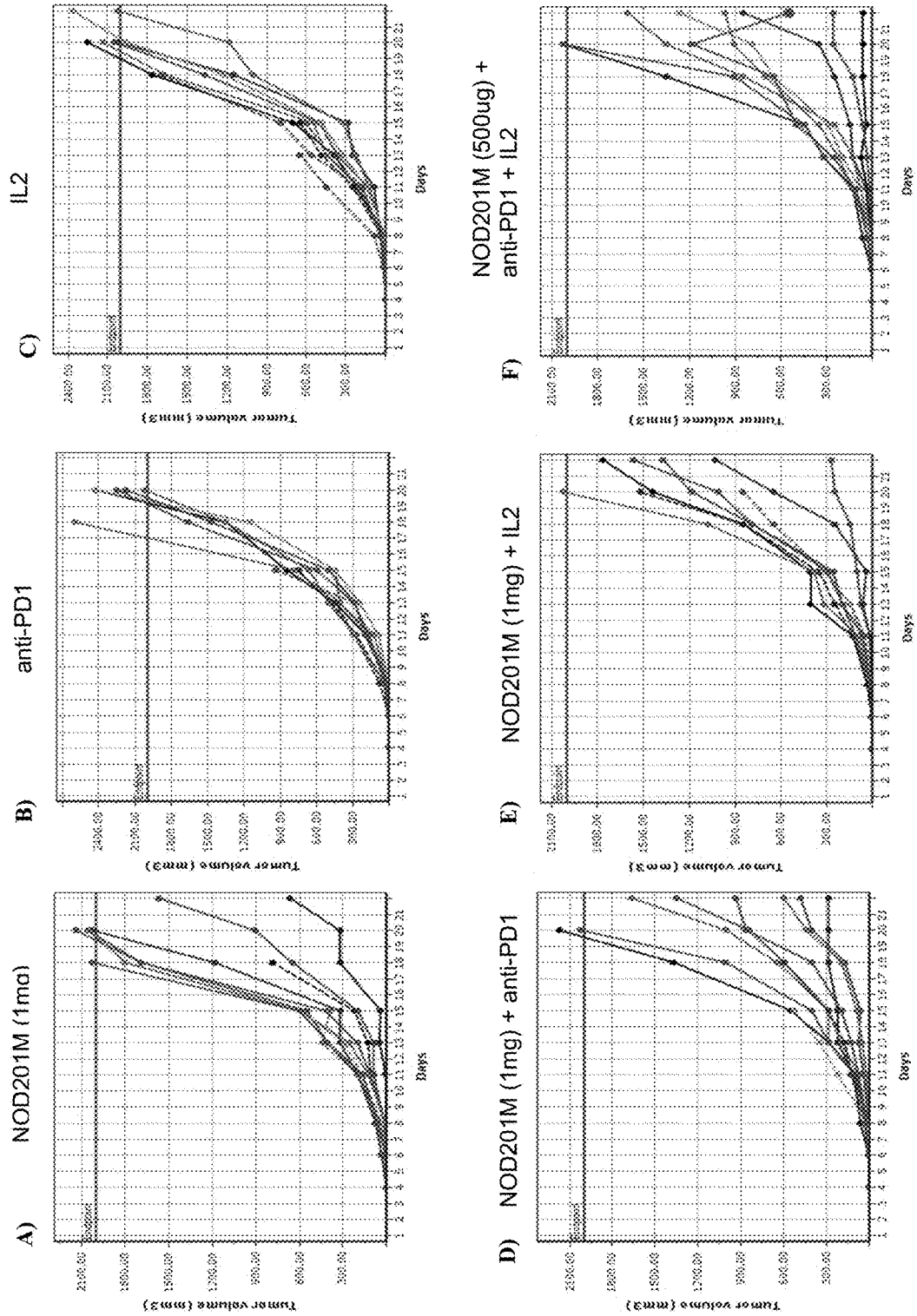
Figures 7G, 7H:
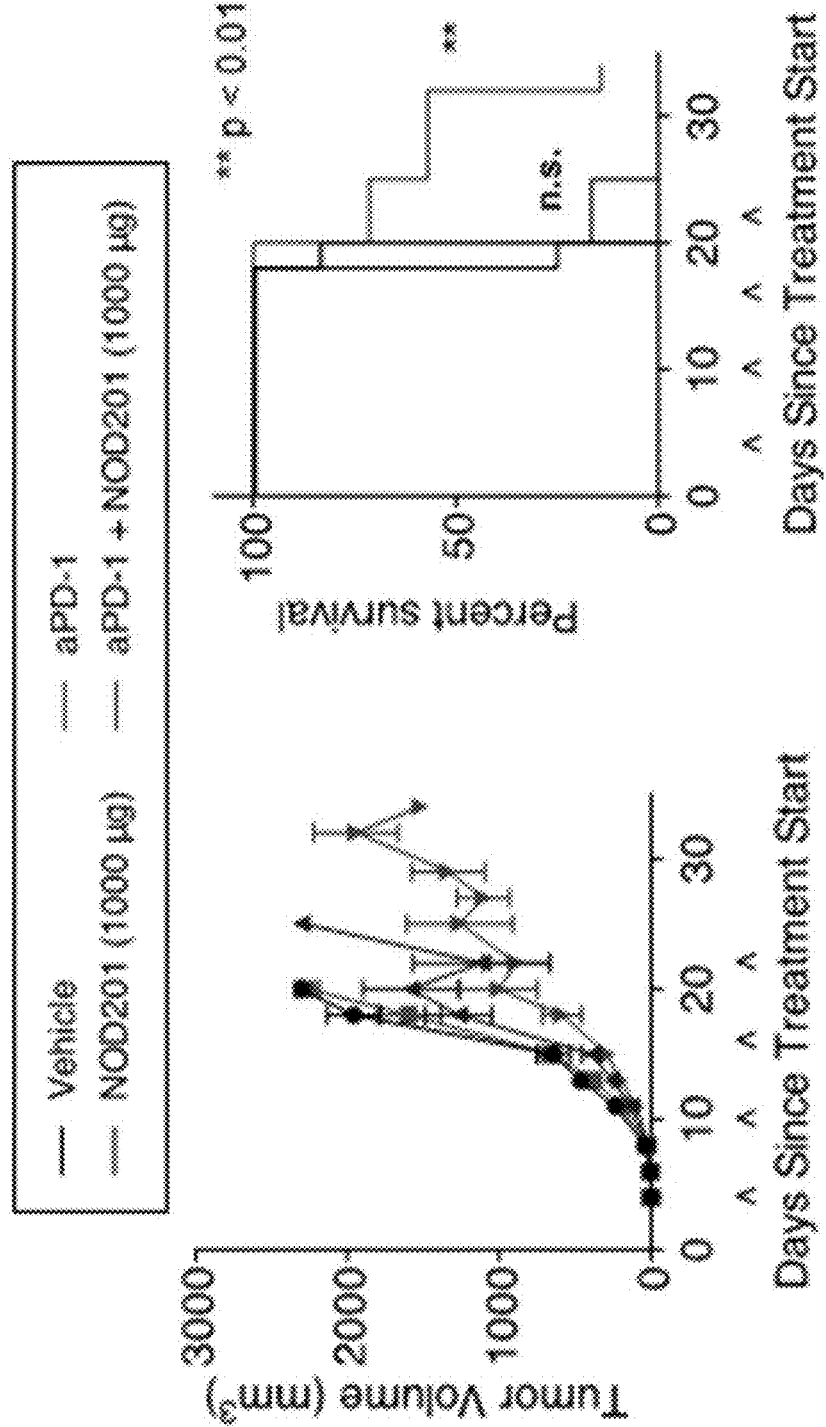
Figures 7I, 7J:
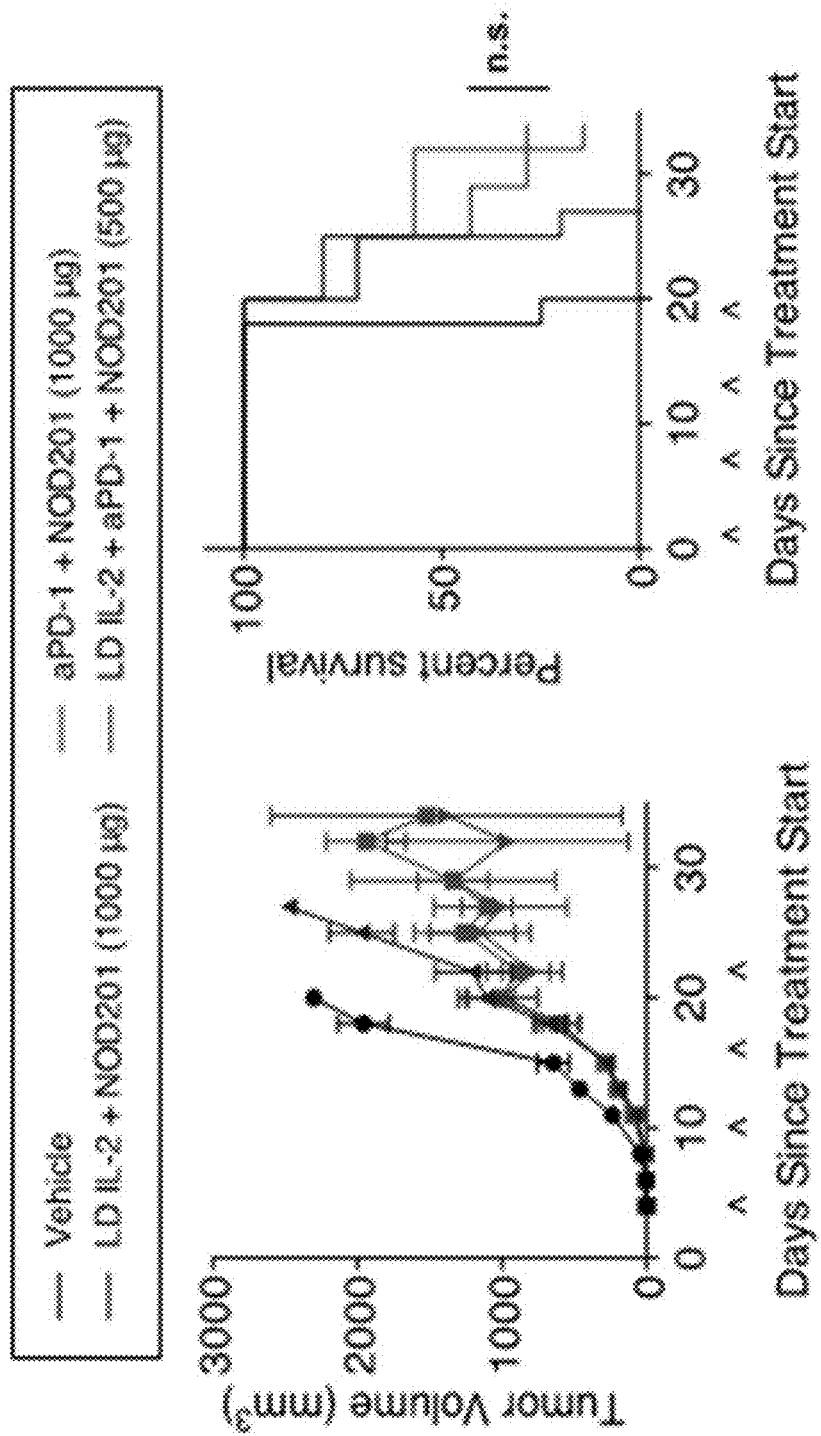

FIG. 5A-FIG. 5B. NOD201M potentiates anti-PD-1. Left, Tumor volume curves. Right, Kaplan-Meier curves. NOD201M was administered IV at doses of 250 µg, 500 µg, or 1000 µg on days 1, 7, 13, 19 after inoculated tumors reached an average size of 60-180 mm$^3$. Anti-PD-1 (200 µg; clone RMP1-14) was administered IV on days 1, 7, 13, 19. Vehicle: phosphate buffered saline. MC38 colon tumor model.

Figures 11A, 11B:
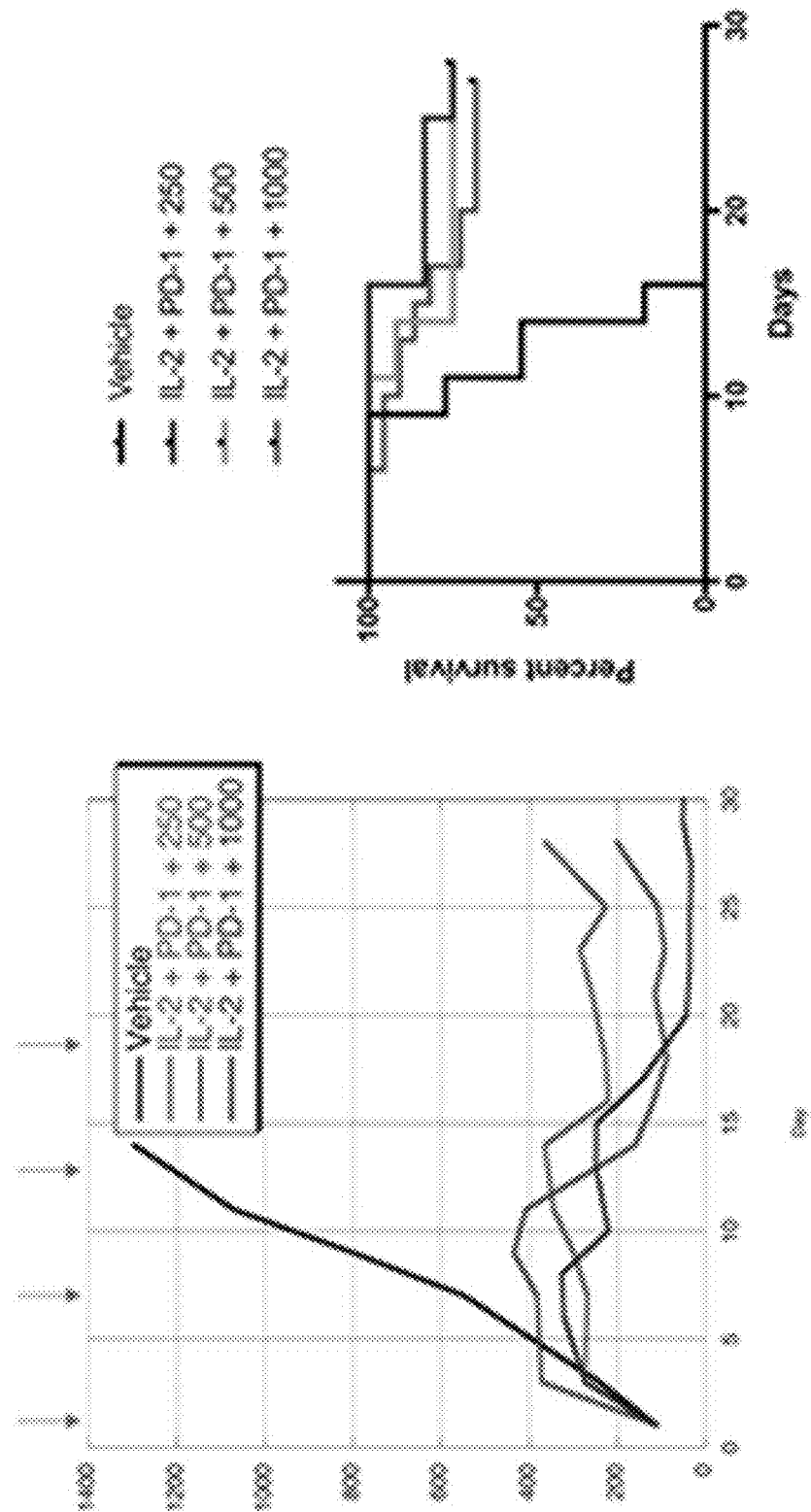
Figures 11C, 11D:
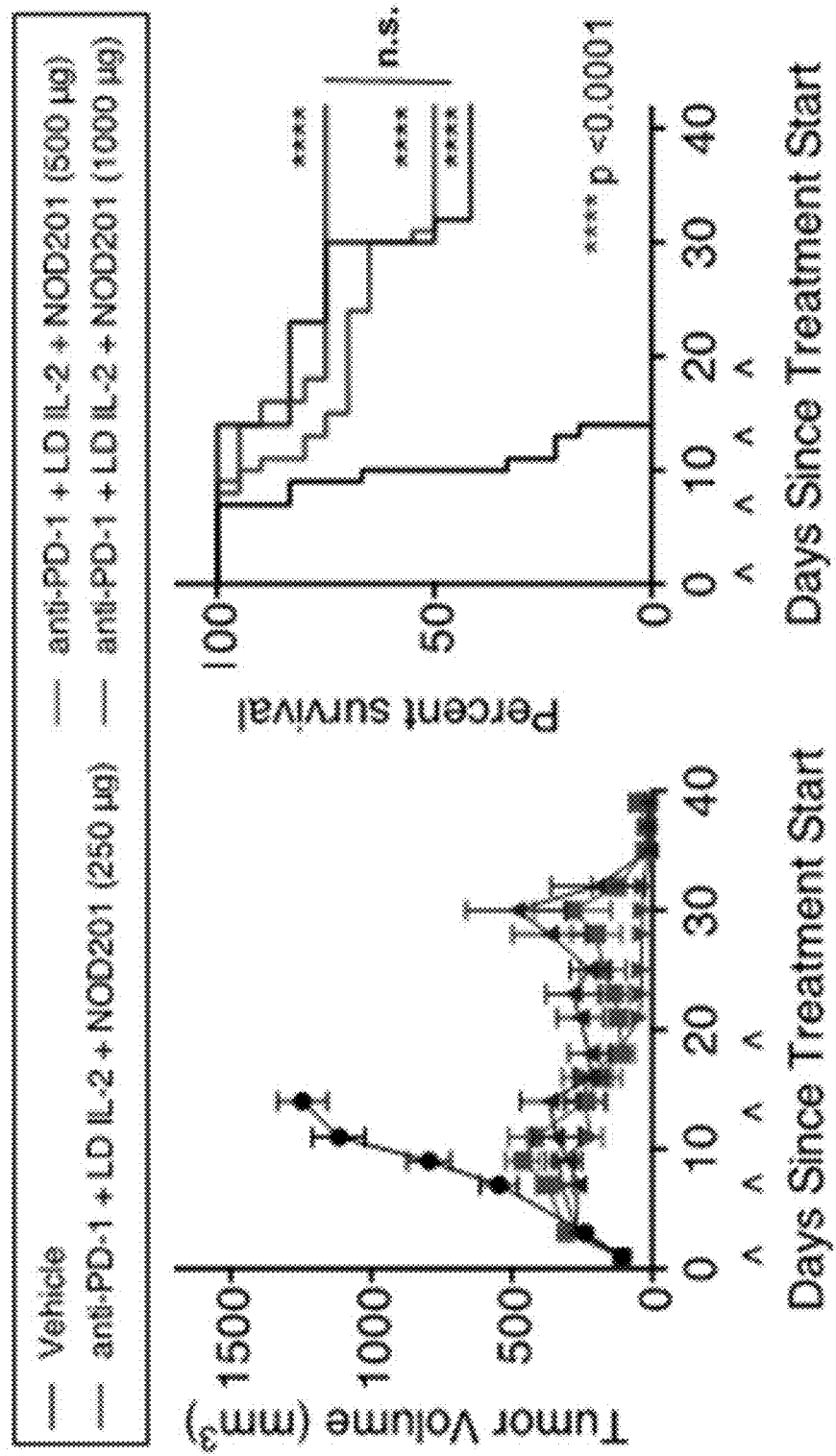

FIG. 6A-FIG. 6E. Tumor cell infiltrates measured following NOD201M combination therapy. NOD201M, anti-PD-1, and low dose IL-2 was administered as described in FIG. 11. Tumors were stained and analyzed for cell surface markers by flow cytometry at day 9; 24 hours post Proleukin dose. Measurements were taken 2 days following 2nd dose cycle. MC38 tumor model. A) NOD201M combination therapy results in a significant increase of CD8+ T cells in the tumor following combination treatment with NOD201M+low dose IL-2 and the NOD201M+anti-PD-1+IL-2 triple combination. B) Myeloid-derived suppressor cells (MDSC) measured in the tumor following treatment indicated. NOD201M+anti-PD-1, NOD201M+low dose IL-2, and NOD201M+anti-PD-1+IL-2 triple combination treatments resulted in a significant decrease in the MDSC in the tumor. The NOD201M+anti-PD-1+IL-2 triple combination treatment resulted in the greatest decrease in MDSC in the tumor. C) NOD201M combination therapy effects on CD4+ T cells in the tumor following treatment indicated. A significant decrease in CD4+ T cells was observed with NOD201M+low dose IL-2 and NOD201M+anti-PD-1+IL-2 triple combination treatments. D) NOD201M combination therapy effects on Tregs in the tumor following treatment indicated. E) NOD201M combination therapy effects on NK cells following treatment indicated.

FIG. 7A-FIG. 7J. NOD201M efficacy in the B16F10 melanoma model. Tumor volume curves for NOD201M+/−IL-2+/−anti-PD-1 combination therapy. A) NOD201M. B) Anti-PD-1 antibody. C) IL-2. D) NOD201M+anti-PD-1 antibody. E) NOD201M+IL-2. F) NOD201M+anti-PD-1 antibody+IL-2. G)/H)/I)/J) Graphical representation of the data. In this experiment, the study start date was the day of tumor implant (Day 1) and not the first day of dosing of established tumors as in MC38 studies. NOD201M was administered IV at doses of 500 µg or 1000 µg (as indicated) on days 4, 10, 16, 22. IL-2 (4 µg; Proleukin) was administered subcutaneously on days 5-7, 11-13, 17-19, 23-25. Anti-PD-1 (200 µg; clone RMP1-14) was administered IV on days 4, 10, 16, 22. B16F10 tumor model.

Figures 8A, 8B:
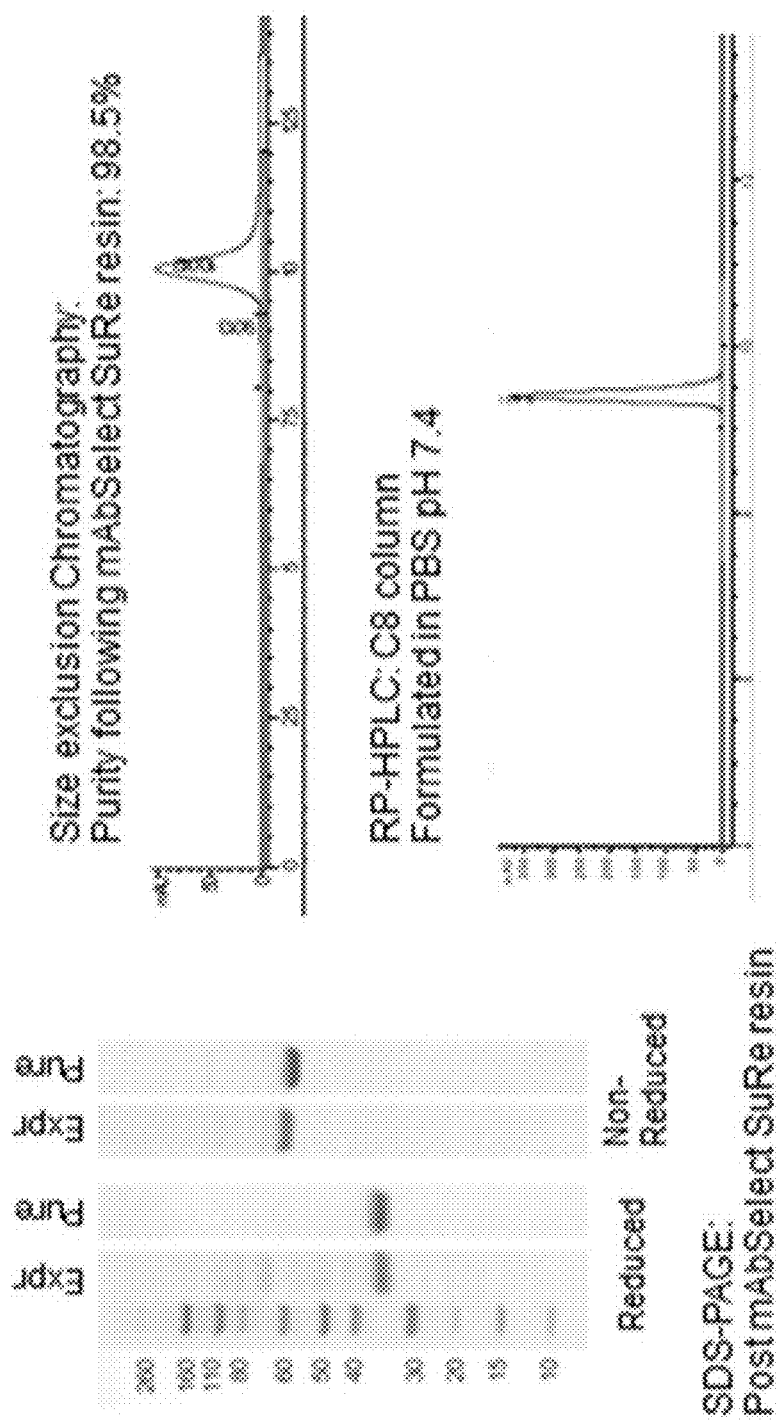
Figures 9A, 9B, 9C, 9D:
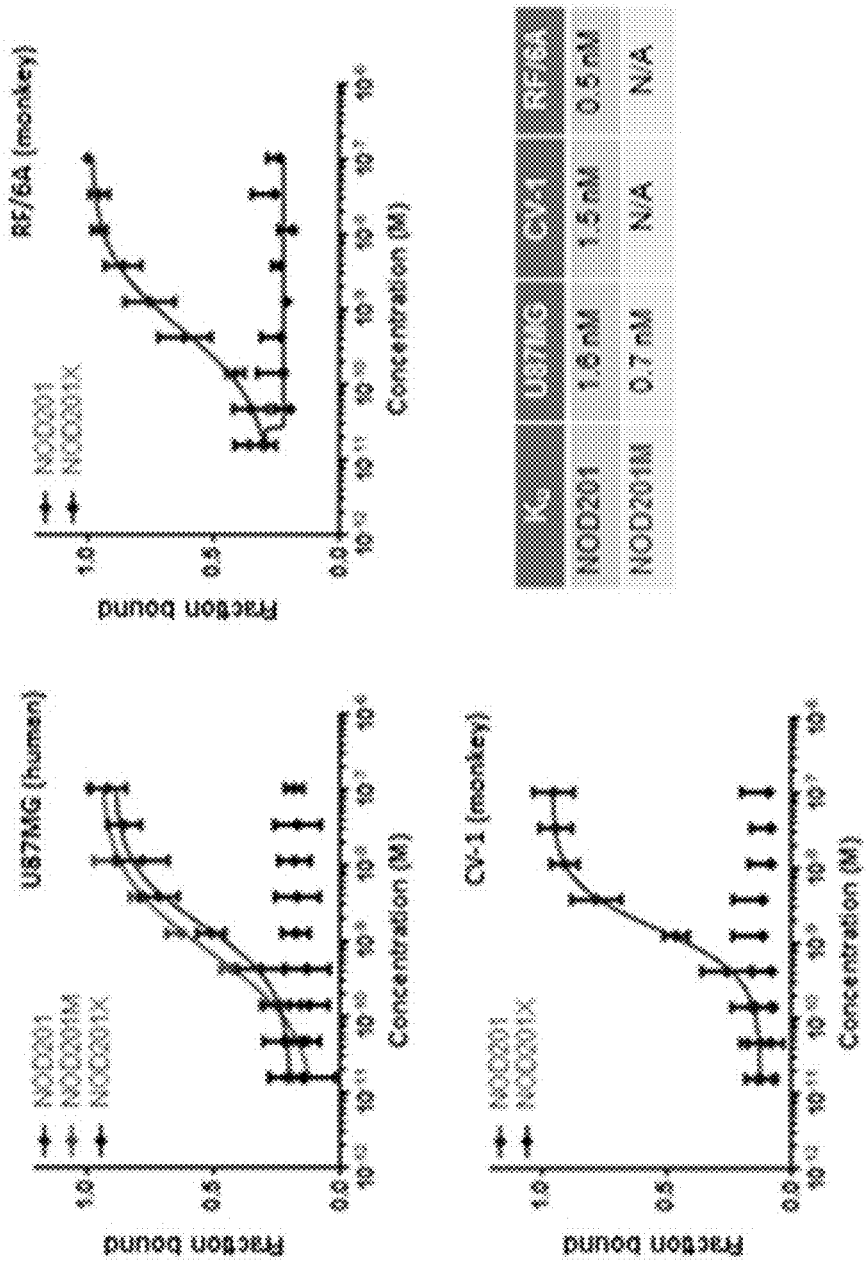

FIG. 8A-FIG. 8B. Analytical characterization of NOD201 produced from a transient HEK expression system. SDS-PAGE of expressed and purified NOD201 showed bands of the expected molecular weight; reduced and non-reduced samples were analyzed. Size exclusion chromatography of purified NOD201 following mAbSelect SuRe resin. RP-HPLC of purified NOD201 formulated in PBS, pH 7.4 using a C8 column. Thermal stability: 68° C. in PBS, pH 7.4 as measured by DSF.

FIG. 9A-FIG. 9D. NOD201 binds with high affinity to cells expressing human and monkey integrins. NOD201X contains a scrambled binding epitope and serves as a negative control. U87MG (human tumor cells); CV-1 (monkey); RF/6A (monkey). Binding was measured using an antibody against the NOD201 or NOD201X Fc domain using flow cytometry. Binding of NOD201M to U87MG cells was also measured for comparison and shows similar binding affinity as NOD201.

Figures 10A, 10B, 10C:
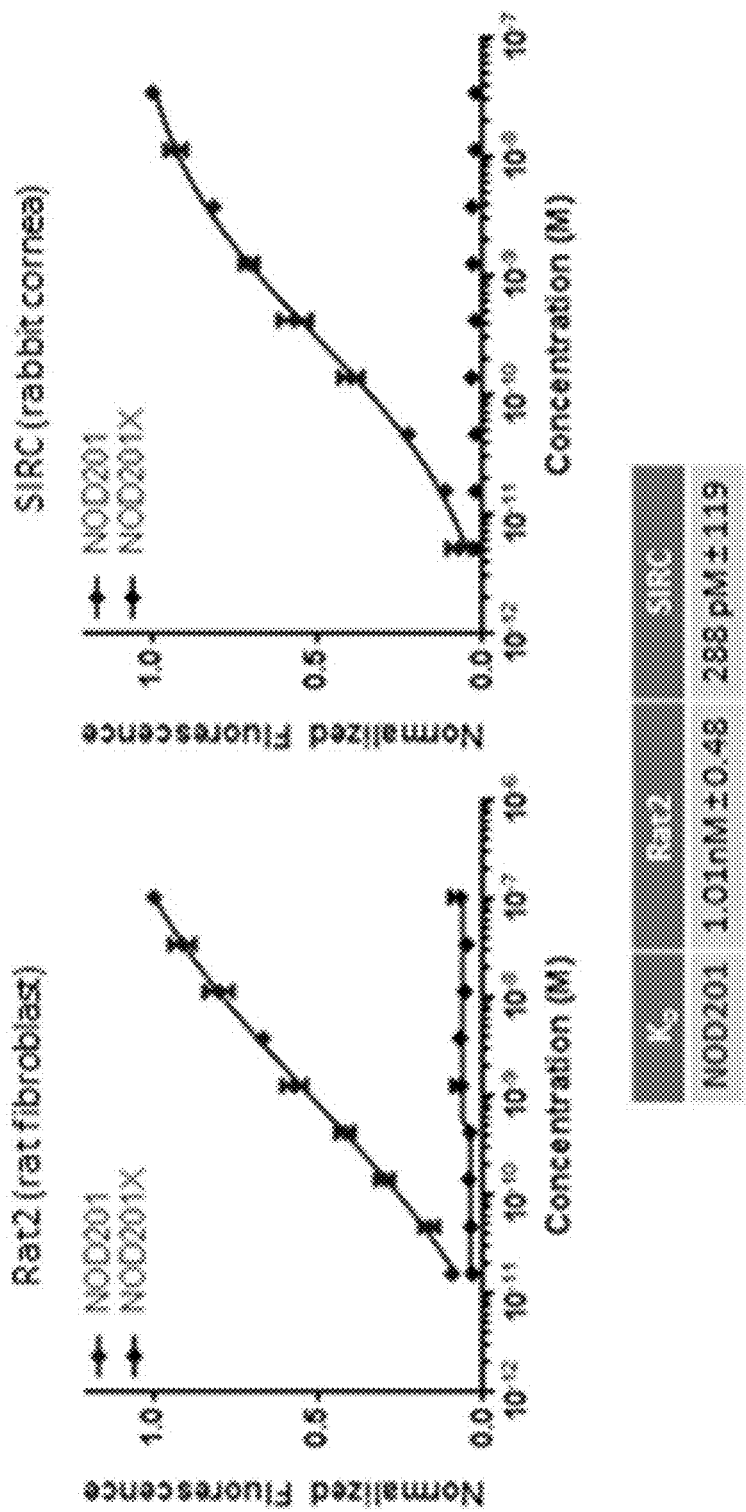

FIG. 10A-FIG. 10C. NOD201 binds with high affinity to cells expressing rat and rabbit integrins. NOD201X contains a scrambled binding epitope and serves as a negative control. Rat2 (rat fibroblasts); SIRC (rabbit corneal cells). Binding was measured using an antibody against the NOD201 or NOD201X Fc domain using flow cytometry.

FIG. 11A-FIG. 11D. Tumor volume (left) and Kaplan-Meier curves (right) for NOD201M+IL-2+anti-PD1 combination therapy. MC38 colon tumor model NOD201M was administered IV at doses of 250 µg, 500 µg, or 1000 µg on days 1, 7, 13, 19 after inoculated tumors reached an average size of 60-180 mm$^3$. IL-2 (4 µg; Proleukin) was administered subcutaneously on days 2-4, 8-10, 14-16, 20-22. Anti-PD1 (200 µg; clone RMP1-14) was administered IV on days 1, 7, 13, 19.

Figures 12A, 12B:
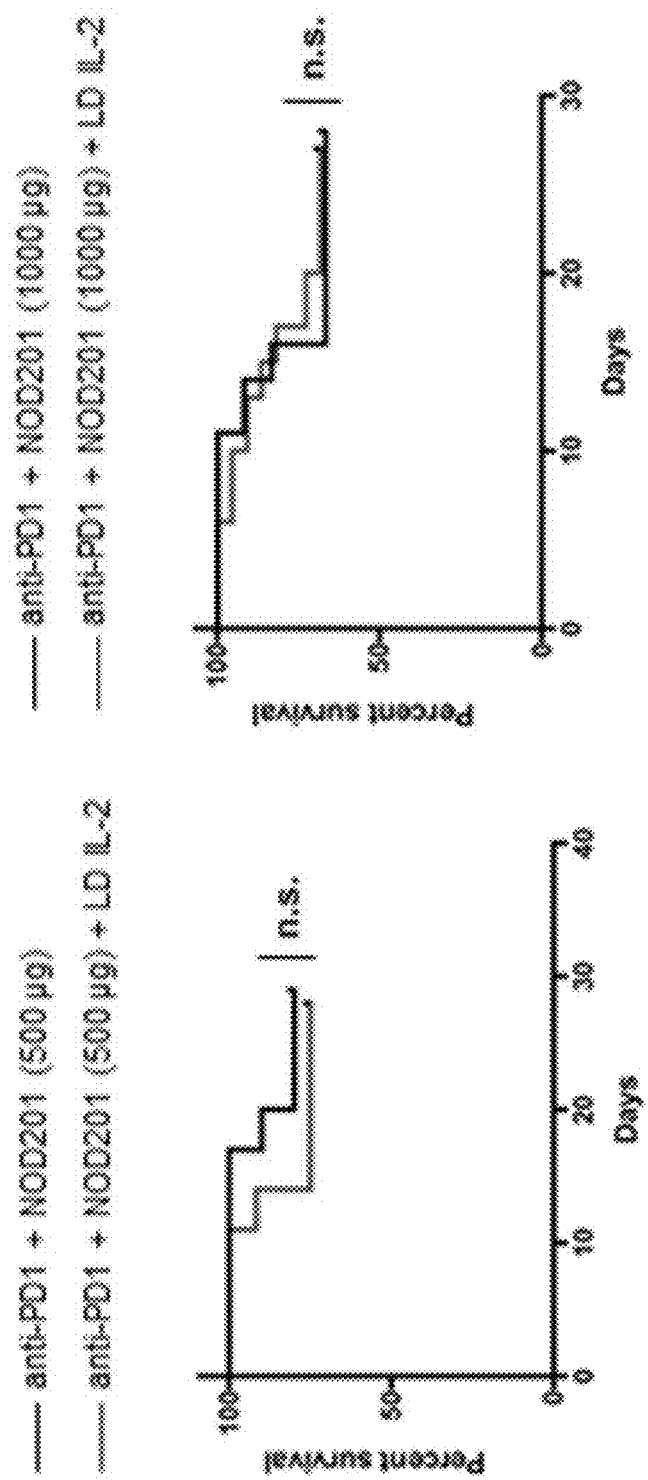

FIG. 12A-FIG. 12B. Addition of IL-2 to NOD201M+anti-PD1 combination therapy does not improve 30-day survival. MC38 colon tumor model.

FIG. 13. Study design to determine the efficacy of NOD201M alone and in combination with high dose or low dose Proleukin, and anti-PD-1 in the MC38-NODU syngeneic colon model using female C57BL/6 mice. Day indicates dosing administered after inoculated tumors reached an average size of 60-180 mm$^3$.

Figures 14A, 14B:
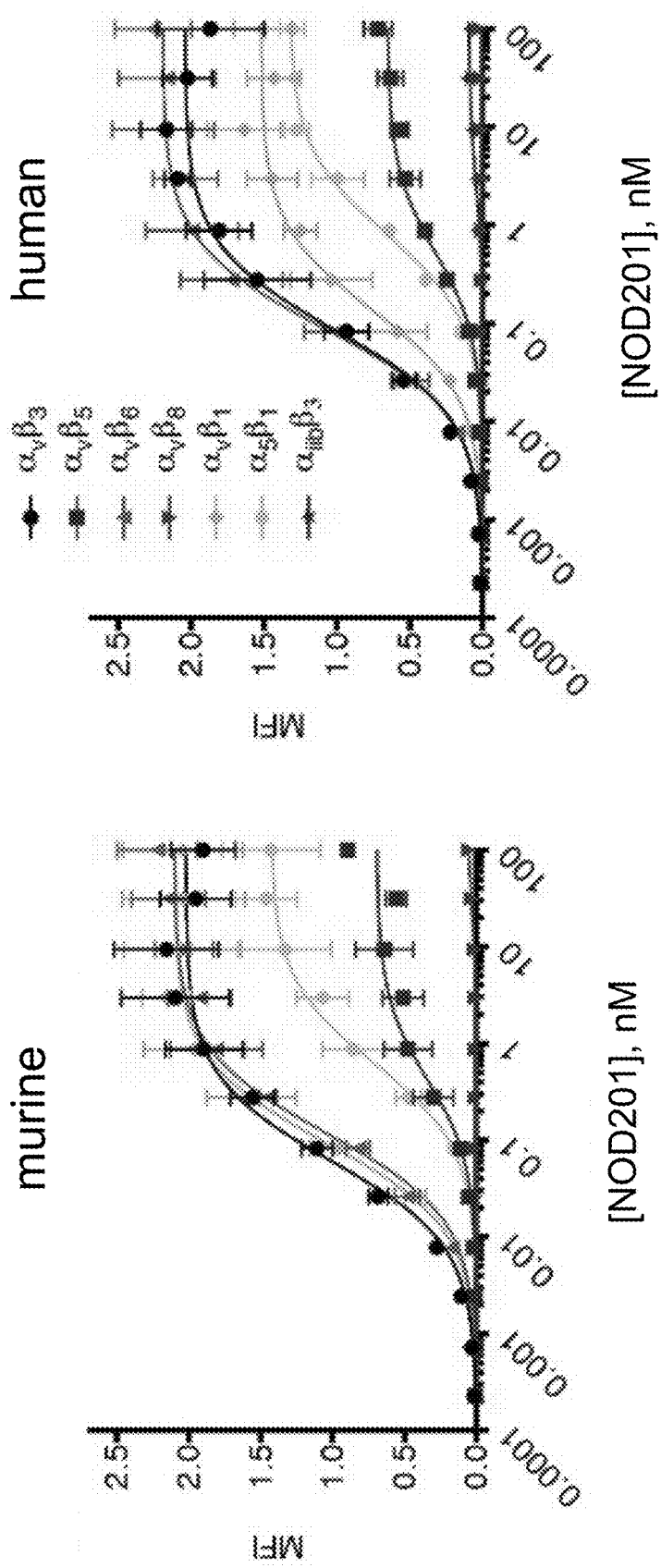

FIG. 14A-FIG. 14B. NOD201 binds to multiple murine and human RGD-binding integrin heterodimers with high affinity.

Figure 15:
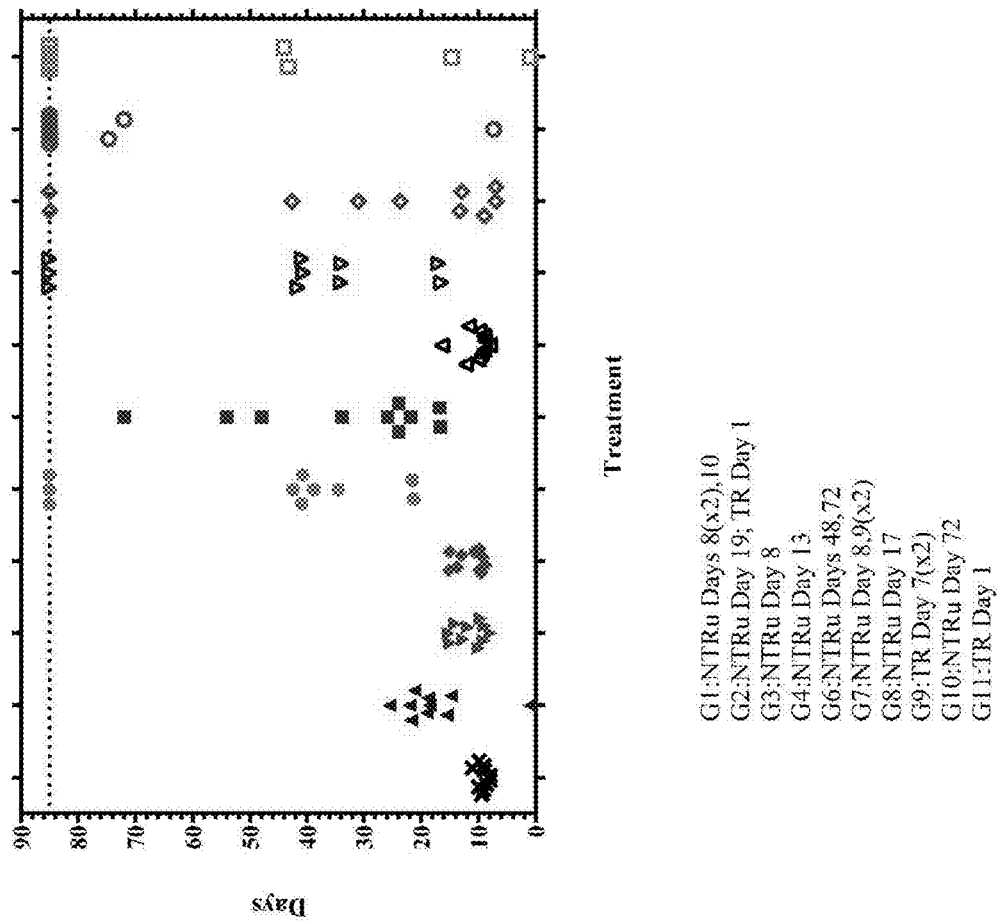

FIG. 15. Individual times to end-point for mice in the study design outlined in FIG. 13. NOD201M, Proleukin, or anti-PD1 were administered as indicated.

Figure 16A:
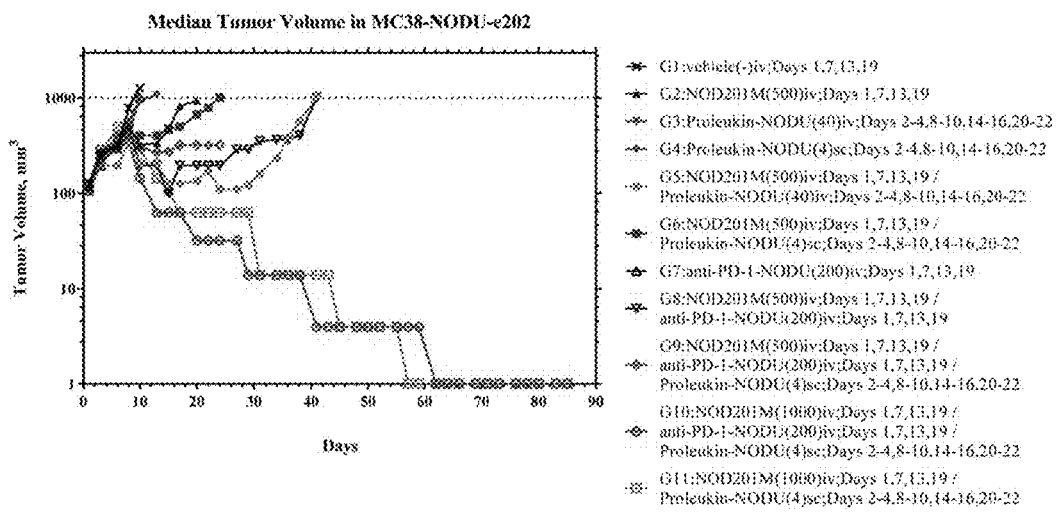
Figure 16B:
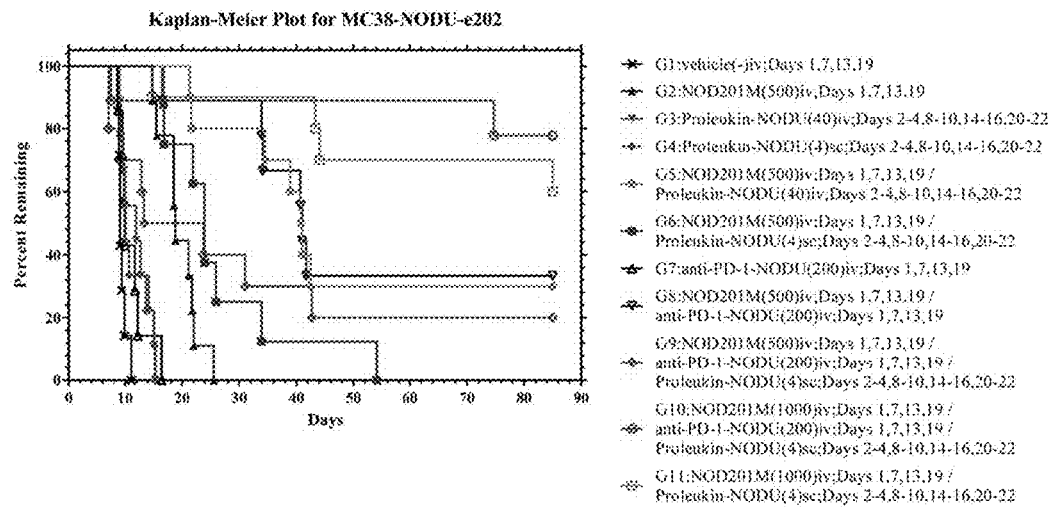

FIG. 16A-FIG. 16B. Median tumor growth and Kaplan-Meier plots for mice in the study design outlined in FIG. 13. NOD201M, Proleukin, or anti-PD1 were administered as indicated.

Figure 17:
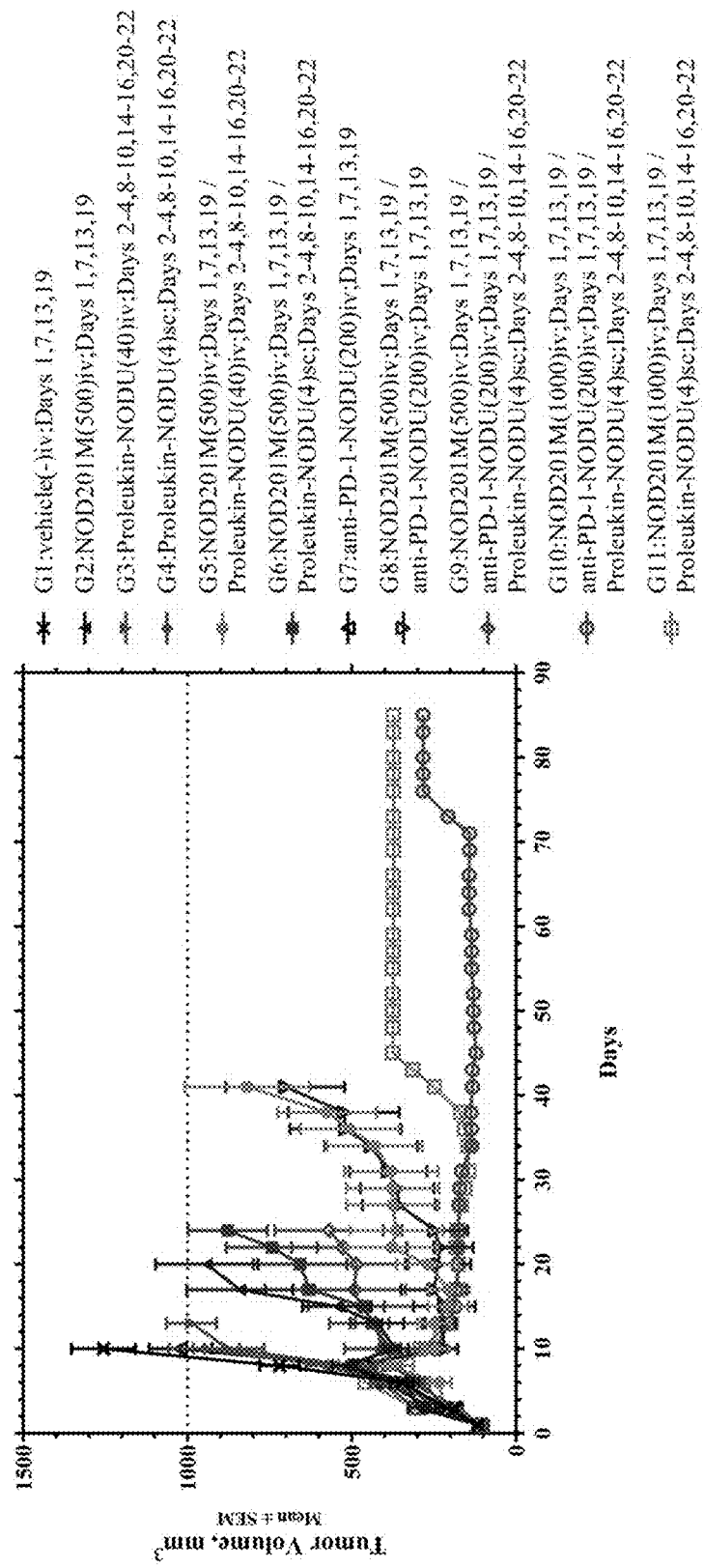
Figure 18A:
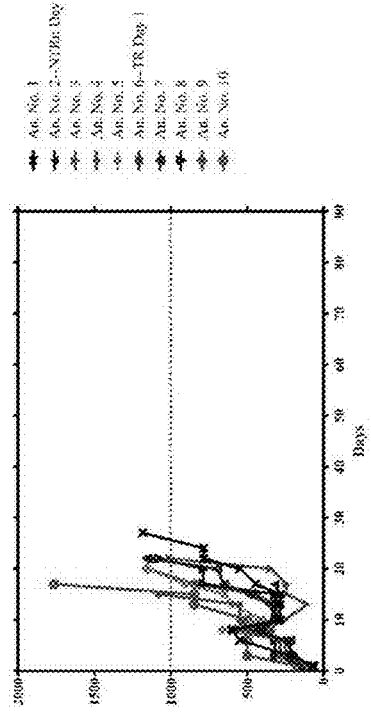
Figure 18B:
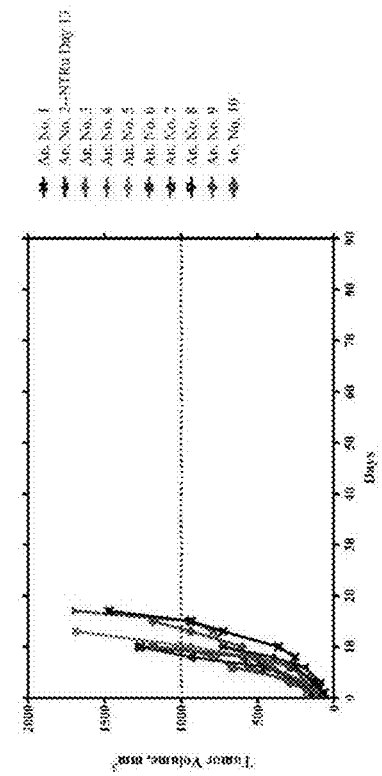
Figure 18C:
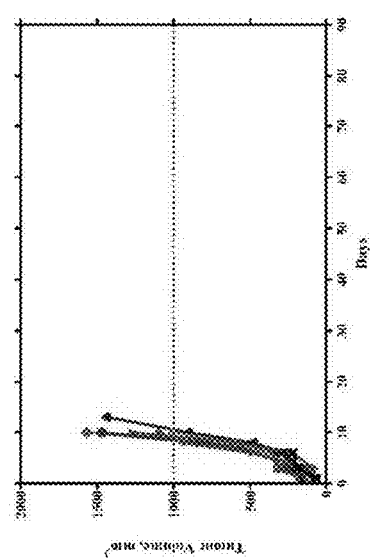
Figure 18D:
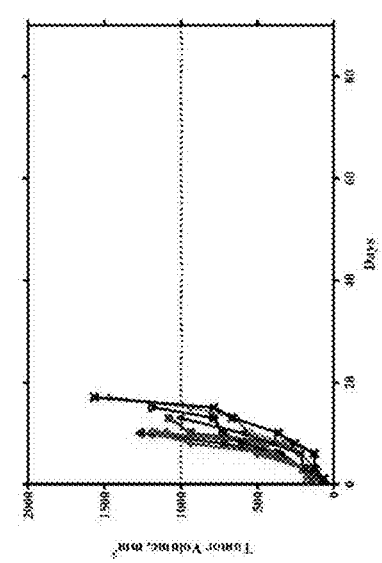
Figures 19A, 19B, 19C, 19D:
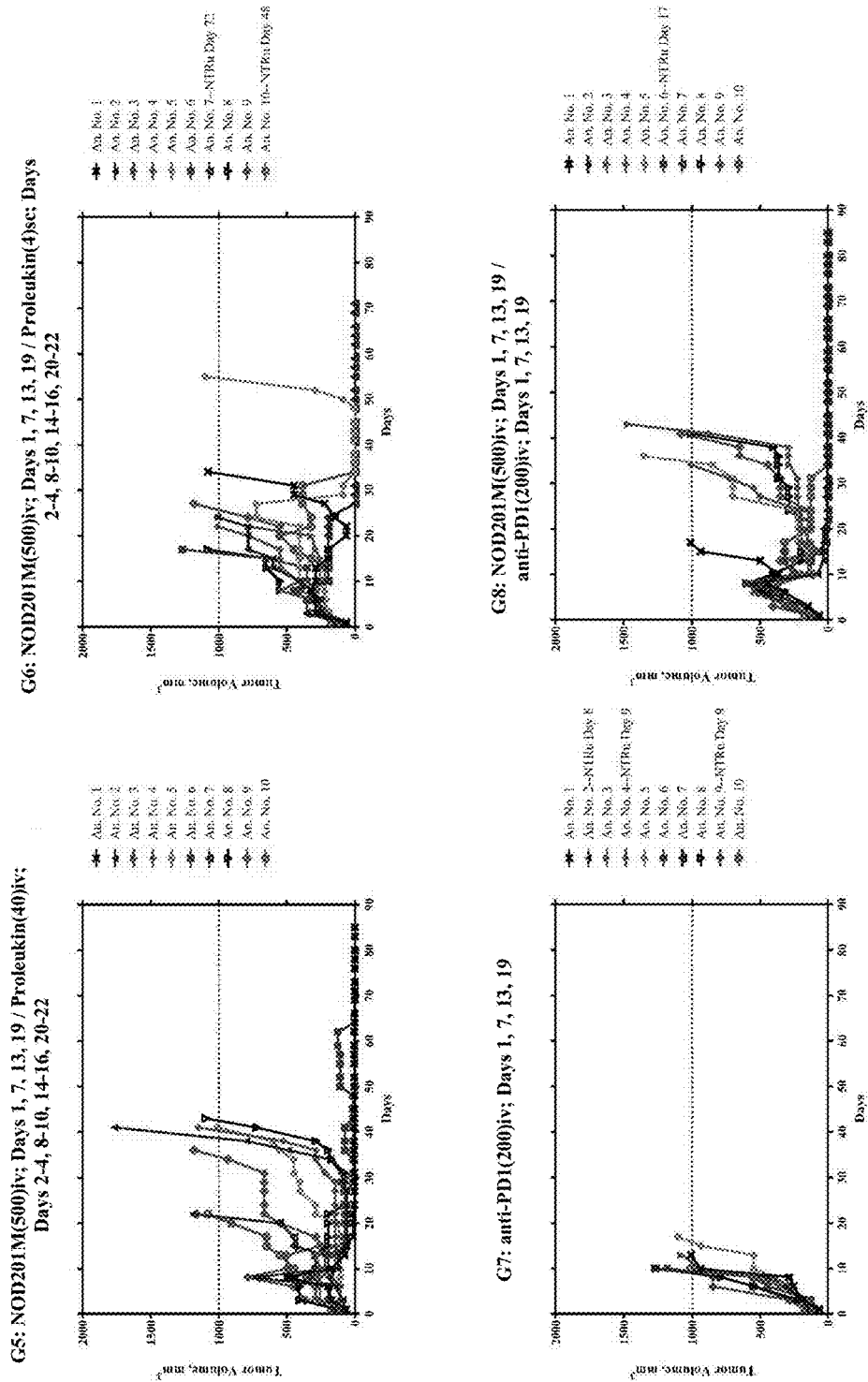

FIG. 17. Mean tumor volume curves for mice in the study design outlined in FIG. 13. NOD201M, Proleukin, or anti-PD1 were administered as indicated.

FIG. 18A-FIG. 18D. Individual tumor volume growth curves for mice in the study design outlined in FIG. 13.

FIG. 19A-FIG. 19D. Individual tumor volume growth curves for mice in the study design outlined in FIG. 13.

Figure 20A:
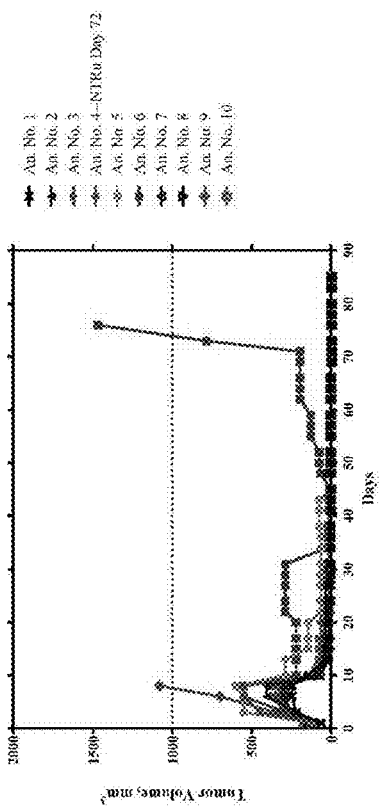
Figure 20B:
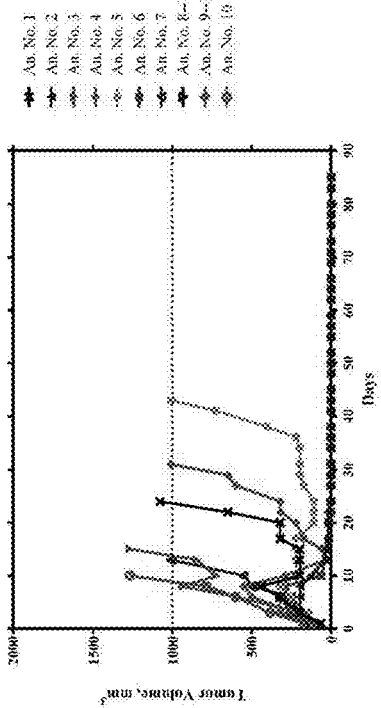
Figure 20C:
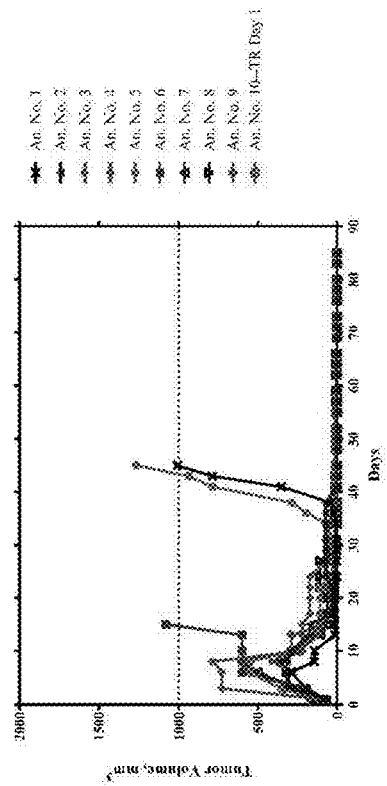

FIG. 20A-FIG. 20C. Individual tumor volume growth curves for mice in the study design outlined in FIG. 13.

Figure 21:
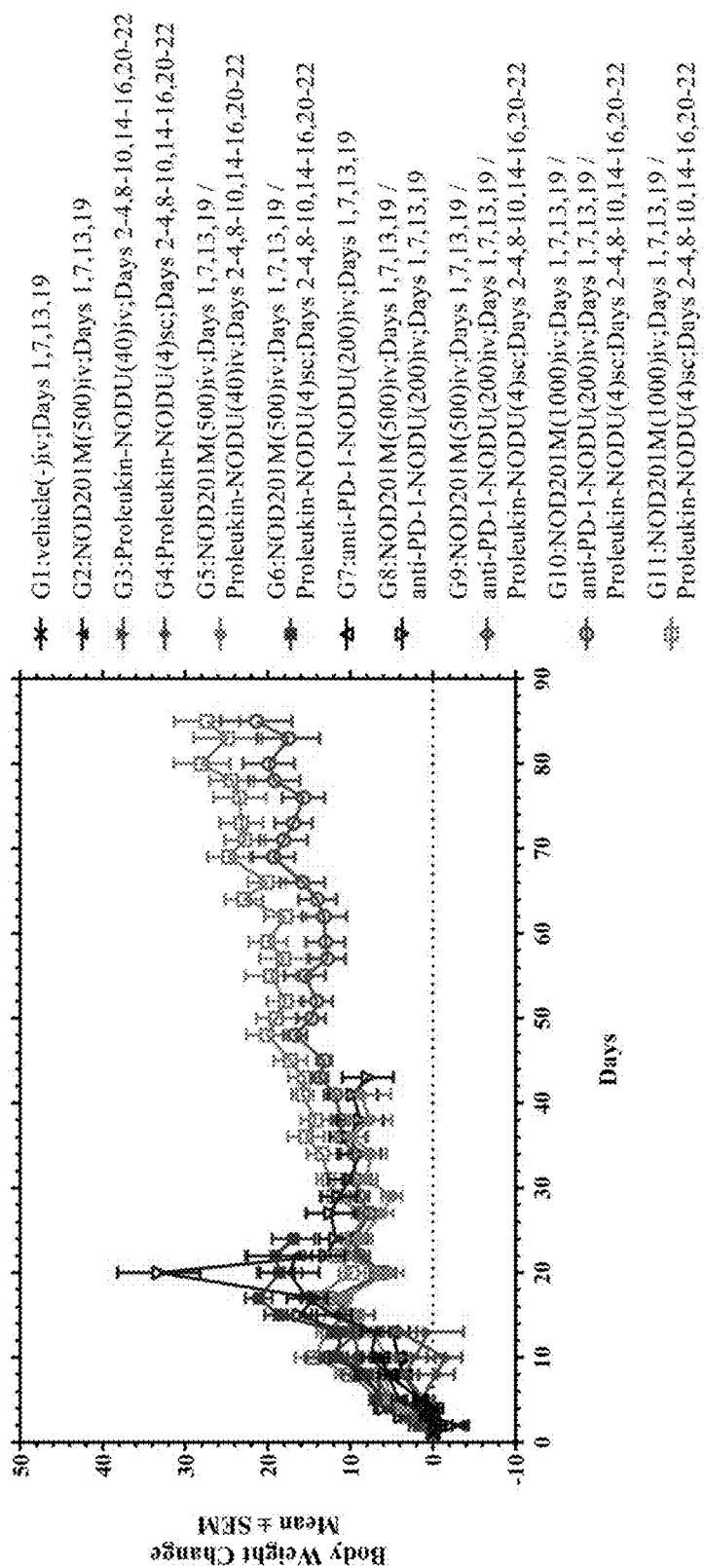
Figures 23A, 23B, 23C:
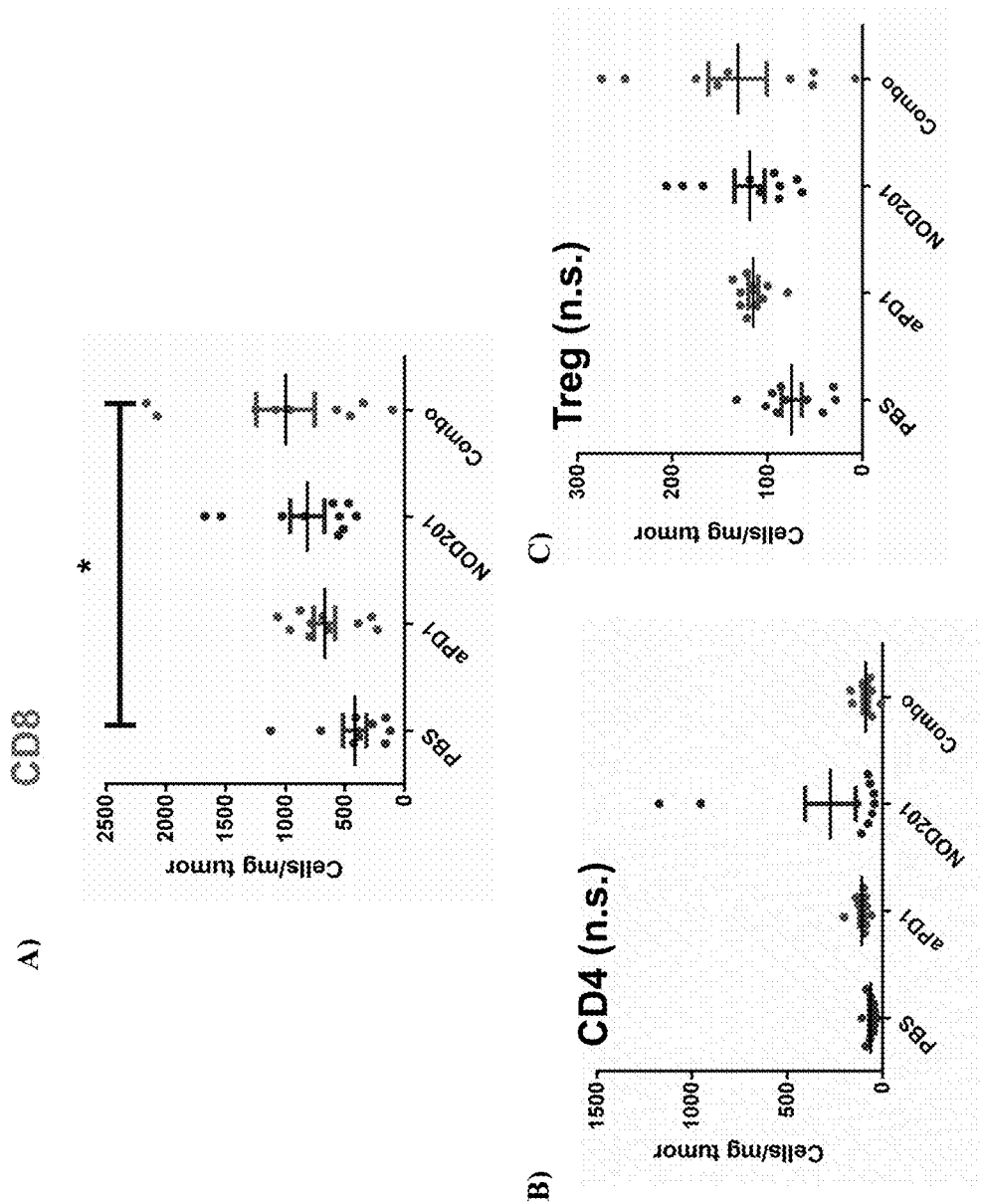
Figure 23D:
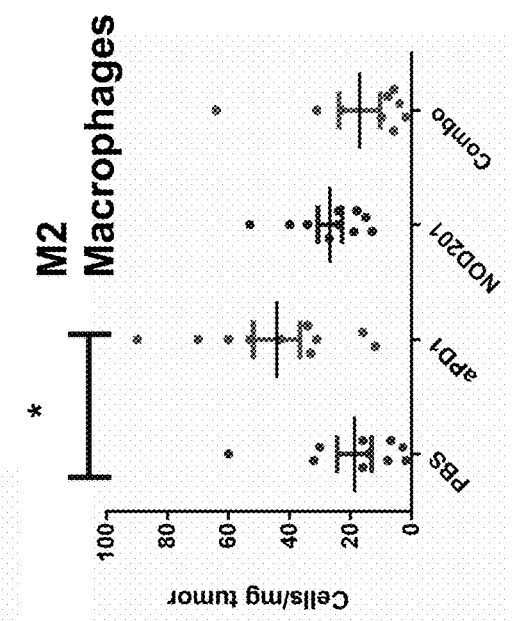
Figure 23E:
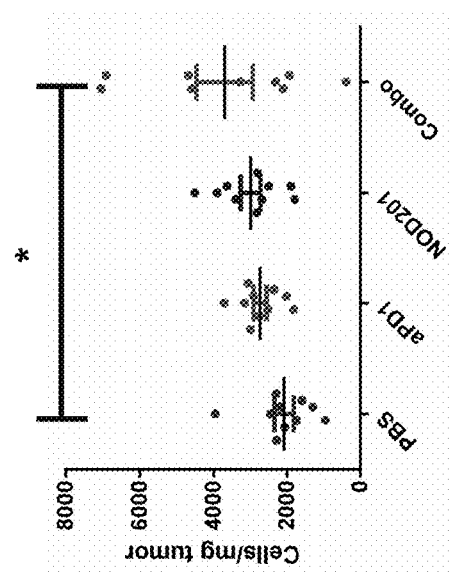
Figure 23F:
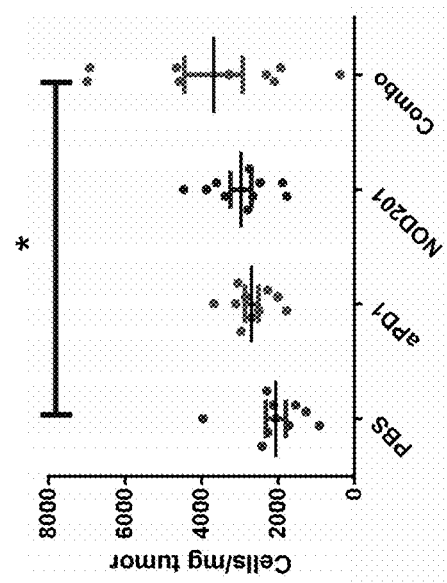
Figures 23G, 23H, 23I, 23J:
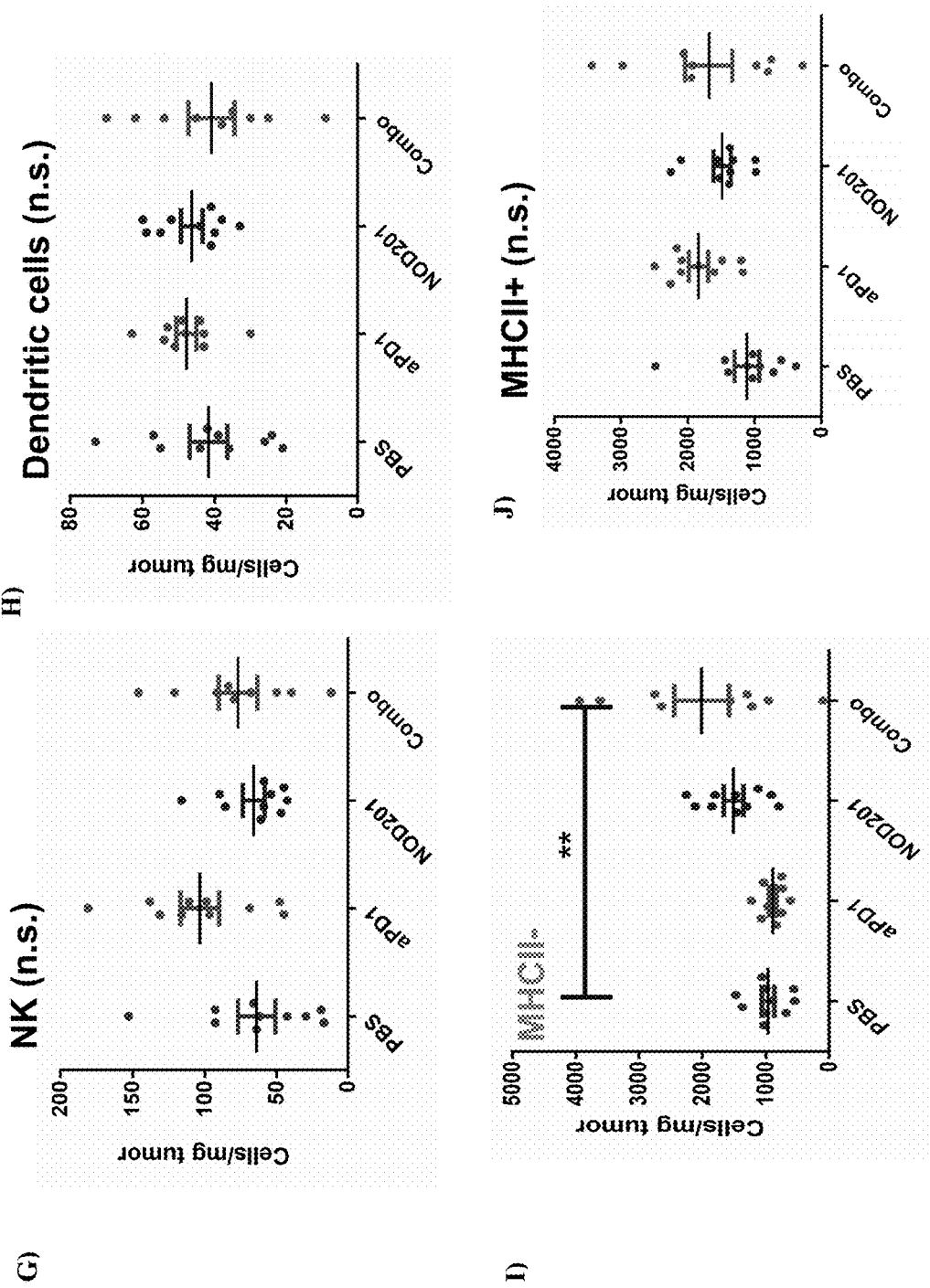
Figures 23K, 23L, 23M:
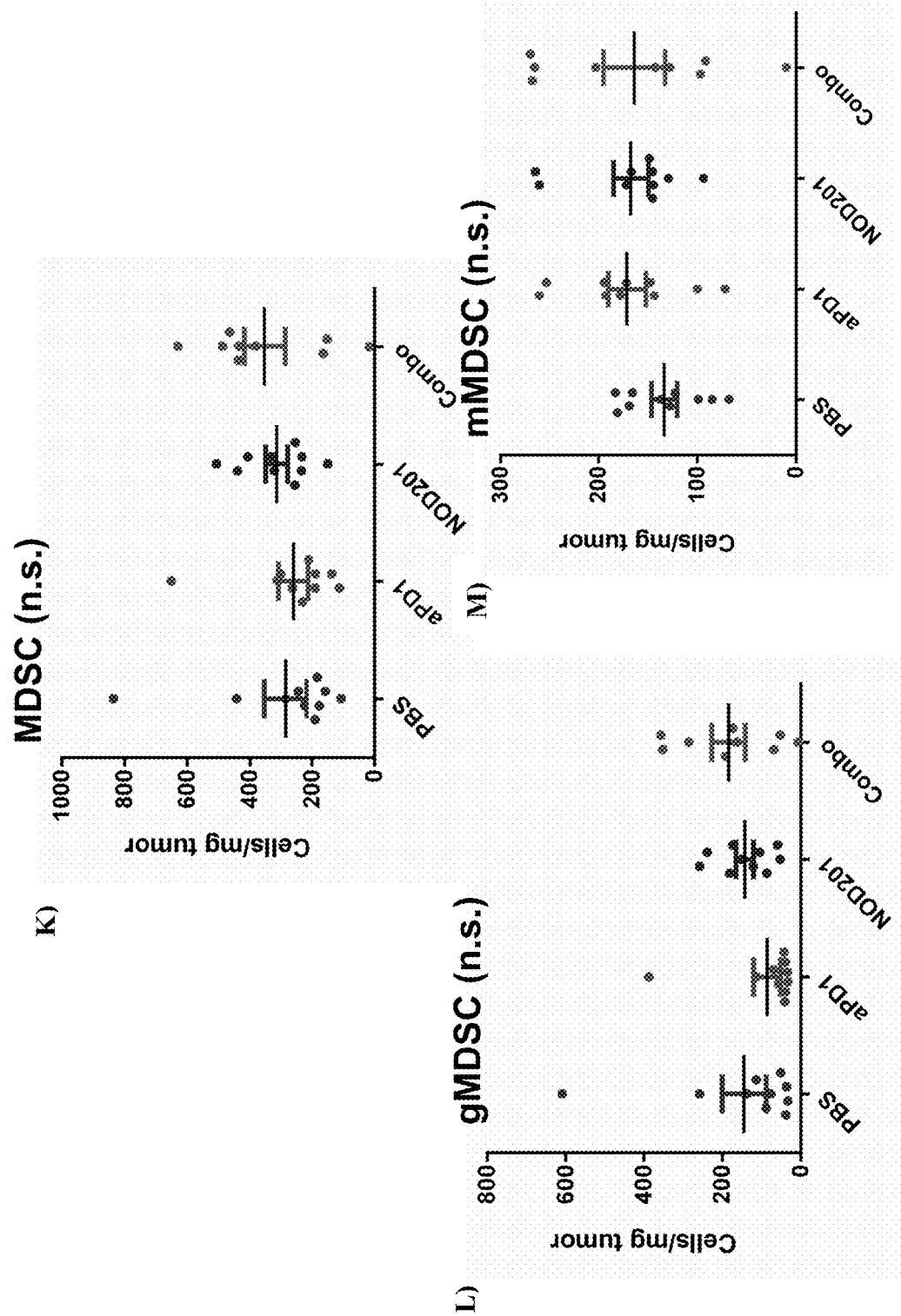

FIG. 21. Percent group mean body weight for mice in the study design outlined in FIG. 13.

Figures 22A, 22B:
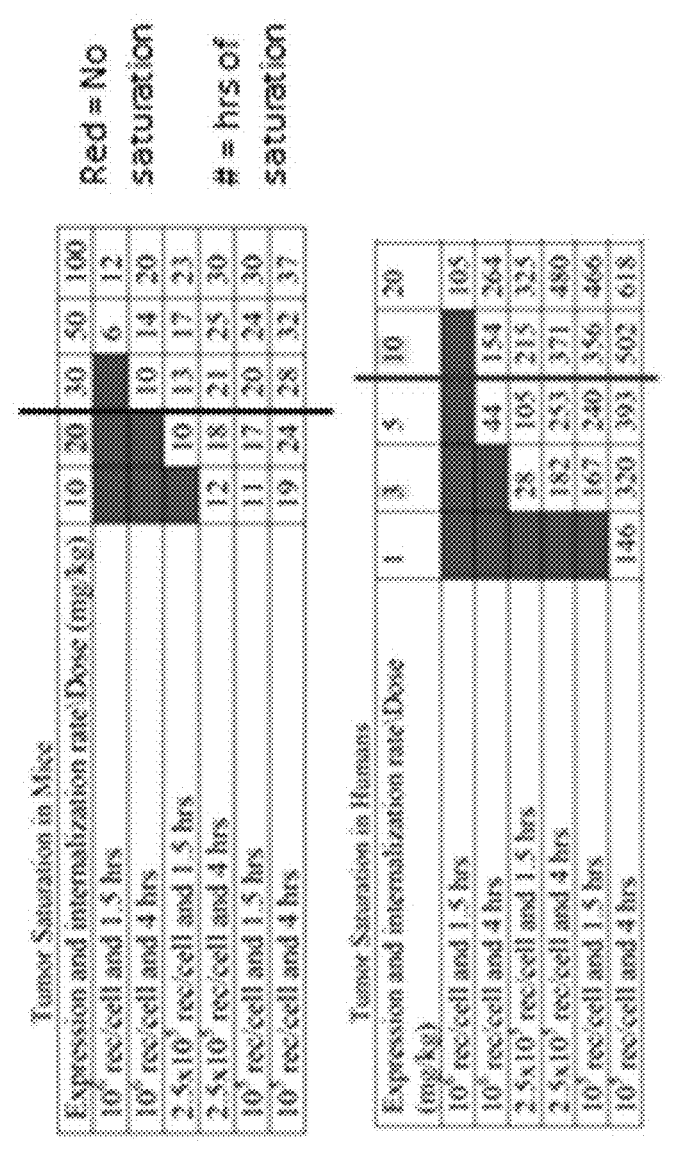

FIG. 22A-FIG. 22B. NOD201 dosing rationale. >25 mg/kg in mice and >10 mg/kg in man required to overcome 1) rapid systemic clearance (~60 kDa), 2) rapid endocytic clearance (~1.5 hr half-life), 3) TMDD (PBMC) Annals of oncology 2013; 24(2):329-36. Model calculations as per J Theor. Biol. 314:57-68 (2012).

FIG. 23A-FIG. 23M. Tumor cell infiltrates resulting from NOD201M combination therapy. A) CD8+, B) CD4+ (n.s.), C) Treg (n.s.), D) Macrophages, E) M1 macrophages, F) M2 macrophages, G) NK (n.s.), H) Dendritic cells (n.s.), I) MHCII−, J) MHCII+ (n.s.), K) MDSC (n.s.), L) gMDSC (n.s.), and M) mMDSC (n.s.). A) CD8+, D) MHCII−, E) M1 macrophages for the combo treatment, and I) M2 macrophages for αPD-1 (anti-PD-1) exhibited statistical significance. CD8+ T-cells and macrophages are involved in the therapeutic effect with NOD201M and αPD-1. However, single agent NOD201M or αPD-1 did not exhibit statistically significant change in the number of CD8+ T-cells or macrophages in the tumor. Cells that did not change significantly upon treatment with single agent or combo were CD4+ T-cells, Tregs, NK cells, MDSC, gMDSC, mMDSC, dendritic cells, and MHCII+. M2 macrophages: these tolerizing or immunosuppressive macrophages were increased with αPD-1 treatment alone. The combo arm was lowered in M2 back down to saline treated levels. M1 macrophages: these highly stimulated tumor killing macrophage type were increased with the combo as compared to no difference with single agents. MHCII– (likely dendritic cells) do change with the combo treatment but not single agent treatment.

DETAILED DESCRIPTION OF THE INVENTION

I. Introduction

Interleukin-2 (IL-2) is a pleiotropic cytokine that activates and induces the proliferation of T cells and NK cells. Although IL-2 is an FDA approved therapy, systemic IL-2 treatment has significant toxicity and the response rate of patients is less than 25%. Combining extended half-life IL-2 and an antibody against a tumor-specific antigen shows promising results for treatment. However, antibody-based therapies often suffer from the fact that many tumors lack known tumor-associated antigens.

Integrins are a family of extracellular matrix adhesion receptors that regulate a diverse array of cellular functions crucial to the initiation, progression and metastasis of solid tumors. The importance of integrins in tumor progression has made them an appealing target for cancer therapy and allows for the treatment of a variety of cancer types. The integrins present on cancerous cells include $\alpha_v\beta_3$, $\alpha_v\beta_5$, and $\alpha_5\beta_1$. A variety of therapeutics have been developed to target individual integrins associated with cancer, including antibodies, linear peptides, cyclic peptides, and peptidomimetics. However, none have utilized small, structured peptide scaffolds or targeted more than two integrins simultaneously. Additionally, current integrin targeting drugs are given as a monotherapy. Novel combination therapies are needed to more effectively combat various cancers.

II. Definitions

Terms used in the claims and specification are defined as set forth below unless otherwise specified. In the case of direct conflict with a term used in a parent provisional patent application, the term used in the instant specification shall control.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid. Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

An "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, the present larger "peptide insertions," can be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

"Polypeptide," "peptide", and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

"Nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed-base and/or deoxyinosine residues (Batzer et al., Nucleic Acid Res. 19:5081, 1991; Ohtsuka et al., Biol. Chem. 260:2605-2608, 1985; and Cassol et al, 1992; Rossolini et al, Mol. Cell. Probes 8:91-98, 1994). For arginine and leucine, modifications at the second base can also be conservative. The term nucleic acid is used interchangeably with gene, cDNA, and mRNA encoded by a gene. Polynucleotides used herein can be composed of any polyribonucleotide or polydeoxribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotide can be composed of triple-stranded regions comprising RNA or DNA or both RNA and DNA. A polynucleotide can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

As used herein, "interleukin (IL)-2," refers to a pleiotropic cytokine that activates and induces proliferation of T cells and natural killer (NK) cells. IL-2 signals by binding its receptor, IL-2R, which is comprised of alpha, beta, and gamma subunits. IL-2 signaling stimulates proliferation of antigen-activated T cells.

As used herein, the term "PK" is an acronym for "pharmacokinetic" and encompasses properties of a compound including, by way of example, absorption, distribution, metabolism, and elimination by a subject. As used herein, an "extended-PK group" refers to a protein, peptide, or moiety that increases the circulation half-life of a biologically active molecule when fused to or administered together with the biologically active molecule. Examples of an extended-PK group include PEG, human serum albumin (HSA) binders (as disclosed in U.S. Publication Nos. 2005/0287153 and 2007/0003549, PCT Publication Nos. WO 2009/083804 and WO 2009/133208, and SABA molecules as described in US Publication No. 2012/094909), human serum albumin, Fc or Fc fragments and variants thereof, and sugars (e.g., sialic acid). Other exemplary extended-PK groups are disclosed in Kontermann et al., Current Opinion in Biotechnology 2011; 22:868-876, which is herein incorporated by reference in its entirety. As used herein, an "extended-PK IL-2" refers to an IL-2 moiety in combination with an extended-PK group. In one embodiment, the extended-PK IL-2 is a fusion protein in which an IL-2 moiety is linked or fused to an extended-PK group. An exemplary fusion protein is an HSA/IL-2 fusion in which one or more IL-2 moieties are linked to HSA.

The term "extended-PK IL-2" is also intended to encompass IL-2 mutants with mutations in one or more amino acid residues that enhance the affinity of IL-2 for one or more of its receptors, for example, CD25. In one embodiment, the IL-2 moiety of extended-PK IL-2 is wild-type IL-2. In another embodiment, the IL-2 moiety is a mutant IL-2 which exhibits greater affinity for CD25 than wild-type IL-2. When a particular type of extended-PK group is indicated, such as HSA-IL-2, it should be understood that this encompasses both HSA or MSA fused to a wild-type IL-2 moiety or HSA or MSA fused to a mutant IL-2 moiety.

In certain aspects, the extended-PK IL-2 or knottin-Fc described can employ one or more "linker domains," such as polypeptide linkers. As used herein, the term "linker" or "linker domain" refers to a sequence which connects two or more domains (e.g., the PK moiety and IL-2) in a linear sequence. As used herein, the term "polypeptide linker" refers to a peptide or polypeptide sequence (e.g., a synthetic peptide or polypeptide sequence) which connects two or more domains in a linear amino acid sequence of a polypeptide chain. For example, polypeptide linkers may be used to connect an IL-2 moiety or an integrin-binding polypeptide to an Fc domain or other PK-extender such as HSA. In some embodiments, such polypeptide linkers can provide flexibility to the polypeptide molecule. Exemplary linkers include Gly-Ser linkers, such as but not limited to [Gly4Ser], comprising 4 glycines followed by 1 serine and [Gly4Ser3], comprising 4 glycines followed by 3 serines.

As used herein, the terms "linked," "fused", or "fusion" are used interchangeably. These terms refer to the joining together of two or more elements or components or domains, by whatever means including chemical conjugation or recombinant means. Methods of chemical conjugation (e.g., using heterobifunctional crosslinking agents) are known in the art.

The term "integrin" means a transmembrane heterodimeric protein important for cell adhesion. Integrins comprise an α and β subunit. These proteins bind to extracellular matrix components (e.g., fibronectin, collagen, laminin, etc.) and respond by inducing signaling cascades. Integrins bind to extracellular matrix components by recognition of an Arg-Gly-Asp (RGD) motif. Certain integrins are found on the surface of tumor cells and therefore make promising therapeutic targets. In certain embodiments, the integrins being targeted are $\alpha_v\beta_3$, $\alpha_v\beta_5$, and $\alpha_5\beta_1$, individually or in combination.

The term "integrin-binding polypeptide" refers to a polypeptide which includes an integrin-binding domain or loop within a knottin polypeptide scaffold. The integrin binding domain or loop includes at least one RGD peptide. In certain embodiments, the RGD peptide is recognized by $\alpha_v\beta_1$, $\alpha_v\beta_3$, $\alpha_v\beta_5$, $\alpha_v\beta_6$, and $\alpha_5\beta_1$ integrins. In certain embodiments the RGD peptide binds to a combination of $\alpha_v\beta_1$, $\alpha_v\beta_3$, $\alpha_v\beta_5$, $\alpha_v\beta_6$, and $\alpha_5\beta_1$ integrins. These specific integrins are found on tumor cells and their vasculature and are therefore the targets of interest.

Integrins are a family of extracellular matrix adhesion proteins that noncovalently associate into α and β heterodimers with distinct cellular and adhesive specificities (Hynes, 1992; Luscinskas and Lawler, 1994). Cell adhesion, mediated though integrin-protein interactions, is responsible for cell motility, survival, and differentiation. Each α and β subunit of the integrin receptor contributes to ligand binding and specificity.

Protein binding to many different cell surface integrins can be mediated through the short peptide motif Arg-Gly-Asp (RGD) (Pierschbacher and Ruoslahti, 1984). These peptides have dual functions: They promote cell adhesion when immobilized onto a surface, and they inhibit cell adhesion when presented to cells in solution. Adhesion proteins that contain the RGD sequence include: fibronectin, vitronectin, osteopontin, fibrinogen, von Willebrand factor, thrombospondin, laminin, entactin, tenascin, and bone sialoprotein (Ruoslahti, 1996). The RGD sequence displays specificity to about half of the 20 known integrins including the $\alpha_5\beta_1$, $\alpha_v\beta_1$, $\alpha_v\beta_1$, $\alpha_v\beta_3$, $\alpha_v\beta_5$, $\alpha_v\beta_6$, $\alpha_v\beta_8$, and $\alpha_v\beta_3$ integrins, and, to a lesser extent, the $\alpha_2\beta_1$, $\alpha_3\beta_1$, $\alpha_4\beta_1$, and $\alpha_7\beta_1$ integrins (Ruoslahti, 1996). In particular, the $\alpha_v\beta_3$ integrin is capable of binding to a large variety of RGD containing proteins including fibronectin, fibrinogen, vitronectin, osteopontin, von Willebrand factor, and thrombospondin (Ruoslahti, 1996; Haubner et al., 1997), while the $\alpha_5\beta_1$ integrin is more specific and has only been shown to bind to fibronectin (D'Souza et al., 1991).

The linear peptide sequence RGD has a much lower affinity for integrins than the proteins from which it is derived (Hautanen et al., 1989). This due to conformational specificity afforded by folded protein domains not present in linear peptides. Increased functional integrin activity has resulted from preparation of cyclic RGD motifs, alteration of the residues flanking the RGD sequence, and synthesis of small molecule mimetics (reviewed in (Ruoslahti, 1996; Haubner et al., 1997)).

The term "loop domain" refers to an amino acid subsequence within a peptide chain that has no ordered secondary structure, and resides generally on the surface of the peptide. The term "loop" is understood in the art as referring to secondary structures that are not ordered as in the form of an alpha helix, beta sheet, etc.

The term "integrin-binding loop" refers to a primary sequence of about 9-13 amino acids which is typically created ab initio through experimental methods such as directed molecular evolution to bind to integrins. In certain embodiments, the integrin-binding loop includes an RGD peptide sequence, or the like, placed between amino acids which are particular to the scaffold and the binding specificity desired. The RGD-containing peptide or similar peptide (such as RYD, etc.) is generally not simply taken from a natural binding sequence of a known protein. The integrin-binding loop is preferably inserted within a knottin polypeptide scaffold between cysteine residues, and the length of the loop adjusted for optimal integrin-binding depending on the three-dimensional spacing between cysteine residues. For example, if the flanking cysteine residues in the knottin scaffold are linked to each other, the optimal loop may be shorter than if the flanking cysteine residues are linked to cysteine residues separated in primary sequence. Otherwise, particular amino acid substitutions can be introduced to constrain a longer RGD-containing loop into an optimal conformation for high affinity integrin binding. The knottin polypeptide scaffolds used herein may contain certain modifications made to truncate the native knottin, or to remove a loop or unnecessary cysteine residue or disulfide bond.

Incorporation of integrin-binding sequences into a molecular (e.g., knottin polypeptide) scaffold provides a framework for ligand presentation that is more rigid and stable than linear or cyclic peptide loops. In addition, the conformational flexibility of small peptides in solution is high, and results in large entropic penalties upon binding. Such constructs have also been described in detail in International Patent Publication WO 2016/025642, incorporated herein by reference in its entirety.

Incorporation of an integrin-binding sequence into a knottin polypeptide scaffold provides conformational constraints that are required for high affinity integrin binding. Furthermore, the scaffold provides a platform to carry out protein engineering studies such as affinity or stability maturation.

As used herein, the term "knottin protein" refers to a structural family of small proteins, typically 25-40 amino acids, which bind to a range of molecular targets like proteins, sugars and lipids. Their three-dimensional structure is essentially defined by a peculiar arrangement of three to five disulfide bonds. A characteristic knotted topology with one disulfide bridge crossing the macro-cycle limited by the two other intra-chain disulfide bonds, which was found in several different microproteins with the same cystine network, lent its name to this class of biomolecules. Although their secondary structure content is generally low, the knottins share a small triple-stranded antiparallel β-sheet, which is stabilized by the disulfide bond framework. Biochemically well-defined members of the knottin family, also called cystine knot proteins, include the trypsin inhibitor EETI-II from *Ecballium elaterium* seeds, the neuronal N-type $Ca^{2+}$ channel blocker co-conotoxin from the venom of the predatory cone snail *Conus geographus*, agouti-related protein (AgRP, See Millhauser et al., "Loops and Links: Structural Insights into the Remarkable Function of the Agouti-Related Protein," Ann. N.Y. Acad. ScL, Jun. 1, 2003; 994(1): 27-35), the omega agatoxin family, etc. A suitable agatoxin sequence [SEQ ID NO: 41] is given in U.S. Pat. No. 8,536,301, having a common inventor with the present application. Other agatoxin sequences suitable for use in the methods disclosed herein include, but are not limited to Omega-agatoxin-Aa4b (GenBank Accession number P37045) and Omega-agatoxin-Aa3b (GenBank Accession number P81744). Other knottin sequences suitable for use in the methods disclosed herein include, knottin [*Bemisia tabaci*] (GenBank Accession number FJ601218.1), Omega-lycotoxin (Genbank Accession number P85079), mu-O conotoxin MrVIA=voltage-gated sodium channel blocker (Genbank Accession number AAB34917) and *Momordica cochinchinensis* Trypsin Inhibitor I (MCoTI-I) or II (MCoTI-II) (Uniprot Accession numbers P82408 and P82409, respectively).

Knottin proteins have a characteristic disulfide linked structure. This structure is also illustrated in Gelly et al., "The KNOTTIN website and database: a new information system dedicated to the knottin scaffold," Nucleic Acids Research, 2004, Vol. 32, Database issue D156-D159. A triple-stranded β-sheet is present in many knottins. The spacing between cysteine residues is important, as is the molecular topology and conformation of the integrin-binding loop.

The term "molecular scaffold" means a polymer having a predefined three-dimensional structure, into which an integrin-binding loop is incorporated, such as an RGD peptide sequence as described herein. The term "molecular scaffold" has an art-recognized meaning (in other contexts), which is also intended here. For example, a review by Skerra, "Engineered protein scaffolds for molecular recognition," J. Mol. Recognit. 2000; 13: 167-187 describes the following scaffolds: single domains of antibodies of the immunoglobulin superfamily, protease inhibitors, helix-bundle proteins, disulfide-knotted peptides and lipocalins. Guidance is given for the selection of an appropriate molecular scaffold.

The term "knottin polypeptide scaffold" refers to a knottin protein suitable for use as a molecular scaffold, as described herein. Characteristics of a desirable knottin polypeptide scaffold for engineering include 1) high stability in vitro and in vivo, 2) the ability to replace amino acid regions of the scaffold with other sequences without disrupting the overall fold, 3) the ability to create multifunctional or bispecific targeting by engineering separate regions of the molecule, and 4) a small size to allow for chemical synthesis and incorporation of non-natural amino acids if desired. Scaffolds derived from human proteins are favored for therapeutic applications to reduce toxicity or immunogenicity concerns, but are not always a strict requirement. Other scaffolds that have been used for protein design include fibronectin (Koide et al., 1998), lipocalin (Beste et al., 1999), cytotoxic T lymphocyte-associated antigen 4 (CTLA-4) (Hufton et al, 2000), and tendamistat (McConnell and Hoess, 1995; Li et al, 2003). While these scaffolds have proved to be useful frameworks for protein engineering, molecular scaffolds such as knottins have distinct advantages: their small size and high stability.

As used herein, the term "NOD201" refers to an integrin-binding polypeptide-Fc fusion comprising the following sequence: GCPRPRGDNPPLTCSQDSDCLAGCVCG-PNGFCG (SEQ ID NO:130; 2.5F peptide) and having no linker between the 2.5F peptide and the Fc domain. In some embodiments, the Fc domain is from IgG1, IgG2, IgG3, or IgG4 and can be mouse or human derived.

As used herein, the term "NOD201modK" refers to an integrin-binding polypeptide-Fc fusion comprising the following sequence: GCPRPRGDNPPLTCKQDSD-CLAGCVCGPNGFCG (SEQ ID NO:131; 2.5FmodK peptide) and having no linker between the 2.5FmodK peptide and the Fc domain. In some embodiments, the Fc domain is from IgG1, IgG2, IgG3, or IgG4 and can be mouse or human derived.

As used herein, the term "NOD203" refers to an integrin-binding polypeptide-Fc fusion comprising the following sequence: GCPRPRGDNPPLTCSQDSDCLAGCVCG-PNGFCGGGGGS (SEQ ID NO:132; 2.5F peptide) and having a Gly$_4$Ser linker between the 2.5F peptide and the Fc domain. In some embodiments, the Fc domain is from IgG1, IgG2, IgG3, or IgG4 and can be mouse or human derived.

As used herein, the term "NOD203modK" refers to an integrin-binding polypeptide-Fc fusion comprising the following sequence: GCPRPRGDNPPLTCKQDSDCLAGCVCGPNGFCGGGGGS (SEQ ID NO:133; 2.5FmodK peptide) and having a Gly$_4$Ser linker between the 2.5FmodK peptide and the Fc domain. In some embodiments, the Fc domain is from IgG1, IgG2, IgG3, or IgG4 and can be mouse or human derived.

As used herein, the term "NOD204" refers to an integrin-binding polypeptide-FC fusion comprising the following sequence: GCPRPRGDNPPLTCSQDSDCLAGCVCGPNGFCGGGGGSGGGGSGGGGS (SEQ ID NO:134; 2.5F peptide) and having a Gly$_4$Ser$_3$ linker between the 2.5F peptide and the Fc domain. In some embodiments, the Fc domain is from IgG1, IgG2, IgG3, or IgG4 and can be mouse or human derived.

As used herein, the term "NOD204modK" refers to an integrin-binding polypeptide-FC fusion comprising the following sequence: CPRPRGDNPPLTCKQDSDCLAGCVCGPNGFCGGGGGSGGGGSGGGGS (SEQ ID NO:135; 2.5FmodK peptide) and having a Gly$_4$Ser$_3$ linker between the 2.5FmodK peptide and the Fc domain. In some embodiments, the Fc domain is from IgG1, IgG2, IgG3, or IgG4 and can be mouse or human derived.

As used herein, the term "AgRP" means PDB entry 1HYK. Its entry in the Knottin database is SwissProt AGRP_HUMAN, where the full-length sequence of 129 amino acids may be found. It comprises the sequence beginning at amino acid 87. An additional G is added to this construct. It also includes a CI 05 A mutation described in Jackson, et al. 2002 Biochemistry, 41, 7565, as well as International Patent Publication WO 2016/025642, incorporated by reference in its entirety; bold and underlined portion, from loop 4, is replaced by the RGD sequences described herein. Loops 1 and 3 are shown between brackets.

As used herein, "integrin-binding polypeptide-Fc fusion" is used interchangeably with "knottin-Fc" and refers to an integrin-binding polypeptide that includes an integrin-binding amino acid sequence within a knottin polypeptide scaffold and is operably linked to an Fc domain. In some embodiments, the Fc domain is fused to the N-terminus of the integrin-binding polypeptide. In some embodiments, the Fc domain is fused to the C-terminus of the integrin-binding polypeptide. In some embodiments, the Fc domain is operably linked to the integrin-binding polypeptide via a linker.

As used herein, the term "Fc region" refers to the portion of a native immunoglobulin formed by the respective Fc domains (or Fc moieties) of its two heavy chains. As used herein, the term "Fc domain" refers to a portion of a single immunoglobulin (Ig) heavy chain wherein the Fc domain does not comprise an Fv domain. As such, an Fc domain can also be referred to as "Ig" or "IgG." In certain embodiments, an Fc domain begins in the hinge region just upstream of the papain cleavage site and ends at the C-terminus of the antibody. Accordingly, a complete Fc domain comprises at least a hinge domain, a CH$_2$ domain, and a CH$_3$ domain. In certain embodiments, an Fc domain comprises at least one of: a hinge (e.g., upper, middle, and/or lower hinge region) domain, a CH$_2$ domain, a CH$_3$ domain, a CH$_4$ domain, or a variant, portion, or fragment thereof. In other embodiments, an Fc domain comprises a complete Fc domain (i.e., a hinge domain, a CH$_2$ domain, and a CH$_3$ domain). In one embodiment, an Fc domain comprises a hinge domain (or portion thereof) fused to a CH$_3$ domain (or portion thereof). In another embodiment, an Fc domain comprises a CH$_2$ domain (or portion thereof) fused to a CH$_3$ domain (or portion thereof). In another embodiment, an Fc domain consists of a CH$_3$ domain or portion thereof. In another embodiment, an Fc domain consists of a hinge domain (or portion thereof) and a CH$_3$ domain (or portion thereof). In another embodiment, an Fc domain consists of a CH$_2$ domain (or portion thereof) and a CH$_3$ domain. In another embodiment, an Fc domain consists of a hinge domain (or portion thereof) and a CH$_2$ domain (or portion thereof). In one embodiment, an Fc domain lacks at least a portion of a CH$_2$ domain (e.g., all or part of a CH$_2$ domain). An Fc domain herein generally refers to a polypeptide comprising all or part of the Fc domain of an immunoglobulin heavy-chain. This includes, but is not limited to, polypeptides comprising the entire CH$_1$, hinge, CH$_2$, and/or CH$_3$ domains as well as fragments of such peptides comprising only, e.g., the hinge, CH$_2$, and CH$_3$ domain. The Fc domain may be derived from an immunoglobulin of any species and/or any subtype, including, but not limited to, a human IgG1, IgG2, IgG3, IgG4, IgD, IgA, IgE, or IgM antibody. A human IgG1 constant region can be found at Uniprot P01857 and in FIG. 1. The Fc domain of human IgG1 with a deletion of the upper hinge region can be found in Table 2, SEQ ID NO: 3 from International Patent Publication No. WO 2016/025642. The Fc domain encompasses native Fc and Fc variant molecules. As with Fc variants and native Fc's, the term Fc domain includes molecules in monomeric or multimeric (e.g., dimeric) form, whether digested from whole antibody or produced by other means. The assignment of amino acid residue numbers to an Fc domain is in accordance with the definitions of Kabat. See, e.g., Sequences of Proteins of Immunological Interest (Table of Contents, Introduction and Constant Region Sequences sections), 5$^{th}$ edition, Bethesda, Md.:NIH vol. 1:647-723 (1991); Kabat et al., "Introduction" Sequences of Proteins of Immunological Interest, US Dept of Health and Human Services, NIH, 5$^{th}$ edition, Bethesda, Md. vol. 1:xiii-xcvi (1991); Chothia & Lesk, J. Mol. Biol. 196:901-917 (1987); Chothia et al, Nature 342:878-883 (1989), each of which is herein incorporated by reference for all purposes. With regard to the integrin-binding polypeptide-Fc fusions described herein, any Fc domain from any IgG as described herein or known can be employed as part of the Fc fusion, including mouse, human and variants thereof, such as hinge deleted (EPKSC deleted; see, SEQ ID NO: 3 from International Patent Publication No. WO 2016/025642).

As set forth herein, it will be understood by one of ordinary skill in the art that any Fc domain may be modified such that it varies in amino acid sequence from the native Fc domain of a naturally occurring immunoglobulin molecule. In certain exemplary embodiments, the Fc domain has increased effector function (e.g., FcγR binding).

The Fc domains of a polypeptide of the invention may be derived from different immunoglobulin molecules. For example, an Fc domain of a polypeptide may comprise a CH$_2$ and/or CH$_3$ domain derived from an IgG1 molecule and a hinge region derived from an IgG3 molecule. In another example, an Fc domain can comprise a chimeric hinge region derived, in part, from an IgG1 molecule and, in part, from an IgG3 molecule. In another example, an Fc domain can comprise a chimeric hinge derived, in part, from an IgG1 molecule and, in part, from an IgG4 molecule.

A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence. Polypeptides derived from another peptide may have one or more mutations relative to the starting polypeptide, e.g., one or more amino acid residues which have been substituted with another amino acid residue or which has one or more amino acid residue insertions or deletions.

A polypeptide can comprise an amino acid sequence which is not naturally occurring. Such variants, in the context of IL-2 or a knottin protein, necessarily have less than 100% sequence identity or similarity with the starting IL-2 or knottin protein. In some embodiments, the variant will have an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and in some embodiments from about 95% to less than 100%, e.g., over the length of the variant molecule.

In one embodiment, there is one amino acid difference between a starting polypeptide sequence and the sequence derived therefrom. Identity or similarity with respect to this sequence is defined herein as the percentage of amino acid residues in the candidate sequence that are identical (i.e., same residue) with the starting amino acid residues, after aligning the sequences and introducing gaps, if necessary, to achieve the maximum percent sequence identity.

In one embodiment, a polypeptide comprising IL-2 or a variant thereof, for use in extended-PK IL-2 consists of, consists essentially of, or comprises an amino acid sequence selected from SEQ ID Nos: 5, 7, 9, 11, 13, 15, 17, 19, 21, 23, 25, 27, 29, 31, 33, and 35 from International Patent Publication No. WO 2016/025642 (copied below). In an embodiment, a polypeptide includes an amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence selected from SEQ ID NOs: 5, 7, 9, 11, 13, 15, 17, 19, 21, 23, 25, 27, 29, 31, 33, and 35 from International Patent Publication No. WO 2016/025642 (copied below). In an embodiment, a polypeptide includes a contiguous amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous amino acid sequence selected from SEQ ID Nos: 5, 7, 9, 11, 13, 15, 17, 19, 21, 23, 25, 27, 29, 31, 33, and 35 from International Patent Publication No. WO 2016/025642 (copied below). In an embodiment, a polypeptide includes an amino acid sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous amino acids of an amino acid sequence selected from SEQ ID Nos: 5, 7, 9, 11, 13, 15, 17, 19, 21, 23, 25, 27, 29, 31, 33, and 35 from International Patent Publication No. WO 2016/025642 (copied below).

In an embodiment, the peptides are encoded by a nucleotide sequence. Nucleotide sequences can be useful for a number of applications, including: cloning, gene therapy, protein expression and purification, mutation introduction, DNA vaccination of a host in need thereof, antibody generation for, e.g., passive immunization, PCR, primer and probe generation, and the like. In an embodiment, the nucleotide sequence of the invention comprises, consists of, or consists essentially of, a nucleotide sequence of IL-2, or a variant thereof, selected from SEQ ID Nos: 4, 6, 8, 10, 12, 14, 16, 18, 20, 22, 24, 26, 28, 30, 32, and 34 from International Patent Publication No. WO 2016/025642 (copied below). In an embodiment, a nucleotide sequence includes a nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence set forth in SEQ ID Nos: 4, 6, 8, 10, 12, 14, 16, 18, 20, 22, 24, 26, 28, 30, 32, and 34 from International Patent Publication No. WO 2016/025642 (copied below). In an embodiment, a nucleotide sequence includes a contiguous nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous nucleotide sequence set forth in SEQ ID Nos: 4, 6, 8, 10, 12, 14, 16, 18, 20, 22, 24, 26, 28, 30, 32, and 34 from International Patent Publication No. WO 2016/025642 (copied below). In an embodiment, a nucleotide sequence includes a nucleotide sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous nucleotides of a nucleotide sequence set forth in SEQ ID Nos: 4, 6, 8, 10, 12, 14, 16, 18, 20, 22, 24, 26, 28, 30, 32, and 34 from International Patent Publication No. WO 2016/025642 (copied below).

TABLE 1

Sequence Summary

| SEQ ID NO | Description | Sequence |
|---|---|---|
| 1 | Human IgG1 constant region (amino acid sequence) | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELL GGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDGSFFLYSKLTV DKSRWQQGNVFSCSVMHEALHNHYTQKSLSLSPGK |
| 2 | Human IgG1 Fc domain (amino acid sequence) | EPKSCDKTHTCPPCPAPELLGGPSVFLFPPKPKDTLMISRTPEVTCVVVDVSHEDPEVK FNWYVDGVEVHNAKTKPREEQYNSTYRVVSVLTVLHQDWLNGKEYKCKVSNKALPAPIE KTISKAKGQPREPQVYTLPPSRDELTKNQVSLTCLVKGFYPSDIAVEWESNGQPENNYK TTPPVLDSDGSFFLYSKLTVDKSRWQQGNVFSCSVMHEALHNHYTQKSLSLSPGK |
| 3 | Human IgG1 Fc domain | DKTHTCPPCPAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKALPAPIEKTISK AKGQPREPQVYTLPPSRDELTKNQVSLTCLVKGFYPSDIAVEWESNGQPENNYKTTPPV |

TABLE 1-continued

Sequence Summary

| SEQ ID NO | Description | Sequence |
|---|---|---|
| | (amino acid sequence) Deletion (ΔEPKSC) Upper Hinge | LDSDGSFFLYSKLTVDKSRWQQGNVFSCSVMHEALHNHYTQKSLSLSPGK |
| 4 | Mouse IL-2 (nucleic acid sequence) | GCACCCACTTCAAGCTCCACTTCAAGCTCTACAGCGGAAGCACAGCAGCAGCAGCA GCAGCAGCAGCAGCAGCAGCACCTGGAGCAGCTGTTGATGGACCTACAGGAGCTCCTGA GCAGGATGGAGAATTACAGGAACCTGAAACTCCCCAGGATGCTCACCTTCAAATTTTAC TTGCCCAAGCAGGCCACAGAATTGAAAGATCTTCAGTGCCTAGAAGATGAACTTGGACC TCTGCGGCATGTTCTGGATTTGACTCAAAGCAAAAGCTTTCAATTGGAAGATGCTGAGA ATTTCATCAGCAATATCAGAGTAACTGTTGTAAAACTAAAGGGCTCTGACAACACATTT GAGTGCCAATTCGATGATGAGTCAGCAACTGTGGTGGACTTTCTGAGGAGATGGATAGC CTTCTGTCAAAGCATCATCTCAACAAGCCCTCAA |
| 5 | Mouse IL-2 (amino acid sequence | APTSSSTSSSTAEAQQQQQQQQQQQQHLEQLLMDLQELLSRMENYRNLKLPRMLTFKFY LPKQATELKDLQCLEDELGPLRHVLDLTQSKSFQLEDAENFISNIRVTVVKLKGSDNTF ECQFDDESATVVDFLRRWIAFCQSIISTSPQ |
| 6 | QQ6210 (nucleic acid sequence) | GCACCCACTTCAAGCTCCACTTCAAGCTCTACAGCGGAAGCACAACAGCAGCAGCAGCA GCAGCAGCAGCAGCAGCACCTGGAGCAGCTGTTGATGGACCTACAGGAACTCCTGA GTAGGATGGAGGATCACAGGAACCTCGAGACTCCCCAGGATGCTCACCTTCAAATTTTAC TTGCCCGAGCAGGCCACAGAATTGGAAGATCTTCAGTGCCTAGAAGATGAACTTGAACC ACTGCGGCAAGTTCTGGATTTGACTCAAAGCAAAAGCTTTCAATTGGAAGATGCTGAGA ATTTCATCAGCAATATCAGAGTAACTGTTGTAAAACTAAAGGGCTCTGACAACACATTT GAGTGCCAATTCGACGATGAGCCAGCAACTGTGGTGGACTTTCTGAGGAGATGGATAGC CTTCTGTCAAAGCATCATCTCAACAAGCCCTCAA |
| 7 | QQ6210 (amino acid sequence) | APTSSSTSSSTAEAQQQQQQQQQQQQHLEQLLMDLQELLSRMEDHRNLRLPRMLTFKFY LPEQATELEDLQCLEDELEPLRQVLDLTQSKSFQLEDAENFISNIRVTVVKLKGSDNTF ECQFDDEPATVVDFLRRWIAFCQSIISTSPQ |
| 8 | E76A (nucleic acid sequence) | GCACCCACTTCAAGCTCCACTTCAAGCTCTACAGCGGAAGCACAGCAGCAGCAGCAGCA GCAGCAGCAGCAGCAGCACCTGGAGCAGCTGTTGATGGACCTACAGGAGCTCCTGA GCAGGATGGAGAATTACAGGAACCTGAAACTCCCCAGGATGCTCACCTTCAAATTTTAC TTGCCCAAGCAGGCCACAGAATTGAAAGATCTTCAGTGCCTAGAAGATGCTCTTGGACC TCTGCGGCATGTTCTGGATTTGACTCAAAGCAAAAGCTTTCAATTGGAAGATGCTGAGA ATTTCATCAGCAATATCAGAGTAACTGTTGTAAAACTAAAGGGCTCTGACAACACATTT GAGTGCCAATTCGATGATGAGTCAGCAACTGTGGTGGACTTTCTGAGGAGATGGATAGC CTTCTGTCAAAGCATCATCTCAACAAGCCCTCAA |
| 9 | E76A (amino acid sequence) | APTSSSTSSSTAEAQQQQQQQQQQQQHLEQLLMDLQELLSRMENYRNLKLPRMLTFKFY LPKQATELKDLQCLEDALGPLRHVLDLTQSKSFQLEDAENFISNIRVTVVKLKGSDNTF ECQFDDESATVVDFLRRWIAFCQSIISTSPQ |
| 10 | E76G (nucleic acid sequence) | GCACCCACTTCAAGCTCCACTTCAAGCTCTACAGCGGAAGCACAGCAGCAGCAGCAGCA GCAGCAGCAGCAGCAGCACCTGGAGCAGCTGTTGATGGACCTACAGGAGCTCCTGA GCAGGATGGAGAATTACAGGAACCTGAAACTCCCCAGGATGCTCACCTTCAAATTTTAC TTGCCCAAGCAGGCCACAGAATTGAAAGATCTTCAGTGCCTAGAAGATGGTCTTGGACC TCTGCGGCATGTTCTGGATTTGACTCAAAGCAAAAGCTTTCAATTGGAAGATGCTGAGA ATTTCATCAGCAATATCAGAGTAACTGTTGTAAAACTAAAGGGCTCTGACAACACATTT GAGTGCCAATTCGATGATGAGTCAGCAACTGTGGTGGACTTTCTGAGGAGATGGATAGC CTTCTGTCAAAGCATCATCTCAACAAGCCCTCAA |
| 11 | E76G (amino acid sequence) | APTSSSTSSSTAEAQQQQQQQQQQQQHLEQLLMDLQELLSRMENYRNLKLPRMLTFKFY LPKQATELKDLQCLEDGLGPLRHVLDLTQSKSFQLEDAENFISNIRVTVVKLKGSDNTF ECQFDDESATVVDFLRRWIAFCQSIISTSPQ |
| 12 | D265A Fc/Flag (nucleic acid sequence) (C-terminal flag tag is underlined) | ATGAGGGTCCCCGCTCAGCTCCTGGGGCTCCTGCTGCTCTGGCTCCCAGGTGCACGATG TGAGCCCAGAGTGCCCATAACACAGAACCCCTGTCCTCCACTCAAAGAGTGTCCCCCAT GCGCAGCTCCAGACCTCTTGGGTGGACCATCCGTCTTCATCTTCCCTCCAAAGATCAAG GATGTACTCATGATCTCCCTGAGCCCCATGGTCACATGTGTGGTGGTGGCCGTGAGCGA GGATGACCCAGACGTCCAGATCAGCTGGTTTGTGAACAACGTGGAAGTACACACAGCTC AGACACAAACCCATAGAGAGGATTACAACAGTACTCTCCGGGTGGTCAGTGCCCTCCCC ATCCAGCACCAGGACTGGATGAGTGGCAAGGAGTTCAAATGCAAGGTCAACAACAGAGC CCTCCCATCCCCCATCGAGAAAACCATCTCAAAACCCAGAGGGCCAGTAAGAGCTCCAC AGGTATATGTCTTGCCTCCACCAGCAGAAGAGATGACTAAGAAAGAGTTCAGTCTGACC TGCATGATCACAGGCTTCTTACCTGCCGAAATTGCTGTGGACTGGACCAGCAATGGGCG TACAGAGCAAAACTACAAGAACACCGCAACAGTCCTGGACTCTGATGGTTCTTACTTCA TGTACAGCAAGCTCAGAGTACAAAAGAGCACTTGGGAAAGAGGAAGTCTTTTCGCCTGC TCAGTGGTCCACGAGGGTCTGCACAATCACCTTACGACTAAGACCATCTCCCGGTCTCT GGGTAAAGGTGGCGGATCT<u>GACTACAAGGACGACGATGACAAG</u>TGATAA |

TABLE 1-continued

Sequence Summary

| SEQ ID NO | Description | Sequence |
|---|---|---|
| 13 | D265A Fc/Flag (amino acid sequence) (C-terminal flag tag is underlined) | MRVPAQLLGLLLLWLPGARCEPRVPITQNPCPPLKECPPCAAPDLLGGPSVFIFPPKIK DVLMISLSPMVTCVVVAVSEDDPDVQISWFVNNVEVHTAQTQTHREDYNSTLRVVSALP IQHQDWMSGKEFKCKVNNRALPSPIEKTISKPRGPVRAPQVYVLPPPAEEMTKKEFSLT CMITGFLPAEIAVDWTSNGRTEQNYKNTATVLDSDGSYFMYSKLRVQKSTWERGSLFAC SVVHEGLHNHLTTKTISRSLGKGGGS<u>DYKDDDDK</u> |
| 14 | D265A Fc/wt mIL-2 (nucleic acid sequence) (C-terminal 6X his tag is underlined) | ATGAGGGTCCCCGCTCAGCTCCTGGGGCTCCTGCTGCTCTGGCTCCCAGGTGCACGATG TGAGCCCAGAGTGCCCATAACACAGAACCCCTGTCCTCCACTCAAAGAGTGTCCCCCAT GCGCAGCTCCAGACCTCTTGGGTGGACCATCCGTCTTCATCTTCCCTCCAAAGATCAAG GATGTACTCATGATCTCCCTGAGCCCCATGGTCACATGTGTGGTGGTGGCCGTGAGCGA GGATGACCCAGACGTCCAGATCAGCTGGTTTGTGAACAACGTGGAAGTACACACAGCTC AGACACAAACCCATAGAGAGGATTACAACAGTACTCTCCGGGTGGTCAGTGCCCTCCCC ATCCAGCACCAGGACTGGATGAGTGGCAAGGAGTTCAAATGCAAGGTCAACAACAGAGC CCTCCCATCCCCCATCGAGAAAACCATCTCAAAACCCAGAGGGCCAGTAAGAGCTCCAC AGGTATATGTCTTGCCTCCACCAGCAGAAGAGATGACTAAGAAAGAGTTCAGTCTGACC TGCATGATCACAGGCTTCTTACCTGCCGAAATTGCTGTGGACTGGACCAGCAATGGGCG TACAGAGCAAAACTACAAGAACACCGCAACAGTCCTGGACTCTGATGGTTCTTACTTCA TGTACAGCAAGCTCAGAGTACAAAAGAGCACTTGGGAAAGAGGAAGTCTTTTCGCCTGC TCAGTGGTCCACGAGGGTCTGCACAATCACCTTACGACTAAGACCATCTCCCGGTCTCT GGGTAAAGGAGGGGGCTCCGCACCCACTTAAGCTCCACTTAAGCTCTACAGCGGAAG CACAGCAGCAGCAGCAGCAGCAGCAGCAGCAGCACCTGGAGCAGCTGTTGATG GACCTACAGGAGCTCCTGAGCAGGATGGAGAATTACAGGAACCTGAAACTCCCCAGGAT GCTCACCTTCAAATTTTACTTGCCCAAGCAGGCCACAGAATTGAAAGATCTTCAGTGCC TAGAAGATGAACTTGGACCTCTGCGGCATGTTCTGGATTTGACTCAAAGCAAAAGCTTT CAATTGGAAGATGCTGAGAATTTCATCAGCAATATCGAGTAACTGTTGTAAAACTAAA GGGCTCTGACAACACATTTGAGTGCCAATTCGATGATGAGTCAGCAACTGTGGTGGACT TTCTGAGGAGATGGATAGCCTTCTGTCAAAGCATCATCTCAACAAGCCCTCAA<u>CACCAT CACCACCATCAC</u>TGATAA |
| 15 | D265A Fc/wt mIL-2 (amino acid sequence) (C-terminal 6x his tag is underlined) | MRVPAQLLGLLLLWLPGARCEPRVPITQNPCPPLKECPPCAAPDLLGGPSVFIFPPKIK DVLMISLSPMVTCVVVAVSEDDPDVQISWFVNNVEVHTAQTQTHREDYNSTLRVVSALP IQHQDWMSGKEFKCKVNNRALPSPIEKTISKPRGPVRAPQVYVLPPPAEEMTKKEFSLT CMITGFLPAEIAVDWTSNGRTEQNYKNTATVLDSDGSYFMYSKLRVQKSTWERGSLFAC SVVHEGLHNHLTTKTISRSLGKGGGSAPTSSSTSSSTAEAQQQQQQQQQQQQHLEQLLM DLQELLSRMENYRNLKLPRMLTFKFYLPKQATELKDLQCLEDELGPLRHVLDLTQSKSF QLEDAENFISNIRVTVVKLKGSDNTFECQFDDESATVVDFLRRWIAFCQSIISTSPQ<u>HH HHHH</u>** |
| 16 | D265A Fc/ QQ6210 (nucleic acid sequence) (C-terminal 6X his tag is underlined) | ATGAGGGTCCCCGCTCAGCTCCTGGGGCTCCTGCTGCTCTGGCTCCCAGGTGCACGATG TGAGCCCAGAGTGCCCATAACACAGAACCCCTGTCCTCCACTCAAAGAGTGTCCCCCAT GCGCAGCTCCAGACCTCTTGGGTGGACCATCCGTCTTCATCTTCCCTCCAAAGATCAAG GATGTACTCATGATCTCCCTGAGCCCCATGGTCACATGTGTGGTGGTGGCCGTGAGCGA GGATGACCCAGACGTCCAGATCAGCTGGTTTGTGAACAACGTGGAAGTACACACAGCTC AGACACAAACCCATAGAGAGGATTACAACAGTACTCTCCGGGTGGTCAGTGCCCTCCCC ATCCAGCACCAGGACTGGATGAGTGGCAAGGAGTTCAAATGCAAGGTCAACAACAGAGC CCTCCCATCCCCCATCGAGAAAACCATCTCAAAACCCAGAGGGCCAGTAAGAGCTCCAC AGGTATATGTCTTGCCTCCACCAGCAGAAGAGATGACTAAGAAAGAGTTCAGTCTGACC TGCATGATCACAGGCTTCTTACCTGCCGAAATTGCTGTGGACTGGACCAGCAATGGGCG TACAGAGCAAAACTACAAGAACACCGCAACAGTCCTGGACTCTGATGGTTCTTACTTCA TGTACAGCAAGCTCAGAGTACAAAAGAGCACTTGGGAAAGAGGAAGTCTTTTCGCCTGC TCAGTGGTCCACGAGGGTCTGCACAATCACCTTACGACTAAGACCATCTCCCGGTCTCT GGGTAAAGGAGGGGGCTCCGCACCCACTTAAGCTCCACTTAAGCTCTACAGCGGAAG CACAACAGCAGCAGCAGCAGCAGCAGCAGCAGCACCTGGAGCAGCTGTTGATG GACCTACAGGAACTCCTGAGTAGGATGGAGGATCACAGGAACCTGAGACTCCCCAGGAT GCTCACCTTCAAATTTTACTTGCCCGAGCAGGCCACAGAATTGGAAGATCTTCAGTGCC TAGAAGATGAACTTGAACCACTGCGGCAAGTTCTGGATTTGACTCAAAGCAAAAGCTTT CAATTGGAAGATGCTGAGAATTTCATCAGCAATATCAGAGTAACTGTTGTAAAACTAAA GGGCTCTGACAACACATTTGAGTGCCAATTCGACGATGAGCCAGCAACTGTGGTGGACT TTCTGAGGAGATGGATAGCCTTCTGTCAAAGCATCATCTCAACAAGCCCTCAA<u>CACCAT CACCACCATCAC</u>TGATAA |
| 17 | D265A Fc/ QQ6210 (amino acid sequence) (C-terminal 6x his tag is underlined) | MRVPAQLLGLLLLWLPGARCEPRVPITQNPCPPLKECPPCAAPDLLGGPSVFIFPPKIK DVLMISLSPMVTCVVVAVSEDDPDVQISWFVNNVEVHTAQTQTHREDYNSTLRVVSALP IQHQDWMSGKEFKCKVNNRALPSPIEKTISKPRGPVRAPQVYVLPPPAEEMTKKEFSLT CMITGFLPAEIAVDWTSNGRTEQNYKNTATVLDSDGSYFMYSKLRVQKSTWERGSLFAC SVVHEGLHNHLTTKTISRSLGKGGGSAPTSSSTSSSTAEAQQQQQQQQQQQQHLEQLLM DLQELLSRMEDHRNLRLPRMLTFKFYLPEQATELEDLQCLEDELEPLRQVLDLTQSKSF QLEDAENFISNIRVTVVKLKGSDNTFECQFDDEPATVVDFLRRWIAFCQSIISTSPQ<u>HH HHHH</u> |
| 18 | D265A Fc / E76A | ATGAGGGTCCCCGCTCAGCTCCTGGGGCTCCTGCTGCTCTGGCTCCCAGGTGCACGATG TGAGCCCAGAGTGCCCATAACACAGAACCCCTGTCCTCCACTCAAAGAGTGTCCCCCAT |

TABLE 1-continued

Sequence Summary

| SEQ ID NO | Description | Sequence |
|---|---|---|
| | (nucleic acid sequence) (C-terminal 6X his tag is underlined) | GCGCAGCTCCAGACCTCTTGGGTGGACCATCCGTCTTCATCTTCCCTCCAAAGATCAAG GATGTACTCATGATCTCCCTGAGCCCCATGGTCACATGTGTGGTGGTGGCCGTGAGCGA GGATGACCCAGACGTCCAGATCAGCTGGTTTGTGAACAACGTGGAAGTACACACAGCTC AGACACAAACCCATAGAGAGGATTACAACAGTACTCTCCGGGTGGTCAGTGCCCTCCCC ATCCAGCACCAGGACTGGATGAGTGGCAAGGAGTTCAAATGCAAGGTCAACAACAGAGC CCTCCCATCCCCCATCGAGAAAACCATCTCAAAACCCAGAGGGCCAGTAAGAGCTCCAC AGGTATATGTCTTGCCTCCACCAGCAGAAGAGATGACTAAGAAAGAGTTCAGTCTGACC TGCATGATCACAGGTTCTTACCTGCCGAAATTGCTGTGGACTGGACCAGCAATGGGCG TACAGAGCAAAACTACAAGAACACCGCAACAGTCCTGGACTCTGATGGTTCTTACTTCA TGTACAGCAAGCTCAGAGTACAAAAGAGCACTTGGGAAAGAGGAAGTCTTTTCGCCTGC TCAGTGGTCCACGAGGGTCTGCACAATCACCTTACGACTAAGACCATCTCCCGGTCTCT GGGTAAAGGAGGGGGCTCCGCACCCACTTCAAGCTCCACTTCAAGCTCTACAGCGGAAG CACAGCAGCAGCAGCAGCAGCAGCAGCAGCAGCAGCACCTGGAGCAGCTGTTGATG GACCTACAGGAGCTCCTGAGCAGGATGGAGAATTACAGGAACCTGAAACTCCCCAGGAT GCTCACCTTCAAATTTTACTTGCCCAAGCAGGCCACAGAATTGAAAGATCTTCAGTGCC TAGAAGATGCTCTTGGACCTCTGCGGCATGTTCTGGATTTGACTCAAAGCAAAAGCTTT CAATTGGAAGATGCTGAGAATTTCATCAGCAATATCAGAGTAACTGTTGTAAAACTAAA GGGCTCTGACAACACATTTGAGTGCCAATTCGATGATGAGTCAGCAACTGTGGTGGACT TTCTGAGGAGATGGATAGCCTTCTGTCAAAGCATCATCTCAACAAGCCCTCAA<u>CACCAT CACCACCATCACTGATAA</u> |
| 19 | D265A Fc / E76A (amino acid sequence) (C-terminal 6x his tag is underlined) | MRVPAQLLGLLLLWLPGARCEPRVPITQNPCPPLKECPPCAAPDLLGGPSVFIFPPKIK DVLMISLSPMVTCVVVAVSEDDPDVQISWFVNNVEVHTAQTQTHREDYNSTLRVVSALP IQHQDWMSGKEFKCKVNNRALPSPIEKTISKPRGPVRAPQVYVLPPPAEEMTKKEFSLT CMITGFLPAEIAVDWTSNGRTEQNYKNTATVLDSDGSYFMYSKLRVQKSTWERGSLFAC SVVHEGLHNHLTTKTISRSLGKGGGSAPTSSSTSSSTAEAQQQQQQQQQQQHLEQLLM DLQELLSRMENYRNLKLPRMLTFKFYLPKQATELKDLQCLEDALGPLRHVLDLTQSKSF QLEDAENFISNIRVTVVKLKGSDNTFECQFDDESATVVDFLRRWIAFCQSIISTSPQ<u>HH HHHH</u> |
| 20 | D265A Fc / E76G (nucleic acid sequence) (C-terminal 6X his tag is underlined) | ATGAGGGTCCCCGCTCAGCTCCTGGGGCTCCTGCTGCTCTGGCTCCCAGGTGCACGATG TGAGCCCAGAGTGCCCCATAACACAGAACCCCTGTCCTCCACTCAAAGAGTGTCCCCCAT GCGCAGCTCCAGACCTCTTGGGTGGACCATCCGTCTTCATCTTCCCTCCAAAGATCAAG GATGTACTCATGATCTCCCTGAGCCCCATGGTCACATGTGTGGTGGTGGCCGTGAGCGA GGATGACCCAGACGTCCAGATCAGCTGGTTTGTGAACAACGTGGAAGTACACACAGCTC AGACACAAACCCATAGAGAGGATTACAACAGTACTCTCCGGGTGGTCAGTGCCCTCCCC ATCCAGCACCAGGACTGGATGAGTGGCAAGGAGTTCAAATGCAAGGTCAACAACAGAGC CCTCCCATCCCCCATCGAGAAAACCATCTCAAAACCCAGAGGGCCAGTAAGAGCTCCAC AGGTATATGTCTTGCCTCCACCAGCAGAAGAGATGACTAAGAAAGAGTTCAGTCTGACC TGCATGATCACAGGTTCTTACCTGCCGAAATTGCTGTGGACTGGACCAGCAATGGGCG TACAGAGCAAAACTACAAGAACACCGCAACAGTCCTGGACTCTGATGGTTCTTACTTCA TGTACAGCAAGCTCAGAGTACAAAAGAGCACTTGGGAAAGAGGAAGTCTTTTCGCCTGC TCAGTGGTCCACGAGGGTCTGCACAATCACCTTACGACTAAGACCATCTCCCGGTCTCT GGGTAAAGGAGGGGGCTCCGCACCCACTTCAAGCTCCACTTCAAGCTCTACAGCGGAAG CACAGCAGCAGCAGCAGCAGCAGCAGCAGCAGCAGCACCTGGAGCAGCTGTTGATG GACCTACAGGAGCTCCTGAGCAGGATGGAGAATTACAGGAACCTGAAACTCCCCAGGAT GCTCACCTTCAAATTTTACTTGCCCAAGCAGGCCACAGAATTGAAAGATCTTCAGTGCC TAGAAGATGGTCTTGGACCTCTGCGGCATGTTCTGGATTTGACTCAAAGCAAAAGCTTT CAATTGGAAGATGCTGAGAATTTCATCAGCAATATCAGAGTAACTGTTGTAAAACTAAA GGGCTCTGACAACACATTTGAGTGCCAATTCGATGATGAGTCAGCAACTGTGGTGGACT TTCTGAGGAGATGGATAGCCTTCTGTCAAAGCATCATCTCAACAAGCCCTCAA<u>CACCAT CACCACCATCACTGATAA</u> |
| 21 | D265A Fc / E76G (amino acid sequence) (C-terminal 6x his tag is underlined) | MRVPAQLLGLLLLWLPGARCEPRVPITQNPCPPLKECPPCAAPDLLGGPSVFIFPPKIK DVLMISLSPMVTCVVVAVSEDDPDVQISWFVNNVEVHTAQTQTHREDYNSTLRVVSALP IQHQDWMSGKEFKCKVNNRALPSPIEKTISKPRGPVRAPQVYVLPPPAEEMTKKEFSLT CMITGFLPAEIAVDWTSNGRTEQNYKNTATVLDSDGSYFMYSKLRVQKSTWERGSLFAC SVVHEGLHNHLTTKTISRSLGKGGGSAPTSSSTSSSTAEAQQQQQQQQQQQHLEQLLM DLQELLSRMENYRNLKLPRMLTFKFYLPKQATELKDLQCLEDGLGPLRHVLDLTQSKSF QLEDAENFISNIRVTVVKLKGSDNTFECQFDDESATVVDFLRRWIAFCQSIISTSPQ<u>HH HHHH</u> |
| 22 | mIL-2 QQ6.2-4 (nucleic acid sequence) | GCACCCACCTCAAGCTCCACTTCAAGCTCTACAGCGGAAGCACAACAGCAGCAGCAGCA GCAGCAGCAGCAGCAGCACCTGGAGCAGCTGTTGATGGACCTACAGGAGCTCCTGA GCAGGATGGAGGATTCCAGGAACCTCCGAGACTCCCCAGGATGCTCACCTTCAAATTTAC TTGCCCAAGCAGGCCACAGAATTGGAAGATCTTCAGTGCCTAGAAGATGAACTTGAACC TCTGCGGCAAGTTCTGGATTTGACTCAAAGCAAAAGCTTTCAATTGGAAGATGCTGAGA ATTTCATCAGCAATATCAGAGTAACTGTTGTAAAACTAAAGGGCTCTGACAACACATTT GAGTGCCAATTCGATGATGAGCCAGCAACTGTGGTGGGCTTTCTGAGGAGATGGATAGC CTTCTGTCAAAGCATCATCTCAACGAGCCCTCAA |
| 23 | mIL-2 QQ6.2-4 (amino acid | APTSSSTSSSTAEAQQQQQQQQQQQHLEQLLMDLQELLSRMEDSRNLRLPRMLTFKFY LPKQATELEDLQCLEDELEPLRQVLDLTQSKSFQLEDAENFISNIRVTVVKLKGSDNTF ECQFDDEPATVVGFLRRWIAFCQSIISTSPQ |

TABLE 1-continued

Sequence Summary

| SEQ ID NO | Description | Sequence |
|---|---|---|
| | sequence) | |
| 24 | mIL-2 QQ6.2-8 (nucleic acid sequence) | GCACCCACCTCAAGCTCCACTTCAAGCTCTACAGCGGAAGCACAACAGCAGCAGCAGCA GCAGCAGCACCTGGAGCAGCTGTTGATGGACCTACAGGAGCTCCTGAGTAGGATGGAGG ATCACAGGAACCTGAGACTCCCCAGGATGCTCACCTTCAAATTTTACTTGCCCAAGCAG GCCACAGAATTGGAAGATCTTCAGTGCCTAGAAGATGAACTTGAACCTCTGCGGCAAGT TCTGGATTTGACTCAAAGCAAAAGCTTTCAATTGGAAGATGCTGAGAATTTCATCAGCA ATATCAGAGTAACTGTTGTAAAACTAAAGGGCTCTGACAACACATTTGAGTGCCAATTC GATGATGAGCCAGCAACTGTGGTGGACTTTCTGAGGAGATGGATAGCCTTCTGTCAAAG CATCATCTCAACAAGCCCTCGA |
| 25 | mIL-2 QQ6.2-8 (amino acid sequence) | APTSSSTSSSTAEAQQQQQQQQHLEQLLMDLQELLSRMEDHRNLRLPRMLTFKFYLPKQ ATELEDLQCLEDELEPLRQVLDLTQSKSFQLEDAENFISNIRVTVVKLKGSDNTFECQF DDEPATVVDFLRRWIAFCQSIISTSPR |
| 26 | mIL-2 QQ6.2-10 (nucleic acid sequence) | GCACCCACCTCAAGCTCCACTTCAAGCTCTACAGCGGAAGCACAACAGCAGCAGCAGCA GCAGCAGCAGCAGCAGCACCTGGAGCAGCTGTTGATGGACCTACAGGAACTCCTGA GTAGGATGGAGGATCACAGGAACCTGAGACTCCCCAGGATGCTCACCTTCAAATTTTAC TTGCCCGAGCAGGCCACAGAATTGGAAGATCTTCAGTGCCTAGAAGATGAACTTGAACC ACTGCGGCAAGTTCTGGATTTGACTCAAAGCAAAAGCTTTCAATTGGAAGATGCTGAGA ATTTCATCAGCAATATCAGAGTAACTGTTGTAAAACTAAAGGGCTCTGACAACACATTT GAGTGCCAATTCGACGATGAGCCAGCAACTGTGGTGGACTTTCTGAGGAGATGGATAGC CTTCTGTCAAAGCATCATCTCAACAAGCCCTCAG |
| 27 | mIL-2 QQ6.2-10 (amino acid sequence) | APTSSSTSSSTAEAQQQQQQQQQQHLEQLLMDLQELLSRMEDHRNLRLPRMLTFKFY LPEQATELEDLQCLEDELEPLRQVLDLTQSKSFQLEDAENFISNIRVTVVKLKGSDNTF ECQFDDEPATVVDFLRRWIAFCQSIISTSPQ |
| 28 | mIL-2 QQ6.2-11 (nucleic acid sequence) | GCACCCACCTCAAGCTCCACTTCAAGCTCTACAGCGGAAGCACAACAGCAGCAGCAGCA GCAGCAGCACCTGGAGCAGCTGTTGATGGACCTACAGGAGCTCCTGAGCAGGATGG AGGATTCCAGGAACCTGAGACTCCCCAGAATGCTCACCTTCAAATTTTACTTGCCCGAG CAGGCCACAGAATTGAAAGATCTCCAGTGCCTAGAAGATGAACTTGAACCTCTGCGGCA AGTTCTGGATTTGACTCAAAGCAAAAGCTTTCAATTGGAAGATGCTGAGAATTTCATCA GCAATATCAGAGTAACTGTTGTAAAACTAAAGGGCTCTGACAACACATTTGAGTGCCAA TTCGACGATGAGCCAGCAACTGTGGTGGACTTTCTGAGGAGATGGATAGCCTTCTGTCA AAGCATCATCTCAACAAGCCCTCAG |
| 29 | mIL-2 QQ6.2-11 (amino acid sequence) | APTSSSTSSSTAEAQQQQQQQQHLEQLLMDLQELLSRMEDSRNLRLPRMLTFKFYLPE QATELKDLQCLEDELEPLRQVLDLTQSKSFQLEDAENFISNIRVTVVKLKGSDNTFECQ FDDEPATVVDFLRRWIAFCQSIISTSPQ |
| 30 | mIL-2 QQ6.2-13 (nucleic acid sequence) | GCACCCACCTCAAGCTCCACTTCAAGCTCTACAGCGGAAGCACAACAGCAGCAGCAGCA GCAGCAGCAGCAGCAGCACCTGGAGCAGCTGTTGATGGACCTACAGGAGCTCCTGA GTAGGATGGAGGATCACAGGAACCTGAGACTCCCCAGGATGCTCACCTTCAAATTTTAC TTGCCCGAGCAGGCCACAGAATTGAAAGATCTCCAGTGCCTAGAAGATGAACTTGAACC TCTGCGGCAGGTTCTGGATTTGACTCAAAGCAAAAGCTTTCAATTGGAAGATGCTGAGA ATTTCATCAGCAATATCAGAGTAACTGTTGTAAAACTAAAGGGCTCTGACAACACATTT GAGTGCCAATTCGATGATGAGCCAGCAACTGTGGTGGACTTTCTGAGGAGATGGATAGC CTTCTGTCAAAGCATCATCTCAACAAGCCCTCAG |
| 31 | mIL-2 QQ6.2-13 (amino acid sequence) | APTSSSTSSSTAEAQQQQQQQQQQHLEQLLMDLQELLSRMEDHRNLRLPRMLTFKFY LPEQATELKDLQCLEDELEPLRQVLDLTQSKSFQLEDAENFISNIRVTVVKLKGSDNTF ECQFDDEPATVVDFLRRWIAFCQSIISTSPQ |
| 32 | Full length human IL-2 (nucleic acid sequence) | ATGTACAGGATGCAACTCCTGTCTTGCATTGCACTAAGTCTTGCACTTGTCACAAACAG TGCACCTACTTCAAGTTCTACAAAGAAAACACAGCTACAACTGGAGCATTTACTGCTGG ATTTACAGATGATTTTGAATGGAATTAATAATTACAAGAATCCCAAACTCACCAGGATG CTCACATTTAAGTTTTACATGCCCAAGAAGGCCACAGAACTGAAACATCTTCAGTGTCT AGAAGAAGAACTCAAACCTCTGGAGGAAGTGCTAAATTTAGCTCAAAGCAAAAACTTTC ACTTAAGACCCAGGGACTTAATCAGCAATATCAACGTAATAGTTCTGGAACTAAAGGGA TCTGAAACAACATTCATGTGTGAATATGCTGATGAGACAGCAACCATTGTAGAATTTCTG AACAGATGGATTACCTTTTGTCAAAGCATCATCTCAACACTGACTTGA |
| 33 | Full length human IL-2 (amino acid sequence) | MYRMQLLSCIALSLALVTNSAPTSSSTKKTQLQLEHLLLDLQMILNGINNYKNPKLTRM LTFKFYMPKKATELKHLQCLEEELKPLEEVLNLAQSKNFHLRPRDLISNINVIVLELKG SETTFMCEYADETATIVEFLNRWITFCQSIISTLT |
| 34 | Human IL-2 without | GCACCTACTTCAAGTTCTACAAAGAAAACACAGCTACAACTGGAGCATTTACTGCTGGA TTTACAGATGATTTTGAATGGAATTAATAATTACAAGAATCCCAAACTCACCAGGATGC |

TABLE 1-continued

Sequence Summary

| SEQ ID NO | Description | Sequence |
|---|---|---|
| | signal peptide (nucleic acid sequence) | TCACATTTAAGTTTTACATGCCCAAGAAGGCCACAGAACTGAAACATCTTCAGTGTCTA GAAGAAGAACTCAAACCTCTGGAGGAAGTGCTAAATTTAGCTCAAAGCAAAAACTTTCA CTTAAGACCCAGGGACTTAATCAGCAATATCAACGTAATAGTTCTGGAACTAAAGGGAT CTGAAACAACATTCATGTGTAATATGCTGATGAGACAGCAACCATTGTAGAATTTCTGA ACAGATGGATTACCTTTTGTCAAAGCATCATCTCAACACTGACTTGA |
| 35 | Human IL-2 without signal peptide (amino acid sequence) | APTSSSTKKTQLQLEHLLLDLQMILNGINNYKNPKLTRMLTFKFYMPKKATELKHLQCL EEELKPLEEVLNLAQSKNFHLRPRDLISNINVIVLELKGSETTFMCEYADETATIVEFL NRWITFCQSIISTLT |
| 36 | Human serum albumin (amino acid sequence) | MDMRVPAQLLGLLLLWLPGARCADAHKSEVAHRFKDLGEENFKALVLIAFAQYLQQCPF EDHVKLVNEVTEFAKTCVADESAENCDKSLHTLFGDKLCTVATLRETYGEMADCCAKQE PERNECFLQHKDDNPNLPRLVRPEVDVMCTAFHDNEETFLKKYLYEIARRHPYFYAPEL LFFAKRYKAAFTECCQAADKAACLLPKLDELRDEGKASSAKQRLKCASLQKFGERAFKA WAVARLSQRFPKAEFAEVSKLVTDLTKVHTECCHGDLLECADDRADLAKYICENQDSIS SKLKECCEKPLLEKSHCIAEVENDEMPADLPSLAADFVESKDVCKNYAEAKDVFLGMFL YEYARRHPDYSVVLLLRLAKTYETTLEKCCAAADPHECYAKVFDEFKPLVEEPQNLIKQ NCELFEQLGEYKFQNALLVRYTKKVPQVSTPTLVEVSRNLGKVGSKCCKHPEAKRMPCA EDYLSVVLNQLCVLHEKTPVSDRVTKCCTESLVNRRPCFSALEVDETYVPKEFNAETFT FHADICTLSEKERQIKKQTALVELVKHKPKATKEQLKAVMDDFAAFVEKCCKADDKETC FAEEGKKLVAASQAALGLGGGSAPTSSSTKKTQLQLEHLLLDLQMILNGINNYKNPKLT RMLTFKFYMPKKATELKHLQCLEEELKPLEEVLNLAQSKNFHLRPRDLISNINVIVLEL KGSETTFMCEYADETATIVEFLNRWITFCQSIISTLTGGGS |
| 37 | Mature HSA (amino acid sequence) | DAHKSEVAHRFKDLGEENFKALVLIAFAQYLQQCPFEDHVKLVNEVTEFAKTCVADESA ENCDKSLHTLFGDKLCTVATLRETYGEMADCCAKQEPERNECFLQHKDDNPNLPRLVRP EVDVMCTAFHDNEETFLKKYLYEIARRHPYFYAPELLFFAKRYKAAFTECCQAADKAAC LLPKLDELRDEGKASSAKQRLKCASLQKFGERAFKAWAVARLSQRFPKAEFAEVSKLVT DLTKVHTECCHGDLLECADDRADLAKYICENQDSISSKLKECCEKPLLEKSHCIAEVEN DEMPADLPSLAADFVESKDVCKNYAEAKDVFLGMFLYEYARRHPDYSVVLLLRLAKTYE TTLEKCCAAADPHECYAKVFDEFKPLVEEPQNLIKQNCELFEQLGEYKFQNALLVRYTK KVPQVSTPTLVEVSRNLGKVGSKCCKHPEAKRMPCAEDYLSVVLNQLCVLHEKTPVSDR VTKCCTESLVNRRPCFSALEVDETYVPKEFNAETFTFHADICTLSEKERQIKKQTALVE LVKHKPKATKEQLKAVMDDFAAFVEKCCKADDKETCFAEEGKKLVAASQAALGLGGGSA PTSSSTKKTQLQLEHLLLDLQMILNGINNYKNPKLTRMLTFKFYMPKKATELKHLQCLE EELKPLEEVLNLAQSKNFHLRPRDLISNINVIVLELKGSETTFMCEYADETATIVEFLN RWITFCQSIISTLTGGGS |
| 38 | Human serum albumin (nucleic acid sequence) | ATGGATATGCGGGTGCCTGCTCAGCTGCTGGGACTGCTGCTGCTGTGGCTGCCTGGGGC TAGATGCGCCGATGCTCACAAAAGCGAAGTCGCACACAGGTTCAAAGATCTGGGGGAGG AAAACTTTAAGGCTCTGGTGCTGATTGCTTTCGCCCAGTACCTGCAGCAGTGCCCCTTT GAGGACCACGTGAAACTGGTCAACGAAGTGACTGAGTTCGCCAAGACCTGCGTGGCCGA CGAATTCTGCTGAGAATTGTGATAAAAGTCTGCATACTCTGTTTGGGGATAAGCTGTGTA CAGTGGCCACTCTGCGAGAAACCTATGGAGAGATGGCAGACTGCTGTGCCAAACAGGAA CCCGAGCGGAACGAATGCTTCCTGCAGCATAAGGACGATAACCCCAATCTGCCTCGCCT GGTGCGACCTGAGGTGGACGTCATGTGTACAGCCTTCCACGATAATGAGGAAACTTTTC TGAAGAAATACCTGTACGAAATCGCTCGGAGACATCCTTACTTTTATGCACCAGAGCTG CTGTTCTTTGCCAAACGCTACAAGGCCGCTTTCACCGAGTGCTGTCAGGCAGCCGATAA AGCTGCATGCCTGCTGCCTAAGCTGGACGAACTGAGGGATGAGGGCAAGGCCAGCTCCG CTAAACAGCGCCTGAAGTGTGCTAGCCTGCAGAAATTCGGGGAGCGAGCCTTCAAGGCT TGGGCAGTGGCACGGCTGAGTCAGAGATTCCCAAAGGCAGAATTTGCCGAGGTCTCAAA ACTGGTGACCGACCTGACAAAGGTGCACACCGAATGCTGTCATGGCGACCTGCTGGAGT GCGCCGACGATCGAGCTGATCTGGCAAAGTATATTTGTGAGAACCAGGACTCCATCTCT AGTAAGCTGAAAGAATGCTGTGAGAAACCACTGCTGGAAAAGTCTCACTGCATTGCCGA AGTGGAGAACGACGAGATGCCAGCTGATCTGCCCTCACTGGCCGCTGACTTCGTCGAAA GCAAAGATGTGTGTAAGAATTACGCTGAGGCAAAGGATGTTCCTGGGAATGTTTCTG TACGAGTATGCCAGGCGCCACCCAGACTACTCCGTGGTCCTGCTGCTGAGGCTGGCTAA AACATATGAAACCACACTGGAGAAGTGCTGTGCAGCCGCTGATCCCCATGAATGCTATG CCAAAGTCTTCGACGAGTTTAAGCCCCTGGTGGAGGAACCTCAGAACCTGATCAAACAG AATTGTGAACTGTTTGAGCAGCTGGGCGAGTACAAGTTCCAGAACGCCCTGCTGGTGCG CTATACCAAGAAAGTCCCACAGGTGTCCACACCCACTCTGGTGGAGGTGAGCCGGAATC TGGGCAAAGTGGGGAGTAAATGCTGTAAGCACCCTGAAGCCAAGAGGATGCCATGCGCT GAGGATTACCTGAGTGTGGTCCTGAATCAGCTGTGTGTCCTGCATGAAAAAACACCTGT CAGCGACCGGGTGACAAAGTGCTGTACTGAGTCACTGGTGAACCGACGGCCCTGCTTTA GCGCCCTGGAAGTCGATGAGACTTATGTGCCTAAAGAGTTCAACGCTGAGACCTTCACA TTTCACGCAGATATTTGTACCCTGAGCGAAAAGGAGAGACAGATCAAGAAACAGACAGC CCTGGTCGAACTGGTGAAGCATAAACCCAAGGCCACAAAAGAGCAGCTGAAGGCTGTCA TGGACGATTTCGCAGCCTTTTGGAAAATGCTGTAAGGCAGACGATAAGGAGACTTGC TTTGCCGAGGAAGGAAAGAAACTGGTGGCTGCATCCCAGGCAGCTCTGGGACTGGGAGG AGGATCTGCCCCCTACCTCAAGCTCCACTAAGAAAACCCAGCTGCAGCTGGAGCACCTGC TGCTGGACCTGCAGATGATTCTGAACGGGATCAACAATTACAAAAATCCAAAGCTGACC |

TABLE 1-continued

Sequence Summary

| SEQ ID NO | Description | Sequence |
|---|---|---|
| | | CGGATGCTGACATTCAAGTTTTATATGCCCAAGAAAGCCACAGAGCTGAAACACCTGCA GTGCCTGGAGGAAGAGCTGAAGCCTCTGGAAGAGGTGCTGAACCTGGCCCAGAGCAAGA ATTTCCATCTGAGACCAAGGGATCTGATCTCCAACATTAATGTGATCGTCCTGGAACTG AAGGGATCTGAGACTACCTTTATGTGCGAATACGCTGACGAGACTGCAACCATTGTGGA GTTCCTGAACAGATGGATCACCTTCTGCCAGTCCATCATTTCTACTCTGACAGGCGGGG GGAGC |
| 39 | EETI-II from Knottin Database | GC PRILMR CKQDSDCLAGCVCGPNGFCG |
| 40 | AgRP from Knottin Database "-" indicates where mini protein can be formed | GCVRLHESCLGQQVPCCDPCATCYCRFFNAFCYCR-KLGTAMNPCSRT |
| 41 | Omega agatoxin from Knottin Database "-" indicates where mini protein can be formed | EDN--CIAEDYGKCTWGGTKCCRGRPCRC SMIGTN CECTPRLIMEGLSFA |
| 42 | EETI-II Library | GCXXXRGDXXXXXCKQDSDCLAGCVCGPNGFCG |
| 43 | EETI-II K15S Mutation Library | GCXXXRGDXXXXXCSQDSDCLAGCVCGPNGFCG |
| 44 | 2.5F-(K15S) mIgG2aFc Nucleic Acid Sequence | GGTTGTCCAAGACCAAGAGGTGATAATCCACCATTGACTTGTTCTCAAGATTCTGATTG TTTGGCTGGTTGTGTTTGTGGTCCAAATGGTTTTTGTGGTGGTCGACTAGAGCCCAGAG TGCCCATAACACAGAACCCCTGTCCTCCACTCAAAGAGTGTCCCCCATGCGCAGCTCCA GACCTCTTGGGTGGACCATCCGTCTTCATCTTCCCTCCAAAGATCAAGGATGTACTCAT GATCTCCCTGAGCCCCATGGTCACATGTGTGGTGGTGGATGTGAGCGAGGATGACCCAG ACGTCCAGATCAGCTGGTTTGTGAACAACGTGGAAGTACACACAGCTCAGACACAAACC CATAGAGAGGATTACAACAGTACTCTCCGGGTGGTCAGTGCCCTCCCCATCCAGCACCA GGACTGGATGAGTGGCAAGGAGTTCAAATGCAAGGTCAACAACAGAGCCCTCCCCATCCC CCATCGAGAAACCATCTCAAAACCCAGAGGGCCAGTAAGAGCTCCACAGGTATATGTC TTGCCTCCACCAGCAGAAGAGATGACTAAGAAAGAGTTCAGTCTGACCTGCATGATCAC AGGCTTCTTACCTGCCGAAATTGCTGTGGACTGGACCAGCAATGGGCGTACAGAGCAAA ACTACAAGAACACCGCAACAGTCCTGGACTCTGATGGTTCTTACTTCATGTACAGCAAG CTCAGAGTACAAAAGAGCACTTGGGAAAGAGGAAGTCTTTTCGCCTGCTCAGTGGTCCA CGAGGGTCTGCACAATCACCTTACGACTAAGACCATCTCCCGGTCTCTGGGTAAA |
| 45 | 2.5F-(K15S) mIgG2aFc Amino Acid Sequence | GCPRPRGDNPPLTCSQDSDCLAGCVCGPNGFCGEPRVPITQNPCPPLKECPPCAAPDLL GGPSVFIFPPKIKDVLMISLSPMVTCVVVDVSEDDPDVQISWFVNNVEVHTAQTQTHRE DYNSTLRVVSALPIQHQDWMSGKEFKCKVNNRALPSPIEKTISKPRGPVRAPQVYVLPP PAEEMTKKEFSLTCMITGFLPAEIAVDWTSNGRTEQNYKNTATVLDSDGSYFMYSKLRV QKSTWERGSLFACSVVHEGLHNHLTTKTISRSLGK |
| 46 | 2.5D-(K15S) mIgG2aFc Nucleic Acid Sequence | GGTTGTCCACAAGGCAGAGGTGATTGGGCTCCAACTTCTTGTTCTCAAGATTCTGATTG TTTGGCTGGTTGTGTTTGTGGTCCAAATGGTTTTTGTGGTGGTCGACTAGAGCCCAGAG TGCCCATAACACAGAACCCCTGTCCTCCACTCAAAGAGTGTCCCCCATGCGCAGCTCCA GACCTCTTGGGTGGACCATCCGTCTTCATCTTCCCTCCAAAGATCAAGGATGTACTCAT GATCTCCCTGAGCCCCATGGTCACATGTGTGGTGGTGGATGTGAGCGAGGATGACCCAG ACGTCCAGATCAGCTGGTTTGTGAACAACGTGGAAGTACACACAGCTCAGACACAAACC CATAGAGAGGATTACAACAGTACTCTCCGGGTGGTCAGTGCCCTCCCCATCCAGCACCA GGACTGGATGAGTGGCAAGGAGTTCAAATGCAAGGTCAACAACAGAGCCCTCCCCATCCC CCATCGAGAAACCATCTCAAAACCCAGAGGGCCAGTAAGAGCTCCACAGGTATATGTC TTGCCTCCACCAGCAGAAGAGATGACTAAGAAAGAGTTCAGTCTGACCTGCATGATCAC AGGCTTCTTACCTGCCGAAATTGCTGTGGACTGGACCAGCAATGGGCGTACAGAGCAAA ACTACAAGAACACCGCAACAGTCCTGGACTCTGATGGTTCTTACTTCATGTACAGCAAG CTCAGAGTACAAAAGAGCACTTGGGAAAGAGGAAGTCTTTTCGCCTGCTCAGTGGTCCA CGAGGGTCTGCACAATCACCTTACGACTAAGACCATCTCCCGGTCTCTGGGTAAA |

TABLE 1-continued

Sequence Summary

| SEQ ID NO | Description | Sequence |
|---|---|---|
| 47 | 2.5D-(K15S) mIgG2aFc Amino Acid Sequence | GCPQGRGDWAPTSCSQDSDCLAGCVCGPNGFCGEPRVPITQNPCPPLKECPPCAAPDLL GGPSVFIFPPKIKDVLMISLSPMVTCVVVDVSEDDPDVQISWFVNNVEVHTAQTQTHRE DYNSTLRVVSALPIQHQDWMSGKEFKCKVNNRALPSPIEKTISKPRGPVRAPQVYVLPP PAEEMTKKEFSLTCMITGFLPAEIAVDWTSNGRTEQNYKNTATVLDSDGSYFMYSKLRV QKSTWERGSLFACSVVHEGLHNHLTTKTISRSLGK |
| 48 | 2.5F-(K15S) hIgG1Fc Amino Acid Sequence | GCPRPRGDNPPLTCSQDSDCLAGCVCGPNGFCGEPKSCDKTHTCPPCPAPELLGGPSVF LFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSREEMT KNQVSLTCLVKGFYPSDIAVEWESNGQPENNYKTTPPVLDSDGSFFLYSKLTVDKSRWQ QGNVFSCSVMHEALHNHYTQKSLSLSPGK |
| 49 | 2.5F-(K15S) hIgG1Fc Fc Upper Hinge Deletion (ΔEPKSC) Amino Acid Sequence | GCPRPRGDNPPLTCSQDSDCLAGCVCGPNGFCGDKTHTCPPCPAPELLGGPSVFLFPPK PKDTLMISRTPEVTCVVVDVSHEDPEVKFNWYVDGVEVHNAKTKPREEQYNSTYRVVSV LTVLHQDWLNGKEYKCKVSNKALPAPIEKTISKAKGQPREPQVYTLPPSREEMTKNQVS LTCLVKGFYPSDIAVEWESNGQPENNYKTTPPVLDSDGSFFLYSKLTVDKSRWQQGNVF SCSVMHEALHNHYTQKSLSLSPGK |
| 50 | 2.5D-(K15S) hIgG1Fc Amino Acid Sequence | GCPQGRGDWAPTSCSQDSDCLAGCVCGPNGFCGEPKSCDKTHTCPPCPAPELLGGPSVF LFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSREEMT KNQVSLTCLVKGFYPSDIAVEWESNGQPENNYKTTPPVLDSDGSFFLYSKLTVDKSRWQ QGNVFSCSVMHEALHNHYTQKSLSLSPGK |
| 51 | 2.5D-(K15S) hIgG1Fc Fc Upper Hinge Deletion (ΔEPKSC) Amino Acid Sequence | GCPQGRGDWAPTSCSQDSDCLAGCVCGPNGFCGDKTHTCPPCPAPELLGGPSVFLFPPK PKDTLMISRTPEVTCVVVDVSHEDPEVKFNWYVDGVEVHNAKTKPREEQYNSTYRVVSV LTVLHQDWLNGKEYKCKVSNKALPAPIEKTISKAKGQPREPQVYTLPPSREEMTKNQVS LTCLVKGFYPSDIAVEWESNGQPENNYKTTPPVLDSDGSFFLYSKLTVDKSRWQQGNVF SCSVMHEALHNHYTQKSLSLSPGK |
| 52 | hPD-1 amino acid sequence | MQIPQAPWPVVWAVLQLGWRPGWFLDSPDPWNPPTFFPALLVVTEGDNATFTCSFSNTS ESFVLNWYRMSPSNQTDKLAAFPEDRSQPGQDCRFRVTQLPNGRDFHMSVVRARRNDSG TYLCGAISLAPKAQIKESLRAELRVTERRAEVPTAHPSPSPRPAGQFQTLVVGVVGGLL GSLVLLVWVLAVICSRAARGTIGARRTGQPLKEDPSAVPVFSVDYGELDFQWREKTPEP PVPCVPEQTEYATIVFPSGMGTSSPARRGSADGPRSAQPLRPEDGHCSWPL |
| 53 | hPD-L1 amino acid sequence | MRIFAVFIFMTYWHLLNAFTVTVPKDLYVVEYGSNMTIECKFPVEKQLDLAALIVYWEM EDKNIIQFVHGEEDLKVQHSSYRQRARLLKDQLSLGNAALQITDVKLQDAGVYRCMISY GGADYKRITVKVNAPYNKINQRILVVDPVTSEHELTCQAEGYPKAEVIWTSSDHQVLSG KTTTTNSKREEKLFNVTSTLRINTTTNEIFYCTFRRLDPEENHTAELVIPELPLAHPPN ERTHLVILGAILLC LGVALTFIFR LRKGRMMDVKKCGIQDTNSK KQSDTHLEET |
| 54 | hCTLA-4 amino acid sequence | MACLGFQRHKAQLNLATRTWPCTLLFFLLFIPVFCKAMHVAQPAVVLASS RGIASFVCEYASPGKATEVRVTVLRQADSQVTEVCAATYM MGNELTFLDDSICTGTSSGNQVNLTIQGLRAMDTGLYICKVELMYPPPYY LGIGNGTQIY VIDPEPCPDS DFLLWILAAVSSGLFFYSFL LTAVSLSKML KKRSPLTTGVYVKMPPTEPE CEKQFQPYFI PIN |
| 55 | hLAG-3 amino acid sequence | MWEAQFLGLLFLQPLWVAPVKPLQPGAEVPVVWAQEGAPAQLPCSPTIPLQDLSLLRRA GVTWQHQPDSGPPAAAPGHPLAPGPHPAAPSSWGPRPRRYTVLSVGPGGLRSGRLPLQP RVQLDERGRQRGDFSLWLRPAR RADAGEYRAAVHLRDRALSCRLRLRLGQASMTASPPGSLR ASDWVILNCSFSRPDRPASVHWFRNRGQGRVPVRESPHHHLAESFLFLPQVSPMDSGPW GCILTYRDGFNVSIMYNLTVLGLEPPTPLTVYAGAGSRVGLPCRLPAGVGTRSFLTAKW TPPGGGPDLLVTGDNGDFTLRL EDVSQAQAGT YTCHIHLQEQ QLNATVTLAI ITVTPKSFGS PGSLGKLLCEVTPVSGQERFVWSSLDTPSQRSFSGPWLEAQEAQLLSQPWQCQLYQGER LLGAAVYFTEL SSPGAQRSGR APGALPAGHL LLFLILGVLS LLLLVTGAFG FHLWRRQWRPRRFSALEQGI HPPQAQSKIE ELEQEPEPEP EPEPEPEPEP EPEQL |
| 56 | hTIM-3 | MFSHLPFDCVLLLLLLLLLTRSSEVEYRAEVGQNAYLPCFYTPAAPGNLVPVCWGKGACP |

TABLE 1-continued

Sequence Summary

| SEQ ID NO | Description | Sequence |
|---|---|---|
| | amino acid sequence | VFECGNVVLRTDERDVNYWTSRYWLNGDFRKGDVSLTIENVTLADSGIYCCRIQIPGIM NDEKFNLKLVIKPAKVTPAPTR QRDFTAAFPR MLTTRGHGPA ETQTLGSLPD INLTQISTLA NELRDSRLANDLRDSGATIRGIYIGAGICAGLALALIFGALIFKWYSHSKEKIQNLSLI SLANLPPSGLANAVAEGIRSEENIYTIEENVYEVEEPNEYYCYVSSRQQPSQPLGCRFA MP |
| 57 | hB7-H3 amino acid sequence | MLRRRGSPGMGVHVGAALGALWFCLTGALEVQVPEDPVVALVGTDATLCC SFSPEPGFSLQLNLIWQLT DTKQLVHSFA EGQDQGSAYA NRTALFPDLLAQGNASLRLQRVRVADEGSFCFVSIRDFGSAAVSLQVAA PYSKPSMTLE PNKDLRPGDT VTITCSSYQG YPEAEVFWQD GQGVPLTGNVTTSQMANEQGLFDVHSILRVVLGANGTYSCLVRNPVLQQD AHSSVTITPQRSPTGAVEVQVPEDPVVALVGTDATLRCSF SPEPGFSLAQLNLIWQLTDTKQLVHSFTEGRDQGSAYANRTALFPDLLAQ GNASLRLQRV RVADEGSFTC FVSIRDFGSA AVSLQVAAPY SKPSMTLEPNKDLRPGDTVTITCSSYRGYPEAEVFWQDGQGVPLTGNVTT SQMANEQGLFDVHSVLRVVLGANGTYSCLVRNPVLQQDAH GSVTITGQPMTFPPEALWVTVGLSVCLIALLVALAFVCWRKIKQSCEEEN AGAEDQDGEGEGSKTALQPLKHSDSKEDDGQEIA |
| 58 | hB7-H4 amino acid sequence | MASLGQILFWSIISIIILAGAIALIIGFGISAFSMPEVNVDYNASSETLRCEAPRWFP QPTVVWASQVDQGANFSEVSNTSFELNSENVTMKVVSVLYN VTINNTYSCM IENDIAKATGDIKVTESEIKRRSHLQLLNS KASLCVSSFFAISWALLPLSPYLMLK |

In one embodiment, an integrin-binding polypeptide or a variant thereof, consists of, consists essentially of, or comprises an amino acid sequence selected from SEQ ID NOs: 59-135. In an embodiment, a polypeptide includes an amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence selected from SEQ ID Nos: 59-135. In an embodiment, a polypeptide includes a contiguous amino acid sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous amino acid sequence selected from SEQ ID NOs: 59-135. In an embodiment, a polypeptide includes an amino acid sequence having at least 10, 15, 20, 25, 30, 35, 40, 45, 50, 55, 60, 65, 70, 75, 80, 85, 90, 95, 100, 200, 300, 400, or 500 (or any integer within these numbers) contiguous amino acids of an amino acid sequence selected from SEQ ID NOs: 59-135.

TABLE 2

Integrin Binding Knottin Sequences

| SEQ ID NO: | Peptide Identifier | Scaffold | Sequence (RGD motif is underlined with flanking residues) |
|---|---|---|---|
| 59 | 1.4A | EETI-II | GCAEPRGDMPWTWCKQDSDCLAGCVCGPNGFCG |
| 60 | 1.4B | EETI-II | GCVGGRGDWSPKWCKQDSDCPAGCVCGPNGFCG |
| 61 | 1.4C | EETI-II | GC AELRGDRSYPE CKQDSDCLAGCVCGPNGFCG |
| 62 | 1.4E | EETI-II | GC RLPRGDVPRPH CKQDSDCQAGCVCGPNGFCG |
| 63 | 1.4H | EETI-II | GC YPLRGDNPYAA CKQDSDCRAGCVCGPNGFCG |
| 64 | 1.5B | EETI-II | GC TIGRGDWAPSE CKQDSDCLAGCVCGPNGFCG |
| 65 | 1.5F | EETI-II | GC HPPRGDNPPVT CKQDSDCLAGCVCGPNGFCG |
| 66 | 2.3A | EETI-II | GC PEPRGDNPPPS CKQDSDCRAGCVCGPNGFCG |
| 67 | 2.3B | EETI-II | GC LPPRGDNPPPS CKQDSDCQAGCVCGPNGFCG |
| 68 | 2.3C | EETI-II | GCHLGRGDWAPVGCKQDSDCPAGCVCGPNGFCG |
| 69 | 2.3D | EETI-II | GC NVGRGDWAPSE CKQDSDCPAGCVCGPNGFCG |
| 70 | 2.3E | EETI-II | GC FPGRGDWAPSS CKQDSDCRAGCVCGPNGFCG |
| 71 | 2.3F | EETI-II | GC PLPRGDNPPTE CKQDSDCQAGCVCGPNGFCG |
| 72 | 2.3G | EETI-II | GC SEARGDNPRLS CKQDSDCRAGCVCGPNGFCG |
| 73 | 2.3H | EETI-II | GCLLGRGDWAPEACKQDSDCRAGCVCPNGFCG |

TABLE 2-continued

Integrin Binding Knottin Sequences

| SEQ ID NO: | Peptide Identifier | Scaffold | Sequence (RGD motif is underlined with flanking residues) |
|---|---|---|---|
| 74 | 2.3I | EETI-II | GCHVGRGDWAPLKCKQDSDCQAGCVCGPNGFCG |
| 75 | 2.3J | EETI-II | GC VRGRGDWAPPSCKQDSDCPAGCVCGPNGFCG |
| 76 | 2.4A | EETI-II | GCLGGRGDWAPPACKQDSDCRAGCVCGPNGFCG |
| 77 | 2.4C | EETI-II | GC FVGRGDWAPLTCKQDSDCQAGCVCGPNGFCG |
| 78 | 2.4D | EETI-II | GC PVGRGDWSPASCKQDSDCRAGCVCGPNGFCG |
| 79 | 2.4E | EETI-II | GC PRPRGDNPPLT CKQDSDCLAGCVCGPNGFCG |
| 80 | 2.4F | EETI-II | GC YQGRGDWSPSSCKQDSDCPAGCVCGPNGFCG |
| 81 | 2.4G | EETI-II | GC APGRGDWAPSECKQDSDCQAGCVCGPNGFCG |
| 82 | 2.4J | EETI-II | GC VQGRGDWSPPSCKQDSDCPAGCVCGPNGFCG |
| 83 | 2.5A | EETI-II | GC HVGRGDWAPEECKQDSDCQAGCVCGPNGFCG |
| 84 | 2.5C | EETI-II | GC DGGRGDWAPPACKQDSDCRAGCVCGPNGFCG |
| 85 | 2.5D | EETI-II | GC PQGRGDWAPTSCKQDSDCRAGCVCGPNGFCG |
| 86 | 2.5F | EETI-II | GC PRPRGDNPPLT CKQDSDCLAGCVCGPNGFCG |
| 87 | 2.5D K15S Mutant | EETI-II | GCPQGRGDWAPTSCSQDSDCLAGCVCGPNGFCG |
| 88 | 2.5F K15S Mutant | EETI-II | GCPRPRGDNPPLTCSQDSDCLAGCVCGPNGFCG |
| 89 | 2.5H | EETI-II | GCPQGRGDWAPEWCKQDSDCPAGCVCGPNGFCG |
| 90 | 2.5J | EETI-II | GCPRGRGDWSPPACKQDSDCQAGCVCGPNGFCG |
| 91 | 3A | AgRp | GCVRLHESCLGQQVPCCDPAATCYCVVRGDWRKRCYCR |
| 92 | 3B | AgRp | GCVRLHESCLGQQVPCCDPAATCYCEERGDMLEKCYCR |
| 93 | 3C | AgRp | GCVRLHESCLGQQVPCCDPAATCYCETRGDGKEKCYCR |
| 94 | 3D | AgRp | GCVRLHESCLGQQVPCCDPAATCYCQWRGDGDVKCYCR |
| 95 | 3E | AgRp | GCVRLHESCLGQQVPCCDPAATCYCSRRGDMRERCYCR |
| 96 | 3F | AgRp | GCVRLHESCLGQQVPCCDPAATCYCQYRGDGMKHCYCR |
| 97 | 3G | AgRp | GCVRLHESCLGQQVPCCDPAATCYCTGRGDTKVLCYCR |
| 98 | 3H | AgRp | GCVRLHESCLGQQVPCCDPAATCYCVERGDMKRRCYCR |
| 99 | 3I | AgRp | GCVRLHESCLGQQVPCCDPAATCYCTGRGDVRMNCYCR |
| 100 | 3J | AgRp | GCVRLHESCLGQQVPCCDPAATCYCVERGDGMSKCYCR |
| 101 | 4A | AgRp | GCVRLHESCLGQQVPCCDPAATCYCRGRGDMRRECYCR |
| 102 | 4B | AgRp | GCVRLHESCLGQQVPCCDPAATCYCEGRGDVKVNCYCR |
| 103 | 4C | AgRp | GCVRLHESCLGQQVPCCDPAATCYCVGRGDEKMSCYCR |

TABLE 2-continued

Integrin Binding Knottin Sequences

| SEQ ID NO: | Peptide Identifier | Scaffold | Sequence (RGD motif is underlined with flanking residues) |
|---|---|---|---|
| 104 | 4D | AgRp | GCVRLHESCLGQQVPCCDPAATCYCVSRGDMRKRCYCR |
| 105 | 4E | AgRp | GCVRLHESCLGQQVPCCDPAATCYCERRGDSVKKCYCR |
| 106 | 4F | AgRp | GCVRLHESCLGQQVPCCDPAATCYCEGRGDTRRRCYCR |
| 107 | 4G | AgRp | GCVRLHESCLGQQVPCCDPAATCYCEGRGDVVRRCYCR |
| 108 | 4H | AgRp | GCVRLHESCLGQQVPCCDPAATCYCKGRGDNKRKCYCR |
| 109 | 4I | AgRp | GCVRLHESCLGQQVPCCDPAXTCYCKGRGDVRRVCYCR |
| 110 | 4J | AgRp | GCVRLHESCLGQQVPCCDPAATCYCVGRGDNKVKCYCR |
| 111 | 5A | AgRp | GCVRLHESCLGQQVPCCDPAATCYCVGRGDNRLKCYCR |
| 112 | 5B | AgRp | GCVRLHESCLGQQVPCCDPAATCYCVERGDGMKKCYCR |
| 113 | 5C | AgRp | GCVRLHESCLGQQVPCCDPAATCYCEGRGDMRRRCYCR |
| 114 | 5D | AgRp | GCVRLHESCLGQQVPCCDPAATCYCQGRGDGDVKCYCR |
| 115 | 5E | AgRp | GCVRLHESCLGQQVPCCDPAATCYCSGRGDNDLVCYCR |
| 116 | 5F | AgRp | GCVRLHESCLGQQVPCCDPAATCYCVERGDGMIRCYCR |
| 117 | 5G | AgRp | GCVRLHESCLGQQVPCCDPAATCYCSGRGDNDLVCYCR |
| 118 | 5H | AgRp | GCVRLHESCLGQQVPCCDPAATCYCEGRGDMKMKCYCR |
| 119 | 5I | AgRp | GCVRLHESCLGQQVPCCDPAATCYCIGRGDVRRRCYCR |
| 120 | 5J | AgRp | GCVRLHESCLGQQVPCCDPAATCYCEERGDGRKKCYCR |
| 121 | 6B | AgRp | GCVRLHESCLGQQVPCCDPAATCYCEGRGDRDMKCYCR |
| 122 | 6C | AgRp | GCVRLHESCLGQQVPCCDPAATCYCTGRGDEKLRCYCR |
| 123 | 6E | AgRp | GCVRLHESCLGQQVPCCDPAATCYCVERGDGNRRCYCR |
| 124 | 6F | AgRp | GCVRLHESCLGQQVPCCDPAATCYCESRGDVVRKCYCR |
| 125 | 7C | AgRp | GCVRLHESCLGQQVPCCDPAATCYCYGRGDNDLRCYCR |

TABLE 3

Integrin Binding Polypeptide Sequences, Signal Sequences, Linkers, Fc fusions

| SEQ ID NO: | Peptide Identifier Scaffold | Sequence |
|---|---|---|
| 130 | NOD201 - 2.5F | GCPRPRGDNPPLTCSQDSDCLAGCVCGPNGFCG |
| 131 | NOD201modK-2.5FmodK | GCPRPRGDNPPLTCKQDSDCLAGCVCGPNGFCG |
| 132 | NOD203 - 2.5F w/GGGGS(SEQ ID NO: 136) | GCPRPRGDNPPLTCSQDSDCLAGCVCGPNGFCGGGGGS |
| 133 | NOD203modK - 2.5FmodK w/GGGGS(SEQ ID NO: 136) | GCPRPRGDNPPLTCKQDSDCLAGCVCGPNGFCGGGGGS |
| 134 | NOD204 - 2.5F w/GGGGSGGGGSGGGGS(SEQ ID NO: 137) | GCPRPRGDNPPLTCSQDSDCLAGCVCGPNGFCGGGGGSGGGGSGGGGS |
| 135 | NOD204modK-2.5FmodK w/GGGGSGGGGSGGGGS(SEQ ID NO: 137) | GCPRPRGDNPPLTCKQDSDCLAGCVCGPNGFCGGGGGSGGGGSGGGGS |
| 136 | Linker (short) | GGGGS |
| 137 | Linker (long) | GGGGSGGGGSGGGGS |
| 138 | Signal sequence (signal peptide A) | MTRLTVLALLAGLLASSR |
| 139 | NOD201 (human Fc; no linker) | GCPRPRGDNPPLTCSQDSDCLAGCVCGPNGFCGEPKSSDKTHTCPPCPA PELLGGPSVFLFPPKPKDTLMISRTPEVTCVVVDVSHEDPEVKFNWYVD GVEVHNAKTKPREEQYNSTYRVVSVLTVLHQDWLNGKEYKCKVSNKALP APIEKTISKAKGQPREPQVYTLPPSRDELTKNQVSLTCLVKGFYPSDIA VEWESNGQPENNYKTTPPVLDSDGSFFLYSKLTVDKSRWQQGNVFSCSV MHEALHNHYTQKSLSLSPG |
| 140 | NOD201X (control sequence - NOD201 with scrambled seq, human Fc; no linker) | GCVTGRDGSPASSCSQDSDCLAGCVCGPNGFCGEPKSSDKTHTCPPCPA PELLGGPSVFLFPPKPKDTLMISRTPEVTCVVVDVSHEDPEVKFNWYVD GVEVHNAKTKPREEQYNSTYRVVSVLTVLHQDWLNGKEYKCKVSNKALP APIEKTISKAKGQPREPQVYTLPPSRDELTKNQVSLTCLVKGFYPSDIA VEWESNGQPENNYKTTPPVLDSDGSFFLYSKLTVDKSRWQQGNVFSCSV MHEALHNHYTQKSLSLSPG |
| 141 | NOD201M (NOD201 with murine Fc domain; no linker) | GCPRPRGDNPPLTCSQDSDCLAGCVCGPNGFCGEPRVPITQNPCPPLKE CPPCAAPDLLGGPSVFIFPPKIKDVLMISLSPMVTCVVVDVSEDDPDVQ ISWFVNNVEVHTAQTQTHREDYNSTLRVVSALPIQHQDWMSGKEFKCKV NNRALPSPIEKTISKPRGPVRAPQVYVLPPPAEEMTKKEFSLTCMITGF LPAEIAVDWTSNGRTEQNYKNTATVLDSDGSYFMYSKLRVQKSTWERGS LFACSVVHEGLHNHLTTKTISRSLG |
| 142 | NOD203 complete (Gly$_4$Ser linker) | GCPRPRGDNPPLTCSQDSDCLAGCVCGPNGFCGGGGGSEPKSSDKTHTC PPCPAPELLGGPSVFLFPPKPKDTLMISRTPEVTCVVVDVSHEDPEVKF NWYVDGVEVHNAKTKPREEQYNSTYRVVSVLTVLHQDWLNGKEYKCKVS NKALPAPIEKTISKAKGQPREPQVYTLPPSRDELTKNQVSLTCLVKGFY PSDIAVEWESNGQPENNYKTTPPVLDSDGSFFLYSKLTVDKSRWQQGNV FSCSVMHEALHNHYTQKSLSLSPG |
| 143 | NOD204 complete ([Gly$_4$Ser]$_3$ linker) | GCPRPRGDNPPLTCSQDSDCLAGCVCGPNGFCGGGGGSGGGGSGGGGSE PKSSDKTHTCPPCPAPELLGGPSVFLFPPKPKDTLMISRTPEVTCVVVD VSHEDPEVKFNWYVDGVEVHNAKTKPREEQYNSTYRVVSVLTVLHQDWL NGKEYKCKVSNKALPAPIEKTISKAKGQPREPQVYTLPPSRDELTKNQV SLTCLVKGFYPSDIAVEWESNGQPENNYKTTPPVLDSDGSFFLYSKLTV DKSRWQQGNVFSCSVMHEALHNHYTQKSLSLSPG |

It will also be understood by one of ordinary skill in the art that the IL-2, extended-PK IL-2 or an integrin-binding polypeptide-Fc fusion used herein may be altered such that they vary in sequence from the naturally occurring or native sequences from which they were derived, while retaining the desirable activity of the native sequences. For example, nucleotide or amino acid substitutions leading to conservative substitutions or changes at "non-essential" amino acid residues may be made. Mutations may be introduced by standard techniques, such as site-directed mutagenesis and PCR-mediated mutagenesis.

The polypeptides described herein (e.g., IL-2, extended-PK IL-2, PK moieties, knottin, Fc, knottin-Fc, integrin-binding polypeptide-Fc fusion, and the like) may comprise conservative amino acid substitutions at one or more amino acid residues, e.g., at essential or non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagines, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a binding polypeptide is preferably replaced with another amino acid residue from the same side chain family. In another embodiment, a string of amino acids can be replaced with a structurally similar string that differs in order and/or composition of side chain family members. Alternatively, in another embodiment, mutations may be introduced randomly along all or part of a coding sequence, such as by saturation mutagenesis, and the resultant mutants can be incorporated into binding polypeptides of the invention and screened for their ability to bind to the desired target.

The "Programmed Death-1 (PD-1)" receptor refers to an immuno-inhibitory receptor belonging to the CD28 family. PD-1 is expressed predominantly on previously activated T-cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. AAC51773 (SEQ ID NO: 52 from International Publication No. WO 2016/025642).

"Programmed Death Ligand-1 (PD-L1)" is one of two cell surface glycoprotein ligands for PD-1 (the other being PD-L2) that downregulates T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7 (SEQ ID NO: 53 from International Publication No. WO 2016/025642).

"Cytotoxic T Lymphocyte Associated Antigen-4 (CTLA-4)" is a T cell surface molecule and is a member of the immunoglobulin superfamily. This protein downregulates the immune system by binding to CD80 and CD86. The term "CTLA-4" as used herein includes human CTLA-4 (hCTLA-4), variants, isoforms, and species homologs of hCTLA-4, and analogs having at least one common epitope with hCTLA-4. The complete hCTLA-4 sequence can be found under GenBank Accession No. P16410 (SEQ ID NO: 54 from International Publication No. WO 2016/025642):

"Lymphocyte Activation Gene-3 (LAG-3)" is an inhibitory receptor associated with inhibition of lymphocyte activity by binding to MHC class II molecules. This receptor enhances the function of Treg cells and inhibits CD8+ effector T cell function. The term "LAG-3" as used herein includes human LAG-3 (hLAG-3), variants, isoforms, and species homologs of hLAG-3, and analogs having at least one common epitope. The complete hLAG-3 sequence can be found under GenBank Accession No. P18627 (SEQ ID NO: 55 from International Publication No. WO 2016/025642).

"T-Cell Membrane Protein-3 (TIM-3)" is an inhibitory receptor involved in the inhibition of lymphocyte activity by inhibition of T-cell and B-cell responses. Its ligand is galectin 9, which is upregulated in various types of cancers. The term "TIM-3" as used herein includes human TIM-3 (hTIM-3), variants, isoforms, and species homologs of hTIM-3, and analogs having at least one common epitope. The complete hTIM-3 sequence can be found under GenBank Accession No. Q8TDQ0 (SEQ ID NO: 56 from International Publication No. WO 2016/025642).

The "B7 family" refers to inhibitory ligands with undefined receptors. The B7 family encompasses B7-H3 and B7-H4, both upregulated on tumor cells and tumor infiltrating cells. The complete hB7-H3 and hB7-H4 sequence can be found under GenBank Accession Nos. Q5ZPR3 and AAZ17406 (SEQ ID NOs: 57 and 58 from International Publication No. WO 2016/025642) respectively.

"Vascular Endothelial Growth Factor (VEGF)" is a secreted disulfide-linked homodimer that selectively stimulates endothelial cells to proliferate, migrate, and produce matrix-degrading enzymes, all of which are processes required for the formation of new vessels. In addition to being the only known endothelial cell specific mitogen, VEGF is unique among angiogenic growth factors in its ability to induce a transient increase in blood vessel permeability to macromolecules. The term "VEGF" or "VEGF-A" is used to refer to the 165-amino acid human vascular endothelial cell growth factor and related 121-, 145-, 189-, and 206-amino acid human vascular endothelial cell growth factors, as described by, e.g., Leung et al. Science, 246: 1306 (1989), and Houck et al. Mol. Endocrin., 5: 1806 (1991), together with the naturally occurring allelic and processed forms thereof. VEGF-A is part of a gene family including VEGF-B, VEGF-C, VEGF-D, VEGF-E, VEGF-F, and P1GF. VEGF-A primarily binds to two high affinity receptor tyrosine kinases, VEGFR-1 (Flt-1) and VEGFR-2 (Flk-1 KDR), the latter being the major transmitter of vascular endothelial cell mitogenic signals of VEGF-A.

As used herein, "immune checkpoint" refers to inhibitory signals that regulate the amplitude and quality of T cell receptor recognition of an antigen. In certain embodiments, the immune checkpoint is an inhibitory signal. In certain embodiments, the inhibitory signal is the interaction between PD-1 and PD-L1. In certain embodiments, the inhibitory signal is the interaction between CTLA-4 and CD80 or CD86 to displace CD28 binding. In certain embodiments the inhibitory signal is the interaction between LAG-3 and MHC class II molecules. In certain embodiments, the inhibitory signal is the interaction between TIM-3 and galectin 9.

As used herein, "immune checkpoint blocker" or "immune checkpoint inhibitor" or "immune checkpoint modulator" refers to a molecule that reduces, inhibits, interferes with or modulates one or more checkpoint proteins or other proteins in the immune system pathways. In certain embodiments, the immune checkpoint inhibitor prevents inhibitory signals associated with the immune checkpoint. In certain embodiments, the immune checkpoint inhibitor is an antibody, or fragment thereof, that disrupts inhibitory signaling associated with the immune checkpoint. In certain embodiments, the immune checkpoint inhibitor is a small molecule that disrupts inhibitory signaling. In certain embodiments, the immune checkpoint inhibitor is an antibody, fragment thereof, or antibody mimic, that prevents the interaction between checkpoint blocker proteins, e.g., an antibody, or fragment thereof, that prevents the interaction between PD-1 and PD-L1. In certain embodiments, the immune checkpoint inhibitor is an antibody, or fragment thereof, that prevents the interaction between CTLA-4 and CD80 or CD86. In certain embodiments, the immune checkpoint inhibitor is an antibody, or fragment thereof, that prevents the interaction between LAG-3 and MHC class II molecules. In certain embodiments the, the immune checkpoint inhibitor is an antibody, or fragment thereof, that prevents the interaction between TIM-3 and galectin9. The checkpoint blocker may also be in the form of the soluble form of the molecules (or mutation thereof) themselves, e.g., a soluble PD-L1 or PD-L1 fusion.

The term "ameliorating" refers to any therapeutically beneficial result in the treatment of a disease state, e.g., cancer, including prophylaxis, lessening in the severity or progression, remission, or cure thereof.

The term "in vivo" refers to processes that occur in a living organism.

The term "mammal" or "subject" or "patient" as used herein includes both humans and non-humans and include but is not limited to humans, non-human primates, canines, felines, murines, bovines, equines, and porcines.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FAST A, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al, J. Mol. Biol. 215:403-410 (1990). Software for performing BLAST analyses is publicly available through the National Center for Biotechnology Information website.

As used herein, the term "gly-ser polypeptide linker" refers to a peptide that consists of glycine and serine residues. An exemplary gly-ser polypeptide linker comprises the amino acid sequence Ser(Gly$_4$Ser)n. In one embodiment, n=1. In one embodiment, n=2. In another embodiment, n=3, i.e., Ser(Gly$_4$Ser)3. In another embodiment, n=4, i.e., Ser(Gly$_4$Ser)4. In another embodiment, n=5. In yet another embodiment, n=6. In another embodiment, n=7. In yet another embodiment, n=8. In another embodiment, n=9. In yet another embodiment, n=10. Another exemplary gly-ser polypeptide linker comprises the amino acid sequence (Gly$_4$Ser)n. In one embodiment, n=1. In one embodiment, n=2. In a preferred embodiment, n=3. In another embodiment, n=4. In another embodiment, n=5. In yet another embodiment, n=6. Another exemplary gly-ser polypeptide linker comprises the amino acid sequence (Gly$_3$Ser)n. In one embodiment, n=1. In one embodiment, n=2. In a preferred embodiment, n=3. In another embodiment, n=4. In another embodiment, n=5. In yet another embodiment, n=6. In some embodiments, the linker is GGGGS (SEQ ID NO:136), and can be used with any sequences disclosed herein. In some embodiments, the linker is GGGGSGGGGSGGGGS (SEQ ID NO:137), and can be used with any sequences disclosed herein.

As used herein, "half-life" refers to the time taken for the serum or plasma concentration of a polypeptide to reduce by 50%, in vivo, for example due to degradation and/or clearance or sequestration by natural mechanisms. The extended-PK IL-2 used herein is stabilized in vivo and its half-life increased by, e.g., fusion to HSA, MSA or Fc, through PEGylation, or by binding to serum albumin molecules (e.g., human serum albumin) which resist degradation and/or clearance or sequestration. The half-life can be determined in any manner known per se, such as by pharmacokinetic analysis. Suitable techniques will be clear to the person skilled in the art, and may for example generally involve the steps of suitably administering a suitable dose of the amino acid sequence or compound of the invention to a subject; collecting blood samples or other samples from said subject at regular intervals; determining the level or concentration of the amino acid sequence or compound of the invention in said blood sample; and calculating, from (a plot of) the data thus obtained, the time until the level or concentration of the amino acid sequence or compound of the invention has been reduced by 50% compared to the initial level upon dosing. Further details are provided in, e.g., standard handbooks, such as Kenneth, A. et al., Chemical Stability of Pharmaceuticals: A Handbook for Pharmacists and in Peters et al., Pharmacokinetic Analysis: A Practical Approach (1996). Reference is also made to Gibaldi, M. et al., Pharmacokinetics, 2$^{nd}$ Rev. Edition, Marcel Dekker (1982).

As used herein, a "small molecule" is a molecule with a molecular weight below about 500 Daltons.

As used herein, "therapeutic protein" refers to any polypeptide, protein, protein variant, fusion protein and/or fragment thereof which may be administered to a subject as a medicament. An exemplary therapeutic protein is an interleukin, e.g., IL-7.

As used herein, "synergy" or "synergistic effect" with regard to an effect produced by two or more individual components refers to a phenomenon in which the total effect produced by these components, when utilized in combination, is greater than the sum of the individual effects of each component acting alone.

The term "sufficient amount" or "amount sufficient to" means an amount sufficient to produce a desired effect, e.g., an amount sufficient to reduce the size of a tumor.

The term "therapeutically effective amount" is an amount that is effective to ameliorate a symptom of a disease. A therapeutically effective amount can be a "prophylactically effective amount" as prophylaxis can be considered therapy.

As used herein, "combination therapy" embraces administration of each agent or therapy in a sequential manner in a regiment that will provide beneficial effects of the combination and co-administration of these agents or therapies in a substantially simultaneous manner. Combination therapy also includes combinations where individual elements may be administered at different times and/or by different routes but which act in combination to provide a beneficial effect by co-action or pharmacokinetic and pharmacodynamics effect of each agent or tumor treatment approaches of the combination therapy.

As used herein, "about" will be understood by persons of ordinary skill and will vary to some extent depending on the context in which it is used. If there are uses of the term which are not clear to persons of ordinary skill given the context in which it is used, "about" will mean up to plus or minus 10% of the particular value.

It must be noted that, as used in the specification and the appended claims, the singular forms "a," "an" and "the" include plural referents unless the context clearly dictates otherwise.

Various aspects described herein are described in further detail in the following subsections.

III. IL-2 and Extended-PK IL-2

The integrin-binding polypeptide-Fc fusions of the invention can be used in absence of IL-2 and/or extended IL-2. In some embodiments, the integrin-binding polypeptide-Fc fusions of the invention can be used in combination with IL-2 and do not require the use of an extended half-life IL-2. In some embodiments, integrin-binding polypeptide-Fc fusions can also be used in combination with half-life extended IL-2.

Interleukin-2 (IL-2) is a cytokine that induces proliferation of antigen-activated T cells and stimulates natural killer (NK) cells. The biological activity of IL-2 is mediated through a multi-subunit IL-2 receptor complex (IL-2R) of three polypeptide subunits that span the cell membrane: p55 (IL-2Ra, the alpha subunit, also known as CD25 in humans), p75 (IL-2Rβ, the beta subunit, also known as CD 122 in humans) and p64 (IL-2Ry, the gamma subunit, also known as CD 132 in humans). T cell response to IL-2 depends on a variety of factors, including: (1) the concentration of IL-2; (2) the number of IL-2R molecules on the cell surface; and (3) the number of IL-2R occupied by IL-2 (i.e., the affinity of the binding interaction between IL-2 and IL-2R (Smith, "Cell Growth Signal Transduction is Quantal" In Receptor Activation by Antigens, Cytokines, Hormones, and Growth Factors 766:263-271, 1995)). The IL-2TL-2R complex is internalized upon ligand binding and the different components undergo differential sorting. IL-2Ra is recycled to the cell surface, while IL-2 associated with the IL-2TL-2Rpγ complex is routed to the lysosome and degraded. When administered as an intravenous (i.v.) bolus, IL-2 has a rapid systemic clearance (an initial clearance phase with a half-life of 12.9 minutes followed by a slower clearance phase with a half-life of 85 minutes) (Konrad et al., Cancer Res. 50:2009-2017, 1990).

Thus, in some embodiments, IL-2 therapy, such as systemic IL-2, is administered to a subject in an effective amount in combination with an integrin-binding-Fc fusion protein, and optionally an immune checkpoint inhibitor.

However, outcomes of systemic IL-2 administration in cancer patients are far from ideal. While 15 to 20 percent of patients respond objectively to high-dose IL-2, the great majority do not, and many suffer severe, life-threatening side effects, including nausea, confusion, hypotension, and septic shock. The severe toxicity associated with IL-2 treatment is largely attributable to the activity of natural killer (NK) cells. NK cells express the intermediate-affinity receptor, IL-2Rβ$y_c$, and thus are stimulated at nanomolar concentrations of IL-2, which do in fact result in patient sera during high-dose IL-2 therapy. Attempts to reduce serum concentration, and hence selectively stimulate IL-2Raβ$y_c$-bearing cells, by reducing dose and adjusting dosing regimen have been attempted, and while less toxic, such treatments were also less efficacious. Given the toxicity issues associated with high dose IL-2 cancer therapy, numerous groups have attempted to improve anti-cancer efficacy of IL-2 by simultaneously administering therapeutic antibodies. Yet, such efforts have been largely unsuccessful, yielding no additional or limited clinical benefit compared to IL-2 therapy alone. Accordingly, novel IL-2 therapies are needed to more effectively combat various cancers.

Applicants recently discovered that the ability of IL-2 to control tumors in various cancer models could be substantially increased by attaching IL-2 to a pharmacokinetic modifying group. The resulting molecule, hereafter referred to as "extended-pharmacokinetic (PK) IL-2," has a prolonged circulation half-life relative to free IL-2. The prolonged circulation half-life of extended-PK IL-2 permits in vivo serum IL-2 concentrations to be maintained within a therapeutic range, leading to the enhanced activation of many types of immune cells, including T cells. Because of its favorable pharmacokinetic profile, extended-PK IL-2 can be dosed less frequently and for longer periods of time when compared with unmodified IL-2. Extended-PK IL-2 is described in detail in International Patent Application NO. PCT/US2013/042057, filed May 21, 2013, and claiming the benefit of priority to U.S. Provisional Patent Application NO. 61/650,277, filed May 22, 2012. The entire contents of the foregoing applications are incorporated by reference herein.

a. IL-2 and Mutants Thereof

In certain embodiments, an effective amount of human IL-2 is administered systemically. In some embodiments, an effective amount of an extended-PK IL-2 is administered systemically. In one embodiment, the IL-2 is a human recombinant IL-2 such as Proleukin® (aldesleukin). Proleukin® is a human recombinant interleukin-2 product produced in E. coli. Proleukin® differs from the native interleukin-2 in the following ways: a) it is not glycosylated; b) it has no N-terminal alanine; and c) it has serine substituted for cysteine at amino acid positions 125. Proleukin® exists as biologicially active, noncovalently bound microaggregates with an average size of 27 recombinant interleukin-2 molecules. Proleukin® (aldesleukin) is administered by intravenous infusion. In some aspects, the IL-2 portion of the extended-PK IL-2 is wild-type IL-2 (e.g., human IL-2 in its precursor form (SEQ ID NO: 33 from International Patent Publication WO 2016/025642, incorporated herein by reference in its entirety) or mature IL-2 (SEQ ID NO: 35 from International Patent Publication WO 2016/025642, incorporated herein by reference in its entirety)).

In certain embodiments, the extended-PK IL-2 is mutated such that it has an altered affinity (e.g., a higher affinity) for the IL-2R alpha receptor compared with unmodified IL-2.

Site-directed mutagenesis can be used to isolate IL-2 mutants that exhibit high affinity binding to CD25, i.e., IL-2Ra, as compared to wild-type IL-2. Increasing the affinity of IL-2 for IL-2Ra at the cell surface will increase receptor occupancy within a limited range of IL-2 concentration, as well as raise the local concentration of IL-2 at the cell surface.

In certain embodiments, the invention features IL-2 mutants, which may be, but are not necessarily, substantially purified and which can function as high affinity CD25 binders. IL-2 is a T cell growth factor that induces proliferation of antigen-activated T cells and stimulation of NK cells. Exemplary IL-2 mutants which are high affinity binders include those described in WO 2013/177187A2 (herein incorporated by reference in its entirety), such as those with amino acid sequences set forth in SEQ ID Nos: 7, 23, 25, 27, 29, and 31. Further exemplary IL-2 mutants with increased affinity for CD25 are disclosed in U.S. Pat. No. 7,569,215, the contents of which are incorporated herein by reference. In one embodiment, the IL-2 mutant does not bind to CD25, e.g., those with amino acid sequences set forth in SEQ ID Nos: 9 and 11.

IL-2 mutants include an amino acid sequence that is at least 80% identical to SEQ ID NO: 33 (from International Patent Publication WO 2016/025642, incorporated herein by reference in its entirety) that bind CD25. For example, an IL-2 mutant can have at least one mutation (e.g., a deletion, addition, or substitution of 1, 2, 3, 4, 5, 6, 7, 8, 9, 10, 11, 12, 13, 14, 15, 16, 17, 18, 19, 20, or more amino acid residues) that increases the affinity for the alpha subunit of the IL-2 receptor relative to wild-type IL-2. It should be understood that mutations identified in mouse IL-2 may be made at corresponding residues in full length human IL-2 (nucleic acid sequence (accession: NM000586) of SEQ ID NO: 32 (from International Patent Publication WO 2016/025642, incorporated herein by reference in its entirety); amino acid sequence (accession: P60568 of SEQ ID NO: 33 from International Patent Publication WO 2016/025642, incorporated herein by reference in its entirety) or human IL-2 without the signal peptide (nucleic acid sequence of SEQ ID NO: 34 (from International Patent Publication WO 2016/025642, incorporated herein by reference in its entirety); amino acid sequence of SEQ ID NO: 35 (from International Patent Publication WO 2016/025642, incorporated herein by reference in its entirety). In some embodiments, the signal peptide is MTRLTVLALLAGLLASSRA (SEQ ID NO:138), and can be used with any sequences disclosed herein. Accordingly, in certain embodiments, the IL-2 moiety of the extended-PK IL-2 is human IL-2. In other embodiments, the IL-2 moiety of the extended-PK IL-2 is a mutant human IL-2.

IL-2 mutants can be at least or about 50%, at least or about 65%, at least or about 70%, at least or about 80%, at least or about 85%, at least or about 87%, at least or about 90%, at least or about 95%, at least or about 97%, at least or about 98%, or at least or about 99% identical in amino acid sequence to wild-type IL-2 (in its precursor form or, preferably, the mature form). The mutation can consist of a change in the number or content of amino acid residues. For example, the IL-2 mutants can have a greater or a lesser number of amino acid residues than wild-type IL-2. Alternatively, or in addition, IL-2 mutants can contain a substitution of one or more amino acid residues that are present in the wild-type IL-2.

By way of illustration, a polypeptide that includes an amino acid sequence that is at least 95% identical to a reference amino acid sequence of SEQ ID NO: 33 is a polypeptide that includes a sequence that is identical to the reference sequence except for the inclusion of up to five alterations of the reference amino acid of SEQ ID NO: 33 (from International Patent Publication WO 2016/025642, incorporated herein by reference in its entirety). For example, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino (N-) or carboxy (C-) terminal positions of the reference amino acid sequence or anywhere between those terminal positions, interspersed either individually among residues in the reference sequence or in one or more contiguous groups within the reference sequence.

The substituted amino acid residue(s) can be, but are not necessarily, conservative substitutions, which typically include substitutions within the following groups: glycine, alanine; valine, isoleucine, leucine; aspartic acid, glutamic acid; asparagines, glutamine; serine, threonine; lysine, arginine; and phenylalanine, tyrosine. These mutations can be at amino acid residues that contact IL-2Ra.

In general, the polypeptides used in the practice of the instant invention will be synthetic, or produced by expression of a recombinant nucleic acid molecule. In the event the polypeptide is an extended-PK IL-2 (e.g., a fusion protein containing at least IL-2 and a heterologous polypeptide, such as a hexa-histidine tag or hemagglutinin tag or an Fc region or human serum albumin), it can be encoded by a hybrid nucleic acid molecule containing one sequence that encodes IL-2 and a second sequence that encodes all or part of the heterologous polypeptide.

The techniques that are required to make IL-2 mutants are routine in the art, and can be performed without resort to undue experimentation by one of ordinary skill in the art. For example, a mutation that consists of a substitution of one or more of the amino acid residues in IL-2 can be created using a PCR-assisted mutagenesis technique (e.g., as known in the art and/or described herein for the creation of IL-2 mutants). Mutations that consist of deletions or additions of amino acid residues to an IL-2 polypeptide can also be made with standard recombinant techniques. In the event of a deletion or addition, the nucleic acid molecule encoding IL-2 is simply digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

In addition to generating IL-2 mutants via expression of nucleic acid molecules that have been altered by recombinant molecular biological techniques, IL-2 mutants can be chemically synthesized. Chemically synthesized polypeptides are routinely generated by those of skill in the art.

As noted above, IL-2 can also be prepared as fusion or chimeric polypeptides that include IL-2 and a heterologous polypeptide (i.e., a polypeptide that is not IL-2). The heterologous polypeptide can increase the circulating half-life of the chimeric polypeptide in vivo, and may, therefore, further enhance the properties of IL-2. As discussed in further detail infra, the polypeptide that increases the circulating half-life may be serum albumin, such as human or mouse serum albumin.

In other embodiments, the chimeric polypeptide can include IL-2 and a polypeptide that functions as an antigenic tag, such as a FLAG sequence. FLAG sequences are recognized by biotinylated, highly specific, anti-FLAG antibodies, as described herein (see also Blanar et al, Science 256: 1014, 1992; LeClair et al, Proc. Natl. Acad. Sci. USA 89:8145, 1992). In certain embodiments, the chimeric polypeptide further comprises a C-terminal c-myc epitope tag.

Chimeric polypeptides can be constructed using no more than conventional molecular biological techniques, which are well within the ability of those of ordinary skill in the art to perform.

b. Nucleic Acid Molecules Encoding IL-2

IL-2, either alone or as a part of a chimeric polypeptide, such as those described herein, can be obtained by expression of a nucleic acid molecule. Thus, nucleic acid molecules encoding polypeptides containing IL-2 or an IL-2 mutant are considered within the scope of the invention, such as those with nucleic acid sequences set forth in SEQ ID Nos: 4, 6, 8, 10, 12, 14, 16, 18, 20, 22, 24, 26, 28, 30, 32, and 34. Just as IL-2 mutants can be described in terms of their identity with wild-type IL-2, the nucleic acid molecules encoding them will necessarily have a certain identity with those that encode wild-type IL-2. For example, the nucleic acid molecule encoding an IL-2 mutant can be at least 50%, at least 65%, preferably at least 75%, more preferably at least 85%, and most preferably at least 95% (e.g., 99%) identical to the nucleic acid encoding full length wild-type IL-2 (e.g., SEQ ID NO: 32 from International Patent Publication WO 2016/025642, incorporated herein by reference in its entirety) or wild-type IL-2 without the signal peptide (e.g., SEQ ID NO: 34 from International Patent Publication WO 2016/025642, incorporated herein by reference in its entirety).

The nucleic acid molecules of the invention can contain naturally occurring sequences, or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

The nucleic acid molecules are not limited to sequences that encode polypeptides; some or all of the non-coding sequences that lie upstream or downstream from a coding sequence (e.g., the coding sequence of IL-2) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

The isolated nucleic acid molecules can include fragments not found as such in the natural state. Thus, the invention encompasses use of recombinant molecules, such as those in which a nucleic acid sequence (for example, a sequence encoding an IL-2 mutant) is incorporated into a vector (e.g., a plasmid or viral vector) or into the genome of a heterologous cell (or the genome of a homologous cell, at a position other than the natural chromosomal location).

As described above, IL-2 mutants of the invention may exist as a part of a chimeric polypeptide. In addition to, or in place of, the heterologous polypeptides described above, a nucleic acid molecule of the invention can contain sequences encoding a "marker" or "reporter." Examples of marker or reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-hsphotransferase (HPH), thymidine kinase (TK), lacz (encoding β-galactosidase), and xanthine guanine phosphoribosyl transferase (XGPRT). As with many of the standard procedures associated with the practice of the invention, skilled artisans will be aware of additional useful reagents, for example, of additional sequences that can serve the function of a marker or reporter.

The nucleic acid molecules of the invention can be obtained by introducing a mutation into IL-2-encoding DNA obtained from any biological cell, such as the cell of a mammal. Thus, the nucleic acids used herein (and the polypeptides they encode) can be those of a mouse, rat, guinea pig, cow, sheep, horse, pig, rabbit, monkey, baboon, dog, or cat. Typically, the nucleic acid molecules will be those of a human.

IV. Extended-PK Groups

As described supra, IL-2 or mutant IL-2 is fused to an extended-PK group, which increases circulation half-life. Non-limiting examples of extended-PK groups are described infra. It should be understood that other PK groups that increase the circulation half-life of IL-2, or variants thereof, are also applicable to extended-PK IL-2.

In certain embodiments, the serum half-life of extended-PK IL-2 is increased relative to IL-2 alone (i.e., IL-2 not fused to an extended-PK group). In certain embodiments, the serum half-life of extended-PK IL-2 is at least 20, 40, 60, 80, 100, 120, 150, 180, 200, 400, 600, 800, or 1000% longer relative to the serum half-life of IL-2 alone. In other embodiments, the serum half-life of the extended-PK IL-2 is at least 1.5-fold, 2-fold, 2.5-fold, 3-fold, 3.5 fold, 4-fold, 4.5-fold, 5-fold, 6-fold, 7-fold, 8-fold, 10-fold, 12-fold, 13-fold, 15-fold, 17-fold, 20-fold, 22-fold, 25-fold, 27-fold, 30-fold, 35-fold, 40-fold, or 50-fold greater than the serum half-life of IL-2 alone. In certain embodiments, the serum half-life of the extended-PK IL-2 is at least 10 hours, 15 hours, 20 hours, 25 hours, 30 hours, 35 hours, 40 hours, 50 hours, 60 hours, 70 hours, 80 hours, 90 hours, 100 hours, 110 hours, 120 hours, 130 hours, 135 hours, 140 hours, 150 hours, 160 hours, or 200 hours.

a. Serum Albumin and Serum Albumin Binding Proteins

In certain embodiments, the extended-PK group is a serum albumin, or fragments thereof. Methods of fusing serum albumin to proteins are disclosed in, e.g., US2010/0144599, US2007/0048282, and US2011/0020345, which are herein incorporated by reference in their entirety. In certain embodiments, the extended-PK group is HSA, or variants or fragments thereof, such as those disclosed in U.S. Pat. No. 5,876,969, WO 2011/124718, WO 2013/075066, and WO 2011/0514789.

In certain embodiments, the extended-PK group is a serum albumin binding protein such as those described in US2005/0287153, US2007/0003549, US2007/0178082, US2007/0269422, US2010/0113339, WO2009/083804, and WO2009/133208, which are herein incorporated by reference in their entirety.

b. PEGylation

In certain embodiments, an extended-PK IL-2 used herein includes a polyethylene glycol (PEG) domain. PEGylation is well known in the art to confer increased circulation half-life to proteins. Methods of PEGylation are well known and disclosed in, e.g., U.S. Pat. Nos. 7,610,156, 7,847,062, all of which are hereby incorporated by reference.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: X-0(CH2CH$_2$O)$_n$-iCH2CH$_2$OH, where n is 20 to 2300 and X is H or a terminal modification, e.g., a $C_1$.4 alkyl. In one embodiment, the PEG of the invention terminates on one end with hydroxy or methoxy, i.e., X is H or CH3 ("methoxy PEG"). PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462, both of which are hereby incorporated by reference. One form of PEGs includes two PEG side-chains (PEG2) linked via the primary amino groups of a lysine (Monfardini et al., Bioconjugate Chem 1995; 6:62-9).

In one embodiment, pegylated IL-2 is produced by site-directed pegylation, particularly by conjugation of PEG to a cysteine moiety at the N- or C-terminus. A PEG moiety may also be attached by other chemistry, including by conjugation to amines.

PEG conjugation to peptides or proteins generally involves the activation of PEG and coupling of the activated PEG-intermediates directly to target proteins/peptides or to a linker, which is subsequently activated and coupled to target proteins/peptides (see Abuchowski et al, JBC 1977; 252:3571 and JBC 1977; 252:3582, and Harris et. al, in: Polyethylene glycol) Chemistry: Biotechnical and Biomedical Applications; (J. M. Harris ed.) Plenum Press: New York, 1992; Chap. 21 and 22).

A variety of molecular mass forms of PEG can be selected, e.g., from about 1,000 Daltons (Da) to 100,000 Da (n is 20 to 2300), for conjugating to IL-2. The number of repeating units "n" in the PEG is approximated for the molecular mass described in Daltons. It is preferred that the combined molecular mass of PEG on an activated linker is suitable for pharmaceutical use. Thus, in one embodiment, the molecular mass of the PEG molecules does not exceed 100,000 Da. For example, if three PEG molecules are attached to a linker, where each PEG molecule has the same molecular mass of 12,000 Da (each n is about 270), then the total molecular mass of PEG on the linker is about 36,000 Da (total n is about 820). The molecular masses of the PEG attached to the linker can also be different, e.g., of three molecules on a linker two PEG molecules can be 5,000 Da each (each n is about 110) and one PEG molecule can be 12,000 Da (n is about 270).

One skilled in the art can select a suitable molecular mass for PEG, e.g., based on how the pegylated IL-2 will be used therapeutically, the desired dosage, circulation time, resistance to proteolysis, immunogenicity, and other considerations. For a discussion of PEG and its use to enhance the properties of proteins, see N. V. Katre, Advanced Drug Delivery Reviews 1993; 10:91-114.

In one embodiment of the invention, PEG molecules may be activated to react with amino groups on IL-2 such as with lysines (Bencham C. O. et al., Anal. Biochem., 131, 25 (1983); Veronese, F. M. et al, Appl. Biochem., 11, 141 (1985); Zalipsky, S. et al, Polymeric Drugs and Drug Delivery Systems, adrs 9-110 ACS Symposium Series 469 (1999); Zalipsky, S. et al, Europ. Polym. J., 19, 1177-1183 (1983); Delgado, C. et al, Biotechnology and Applied Biochemistry, 12, 119-128 (1990)).

In one embodiment, carbonate esters of PEG are used to form the PEG-IL-2 conjugates. N,N'-disuccinimidylcarbonate (DSC) may be used in the reaction with PEG to form active mixed PEG-succinimidyl carbonate that may be subsequently reacted with a nucleophilic group of a linker or an amino group of IL-2 (see U.S. Pat. Nos. 5,281,698 and 5,932,462). In a similar type of reaction, 1,1'-(dibenzotriazolyl)carbonate and di-(2-pyridyl)carbonate may be reacted with PEG to form PEG-benzotriazolyl and PEG-pyridyl mixed carbonate (U.S. Pat. No. 5,382,657), respectively.

Pegylation of IL-2 can be performed according to the methods of the state of the art, for example by reaction of IL-2 with electrophilically active PEGs (Shearwater Corp., USA, www.shearwatercorp.com). Preferred PEG reagents are, e.g., N-hydroxysuccinimidyl propionates (PEG-SPA), butanoates (PEG-SBA), PEG-succinimidyl propionate or branched N-hydroxysuccinimides such as mPEG2-NHS (Monfardini, C, et al., Bioconjugate Chem. 6 (1995) 62-69).

In another embodiment, PEG molecules may be coupled to sulfhydryl groups on IL-2 (Sartore, L., et al., Appl. Biochem. Biotechnol., 27, 45 (1991); Morpurgo et al., Biocon. Chem., 7, 363-368 (1996); Goodson et al, Bio/Technology (1990) 8, 343; U.S. Pat. No. 5,766,897). U.S. Pat. Nos. 6,610,281 and 5,766,897 describe exemplary reactive PEG species that may be coupled to sulfhydryl groups.

In certain embodiments where PEG molecules are conjugated to cysteine residues on IL-2 the cysteine residues are native to IL-2 whereas in other embodiments, one or more cysteine residues are engineered into IL-2. Mutations may be introduced into the coding sequence of IL-2 to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or a protein.

In another embodiment, pegylated IL-2 comprises one or more PEG molecules covalently attached to a linker.

In some embodiments, the pegylated IL-2 is NKTR-214. NKTR-12 is an IL-2 conjugated to 6 releasable polyethylene glycol PEG chains. In vivo, the PEG chains slowly release to generate active IL-2 conjugates, as described in Charych, D. H., et al., Clinical Cancer Res.; 22(3): 680-690 (2016).

In one embodiment, IL-2 is pegylated at the C-terminus. In a specific embodiment, a protein is pegylated at the C-terminus by the introduction of C-terminal azido-methionine and the subsequent conjugation of a methyl-PEG-triarylphosphine compound via the Staudinger reaction. This C-terminal conjugation method is described in Cazalis et al., C-Terminal Site-Specific PEGylation of a Truncated Thrombomodulin Mutant with Retention of Full Bioactivity, Bioconjug Chem. 2004; 15(5): 1005-1009.

Monopegylation of IL-2 can also be achieved according to the general methods described in WO 94/01451. WO 94/01451 describes a method for preparing a recombinant polypeptide with a modified terminal amino acid alpha-carbon reactive group. The steps of the method involve forming the recombinant polypeptide and protecting it with one or more biologically added protecting groups at the N-terminal alpha-amine and C-terminal alpha-carboxyl. The polypeptide can then be reacted with chemical protecting agents to selectively protect reactive side chain groups and thereby prevent side chain groups from being modified. The polypeptide is then cleaved with a cleavage reagent specific for the biological protecting group to form an unprotected terminal amino acid alpha-carbon reactive group. The unprotected terminal amino acid alpha-carbon reactive group is modified with a chemical modifying agent. The side chain protected terminally modified single copy polypeptide is then deprotected at the side chain groups to form a terminally modified recombinant single copy polypeptide. The number and sequence of steps in the method can be varied to achieve selective modification at the N- and/or C-terminal amino acid of the polypeptide.

The ratio of IL-2 to activated PEG in the conjugation reaction can be from about 1:0.5 to 1:50, between from about 1:1 to 1:30, or from about 1:5 to 1:15. Various aqueous buffers can be used to catalyze the covalent addition of PEG to IL-2, or variants thereof. In one embodiment, the pH of a buffer used is from about 7.0 to 9.0. In another embodiment, the pH is in a slightly basic range, e.g., from about 7.5 to 8.5. Buffers having a pKa close to neutral pH range may be used, e.g., phosphate buffer.

Conventional separation and purification techniques known in the art can be used to purify PEGylated IL-2, such as size exclusion (e.g. gel filtration) and ion exchange chromatography. Products may also be separated using SDS-PAGE. Products that may be separated include mono-, di-, tri- poly- and un-pegylated IL-2 as well as free PEG. The percentage of mono-PEG conjugates can be controlled by pooling broader fractions around the elution peak to increase the percentage of mono-PEG in the composition.

In one embodiment, PEGylated IL-2 of the invention contains one, two or more PEG moieties. In one embodiment, the PEG moiety(ies) are bound to an amino acid residue which is on the surface of the protein and/or away from the surface that contacts CD25. In one embodiment, the combined or total molecular mass of PEG in PEG-IL-2 is from about 3,000 Da to 60,000 Da, optionally from about 10,000 Da to 36,000 Da. In one embodiment, PEG in pegylated IL-2 is a substantially linear, straight-chain PEG.

In one embodiment, PEGylated IL-2 of the invention will preferably retain at least 25%, 50%, 60%, 70%, 80%, 85%, 90%, 95% or 100% of the biological activity associated with the unmodified protein. In one embodiment, biological activity refers to the ability to bind CD25. The serum clearance rate of PEG-modified IL-2 may be decreased by about 10%, 20%, 30%, 40%, 50%, 60%, 70%, 80%, or even 90%, relative to the clearance rate of the unmodified IL-2. PEG-modified IL-2 may have a circulation half-life which is enhanced relative to the half-life of unmodified IL-2. The half-life of PEG-IL-2, or variants thereof, may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of unmodified IL-2. In certain embodiments, the protein half-life is determined in vitro, such as in a buffered saline solution or in serum. In other embodiments, the protein half-life is an in vivo circulation half-life, such as the half-life of the protein in the serum or other bodily fluid of an animal.

c. Other Extended-PK Groups

In certain embodiments, the extended-PK group is transferrin, as disclosed in U.S. Pat. Nos. 7,176,278 and 8,158,579, which are herein incorporated by reference in their entirety.

In certain embodiments, the extended-PK group is a serum immunoglobulin binding protein such as those disclosed in US2007/0178082, which is herein incorporated by reference in its entirety.

In certain embodiments, the extended-PK group is a fibronectin (Fn)-based scaffold domain protein that binds to serum albumin, such as those disclosed in US2012/0094909, which is herein incorporated by reference in its entirety. Methods of making fibronectin-based scaffold domain proteins are also disclosed in US2012/0094909. A non-limiting example of a Fn3-based extended-PK group is Fn3(HSA), i.e., a Fn3 protein that binds to human serum albumin.

d. Fc Domains

In certain embodiments, an extended-PK IL-2 includes an Fc domain, as described in International Patent Publication No. WO 2013/177187. The Fc domain does not contain a variable region that binds to antigen. Fc domains useful for producing the extended-PK IL-2 described herein may be obtained from a number of different sources. In certain embodiments, an Fc domain of the extended-PK IL-2 is derived from a human immunoglobulin. In a certain embodiment, the Fc domain is from a human IgG1 constant region (for example, SEQ ID NO:126). The Fc domain of human IgG1 is set forth in SEQ ID NO: 126. In certain embodiments, the Fc domain of human IgG1 does not have the upper hinge region (SEQ ID NO: 3 from International Patent Publication WO 2016/025642, incorporated herein by reference in its entirety). It is understood, however, that the Fc domain may be derived from an immunoglobulin of another mammalian species, including for example, a rodent (e.g. a mouse, rat, rabbit, guinea pig) or non-human primate (e.g. chimpanzee, macaque) species. Moreover, the Fc domain or portion thereof may be derived from any immunoglobulin class, including IgM, IgG, IgD, IgA, and IgE, and any immunoglobulin isotype, including IgG1 (for example, SEQ ID NO:126), IgG2 for example, SEQ ID NO:127, IgG3 (for example, SEQ ID NO:128), and IgG4 (for example, SEQ ID NO:129).

In some aspects, an extended-PK IL-2 includes a mutant Fc domain. In some aspects, an extended-PK IL-2 includes a mutant, IgG1 Fc domain. In some aspects, a mutant Fc domain comprises one or more mutations in the hinge, $CH_2$, and/or $CH_3$ domains. In some aspects, a mutant Fc domain includes a D265A mutation.

In one embodiment, the extended-PK IL-2 of the invention lacks one or more constant region domains of a complete Fc region, i.e., they are partially or entirely deleted. In certain embodiments, the extended-PK IL-2 of the invention will lack an entire $CH_2$ domain. In certain embodiments, the extended-PK IL-2 of the invention comprise $CH_2$ domain-deleted Fc regions derived from a vector (e.g., from IDEC Pharmaceuticals, San Diego) encoding an IgG1 human constant region domain (see, e.g., WO 02/060955A2 and WO 02/096948A2).

This exemplary vector is engineered to delete the CH2 domain and provide a synthetic vector expressing a domain-deleted IgG1 constant region. It will be noted that these exemplary constructs are preferably engineered to fuse a binding $CH_3$ domain directly to a hinge region of the respective Fc domain.

V. Integrin and Knottin Polypeptides and Fc-Fusions

Integrins are a family of extracellular matrix adhesion receptors that regulate a diverse array of cellular functions crucial to the initiation, progression and metastasis of solid tumors. The importance of integrins in tumor progression has made them an appealing target for cancer therapy and allows for the treatment of a variety of cancer types. The integrins present on cancerous cells include $\alpha_v\beta_1$, $\alpha_v\beta_3$, $\alpha_v\beta_5$, $\alpha_v\beta_6$, and $\alpha_5\beta_1$.

Knottin proteins are small compact peptides that have high thermal and proteolytic stability and are tolerant to mutagenesis, making them good molecular scaffolds. These peptides contain at least 3 disulfide bonds that form a "knot" core. They also contain several loops exposed to the surface, allowing these loops to bind targets. These loops can be engineered to bind specific targets with high affinity, making them a useful tool for therapy.

The present invention involves the use of a knottin polypeptide scaffold engineered with an RGD sequence capable of binding integrins, fused to an Fc donor, which confers a therapeutic benefit (also referred to as "knottin-Fc"), herein collectively referred to as an integrin-binding polypeptide-Fc fusion. As described supra, Fc fragments have been added to proteins and/or therapeutics to extend half-life. In the context of integrin-binding polypeptide-Fc fusion as used herein, the effector function of Fc contributes to the treatment of a variety of cancers. In some embodiments, this effect can find further use and/or be enhanced when used in conjunction with IL-2, including Proleukin and/or extended-PK IL-2. In some embodiments, an integrin-binding polypeptide-Fc fusion (also sometimes referred to as a knottin-Fc) that binds three integrins simultaneously, is used for example, an integrin-binding polypeptide-Fc fusion that is selected from the group consisting of NOD201 (SEQ ID NO:139), NOD203 (SEQ ID NO:142), and NOD204 (SEQ ID NO:143). In some embodiments, the integrin-binding polypeptide-Fc fusion is NOD201 (SEQ ID NO:139). In some embodiments, the integrin-binding polypeptide-Fc fusion is NOD203 (SEQ ID NO:142). In some embodiments, the integrin-binding polypeptide-Fc fusion is NOD204 (SEQ ID NO:143). In some embodiments, the integrin-binding polypeptide-Fc fusion comprises GCPRPRGDNPPLTCSQDSDCLAGCVCGPNGFCG, 2.5F, SEQ ID NO:130; GCPRPRGDNPPLTCKQDSDCLAGCVCGPNGFCG, 2.5FmodK, SEQ ID NO:131; GCPRPRGDNPPLTCSQDSDCLAGCVCGPNGFCGGGGGS (SEQ ID NO:132); GCPRPRGDNPPLTCKQDSDCLAGCVCGPNGFCGGGGGS (SEQ ID NO:133); GCPRPRGDNPPLTCSQDSDCLAGCVCGPNGFCGGGGGSGGGGSGGGGS (SEQ ID NO:134); or GCPRPRGDNPPLTCKQDSDCLAGCVCGPNGFCGGGGGSGGGGSGGGGS (SEQ ID NO:135), operatively linked to an Fc domain. In some embodiments, the integrin-binding polypeptide-Fc fusion comprises GCPRPRGDNPPLTCSQDSDCLAGCVCGPNGFCG, 2.5F, SEQ ID NO:130; GCPRPRGDNPPLTCKQDSDCLAGCVCGPNGFCG, 2.5FmodK, SEQ ID NO:131; GCPRPRGDNPPLTCSQDSDCLAGCVCGPNGFCGGGGGS (SEQ ID NO:132); GCPRPRGDNPPLTCKQDSDCLAGCVCGPNGFCGGGGGS (SEQ ID NO:133), GCPRPRGDNPPLTCSQDSDCLAGCVCGPNGFCGGGGGSGGGGSGGGGS (SEQ ID NO:134); or GCPRPRGDNPPLTCKQDSDCLAGCVCGPNGFCGGGGGSGGGGSGGGGS (SEQ ID NO:135) operatively linked to an Fc domain, wherein said Fc domains is from IgG1, IgG2, IgG3, and IgG4, including mouse or human. Exemlary IgG sequences are known in the art and can be found in FIG. 1 and Table 1 above. Selected sequences of importance are also copied below:

```
Sequence Set 1:
Signal peptide:
                                            (SEQ ID NO: 138)
MTRLTVLALLAGLLASSRA NOD201: human Fc
                                            (SEQ ID NO: 139)
GCPRPRGDNPPLTCSQDSDCLAGCVCGPNGFCGEPKSSDKTHTCPPCPAP

ELLGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHEAL

HNHYTQKSLSLSPG

Sequence Set 2:
Signal peptide:
                                            (SEQ ID NO: 138)
MTRLTVLALLAGLLASSRA NOD201X (control sequence - NOD201 with scrambled
seq, human Fc)
                                            (SEQ ID NO: 140)
GCVTGRDGSPASSCSQDSDCLAGCVCGPNGFCGEPKSSDKTHTCPPCPAP

ELLGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVEWE

NGQPENNYKTTPPVLDSDGSFFLYSKLTVDKSRWQQGNVFSCSVMHEALH

NHYTQKSLSLSPG

Theoretical pI/Mw: 6.19 / 58065.44

Sequence Set 3:
Signal peptide:
                                            (SEQ ID NO: 138)
MTRLTVLALLAGLLASSRA NOD201M (NOD201 with murine Fc domain)
                                            (SEQ ID NO: 141)
GCPRPRGDNPPLTCSQDSDCLAGCVCGPNGFCGEPRVPITQNPCPPLKEC

PPCAAPDLLGGPSVFIFPPKIKDVLMISLSPMVTCVVVDVSEDDPDVQIS

WFVNNVEVHTAQTQTHREDYNSTLRVVSALPIQHQDWMSGKEFKCKVNNR

ALPSPIEKTISKPRGPVRAPQVYVLPPPAEEMTKKEFSLTCMITGFLPAE

IAVDWTSNGRTEQNYKNTATVLDSDGSYFMYSKLRVQKSTWERGSLFACS

VVHEGLHNHLTTKTISRSLG

Theoretical pI/Mw: 6.34 / 59357.92
Ext. coefficient 60525
Abs 0.1% (= 1 g/l) 1.020, assuming all pairs of
Cys residues form cystines Sequence Set 4:
NOD203 complete (with Gly4Ser linker - bold/
underlined)
                                            (SEQ ID NO: 142)
GCPRPRGDNPPLTCSQDSDCLAGCVCGPNGFCGGGGGSEPKSSDKTHTCP

PCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKA
```

```
-continued
LPAPIEKTISKAKGQPREPQVYTLPPSRDELTKNQVSLTCLVKGFYPSDI

AVEWESNGQPENNYKTTPPVLDSDGSFFLYSKLTVDKSRWQQGNVFSCSV

MHEALHNHYTQKSLSLSPG

Sequence Set 5:
NOD204 complete (with [Gly4Ser]3 linker - bold/
underlined)
                                        (SEQ ID NO: 143)
GCPRPRGDNPPLTCSQDSDCLAGCVCGPNGFCGGGGSGGGGSGGGGSEP

KSSDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPG
```

In some embodiments, the integrin-binding polypeptide-Fc fusions bind to one more integrins selected from $\alpha_v\beta_1 \alpha_v\beta_3$, $\alpha_v\beta_5$, $\alpha_v\beta_6$, and $\alpha_5\beta_1$ with high affinity. In some embodiments, the integrin-binding polypeptide-Fc fusions bind to two integrins selected from $\alpha_v\beta_1$, $\alpha_v\beta_3$, $\alpha_v\beta_5$, $\alpha_v\beta_6$, and $\alpha_5\beta_1$ with high affinity. In some embodiments, the integrin-binding polypeptide-Fc fusions bind to three integrins selected from $\alpha_v\beta_1$, $\alpha_v\beta_3$, $\alpha_v\beta_5$, $\alpha_v\beta_6$, and $\alpha_5\beta_1$ with high affinity. In some embodiments, the binding affinity is less than about 100 nM, less than about 50 nM, less than about 40 nM, less than about 30 nM, less than about 20 nM, less thank about 20 nM, less than about 10 nM, less than about 5 nM, less than about 4 nM, less than about 3 nM, less than about 2 nM, or less than about 1 nM. In some embodiments, the binding affinity is less than 5 nM. In some embodiments, the binding affinity is less than about 4 nM. In some embodiments, the binding affinity is less than about 3 nM. In some embodiments, the binding affinity is less than about 2 nM. In some embodiments, the binding affinity is less than about 1 nM. In some embodiments, the binding affinity is about 1.6 nM. In some embodiments, the binding affinity is about 1.5 nM. In some embodiments, the binding affinity is about 1 nM. In some embodiments, the binding affinity is about 0.7 nM.

a. Fc Domains

Figure 1A:
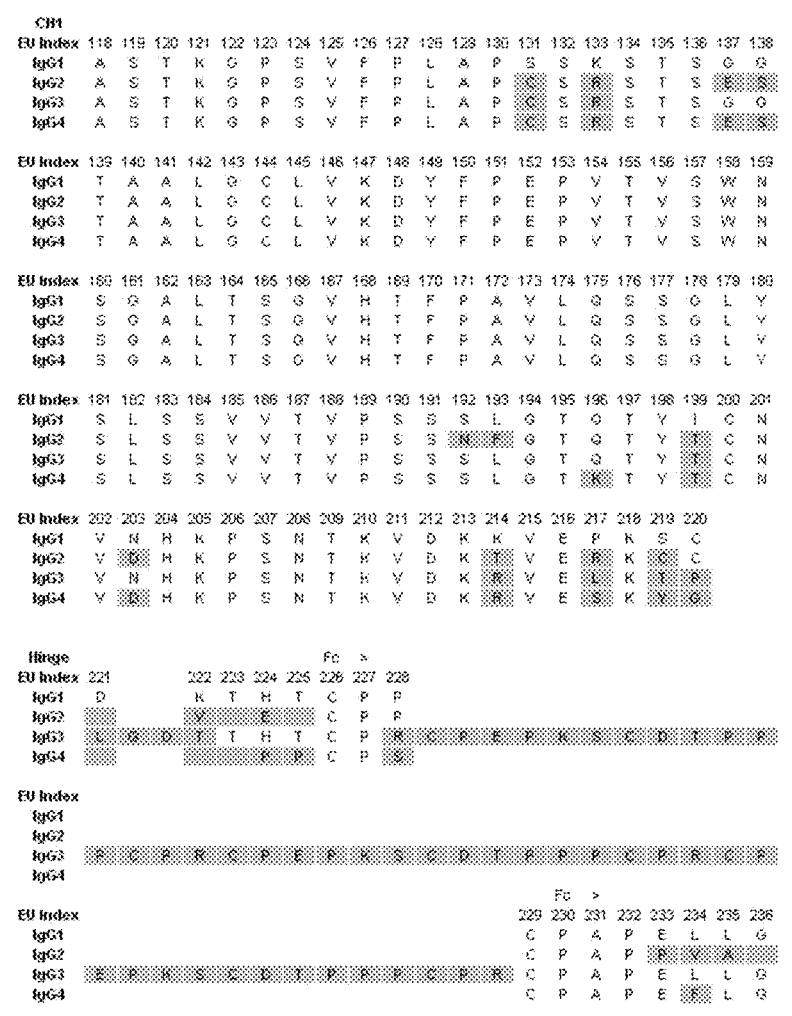
Figure 1B:
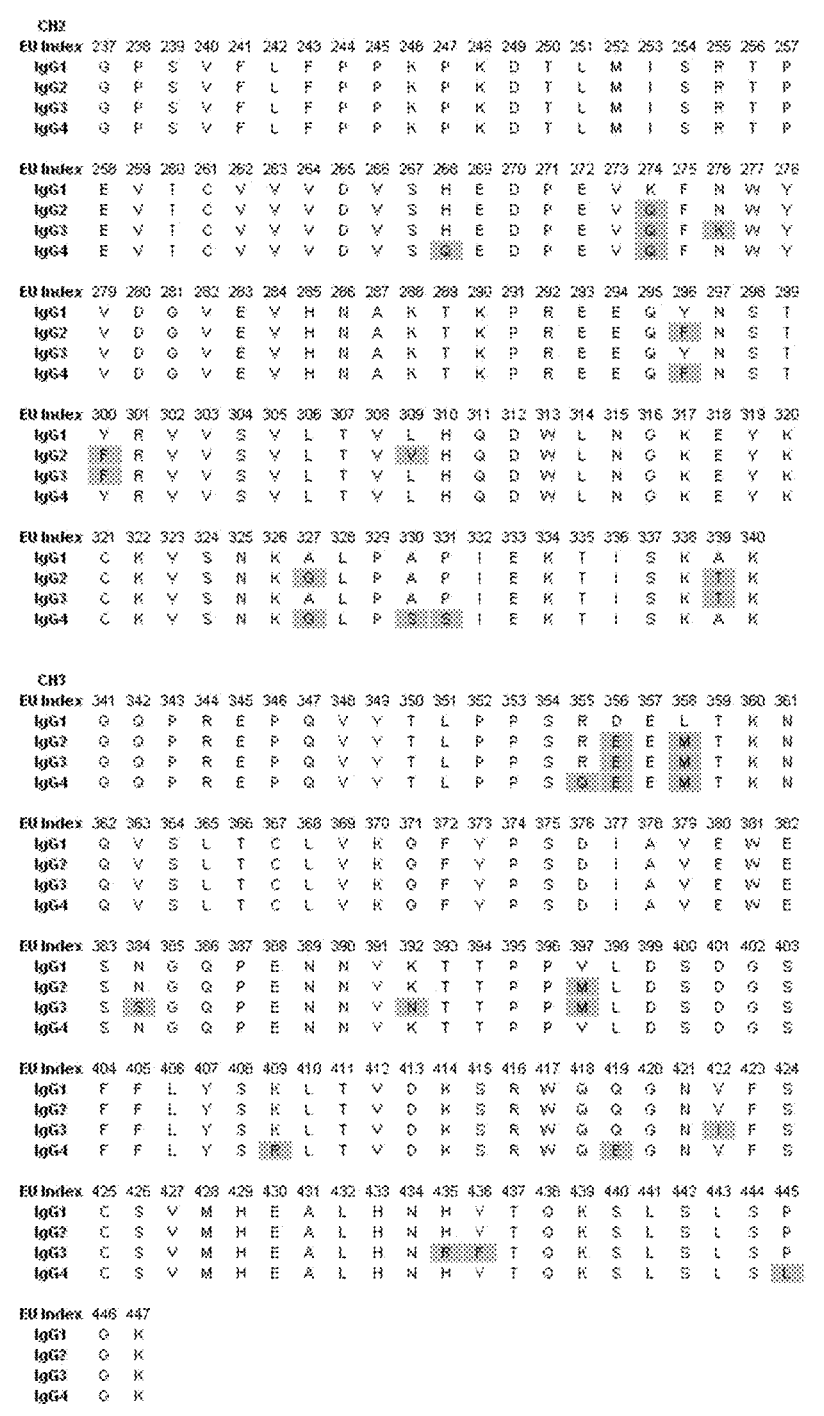

The Fc domain does not contain a variable region that binds to antigen. Fc domains useful for the integrin-binding polypeptide-Fc fusions described herein may be obtained from a number of different sources. In certain embodiments, an Fc domain of the extended-PK IL-2 is derived from a human immunoglobulin. In a certain embodiment, the Fc domain is from a human IgG1 constant region (FIG. 1; SEQ ID NO:126). An exemplary Fc domain of human IgG1 is set forth in SEQ ID NO: 126 (FIG. 1). In certain embodiments, the Fc domain of human IgG1 does not have the upper hinge region (FIG. 1 and Table 1). It is understood, however, that the Fc domain may be derived from an immunoglobulin of another mammalian species, including for example, a rodent (e.g. a mouse, rat, rabbit, guinea pig) or non-human primate (e.g. chimpanzee, macaque) species. Moreover, the Fc domain or portion thereof can be derived from any immunoglobulin class, including IgM, IgG, IgD, IgA, and IgE, and any immunoglobulin isotype, including IgG1, IgG2, IgG3, and IgG4. The Fc domain can be mouse or human.

In some embodiments, the integrin-binding polypeptide-Fc fusion includes a mutant Fc domain. In some embodiments, the integrin-binding polypeptide-Fc fusion includes a mutant, IgG1 Fc domain. In some embodiments, a mutant Fc domain comprises one or more mutations in the hinge, $CH_2$, and/or $CH_3$ domains. In some embodiments, a mutant Fc domain includes a D265A mutation.

In some embodiments, the integrin-binding polypeptide-Fc fusion of the invention lacks one or more constant region domains of a complete Fc region, i.e., they are partially or entirely deleted. In certain embodiments, the integrin-binding polypeptide-Fc fusion of the invention will lack an entire $CH_2$ domain. In some embodiments, the integrin-binding polypeptide-Fc fusion of the invention comprise $CH_2$ domain-deleted Fc regions derived from a vector (e.g., from IDEC Pharmaceuticals, San Diego) encoding an IgG1 human constant region domain (see, e.g., WO 02/060955A2 and WO 02/096948A2).

In some embodiments, an exemplary vector is engineered to delete the $CH_2$ domain and provide a synthetic vector expressing a domain-deleted IgG1 constant region. It will be noted that these exemplary constructs are preferably engineered to fuse a binding $CH_3$ domain directly to a hinge region of the respective Fc domain.

b. Methods of Engineering Knottin Polypeptide Scaffolds

Knottin polypeptide scaffolds are used to insert an integrin-binding sequence, preferably in the form of a loop, to confer specific integrin binding. Integrin-binding is preferably engineered into a knottin polypeptide scaffold by inserting an integrin-binding peptide sequence, such as an RGD peptide. In some embodiments, insertion of an integrin-binding peptide sequence results in replacement of portion of the native knottin protein. For example, in one embodiment an RGD peptide sequence is inserted into a native solvent exposed loop by replacing all or a portion of the loop with an RGD-containing peptide sequence (e.g., 5-12 amino acid sequence) that has been selected for binding to one or more integrins. The solvent-exposed loop (i.e., on the surface) will generally be anchored by disulfide-linked cysteine residues in the native knottin protein sequence. The integrin-binding replacement amino acid sequence can be obtained by randomizing codons in the loop portion, expressing the engineered peptide, and selecting the mutants with the highest binding to the predetermined ligand. This selection step may be repeated several times, taking the tightest binding proteins from the previous step and re-randomizing the loops.

Integrin-binding polypeptides may be modified in a number of ways. For example, the polypeptide may be further cross-linked internally, or may be cross-linked to each other, or the RGD loops may be grafted onto other cross linked molecular scaffolds. There are a number of commercially available crosslinking reagents for preparing protein or peptide bioconjugates. Many of these crosslinkers allow dimeric homo- or heteroconjugation of biological molecules through free amine or sulfhydryl groups in protein side chains. More recently, other crosslinking methods involving coupling through carbohydrate groups with hydrazide moieties have been developed. These reagents have offered convenient, facile, crosslinking strategies for researchers with little or no chemistry experience in preparing bioconjugates.

The EETI-II knottin protein (SEQ ID NO: 39 from U.S. Pat. No. 8,536,301, the contents of which are incorporated herein by reference) contains a disulfide knotted topology and possesses multiple solvent-exposed loops that are amenable to mutagenesis. Some embodiments use EETI-II as the molecular scaffold.

Another example of a knottin protein which can be used as a molecular scaffold is AgRP or agatoxin. The amino acid sequences of AgRP (SEQ ID NO: 40 from U.S. Pat. No.

8,536,301) and agatoxin (SEQ ID NO: 41 from U.S. Pat. No. 8,536,301) differ but their structure is identical. Exemplary AgRP knottins are found in Table 1 from U.S. Pat. No. 8,536,301.

Additional AgRP engineered knottins can be made as described in the above-referenced US 2009/0257952 to Cochran et al. (the contents of which are incorporated herein by reference). AgRP knottin fusions can be prepared using AgRP loops 1, 2 and 3, as well as loop 4.

The present polypeptides may be produced by recombinant DNA or may be synthesized in solid phase using a peptide synthesizer, which has been done for the peptides of all three scaffolds described herein. They may further be capped at their N-termini by reaction with fluorescein isothiocyanate (FITC) or other labels, and, still further, may be synthesized with amino acid residues selected for additional crosslinking reactions. TentaGel S RAM Fmoc resin (Advanced ChemTech) may be used to give a C-terminal amide upon cleavage. B-alanine is used as the N-terminal amino acid to prevent thiazolidone formation and release of fluorescein during peptide deprotection (Hermanson, 1996). Peptides are cleaved from the resin and side-chains are deprotected with 8% trifluoroacetic acid, 2% triisopropylsilane, 5% dithiothreitol, and the final product is recovered by ether precipitation. Peptides are purified by reverse phase HPLC using an acetonitrile gradient in 0.1% trifluoroacetic acid and a C4 or C18 column (Vydac) and verified using matrix-assisted laser desorption/ionization time-of-flight mass spectrometry (MALDI-TOF) or electrospray ionization-mass spectrometry (ESI-MS).

When the present peptides are produced by recombinant DNA, expression vectors encoding the selected peptide are transformed into a suitable host. The host should be selected to ensure proper peptide folding and disulfide bond formation as described above. Certain peptides, such as EETI-II, can fold properly when expressed in prokaryotic hosts such as bacteria.

Dimeric, trimeric, and tetrameric complexes of the present peptides can be formed through genetic engineering of the above sequences or by reaction of the synthetic crosslinkers with engineered peptides carrying an introduced cysteine residue, for example on the C-terminus of the peptide. These oligomeric peptide complexes can be purified by gel filtration. Oligomers of the present peptides can be prepared by preparing vectors encoding multiple peptide sequences end-to-end. Also, multimers may be prepared by complexing the peptides, such as, e.g., described in U.S. Pat. No. 6,265,539. There, an active HJV peptide is prepared in multimer form by altering the amino-terminal residue of the peptide so that it is peptide-bonded to a spacer peptide that contains an amino-terminal lysyl residue and one to about five amino acid residues such as glycyl residues to form a composite polypeptide. Alternatively, each peptide is synthesized to contain a cysteine (Cys) residue at each of its amino- and carboxy-termini. The resulting di-cysteine-terminated (di-Cys) peptide is then oxidized to polymerize the di-Cys peptide monomers into a polymer or cyclic peptide multimer. Multimers may also be prepared by solid phase peptide synthesis utilizing a lysine core matrix. The present peptides may also be prepared as nanoparticles. See, "Multivalent Effects of RGD Peptides Obtained by Nanoparticle Display," Montet, et al., J. Med. Chem.; 2006; 49(20) pp 6087-6093. EETI dimerization may be carried out with the present EETI-II peptides according to the EETI-II dimerization paper: "Grafting of thrombopoietin-mimetic peptides into cystine knot miniproteins yields high-affinity thrombopoietin antagonist and agonists," Krause, et al., FEBS Journal; 2006; 274 pp 86-95. This is further described in PCT application No. PCT/US2013/065610, herein incorporated by reference.

Synergistic sites on fibronectin and other adhesion proteins have been identified for enhanced integrin binding (Ruoslahti, 1996; Koivunen et al., 1994; Aota et al., 1994; Healy et al., 1995). The ability to incorporate different integrin-specific motifs into one soluble molecule would have an important impact on therapeutic development. Crosslinkers with heterofunctional specificity may be used for creating integrin-binding proteins with synergistic binding effects. In addition, these same crosslinkers could easily be used to create bispecific targeting molecules, or as vehicles for delivery of radionuclides or toxic agents for therapeutic applications.

c. Integrin-Binding Polypeptides

The integrin-binding polypeptides for use in Fc fusions include an integrin-binding loop (e.g., RGD peptide sequence) and a knottin polypeptide scaffold. Such integrin-binding polypeptides are described in U.S. Pat. No. 8,536,301, the contents of which are incorporated herein by reference. As described in U.S. Pat. No. 8,536,301, integrin-binding polypeptides may be varied in the non-RGD residues to a certain degree without affecting binding specificity and potency. For example, if three of the eleven residues were varied, one would have about 70% identity to 2.5D. Table 1 shows exemplary integrin-binding polypeptides within the scope of the invention, and their specific knottin polypeptide scaffold (e.g., EETI-II or AgRP). In some embodiments, integrin-binding polypeptides for use in Fc fusions are peptides 2.5F and 2.5FmodK, as described herein (GCPRPRGDNPPLTCSQDSDCLAGCVCGPNGFCG, 2.5F, SEQ ID NO:130 and GCPRPRGDNPPLTCKQDSDCLAGCVCGPNGFCG, 2.5FmodK, SEQ ID NO:131), as well as GCPRPRGDNPPLTCSQDSDCLAGCVCGPNGFCGGGGGS (SEQ ID NO:132), GCPRPRGDNPPLTCKQDSDCLAGCVCGPNGFCGGGGGS (SEQ ID NO:133), GCPRPRGDNPPLTCSQDSDCLAGCVCGPNGFCGGGGGSGGGGSGGGGS (SEQ ID NO:134), and/or GCPRPRGDNPPLTCKQDSDCLAGCVCGPNGFCGGGGGSGGGGSGGGGS (SEQ ID NO:135).

In certain embodiments, the integrin-binding polypeptide binds to $\alpha_v\beta3$, $\alpha_v\beta5$, or $\alpha5\beta1$ separately.

In certain embodiments, the integrin-binding polypeptide binds to $\alpha_v\beta3$ and $\alpha_v\beta5$ simultaneously.

In certain embodiments, the integrin-binding polypeptide binds to $\alpha_v\beta3$, $\alpha_v\beta5$, and $\alpha5\beta1$ simultaneously.

In certain embodiments, the integrin-binding polypeptide is 2.5F or 2.5FmodK, as described herein (GCPRPRGDNPPLTCSQDSDCLAGCVCGPNGFCG, 2.5F, SEQ ID NO:130 and GCPRPRGDNPPLTCKQDSDCLAGCVCGPNGFCG, 2.5FmodK, SEQ ID NO:131), as well as GCPRPRGDNPPLTCSQDSDCLAGCVCGPNGFCGGGGGS (SEQ ID NO:132), GCPRPRGDNPPLTCKQDSDCLAGCVCGPNGFCGGGGGS (SEQ ID NO:133), GCPRPRGDNPPLTCSQDSDCLAGCVCGPNGFCGGGGGSGGGGSGGGGS (SEQ ID NO:134), and/or GCPRPRGDNPPLTCKQDSDCLAGCVCGPNGFCGGGGGSGGGGSGGGGS (SEQ ID NO:135). In some embodiments, an integrin-binding polypeptide as recited in Table 1 of U.S. Pat. No. 8,536,301 can also be used in Fc fusion as described herein.

The present polypeptides target $\alpha_v\beta1$, $\alpha_v\beta3$, $\alpha_v\beta5$, $\alpha_v\beta6$, and $\alpha5\beta1$ integrin receptors. They do not bind to other integrins tested, such as $\alpha_{iib}\beta3$, where there was little to no affinity (as described in US. Thus, these engineered integrin-binding polypeptides have broad diagnostic and therapeutic applications in a variety of human cancers that specifically overexpress the above named integrins. As described below, these polypeptides bind with high affinity to both detergent-solubilized and tumor cell surface integrin receptors.

The $\alpha_v\beta_3$ (and $\alpha_v\beta_5$) integrins are also highly expressed on many tumor cells including osteosarcomas, neuroblastomas, carcinomas of the lung, breast, prostate, and bladder, glioblastomas, and invasive melanomas The $\alpha_v\beta_3$ integrin has been shown to be expressed on tumor cells and/or the vasculature of breast, ovarian, prostate, and colon carcinomas, but not on normal adult tissues or blood vessels. Also, the $\alpha_5\beta_1$ integrin has been shown to be expressed on tumor cells and/or the vasculature of breast, ovarian, prostate, and colon carcinomas, but not on normal adult tissue or blood vessels. The present, small, conformationally-constrained polypeptides (about 33 amino acids) are so constrained by intramolecular bonds. For example, EETI-II has three disulfide linkages. This will make it more stable in vivo.

Until now, it is believed that the development of a single agent that can bind $\alpha_v\beta_3$, $\alpha_v\beta_5$, and $\alpha_5\beta_1$ integrins with high affinity and specificity has not been achieved. Since all three of these integrins are expressed on tumors and are involved in mediating angiogenesis and metastasis, a broad spectrum targeting agent (i.e., $\alpha_v\beta_3$, $\alpha_v\beta_5$, and $\alpha_5\beta_1$) will likely be more effective for diagnostic and therapeutic applications.

The present engineered knottin-Fc fusions have several advantages over previously identified integrin-targeting compounds. They possess a compact, disulfide-bonded core that confers proteolytic resistance and exceptional in vivo stability.

Our studies indicate the half-life of integrin-binding-Fc fusion protein in mouse serum to be greater than 90 hours. Their larger size ($^{18}$3-4 kDa) and enhanced affinity compared to RGD-based cyclic peptides confer enhanced pharmacokinetics and biodistribution for molecular imaging and therapeutic applications. These integrin-binding-Fc fusion proteins are small enough to allow for chemical synthesis and site-specific conjugation of imaging probes, radioisotopes, or chemotherapeutic agents. Furthermore, they can easily be chemically modified to further improve in vivo properties if necessary.

d. Integrin-Binding Polypeptide-Fc Fusion

The integrin-binding polypeptide-Fc fusions (knottin-Fc fusions) described herein and in U.S. Patent Application No. 2014/0073518, herein incorporated by reference in its entirety, combine an engineered integrin-binding polypeptide (within a knottin scaffold) and an Fc domain or antibody like construct capable of binding FcγR and inducing ADCC.

The Fc portion of an antibody is formed by the two carboxy terminal domains of the two heavy chains that make up an immunoglobin molecule. The IgG molecule contains 2 heavy chains (~50 kDa each) and 2 light chains (~25 kDa each). The general structure of all antibodies is very similar, a small region at the tip of the protein is extremely variable, allowing millions of antibodies with slightly different tip structures to exist. This region is known as the hypervariable region (Fab). The other fragment contains no antigen-binding activity but was originally observed to crystallize readily, and for this reason was named the Fc fragment, for Fragment crystallizable. This fragment corresponds to the paired C¾ and C¾ domains and is the part of the antibody molecule that interacts with effector molecules and cells. The functional differences between heavy-chain isotypes lie mainly in the Fc fragment. The hinge region that links the Fc and Fab portions of the antibody molecule is in reality a flexible tether, allowing independent movement of the two Fab arms, rather than a rigid hinge. This has been demonstrated by electron microscopy of antibodies bound to haptens. Thus the present fusion proteins can be made to contain two knottin peptides, one on each arm of the antibody fragment.

The Fc portion varies between antibody classes (and subclasses) but is identical within that class. The C-terminal end of the heavy chain forms the Fc region. The Fc region plays an important role as a receptor binding portion. The Fc portion of antibodies will bind to Fc receptors in two different ways. For example, after IgG and IgM bind to a pathogen by their Fab portion their Fc portions can bind to receptors on phagocytic cells (like macrophages) inducing phagocytosis.

The present integrin-binding polypeptide-Fc fusions can be implemented such that the Fc portion is used to provide dual binding capability, and/or for half-life extension, for improving expression levels, etc. The Fc fragment in the integrin-binding polypeptide-Fc fusion can be, for example, from murine IgG2a or human IgG1. In some embodiments, the Fc fragment can be from mouse IgG1, IgG2, IgG3, or mouse IgG4, as well as variants thereof. In some embodiments, the Fc fragment can be from human IgG1, IgG2, IgG3, or mouse IgG4, as well as variants thereof. See, for example, FIG. 1. Linkers can be optionally used to connect the integrin binding portion (knottin) to the Fc portion.

In some embodiments, the linkers do not affect the binding affinity of the integrin-binding polypeptide-Fc fusions to integrins or Fc receptors. A variety of Fc domain gene sequences (e.g., mouse and human constant region gene sequences) are available in the form of publicly accessible deposits.

e. Fc-Domains

A variety of Fc domain gene sequences (e.g., mouse and human constant region gene sequences) are available in the form of publicly accessible deposits. Constant region domains comprising an Fc domain sequence can be selected lacking a particular effector function and/or with a particular modification to reduce immunogenicity. Many sequences of antibodies and antibody-encoding genes have been published and suitable Fc domain sequences (e.g., hinge, $CH_2$, and/or $CH_3$ sequences, or portions thereof) can be derived from these sequences using art recognized techniques. The genetic material obtained using any of the foregoing methods may then be altered or synthesized to obtain polypeptides used herein. It will further be appreciated that alleles, variants and mutations of constant region DNA sequences are suitable for use in the methods disclosed herein.

Integrin-binding polypeptide-Fc fusions suitable for use in the methods disclosed herein may comprise one or more Fc domains (e.g., 2, 3, 4, 5, 6, 7, 8, 9, 10, or more Fc domains). In some embodiments, the Fc domains may be of different types. In some embodiments, at least one Fc domain present in an integrin-binding polypeptide-Fc fusion comprises a hinge domain or portion thereof. In another embodiment, an integrin-binding polypeptide-Fc fusion comprises at least one Fc domain which comprises at least one CH2 domain or portion thereof. In another embodiment, an integrin-binding polypeptide-Fc fusion comprises at least one Fc domain which comprises at least one $CH_3$ domain or portion thereof. In another embodiment, an integrin-binding polypeptide-Fc fusion comprises at least one Fc domain which comprises at least one $CH_4$ domain or portion thereof. In another embodiment, an integrin-binding polypeptide-Fc fusion comprises at least one Fc domain which comprises at least one hinge domain or portion thereof and at least one CH$_2$ domain or portion thereof (e.g., in the hinge-CH$_2$ orientation). In another embodiment, an integrin-binding polypeptide-Fc fusion comprises at least one Fc domain which comprises at least one CH$_2$ domain or portion thereof and at least one CH$_3$ domain or portion thereof (e.g., in the CH$_2$—CH$_3$ orientation). In another embodiment, an integrin-binding polypeptide-Fc fusion comprises at least one Fc domain comprising at least one hinge domain or portion thereof, at least one CH$_2$ domain or portion thereof, and least one CH$_3$ domain or portion thereof, for example in the orientation hinge-CH$_2$—CH$_3$, hinge-CH$_3$—CH$_2$, or CH$_2$—CH$_3$-hinge.

In some embodiments, an integrin-binding polypeptide-Fc fusion comprises at least one complete Fc region derived from one or more immunoglobulin heavy chains (e.g., an Fc domain including hinge, CH$_2$, and CH$_3$ domains, although these need not be derived from the same antibody). In other embodiments an integrin-binding polypeptide-Fc fusion comprises at least two complete Fc domains derived from one or more immunoglobulin heavy chains. In certain embodiments, the complete Fc domain is derived from a human IgG immunoglobulin heavy chain (e.g., human IgG1).

In another embodiment, an integrin-binding polypeptide-Fc fusion comprises at least one Fc domain comprising a complete CH$_3$ domain. In another embodiment, an integrin-binding polypeptide-Fc fusion comprises at least one Fc domain comprising a complete CH$_2$ domain. In another embodiment, an integrin-binding polypeptide-Fc fusion comprises at least one Fc domain comprising at least a CH$_3$ domain, and at least one of a hinge region, and a CH$_2$ domain. In one embodiment, an integrin-binding polypeptide-Fc fusion comprises at least one Fc domain comprising a hinge and a CH$_3$ domain. In another embodiment, an integrin-binding polypeptide-Fc fusion comprises at least one Fc domain comprising a hinge, a CH$_2$, and a CH$_3$ domain. In some embodiments, the Fc domain is derived from a human IgG immunoglobulin heavy chain (e.g., human IgG1). In some embodiments, a human IgG1 Fc domain is used with a hinge region mutation, substitution, or deletion to remove or substitute one or more hinge region cysteine residues.

The constant region domains or portions thereof making up an Fc domain of an integrin-binding polypeptide-Fc fusion may be derived from different immunoglobulin molecules. For example, a polypeptide used in the invention may comprise a CH$_2$ domain or portion thereof derived from an IgG1 molecule and a CH$_3$ region or portion thereof derived from an IgG3 molecule. In some embodiments, an integrin-binding polypeptide-Fc fusion can comprise an Fc domain comprising a hinge domain derived, in part, from an IgG1 molecule and, in part, from an IgG3 molecule. As set forth herein, it will be understood by one of ordinary skill in the art that an Fc domain may be altered such that it varies in amino acid sequence from a naturally occurring antibody molecule.

In other constructs it may be desirable to provide a peptide spacer between one or more constituent Fc domains. For example, in some embodiments, a peptide spacer may be placed between a hinge region and a CH$_2$ domain and/or between a CH$_2$ and a CH$_3$ domain. For example, compatible constructs could be expressed wherein the CH$_2$ domain has been deleted and the remaining CH$_3$ domain (synthetic or unsynthetic) is joined to the hinge region with a 1-20, 1-10, or 1-5 amino acid peptide spacer. Such a peptide spacer may be added, for instance, to ensure that the regulatory elements of the constant region domain remain free and accessible or that the hinge region remains flexible. Preferably, any linker peptide compatible with the instant invention will be relatively non-immunogenic and not prevent proper folding of the Fc.

f. Changes to Fc Amino Acids

In some embodiments, an Fc domain is altered or modified, e.g., by amino acid mutation (e.g., addition, deletion, or substitution). As used herein, the term "Fc domain variant" refers to an Fc domain having at least one amino acid modification, such as an amino acid substitution, as compared to the wild-type Fc from which the Fc domain is derived. For example, wherein the Fc domain is derived from a human IgG1 antibody, a variant comprises at least one amino acid mutation (e.g., substitution) as compared to a wild type amino acid at the corresponding position of the human IgG1 Fc region.

In some embodiments, the hinge region of human IgG1 Fc domain is altered by an amino acid substitution or deletion to mutate or remove one or more of three hinge region cysteine residues (located at residues 220, 226, and 229 by EU numbering). In some aspects, the upper hinge region is deleted to remove a cysteine that pairs with the light chain. For example, in some embodiments, amino acids "EPKSC" in the upper hinge region are deleted, as set forth in SEQ ID NO: 3 from U.S. Pat. No. 8,536,301. In other aspects, one or more of three hinge region cysteines is mutated (e.g., to serine). In certain embodiments, cysteine 220 is mutated to serine.

In some embodiments, the Fc variant comprises a substitution at an amino acid position located in a hinge domain or portion thereof. In some embodiments, the Fc variant comprises a substitution at an amino acid position located in a CH$_2$ domain or portion thereof. In another embodiment, the Fc variant comprises a substitution at an amino acid position located in a CH$_3$ domain or portion thereof. In another embodiment, the Fc variant comprises a substitution at an amino acid position located in a CH$_4$ domain or portion thereof.

In some embodiments, an integrin-binding polypeptide-Fc fusion comprises an Fc variant comprising more than one amino acid substitution. The an integrin-binding polypeptide-Fc fusion used in the methods described herein may comprise, for example, 2, 3, 4, 5, 6, 7, 8, 9, 10 or more amino acid substitutions.

In some embodiments, the amino acid substitutions are spatially positioned from each other by an interval of at least 1 amino acid position or more, for example, at least 2, 3, 4, 5, 6, 7, 8, 9, or 10 amino acid positions or more. In some embodiments, the engineered amino acids are spatially positioned apart from each other by an interval of at least 5, 10, 15, 20, or 25 amino acid positions or more.

In some embodiments, an integrin-binding polypeptide-Fc fusion comprises an amino acid substitution to an Fc domain which alters the antigen-independent effector functions of the polypeptide, in particular the circulating half-life of the polypeptide.

In one embodiment, the integrin-binding polypeptide-Fc fusion exhibits enhanced binding to an activating FcγR (e.g. Fcγ1, Fcγ1α, or FcγRIIIα). Exemplary amino acid substitutions which altered FcR or complement binding activity are disclosed in International PCT Publication No. WO 2005/063815 which is incorporated by reference herein. In certain embodiments the Fc region contains at least one of the following mutations: S239D, S239E, L261A, H268D, S298A, A330H, A330L, I332D, I332E, I332Q, K334V, A378F, A378K, A378W, A378Y, H435S, or H435G. In certain embodiments, the Fc region contains at least one of the following mutations: S239D, S239E, I332D or I332E or H268D. In certain embodiments, the Fc region contains at least one of the following mutations: I332D or I332E or H268D.

The integrin-binding polypeptide-Fc fusion used herein may also comprise an amino acid substitution which alters the glycosylation of the integrin-binding polypeptide-Fc fusion. For example, the Fc domain of the integrin-binding polypeptide-Fc fusion may comprise an Fc domain having a mutation leading to reduced glycosylation (e.g., N- or O-linked glycosylation) or may comprise an altered glycoform of the wild-type Fc domain (e.g., a low fucose or fucose-free glycan). In another embodiment, the integrin-binding polypeptide-Fc fusion has an amino acid substitution near or within a glycosylation motif, for example, an N-linked glycosylation motif that contains the amino acid sequence NXT or NXS. Exemplary amino acid substitutions which reduce or alter glycosylation are disclosed in WO 05/018572 and US 2007/0111281, which are incorporated by reference herein. In other embodiments, the integrin-binding polypeptide-Fc fusion used herein comprises at least one Fc domain having engineered cysteine residue or analog thereof which is located at the solvent-exposed surface. In some embodiments, the integrin-binding polypeptide-Fc fusion used herein comprises an Fc domain comprising at least one engineered free cysteine residue or analog thereof that is substantially free of disulfide bonding with a second cysteine residue. Any of the above engineered cysteine residues or analogs thereof may subsequently be conjugated to a functional domain using art-recognized techniques (e.g., conjugated with a thiol-reactive heterobifunctional linker).

In one embodiment, the integrin-binding polypeptide-Fc fusion used herein may comprise a genetically fused Fc domain having two or more of its constituent Fc domains independently selected from the Fc domains described herein. In one embodiment, the Fc domains are the same. In another embodiment, at least two of the Fc domains are different. For example, the Fc domains of the integrin-binding polypeptide-Fc fusion used herein comprise the same number of amino acid residues or they may differ in length by one or more amino acid residues (e.g., by about 5 amino acid residues (e.g., 1, 2, 3, 4, or 5 amino acid residues), about 10 residues, about 15 residues, about 20 residues, about 30 residues, about 40 residues, or about 50 residues). In some embodiments, the Fc domains of the integrin-binding polypeptide-Fc fusion used herein may differ in sequence at one or more amino acid positions. For example, at least two of the Fc domains may differ at about 5 amino acid positions (e.g., 1, 2, 3, 4, or 5 amino acid positions), about 10 positions, about 15 positions, about 20 positions, about 30 positions, about 40 positions, or about 50 positions).

VI. Nucleic Acid Compositions

Nucleic acid compositions encoding the integrin-binding polypeptide-Fc fusions of the invention are also provided, as well as expression vectors containing the nucleic acids and host cells transformed with the nucleic acid and/or expression vector compositions.

The nucleic acid compositions that encode the integrin-binding polypeptide-Fc are generally put into a single expression vectors is known in the art, transformed into host cells, where they are expressed to form the integrin-binding polypeptide-Fc of the invention. The nucleic acids can be put into expression vectors that contain the appropriate transcriptional and translational control sequences, including, but not limited to, signal and secretion sequences, regulatory sequences, promoters, origins of replication, selection genes, etc.

For example, to express the protein DNA, DNAs can be obtained by standard molecular biology techniques (e.g., PCR amplification or gene synthesis) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The protein genes are inserted into the expression vector by standard methods (e.g., ligation of complementary restriction sites on the gene fragment and vector, or blunt end ligation if no restriction sites are present). Additionally or alternatively, the recombinant expression vector can encode a signal peptide that facilitates secretion of the protein (including fusion proteins) from a host cell. The gene can be cloned into the vector such that the signal peptide is linked in-frame to the amino terminus of the gene. The signal peptide can be an immunoglobulin signal peptide or a heterologous signal peptide (i.e., a signal peptide from a non-immunoglobulin protein). Exemplary signal peptides include but are not limited to MTRLTVLAL-LAGLLASSRA (SEQ ID NO:138).

In addition to the protein genes, the recombinant expression vectors according to at least some embodiments of the invention carry regulatory sequences that control the expression of the genes in a host cell. The term "regulatory sequence" is intended to include promoters, enhancers and other expression control elements (e.g., polyadenylation signals) that control the transcription or translation of the genes. Such regulatory sequences are described, for example, in Goeddel ("Gene Expression Technology", *Methods in Enzymology* 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SR α promoter system, which contains sequences from the SV40 early promoter and the long terminal repeat of human T cell leukemia virus type 1 (Takebe, Y. et al. (1988) *Mol. Cell. Biol.* 8:466-472).

In addition to the protein genes and regulatory sequences, the recombinant expression vectors according to at least some embodiments of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the proteins of the invention, an expression vector encoding the protein is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the proteins according to at least some embodiments of the invention in either prokaryotic or eukaryotic host cells, expression of antibodies in eukaryotic cells, and most preferably mammalian host cells, is the most preferred.

In some embodiments, mammalian host cells for expressing the recombinant proteins include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. In particular, for use with NS0 myeloma cells, another preferred expression system is the GS gene expression system disclosed in WO 87/04462, WO 89/01036 and EP 338,841. When recombinant expression vectors encoding protein genes are introduced into mammalian host cells, the proteins are produced by culturing the host cells for a period of time sufficient to allow for expression of the protein in the host cells or, more preferably, secretion of the protein into the culture medium in which the host cells are grown.

VII. Immune Checkpoint Inhibitor

In certain embodiments, immune checkpoint modulators are used in combination with other therapeutic agents described herein (e.g., IL-2, extended-PK IL-2, and/or integrin binding-Fc fusion proteins). T cell activation and effector functions are balanced by various signals, referred to as "immune checkpoints." Inhibitory ligands and receptors that regulate T cell effector functions are overexpressed on tumor cells. Subsequently, agonists of stimulatory receptors or antagonists of inhibitory signals, result in the amplification of antigen-specific T cell responses.

VIII. Immune Checkpoint Inhibitors

In certain embodiments, the immune checkpoint modulator is an immune checkpoint inhibitor. In contrast to therapeutic antibodies which target tumor cells directly, immune checkpoint inhibitors enhance endogenous anti-tumor activity. In certain embodiments, the immune checkpoint inhibitor suitable for use in the methods disclosed herein, is an antagonist of inhibitory signals, e.g., an antibody which targets, for example, PD-1 and/or PD-L1. These ligands and receptors are reviewed in Pardoll, D., Nature. 12: 252-264, 2012.

In some embodiments, the immune checkpoint inhibitor is selected from the group consisting of an anti-PD-1 antibody and an anti-PD-L1 antibody. In some embodiments, the immune checkpoint inhibitor is an anti-PD-1 antibody. In some embodiments, the immune checkpoint inhibitor is an anti-PD-L1 antibody.

Disclosed herein are methods for treating a subject afflicted with diseases such as cancer, which methods comprise administering to the subject a composition comprising a therapeutically effective amount of an integrin-binding-Fc fusion protein as described herein. In some embodiments, the method comprising administering an integrin-binding-Fc fusion protein such as NOD201, NOD203, and/or NOD204, as well as combinations thereof. In some embodiments, the integrin-binding-Fc fusion protein is combined with molecule which blocks the immune checkpoint, and an integrin-binding-Fc fusion protein. In some embodiments, the methods for treating a subject afflicted with diseases such as cancer, which methods comprise administering to the subject a composition comprising a therapeutically effective amount of a molecule which blocks the immune checkpoint, an integrin-binding-Fc fusion protein, and IL-2 (e.g., wild-type IL-2, Proleukin, and/or extended-PK IL-2). In some embodiments, the immune checkpoint inhibitor is an antibody or an antigen-binding portion thereof, that disrupts or inhibits signaling from an inhibitory immunoregulator. In some embodiments, the immune checkpoint inhibitor is a small molecule that disrupts or inhibits signaling from an inhibitory immunoregulator.

In some embodiments, the inhibitory immunoregulator (immune checkpoint inhibitor) is a component of the PD-1/PD-L1 signaling pathway. Accordingly, some embodiments provide methods for immunotherapy of a subject afflicted with cancer, which methods comprise administering to the subject a therapeutically effective amount of an antibody or an antigen-binding portion thereof that disrupts the interaction between the PD-1 receptor and its ligand, PD-L1. Antibodies known in the art which bind to PD-1 and disrupt the interaction between the PD-1 and its ligand, PD-L1, and stimulates an anti-tumor immune response, are suitable for use in the methods disclosed herein. In some embodiments, the antibody or antigen-binding portion thereof binds specifically to PD-1. For example, antibodies that target PD-1 and which can find used in the methods of the present invention include, e.g., but are not limited to nivolumab (BMS-936558, Bristol-Myers Squibb), pembrolizumab (lambrolizumab, MK03475 or MK-3475, Merck), humanized anti-PD-1 antibody JS001 (ShangHai JunShi), monoclonal anti-PD-1 antibody TSR-042 (Tesaro, Inc.), Pidilizumab (anti-PD-1 mAb CT-011, Medivation), anti-PD-1 monoclonal Antibody BGB-A317 (BeiGene), and/or anti-PD-1 antibody SHR-1210 (ShangHai HengRui), human monoclonal antibody REGN2810 (Regeneron), human monoclonal antibody MDX-1106 (Bristol-Myers Squibb), and/or humanized anti-PD-1 IgG4 antibody PDR001 (Novartis). In some embodiments, the PD-1 antibody is from clone: RMP1-14 (rat IgG)—BioXcell cat #BP0146. Other suitable antibodies for use in the methods disclosed herein are anti-PD-1 antibodies disclosed in U.S. Pat. No. 8,008,449, herein incorporated by reference. In some embodiments, the antibody or antigen-binding portion thereof binds specifically to PD-L1 and inhibits its interaction with PD-1, thereby increasing immune activity. Any antibodies known in the art which bind to PD-L1 and disrupt the interaction between the PD-1 and PD-L1, and stimulates an anti-tumor immune response, are suitable for use in the methods disclosed herein. For example, antibodies that target PD-L1 and are in clinical trials, include BMS-936559 (Bristol-Myers Squibb) and MPDL3280A (Genetech). Other suitable antibodies that target PD-L1 are disclosed in U.S. Pat. No. 7,943,743, herein incorporated by reference. It will be understood by one of ordinary skill that any antibody which binds to PD-1 or PD-L1, disrupts the PD-1/PD-L1 interaction, and stimulates an anti-tumor immune response, are suitable for use in the methods disclosed herein.

In some embodiments, the inhibitory immunoregulator is a component of the CTLA-4 signaling pathway. Accordingly, some embodiments provide methods for immunotherapy of a subject afflicted with cancer, which methods comprise administering to the subject a therapeutically effective amount of an antibody or an antigen-binding portion thereof that targets CTLA-4 and disrupts its interaction with CD80 and CD86. Exemplary antibodies that target CTLA-4 include ipilimumab (MDX-010, MDX-101, Bristol-Myers Squibb), which is FDA approved, and tremelimumab (ticilimumab, CP-675, 206, Pfizer), currently undergoing human trials. Other suitable antibodies that target CTLA-4 are disclosed in WO 2012/120125, U.S. Pat. Nos. 6,984,720, 6,682,7368, and U.S. Patent Applications 2002/0039581, 2002/0086014, and 2005/0201994, herein incorporated by reference. It will be understood by one of ordinary skill that any antibody which binds to CTLA-4, disrupts its interaction with CD80 and CD86, and stimulates an anti-tumor immune response, are suitable for use in the methods disclosed herein.

In certain embodiments, the inhibitory immunoregulator is a component of the LAG-3 (lymphocyte activation gene 3) signaling pathway. Accordingly, certain embodiments provide methods for immunotherapy of a subject afflicted with cancer, which methods comprise administering to the subject a therapeutically effective amount of an antibody or an antigen-binding portion thereof that targets LAG-3 and disrupts its interaction with MHC class II molecules. An exemplary antibody that targets LAG-3 is IMP321 (Immutep), currently undergoing human trials. Other suitable antibodies that target LAG-3 are disclosed in U.S. Patent Application 2011/0150892, herein incorporated by reference. It will be understood by one of ordinary skill that any antibody which binds to LAG-3, disrupts its interaction with MHC class II molecules, and stimulates an anti-tumor immune response, are suitable for use in the methods disclosed herein.

In some embodiments, the inhibitory immunoregulator is a component of the B7 family signaling pathway. In some embodiments, the B7 family members are B7-H3 and B7-H4. Accordingly, some embodiments provide methods for immunotherapy of a subject afflicted with cancer, which methods comprise administering to the subject a therapeutically effective amount of an antibody or an antigen-binding portion thereof that targets B7-H3 or -H4. The B7 family does not have any defined receptors but these ligands are unregulated on tumor cells or tumor-infiltrating cells. Preclinical mouse models have shown that blockade of these ligands can enhance anti-tumor immunity. An exemplary antibody that targets B7-H3 is MGA271 (Macrogenics), currently undergoing human trials. Other suitable antibodies that target B7 family members are disclosed in U.S. Patent Application 2013/0149236, herein incorporated by reference. It will be understood by one of ordinary skill that any antibody which binds to B7-H3 or H4, and stimulates an anti-tumor immune response, are suitable for use in the methods disclosed herein.

In certain embodiments, the inhibitory immunoregulator is a component of the TIM-3 (T cell membrane protein 3) signaling pathway. Accordingly, certain embodiments provide methods for immunotherapy of a subject afflicted with cancer, which methods comprise administering to the subject a therapeutically effective amount of an antibody or an antigen-binding portion thereof that targets TIM-3 and disrupts its interaction with galectin 9. Suitable antibodies that target TIM-3 are disclosed in U.S. Patent Application 2013/0022623, herein incorporated by reference. It will be understood by one of ordinary skill that any antibody which binds to TIM-3, disrupts its interaction with galectin 9, and stimulates an anti-tumor immune response, are suitable for use in the methods disclosed herein.

It should be understood that antibodies targeting immune checkpoints suitable for use in the methods disclosed herein are not limited to those described herein. Moreover, it will be understood by one of ordinary skill in the art that other immune checkpoint targets can also be targeted by antagonists or antibodies in the methods described herein, provided that the targeting results in the stimulation of an anti-tumor immune response as reflected in, e.g., an increase in T cell proliferation, enhanced T cell activation, and/or increased cytokine production (e.g., IFN-γ, IL-2).

IX. Alternatives to Immune Checkpoint Modulators

In certain embodiments, an antagonist of vascular endothelial growth factor (VEGF) is used in place of an immune checkpoint inhibitor. VEGF has recently been demonstrated to play a role in immune suppression (Liang, W.-C. et al. J. Biol. Chem. (2006) Vol 281: 951-961; Voron, T. et al. Front Oncol (2014) Vol. 4: Article 70; Terme, M. et al, Clin Dev Immunol (2012) Vol. 2012: Article ID 492920; Kandalaft, E. et &\., Curr Top Microbiol Immunol (2011) Vol 344: 129-48), therefore blocking its activity would enhance the immune response, similar to that of an immune checkpoint inhibitor. A "VEGF antagonist" refers to a molecule capable of neutralizing, blocking, inhibiting, abrogating, reducing or interfering with VEGF activities including its binding to one or more VEGF receptors. Non-limiting examples of VEGF antagonists include anti-VEGF antibodies and antigen-binding fragments thereof, receptor molecules and derivatives which bind specifically to VEGF thereby sequestering its binding to one or more receptors (e.g., a VEGF receptor), anti-VEGF receptor antibodies, VEGF receptor antagonists such as small molecule inhibitors of the VEGFR tyrosine kinases, or a dominant negative VEGF.

In certain embodiments, the VEGF antagonist is an antibody. An "anti-VEGF antibody" is an antibody that binds to VEGF with sufficient affinity and specificity. Non-limiting examples of anti-VEGF antibodies are described in U.S. Pat. Nos. 6,884,879, 7,060,269, 6,582,959, 6,703,030, 6,054,297, US Patent Application Nos. 2006009360, 20050186208, 20030206899, 20030190317, 20030203409, 20050112126, and PCT Publication Nos. WO 98/45332, 96/30046, 94/10202, 05/044853, 13/181452. The contents of these patents and patent applications are herein incorporated by reference. In certain embodiments the VEGF antibody is bevacizumab (Avastin® Genentech/Roche) or ranibizumab (Lucentis® Genentech/Roche).

VEGF receptors, or fragments thereof, that specifically bind to VEGF can be used to bind to and sequester the VEGF protein, thereby preventing it from activating downstream signaling. In certain embodiments, the VEGF receptor, or VEGF binding fragment thereof, is a soluble VEGF receptor, such as sFlt-1. The soluble form of the receptor exerts an inhibitory effect on the biological activity of VEGF by binding to VEGF, thereby preventing it from binding to its natural receptors present on the surface of target cells. Non-limiting examples of VEGF antagonists which bind the VEGF receptor are disclosed in PCT Application Nos. 97/44453, 05/000895 and U.S. Patent Application No. 20140057851. In certain embodiments the VEGF antagonist is a polypeptide with a bifunctional single-chain antagonistic human VEGF variant comprising a modified VEGF wherein the modified VEGF comprises a loop with an integrin-recognition RGD sequence, as described in U.S. Pat. No. 8,741,839, herein incorporated by reference.

In certain embodiments, the VEGF antagonist binds to the VEGF receptor, and can include an antibody or VEGF fragment.

X. Linkers

In certain embodiments, the extended-PK group is optionally fused to IL-2 via a linker. In certain embodiments, an integrin-binding polypeptide is fused to an Fc fragment via a linker. Suitable linkers are well known in the art, such as those disclosed in, e.g., US2010/0210511 US2010/0179094, and US2012/0094909, which are herein incorporated by reference in its entirety. Exemplary linkers include gly-ser polypeptide linkers, glycine-proline polypeptide linkers, and proline-alanine polypeptide linkers. In a certain embodiment, the linker is a gly-ser polypeptide linker, i.e., a peptide that consists of glycine and serine residues.

Exemplary gly-ser polypeptide linkers comprise the amino acid sequence Ser(Gly$_4$Ser)$_n$, as well as (Gly$_4$Ser)$_n$ and/or (Gly$_4$Ser$_3$)$_n$. In some embodiments, n=1. In some embodiments, n=2. In some embodiments, n=3, i.e., Ser(Gly$_4$Ser)$_3$. In some embodiments, n=4, i.e., Ser(Gly$_4$Ser)$_4$. In some embodiments, n=5. In some embodiments, n=6. In some embodiments, n=7. In some embodiments, n=8. In some embodiments, n=9. In some embodiments, n=10. Another exemplary gly-ser polypeptide linker comprises the amino acid sequence Ser(Gly$_4$Ser)$_n$. In some embodiments, n=1. In some embodiments, n=2. In some embodiments, n=3. In another embodiment, n=4. In some embodiments, n=5. In some embodiments, n=6. Another exemplary gly-ser polypeptide linker comprises (Gly$_4$Ser)n. In some embodiments, n=1. In some embodiments, n=2. In some embodiments, n=3. In some embodiments, n=4. In some embodiments, n=5. In some embodiments, n=6. Another exemplary gly-ser polypeptide linker comprises (Gly$_3$Ser)$_n$. In some embodiments, n=1. In some embodiments, n=2. In some embodiments, n=3. In some embodiments, n=4. In another embodiment, n=5. In yet another embodiment, n=6. Another exemplary gly-ser polypeptide linker comprises (Gly$_4$Ser$_3$) n. In some embodiments, n=1. In some embodiments, n=2. In some embodiments, n=3. In some embodiments, n=4. In some embodiments, n=5. In some embodiments, n=6. Another exemplary gly-ser polypeptide linker comprises (Gly$_3$Ser)$_n$. In some embodiments, n=1. In some embodiments, n=2. In some embodiments, n=3. In some embodiments, n=4. In another embodiment, n=5. In yet another embodiment, n=6.

In some embodiments, the linker polypeptide is selected from the group consisting of GGGGS (SEQ ID NO:136) and GGGGSGGGGSGGGGS (SEQ ID NO:137). In some embodiments, the linker polypeptide is GGGGS (SEQ ID NO:136). In some embodiments, the linker polypeptide is GGGGSGGGGSGGGGS (SEQ ID NO:137).

XI. Other Therapeutic Agents

The integrin-binding-Fc fusion protein suitable for use in the methods disclosed herein, can be used in conjunction with one or more therapeutic agents. In one embodiment, the therapeutic agent is a therapeutic antibody. In another embodiment, the therapeutic agent is a therapeutic protein. In another embodiment, the therapeutic agent is a small molecule. In another embodiment, the therapeutic agent is an antigen. In another embodiment, the therapeutic agent is a population of cells.

XII. Engineered Fusion Molecules

Also provided herein are engineered molecules that comprise two or more of IL-2, and an antibody (e.g., a therapeutic antibody, an immune checkpoint inhibitor, or an antibody that antagonizes VEGF) or antibody fragment described herein. Such engineered molecules can effectively reduce the number of components to be administered to a subject (e.g., a cancer patient) in the methods described herein. In some embodiments, the antibody or antibody fragment serves as the scaffold for conjugation with other components (e.g., IL-2).

Accordingly, in certain embodiments, the engineered molecule comprises IL-2 and an antibody or antibody fragment. In a particular embodiment, the antibody for use in the engineered protein is a bispecific antibody, wherein one component is a therapeutic antibody and the other component is an antibody that binds to an immune checkpoint inhibitor or an antibody that antagonizes VEGF activity. Methods for generating bispecific antibodies are known in the art.

Accordingly, in certain embodiments, the engineered molecule comprises IL-2 and a bispecific antibody which binds to a therapeutic target and an immune checkpoint inhibitor or an antibody that antagonizes VEGF.

In certain embodiments, the IL-2 component for use in the engineered protein is an IL-2 lacking a pharmacokinetic moiety (i.e., a non-extended-PK IL-2). In other embodiments, the IL-2 comprises a pharmacokinetic moiety (an extended-PK IL-2).

In certain embodiments, the components of the engineered molecule are conjugated to the antibody or bispecific antibody with or without a linker. Suitable linkers for conjugation are described herein and extensively described in the art.

Regions to which polypeptide-based components (e.g., IL-2) of the engineered molecule can be fused, with or without a linker, to the antibody are generally known in the art, and include, for example, the C-terminus of the antibody heavy chain, and the C-terminus of the antibody light chain.

In certain embodiments, components of the engineered molecule do not interfere with the function of the other components. By way of example, when the engineered protein comprises a therapeutic antibody and IL-2, the IL-2 will be fused to the therapeutic antibody in a manner such that the antibody retains its antigen-binding function, and IL-2 retains the ability to interact with its receptor. The methods described herein, e.g., in the Examples, can be used to determine whether components of the engineered protein retain their respective functions.

XIII. Methods of Making Polypeptides

In some aspects, the polypeptides described herein (e.g., IL-2, such as extended-PK IL-2, knottin-Fc, integrin binding-protein Fc fusion) are made in transformed host cells using recombinant DNA techniques. To do so, a recombinant DNA molecule coding for the peptide is prepared. Methods of preparing such DNA molecules are well known in the art. For instance, sequences coding for the peptides could be excised from DNA using suitable restriction enzymes. Alternatively, the DNA molecule could be synthesized using chemical synthesis techniques, such as the phosphoramidate method. Also, a combination of these techniques could be used.

The methods of making polypeptides also include a vector capable of expressing the peptides in an appropriate host. The vector comprises the DNA molecule that codes for the peptides operatively linked to appropriate expression control sequences. Methods of affecting this operative linking, either before or after the DNA molecule is inserted into the vector, are well known. Expression control sequences include promoters, activators, enhancers, operators, ribosomal nuclease domains, start signals, stop signals, cap signals, polyadenylation signals, and other signals involved with the control of transcription or translation.

The resulting vector having the DNA molecule thereon is used to transform an appropriate host. This transformation may be performed using methods well known in the art.

Any of a large number of available and well-known host cells may be used in the practice of this invention. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial hosts include bacteria (such as *E. coli* sp.), yeast (such as *Saccharomyces* sp.) and other fungi, insects, plants, mammalian (including human) cells in culture, or other hosts known in the art.

Next, the transformed host is cultured and purified. Host cells may be cultured under conventional fermentation conditions so that the desired compounds are expressed. Such fermentation conditions are well known in the art. Finally, the peptides are purified from culture by methods well known in the art.

The compounds may also be made by synthetic methods. For example, solid phase synthesis techniques may be used. Suitable techniques are well known in the art, and include those described in Merrifield (1973), Chem. Polypeptides, pp. 335-61 (Katsoyannis and Panayotis eds.); Merrifield (1963), J. Am. Chem. Soc. 85: 2149; Davis et al. (1985), Biochem. Intl. 10: 394-414; Stewart and Young (1969), Solid Phase Peptide Synthesis; U.S. Pat. No. 3,941,763; Finn et al. (1976), The Proteins ($3^{rd}$ ed.) 2: 105-253; and Erickson et al. (1976), The Proteins ($3^{rd}$ ed.) 2: 257-527. Solid phase synthesis is the preferred technique of making individual peptides since it is the most cost-effective method of making small peptides. Compounds that contain derivatized peptides or which contain non-peptide groups may be synthesized by well-known organic chemistry techniques.

Other methods are of molecule expression/synthesis are generally known in the art to one of ordinary skill.

XIV. Expression of Polypeptides

The nucleic acid molecules described above can be contained within a vector that is capable of directing their expression in, for example, a cell that has been transduced with the vector. Accordingly, in addition to extended-PK IL-2 and knottin-Fc mutants, expression vectors containing a nucleic acid molecule encoding an extended-PK IL-2 or knottin-Fc mutant and cells transfected with these vectors are among the certain embodiments.

Vectors suitable for use include T7-based vectors for use in bacteria (see, for example, Rosenberg et al., Gene 56: 125, 1987), the pMSXND expression vector for use in mammalian cells (Lee and Nathans, J. Biol. Chem. 263:3521, 1988), and baculovirus-derived vectors (for example the expression vector pBacPAKS from Clontech, Palo Alto, Calif.) for use in insect cells. The nucleic acid inserts, which encode the polypeptide of interest in such vectors, can be operably linked to a promoter, which is selected based on, for example, the cell type in which expression is sought. For example, a T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

In addition to sequences that facilitate transcription of the inserted nucleic acid molecule, vectors can contain origins of replication, and other genes that encode a selectable marker. For example, the neomycin-resistance (neo) gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that can be used in the invention include, for example, retroviral, adenoviral, and adeno-associated vectors, herpes virus, simian virus 40 (SV40), and bovine papilloma virus vectors (see, for example, Gluzman (Ed.), Eukaryotic Viral Vectors, CSH Laboratory Press, Cold Spring Harbor, N.Y.).

Prokaryotic or eukaryotic cells that contain and express a nucleic acid molecule that encodes an extended-PK IL-2 or an integrin binding-protein Fc fusion mutant are also features of the invention. A cell of the invention is a transfected cell, i.e., a cell into which a nucleic acid molecule, for example a nucleic acid molecule encoding an extended-PK IL-2 mutant or integrin binding-protein Fc fusion, has been introduced by means of recombinant DNA techniques. The progeny of such a cell are also considered within the scope of the invention.

The precise components of the expression system are not critical. For example, an extended-PK IL-2 or integrin binding-protein Fc fusion mutant can be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

The expressed polypeptides can be purified from the expression system using routine biochemical procedures, and can be used, e.g., as therapeutic agents, as described herein.

XV. Pharmaceutical Compositions and Modes of Administration

In some embodiments, the integrin-binding polypeptide-Fc fusion is administered alone. In some embodiments, IL-2 is administered together (simultaneously or sequentially) with an integrin-binding polypeptide-Fc fusion. In some embodiments, IL-2 is administered prior to the administration of an integrin-binding polypeptide-Fc fusion. In some embodiments, IL-2 is administered concurrently with the administration of an integrin-binding polypeptide-Fc fusion. In some embodiments, IL-2 is administered subsequent to the administration of an integrin-binding polypeptide-Fc fusion. In some embodiments, the IL-2 and an integrin-binding polypeptide-Fc fusion are administered simultaneously. In other embodiments, the IL-2 and an integrin-binding polypeptide-Fc fusion are administered sequentially. In some embodiments, the IL-2 and an integrin-binding polypeptide-Fc fusion are administered within one, two, or three days of administration of the other. In some embodiments, the IL-2 is administered at day 2, day 3, and/or day 4 before administration of the integrin-binding polypeptide-Fc fusion. In some embodiments, the IL-2 is administered at day 2, day 3, and/or day 4 after administration of the integrin-binding polypeptide-Fc fusion. In some embodiments, the IL-2 is administered at day 2 after administration of the integrin-binding polypeptide-Fc fusion. In some embodiments, the IL-2 is administered at day 3 after administration of the integrin-binding polypeptide-Fc fusion. In some embodiments, the IL-2 is administered at day 4 after administration of the integrin-binding polypeptide-Fc fusion.

Figures 4A, 4B:
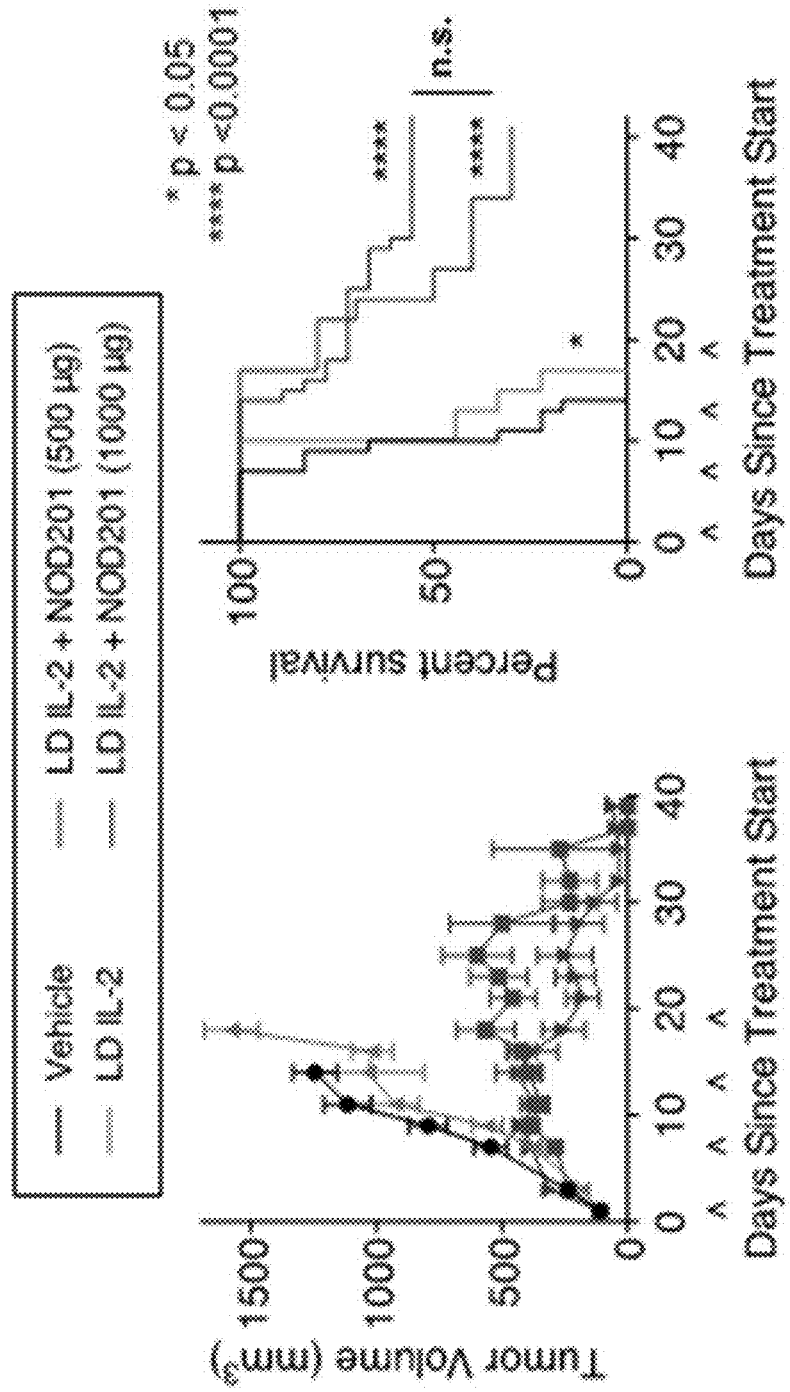
FIG. 4A-FIG. 4B. NOD201M potentiates low dose IL-2 (4 µg; Proleukin). Left, Tumor volume curves. Right, Kaplan-Meier curves. NOD201M was administered IV at doses of 500 µg or 1000 µg on days 1, 7, 13, 19 after inoculated tumors reached an average size of 60-180 mm³.

While not being bound by theory, the hypothesized therapeutic mechanism of action for IL-2 in combination with an Fc-containing tumor-targeting moiety such as an antibody or integrin-binding polypeptide-Fc fusion is to activate and amplify the CD8+ T cell response following treatment with the integrin-binding polypeptide-Fc fusion (Cancer Cell. 2015 Apr. 13; 27(4):489-501.). IL-2 is well known to cause numerous significant clinical toxicities, and so it is desirable to minimize the dose and frequency of IL-2 administration. Consequently, clinical protocols involving subcutaneous administration of low dose IL-2 have been tested and found to be much better tolerated albeit with somewhat reduced efficacy (Journal of Clinical Oncology, Vol 21, No 16 (August 15), 2003: pp 3127-3132). This lower dose may be tested in mice by using a suitable allometric scaling algorithm for administration of Proleukin (http://www.fda.gov/downloads/Drugs/ . . . /Guidances/UCM078932.pdf), leading to a dose of about 4 micrograms administered subcutaneously. In lieu of extended-PK IL-2, we show that it is possible to administer a better-tolerated schedule of subcutaneous low dose IL-2 on a daily basis starting one day after administration of an integrin-binding polypeptide-Fc fusion. Low dose IL-2 preferentially stimulates cells expressing the high affinity IL-2 receptor subunit alpha, also known as CD25. Immunosuppressive regulatory CD4+ T cells (Tregs) are known to express CD25 at a high level, and activated cytolytic CD8+ T cells (CTLs) also transiently express CD25. In an attempt to preferentially stimulate Tregs, chronic subcutaneous low dose IL-2 has been tested successfully in patients with graft versus host disease (Science Translational Medicine Vol 5 Issue 179 179ra43). One skilled in the art might therefore expect this immunosuppressive effect mediated by Tregs to interfere with the desired activating CTL response to subcutaneous IL-2. However, we do in fact find that combining an integrin-binding polypeptide-Fc fusion with daily subcutaneous low-dose IL-2 for three days leads to significant therapeutic effects in animal models of cancer (see, FIG. 4 and FIG. 7).

In some embodiments, integrin-binding polypeptide-Fc fusion and IL-2 are administered with an immune checkpoint inhibitor. In some embodiments the immune checkpoint inhibitor is an anti-PD-1 antibody. In some embodiments, the anti PD-1 antibody can include but is not limited to nivolumab (BMS-936558, Bristol-Myers Squibb), pembrolizumab (lambrolizumab, MK03475 or MK-3475, Merck), humanized anti-PD-1 antibody JS001 (ShangHai JunShi), monoclonal anti-PD-1 antibody TSR-042 (Tesaro, Inc.), pidilizumab (anti-PD-1 mAb CT-011, Medivation), anti-PD-1 monoclonal antibody BGB-A317 (BeiGene), and/or anti-PD-1 antibody SHR-1210 (ShangHai HengRui), human monoclonal antibody REGN2810 (Regeneron), human monoclonal antibody MDX-1106 (Bristol-Myers Squibb), and/or humanized anti-PD-1 IgG4 antibody PDR001 (Novartis). In some embodiments, the PD-1 antibody is from clone: RMP1-14 (rat IgG)—BioXcell cat #BP0146.

In some embodiments, the immune checkpoint inhibitor is an anti-CTLA-4 antibody, such as for example ipilimumab (Yervoy, Bristol-Myers Squibb). In some embodiments, an antagonist of VEGF is used in place of an immune checkpoint inhibitor.

Pharmaceutical compositions of the invention can be administered in combination therapy, i.e., combined with other agents. Agents include, but are not limited to, in vitro synthetically prepared chemical compositions, antibodies, antigen binding regions, and combinations and conjugates thereof. In certain embodiments, an agent can act as an agonist, antagonist, allosteric modulator, or toxin.

In some embodiments, the invention provides for separate pharmaceutical compositions comprising extended-PK IL-2 with a pharmaceutically acceptable diluent, carrier, solubilizer, emulsifier, preservative and/or adjuvant, and another pharmaceutical composition comprising a integrin-binding polypeptide-Fc fusion with a pharmaceutically acceptable diluent, carrier, solubilizer, emulsifier, preservative and/or adjuvant. In certain embodiments, the invention further provides for a separate pharmaceutical composition comprising an immune checkpoint inhibitor (or an antagonist of VEGF) with a pharmaceutically acceptable diluent, carrier, solubilizer, emulsifier, preservative and/or adjuvant. In certain embodiments, the pharmaceutical compositions comprise both IL-2 or extended-PK IL-2 and integrin-binding polypeptide-Fc fusion with a pharmaceutically acceptable diluents, carrier, solubilizer, emulsifier, preservative and/or adjuvant. In certain embodiments, the pharmaceutical composition comprises IL-2 or extended-PK IL-2, integrin-binding polypeptide-Fc fusion, and an immune checkpoint modulator, including inhibitors (or an antagonist of VEGF) with a pharmaceutically acceptable diluents, carrier, solubilizer, emulsifier, preservative and/or adjuvant.

In some embodiments, the invention provides for pharmaceutical compositions comprising 11-2 or extended-PK IL-2, together with a pharmaceutically acceptable diluent, carrier, solubilizer, emulsifier, preservative and/or adjuvant, and another pharmaceutical composition comprises an integrin-binding polypeptide-Fc fusion, together with a pharmaceutically acceptable diluent, carrier, solubilizer, emulsifier, preservative and/or adjuvant. In certain embodiments, the invention provides for pharmaceutical compositions comprising an immune checkpoint inhibitor, together with a pharmaceutically acceptable diluent, carrier, solubilizer, emulsifier, preservative and/or adjuvant. In certain embodiments, each of the agents, e.g., IL-2, extended-PK IL-2, an integrin-binding polypeptide-Fc fusion, and optionally an immune checkpoint inhibitor (or an antagonist of VEGF), can be formulated as separate compositions. In some embodiments, acceptable formulation materials preferably are nontoxic to recipients at the dosages and concentrations employed. In certain embodiments, the formulation material(s) are for s.c. and/or I.V. administration. In certain embodiments, the pharmaceutical composition can contain formulation materials for modifying, maintaining or preserving, for example, the pH, osmolality, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18$^{th}$ Edition, A. R. Gennaro, ed., Mack Publishing Company (1995). In certain embodiments, the formulation comprises PBS; 20 mM NaOAC, pH 5.2, 50 mM NaCl; and/or 10 mM NAOAC, pH 5.2, 9% Sucrose. In certain embodiments, the optimal pharmaceutical composition will be determined by one skilled in the art depending upon, for example, the intended route of administration, delivery format and desired dosage. See, for example, Remington's Pharmaceutical Sciences, supra. In certain embodiments, such compositions may influence the physical state, stability, rate of in vivo release and rate of in vivo clearance of extended-PK IL-2, a knottin-Fc, and optionally an immune checkpoint inhibitor (or an antagonist of VEGF).

In some embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In certain embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In some embodiments, a composition comprising IL-2 or extended-PK IL-2, an integrin-binding polypeptide-Fc fusion, and optionally an immune checkpoint inhibitor (or an antagonist of VEGF), can be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising IL-2 or extended-PK IL-2, an integrin-binding polypeptide-Fc fusion, and optionally an immune checkpoint inhibitor (or an antagonist of VEGF), can be formulated as a lyophilizate using appropriate excipients such as sucrose.

In some embodiments, the pharmaceutical composition can be selected for parenteral delivery. In some embodiments, the compositions can be selected for inhalation or for delivery through the digestive tract, such as orally. The preparation of such pharmaceutically acceptable compositions is within the ability of one skilled in the art.

In some embodiments, the formulation components are present in concentrations that are acceptable to the site of administration. In some embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising a desired extended-PK IL-2, a knottin-Fc, and optionally an immune checkpoint inhibitor (or an antagonist of VEGF), in a pharmaceutically acceptable vehicle. In certain embodiments, a vehicle for parenteral injection is sterile distilled water in which IL-2 or extended-PK IL-2, integrin-binding polypeptide-Fc fusion and optionally an immune checkpoint inhibitor (or an antagonist of VEGF), are formulated as a sterile, isotonic solution, and properly preserved. In some embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In some embodiments, hyaluronic acid can also be used, and can have the effect of promoting sustained duration in the circulation. In certain embodiments, implantable drug delivery devices can be used to introduce the desired molecule.

In some embodiments, a pharmaceutical composition can be formulated for inhalation. In some embodiments, IL-2 or extended-PK IL-2, an integrin-binding polypeptide-Fc fusion, and optionally an immune checkpoint inhibitor (or an antagonist of VEGF), can be formulated as a dry powder for inhalation. In some embodiments, an inhalation solution comprising IL-2 or extended-PK IL-2, an integrin-binding polypeptide-Fc fusion, and optionally an immune checkpoint inhibitor (or an antagonist of VEGF), can be formulated with a propellant for aerosol delivery. In certain embodiments, solutions can be nebulized. Pulmonary administration is further described in PCT application No. PCT/US94/001875, which describes pulmonary delivery of chemically modified proteins.

In certain embodiments, it is contemplated that formulations can be administered orally. In certain embodiments, IL-2 or extended-PK IL-2, an integrin-binding polypeptide-Fc fusion, and optionally an immune checkpoint inhibitor (or an antagonist of VEGF), that is administered in this fashion can be formulated with or without those carriers customarily used in the compounding of solid dosage forms such as tablets and capsules. In some embodiments, a capsule can be designed to release the active portion of the formulation at the point in the gastrointestinal tract when bioavailability is maximized and pre-systemic degradation is minimized. In some embodiments, at least one additional agent can be included to facilitate absorption of IL-2 or extended-PK IL-2, an integrin-binding polypeptide-Fc fusion, and optionally an immune checkpoint inhibitor (or an antagonist of VEGF). In some embodiments, diluents, flavorings, low melting point waxes, vegetable oils, lubricants, suspending agents, tablet disintegrating agents, and binders can also be employed.

In some embodiments, a pharmaceutical composition can involve an effective quantity of IL-2 extended-PK IL-2, an integrin-binding polypeptide-Fc fusion, and optionally an immune checkpoint inhibitor (or an antagonist of VEGF), in a mixture with non-toxic excipients which are suitable for the manufacture of tablets. In some embodiments, by dissolving the tablets in sterile water, or another appropriate vehicle, solutions can be prepared in unit-dose form. In some embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving IL-2 or extended-PK IL-2, an integrin-binding polypeptide-Fc fusion, and optionally an immune checkpoint inhibitor (or an antagonist of VEGF), in sustained- or controlled-delivery formulations. In some embodiments, techniques for formulating a variety of other sustained- or controlled-delivery means, such as liposome carriers, bio-erodible microparticles or porous beads and depot injections, are also known to those skilled in the art. See, for example, PCT Application No. PCT/US93/00829 which describes the controlled release of porous polymeric microparticles for the delivery of pharmaceutical compositions, incorporated by reference herein. In some embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481, incorporated by reference herein), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15: 167-277 (1981) and Langer, Chem. Tech., 12:98-105 (1982)), ethylene vinyl acetate (Langer et al., supra) or poly-D(–)-3-hydroxybutyric acid (EP 133,988). In certain embodiments, sustained release compositions can also include liposomes, which can be prepared by any of several methods known in the art. See, e.g., Eppstein et al, Proc. Natl. Acad. Sci. USA, 82:3688-3692 (1985); EP 036,676; EP 088,046 and EP 143,949.

The pharmaceutical composition to be used for in vivo administration typically is sterile. In certain embodiments, this can be accomplished by filtration through sterile filtration membranes. In some embodiments, where the composition is lyophilized, sterilization using this method can be conducted either prior to or following lyophilization and reconstitution. In certain embodiments, the composition for parenteral administration can be stored in lyophilized form or in a solution. In some embodiments, parenteral compositions generally are placed into a container having a sterile access port, for example, an intravenous solution bag or vial having a stopper pierceable by a hypodermic injection needle.

In some embodiments, once the pharmaceutical composition has been formulated, it can be stored in sterile vials as a solution, suspension, gel, emulsion, solid, or as a dehydrated or lyophilized powder. In some embodiments, such formulations can be stored either in a ready-to-use form or in a form (e.g., lyophilized) that is reconstituted prior to administration.

In some embodiments, kits are provided for producing a single-dose administration unit. In certain embodiments, the kit can contain both a first container having a dried protein and a second container having an aqueous formulation. In some embodiments, kits containing single and multi-chambered pre-filled syringes (e.g., liquid syringes and lyosyringes) are included.

In some embodiments, the effective amount of a pharmaceutical composition comprising extended-PK IL-2 and/or one or more pharmaceutical compositions comprising a knottin-Fc, and optionally an immune checkpoint inhibitor (or an antagonist of VEGF), to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which IL-2 or extended-PK IL-2, an integrin-binding polypeptide-Fc fusion, and optionally an immune checkpoint inhibitor (or an antagonist of VEGF), are being used, the route of administration, and the size (body weight, body surface or organ size) and/or condition (the age and general health) of the patient. In some embodiments, the clinician can titer the dosage and modify the route of administration to obtain the optimal therapeutic effect. In certain embodiments, a typical dosage of IL-2 or extended-PK IL-2 and an integrin-binding polypeptide-Fc fusion can each range from about 0.1 µg/kg to up to about 100 mg/kg or more, depending on the factors mentioned above. In certain embodiments, the dosage can range from 0.1 µg/kg up to about 100 mg/kg; or 1 µg/kg up to about 100 mg/kg; or 5 µg/kg up to about 100 mg/kg. In some embodiments, the dosage of an integrin-binding polypeptide-Fc fusion can range from about 5 mg/kg to about 50 mg/kg. In some embodiments, the dosage can range from about 10 mg/kg to about 40 mg/kg, about 10 mg/kg to about 30 mg/kg, about 10 mg/kg to about 25 mg/kg, about 5 mg/kg to about 20 mg/kg, about 5 mg/kg to about 15 mg/kg, or about 5 mg/kg to about 10 mg/kg. In some embodiments, the dosage is about 10 mg/kg.

IL-2 dosages can include but are not limited to high doses (HD): 0.72 MIU/kg every 8 hr×15 (80 MIU/m2/d); low dosages (LD): 8 MIU/m2/d; and subcutaneous dosages (SC): 250,000 U/kg/dose (9.25 MIU/m2/d, 5 days per week, dose halved in weeks 2-6). MIU refers to million international units. Subcutaneous IL-2 has been shown to be well tolerated and to exhibit a 10% response rate to subcutaneous IL-2 (see, for example, *J Clin Oncol* 21:3127-3132, 2003). As such, Other subcutaneous IL-2 dosages can include 1 MIU/m2 d 2-7, 12-21; 12 MIU/m2 d 9-11 & 1-3 subsequent cycles (see, for example, Mani et al., *Breast Cancer Research and Treatment*, 117(1), 83-89. 2009) and 8.8 MIU/m2/d, 6.25 MIU/m2/d (14 MIU s.c. thrice weekly during weeks 2 to 5 and 10 MIU s.c. thrice weekly during weeks 6 to 9; see, for example, *Clinical Cancer Research* 12(23), 7046-7053, 2006). While the examples provide herein are directed to mice studies, such studies can be translated to human patients, including the IL-2 dosing. For example, 9 MIU/m2 in humans is equivalent to 3.6 µg in mice. The FDA human equivalent dose (HED) based on body area (see, for example, http://www.fda.gov/downloads/drugs/guidances/ucm078932.pdf; incorporated by reference herein; see tables 4 and 5 copied below). For example, 9 MIU/m2/(37 kg/m2)=0.24 MIU/kg×12.3 (from table 3)=2.95 MIU/kg in mice and 2.95 MIU/kg/(16.4 MIU/mg)*0.02 kg/mouse=3.6 µg in mice.

TABLE 4

Conversion of Animal Doses to Human Equivalent Doses Based on Body Surface Area

| Species | To Convert Animal Dose in mg/kg to Dose in mg/m², Multiply by $k_m$ | To Convert Animal Dose in mg/kg to HED$^a$ in mg/kg, Either: | |
|---|---|---|---|
| | | Divide Animal Dose By | Multiply Animal Dose By |
| Human | 37 | — | — |
| Child (20 kg)$^b$ | 25 | — | — |
| Mouse | 3 | 12.3 | 0.08 |
| Hamster | 5 | 7.4 | 0.13 |
| Rat | 6 | 6.2 | 0.16 |
| Ferret | 7 | 5.3 | 0.19 |
| Guinea pig | 8 | 4.6 | 0.22 |
| Rabbit | 12 | 3.1 | 0.32 |
| Dog | 20 | 1.8 | 0.54 |
| Primates: | | | |
| Monkeys$^c$ | 12 | 3.1 | 0.32 |
| Marmoset | 6 | 6.2 | 0.16 |
| Squirrel monkey | 7 | 5.3 | 0.19 |
| Baboon | 20 | 1.8 | 0.54 |
| Micro-pig | 27 | 1.4 | 0.73 |
| Mini-pig | 35 | 1.1 | 0.95 |

$^a$Assumes 60 kg human. For species not listed or for weight outside the standard ranges. HED can be calculated from the following formula.
HED = animal dose in mg/kg × (animal weight in kg/human weight in kg)$^{0.33}$
$^b$This $k_m$ value is provided for reference only since healthy children will rarely be volunteers for phase 1 trials.
$^c$For example, cynomolgus, rhesus, and stamptail.

TABLE 5

Conversion of Animal Doses to Human Equivalent Doses Based on Body Surface Area

| Species | Reference Body Weight (kg) | Working Weight Range$^a$ (kg) | Body Surface Area (m²) | To Convert Dose in mg/kg to Dose in mg/m² Multiply by $k_m$ | To Convert Animal Dose in mg/kg to HED$^b$ in mg/kg, Either: | |
|---|---|---|---|---|---|---|
| | | | | | Divide Animal Dose By | Multiply Animal Dose By |
| Human | 60 | — | 1.62 | 37 | — | — |
| Child$^c$ | 20 | — | 0.80 | 25 | — | — |
| Mouse | 0.020 | 0.011-0.034 | 0.007 | 3 | 12.3 | 0.081 |
| Hamster | 0.080 | 0.047-0.157 | 0.016 | 5 | 7.4 | 0.135 |
| Rat | 0.150 | 0.080-0.270 | 0.025 | 6 | 6.2 | 0.162 |
| Ferret | 0.300 | 0.160-0.540 | 0.043 | 7 | 5.3 | 0.189 |
| Guinea pig | 0.400 | 0.208-0.700 | 0.05 | 8 | 4.6 | 0.216 |
| Rabbit | 1.8 | 0.9-3.0 | 0.15 | 12 | 3.1 | 0.324 |
| Dog | 10 | 5-17 | 0.50 | 20 | 1.8 | 0.541 |
| Primates: | | | | | | |
| Monkeys$^d$ | 3 | 1.4-4.9 | 0.25 | 12 | 3.1 | 0.324 |
| Marmoset | 0.350 | 0.140-0.720 | 0.06 | 6 | 6.2 | 0.162 |
| Squirrel monkey | 0.600 | 0.290-0.970 | 0.09 | 7 | 5.3 | 0.189 |
| Baboon | 12 | 7-23 | 0.60 | 20 | 1.8 | 0.541 |
| Micro-pig | 20 | 10-33 | 0.74 | 27 | 1.4 | 0.730 |
| Mini-pig | 40 | 25-64 | 1.14 | 35 | 1.1 | 0.946 |

$^a$For animal weights within the specified ranges, the HED for a 60 kg human calculated using the standard $k_m$ value will not vary more than ±20 percent from the HED calculated using a $k_m$ value based on the exact animal weight.
$^b$Assumes 60 kg human. For species listed or for weight outside the standard ranges, human equivalent dose can be calculated from the formula: HED = animal dose in mg/kg × (animal weight in kg/human weight in kg)$^{0.33}$.
$^c$The $k_m$ value is provided for reference only since healthy children will rarely be volunteers for phase 1 trials.
$^d$For example, cynomolgus, rhesus, and stamptail.

Subcutaneous IL-2 has a plasma peak when 0.7 nM per MIU/m2 SC is dosed. The calculation is as follows:

10.6 CU/mL per MCU/m2;

10.6 CU/mL/(4×10^6 CU/mg)*1000 mL/L/(15,300 mg/mmol)×10^6 nmol/mmol=0.17 nM 16.4 MIU/mg/(4 MCU/mg)=4.1 MIU/MCU This has been described in, for example, Cancer Research 50. 2009-2017, '90, Table 4 of which is copied below as Table 6.

TABLE 6

Peak serum elvels after s.c. injections
IL-2 was administered by s.c. injection at doses of 0.5 or 1.0 MU/m$^2$,
and the activity was determined in serum taken at 0.5, 1, 2, 3, 4, 6, 8,
and 24 h after injection. The median dose normalized peak level of
10.7 units/ml and time to peak of 180 min are similar to the
corresponding values of 14.0 units/ml and 150 min observed after i.m.
administration (Table 3). The dose levels were lower in this
study as compared to the i.m. trial, and meaningful values
for AUC could not be obtained.

| Patient | Dose level (MU/m$^2$) | Last time point (min) | Peak time (min) | Peak level (units/ml) | Peak level/dose |
|---|---|---|---|---|---|
| 1 | 0.5 | 1440 | 120 | 6.7 | 13.4 |
| 2 | 0.5 | 1440 | 240 | 4.5 | 9.0 |
| 3 | 0.5 | 1440 | 360 | 7.5 | 15.0 |
| 4 | 1.0 | 1440 | 120 | 5.7 | 5.7 |
| 5 | 1.0 | 1440 | 120 | 11.8 | 11.8 |
| 7 | 1.0 | 1440 | 240 | 9.5 | 9.5 |
| Median | 0.8 | 1440 | 180 | 7.1 | 10.7 |
| Minimum | 0.5 | 1440 | 120 | 4.5 | 5.7 |
| Maximum | 1.0 | 1440 | 360 | 11.8 | 15.0 |
| Mean ± SD | | | | | 10.6 ± 3.5 |

With regard to Proleukin, it has a MW 15.3 kD and can be dosed at 16.4 MIU/mg. Other dosage units have been described, including "Cetus Units" and "Roche Units", and 1 Cetus Unit=3-6 IU (see, for example, http://cancerguide.org/rcc_il2.html Cancer Research 50. 2009-2017, '90).

With regard to surface area dosage conversion factors in IL-2 dosing, the following is applicable to the methods described herein. In adult humans, 100 mg/kg is equivalent to 100 mg/kg×37 kg/sq.m.=3700 mg/m2. A given mg/kg dose in mice can be divided by 12 to give an equivalent dose in man in terms of mg/m2. For example, a 60 kg human has 1.6 m2 surface area. See, for example, https://ncifrederick.cancer.gov/Lasp/Acuc/Frederick/Media/Documents/ACUC42.pdf.

In some embodiments, a typical dosage for an immune checkpoint inhibitor can range from about 0.1 mg/kg to up to about 300 mg/kg or more, depending on the factors mentioned above. In some embodiments, the dosage can range from 1 mg/kg up to about 300 mg/kg; or 5 mg/kg up to about 300 mg/kg; or 10 mg/kg up to about 300 mg/kg.

In some embodiments, the frequency of dosing will take into account the pharmacokinetic parameters of IL-2 or extended-PK IL-2, an integrin-binding polypeptide-Fc fusion, and optionally an immune checkpoint inhibitor (or an antagonist of VEGF), in the formulation used. In some embodiments, a clinician will administer the composition until a dosage is reached that achieves the desired effect. In some embodiments, the composition can therefore be administered as a single dose, or as two or more doses (which may or may not contain the same amount of the desired molecule) over time, or as a continuous infusion via an implantation device or catheter. Further refinement of the appropriate dosage can be made by those of ordinary skill in the art and is within the ambit of tasks routinely performed by them. In some embodiments, appropriate dosages can be ascertained through use of appropriate dose-response data. In some embodiments, IL-2 is administered before, after, and/or simultaneously with the integrin-binding polypeptide-Fc fusion. In some embodiments, IL-2 is administered 1 day, 2 days, 3 days, 4 days, 5, days, 6 days, or more after administration of the integrin-binding polypeptide-Fc fusion. In some embodiments, IL-2 is administered 2 days after administration of the integrin-binding polypeptide-Fc fusion. In some embodiments, IL-2 is administered 3 days after administration of the integrin-binding polypeptide-Fc fusion. In some embodiments, IL-2 is administered 4 days after administration of the integrin-binding polypeptide-Fc fusion.

In some embodiments, the IL-2 is administered at a 12 MIU/m2 or lower daily dose. In some embodiments, the IL-2 dose is less than 14 MIU/m2, less than 12 MIU/m2, less than 10 MIU/m2, less than 8 MIU/m2, less than 6 MIU/m2, less than 4 MIU/m2, less than 2 MIU/m2 per day. In some embodiments, the IL-2 dose is about 14 MIU/m2 to about 6 MIU/m2 per day. In some embodiments, the IL-2 dose is about 12 MIU/m2 to about 8 MIU/m2 per day. In some embodiments, the IL-2 dose is about 12 MIU/m2 to about 10 MIU/m2 per day.

In some embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intra-ocular, intraarterial, intraportal, or intralesional routes; by sustained release systems or by implantation devices. In some embodiments, the compositions can be administered by bolus injection or continuously by infusion, or by implantation device. In certain embodiments, individual elements of the combination therapy may be administered by different routes.

In some embodiments, the composition can be administered locally via implantation of a membrane, sponge or another appropriate material onto which the desired molecule has been absorbed or encapsulated. In some embodiments, where an implantation device is used, the device can be implanted into any suitable tissue or organ, and delivery of the desired molecule can be via diffusion, timed-release bolus, or continuous administration. In some embodiments, it can be desirable to use a pharmaceutical composition comprising IL-2 or extended-PK IL-2, an integrin-binding polypeptide-Fc fusion, and optionally an immune checkpoint inhibitor (or an antagonist of VEGF), in an ex vivo manner. In such instances, cells, tissues and/or organs that have been removed from the patient are exposed to a pharmaceutical composition comprising IL-2 or extended-PK IL-2, an integrin-binding polypeptide-Fc fusion, and optionally an immune checkpoint inhibitor (or an antagonist of VEGF), after which the cells, tissues and/or organs are subsequently implanted back into the patient.

In some embodiments, IL-2 or extended-PK IL-2, an integrin-binding polypeptide-Fc fusion, and optionally an immune checkpoint inhibitor (or an antagonist of VEGF), can be delivered by implanting certain cells that have been genetically engineered, using methods such as those described herein, to express and secrete the polypeptides. In certain embodiments, such cells can be animal or human cells, and can be autologous, heterologous, or xenogeneic. In some embodiments, the cells can be immortalized. In some embodiments, in order to decrease the chance of an immunological response, the cells can be encapsulated to avoid infiltration of surrounding tissues. In some embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

XVI. Methods of Treatment

The integrin-binding polypeptide-Fc fusions and/or nucleic acids expressing them, as described herein, are useful for treating a disorder associated with abnormal apoptosis or a differentiative process (e.g., cellular proliferative disorders or cellular differentiative disorders, such as cancer). Additionally, the IL-2 or extended-PK IL-2, an integrin-binding polypeptide-Fc fusion, and optionally an immune checkpoint modulator, including an inhibitor (or an antagonist of VEGF), and/or nucleic acids expressing them, as described herein, are useful for treating a disorder associated with abnormal apoptosis or a differentiative process (e.g., cellular proliferative disorders or cellular differentiative disorders, such as cancer). Non-limiting examples of cancers that are amenable to treatment with the methods of the present invention are described below.

Examples of cellular proliferative and/or differentiative disorders include cancer (e.g., carcinoma, sarcoma, metastatic disorders or hematopoietic neoplastic disorders, e.g., leukemias). A metastatic tumor can arise from a multitude of primary tumor types, including but not limited to those of prostate, colon, lung, breast and liver. Accordingly, the compositions used herein, comprising, e.g., extended-PK IL-2, a knottin-Fc, and optionally an immune checkpoint inhibitor (or an antagonist of VEGF), can be administered to a patient who has cancer.

As used herein, we may use the terms "cancer" (or "cancerous"), "hyperproliferative," and "neoplastic" to refer to cells having the capacity for autonomous growth (i.e., an abnormal state or condition characterized by rapidly proliferating cell growth).

Hyperproliferative and neoplastic disease states may be categorized as pathologic (i.e., characterizing or constituting a disease state), or they may be categorized as non-pathologic (i.e., as a deviation from normal but not associated with a disease state). The terms are meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. In some embodiments, the diseases arise from poorly differentiated acute leukemias (e.g., erythroblastic leukemia and acute megakaryoblastic leukemia). Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit. Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macro globulinemia (WM). Additional forms of malignant lymphomas include, but are not limited to non-Hodgkin lymphoma and variants thereof, peripheral T cell lymphomas, adult T cell leukemia/lymphoma (ATL), cutaneous T cell lymphoma (CTCL), large granular lymphocytic leukemia (LGF), Hodgkin's disease and Reed-Sternberg disease.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The mutant IL-2 polypeptides can be used to treat patients who have, who are suspected of having, or who may be at high risk for developing any type of cancer, including renal carcinoma or melanoma, or any viral disease. Exemplary carcinomas include those forming from tissue of the cervix, lung, prostate, breast, head and neck, colon and ovary. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures.

"Cancer," as used herein, refers broadly to any neoplastic disease (whether invasive non-invasive or metastatic) characterized by abnormal and uncontrolled cell division causing malignant growth or tumor (e.g., unregulated cell growth). Non-limiting examples of which are described herein. This includes any physiological condition in mammals that is typically characterized by unregulated cell growth. Examples of cancer are exemplified in the working examples and also are described within the specification. The terms "cancer" or "neoplasm" are used to refer to malignancies of the various organ systems, including those affecting the lung, breast, thyroid, lymph glands and lymphoid tissue, gastrointestinal organs, and the genitourinary tract, as well as to adenocarcinomas which are generally considered to include malignancies such as most colon cancers, renal-cell carcinoma, prostate cancer and/or testicular tumors, non-small cell carcinoma of the lung, cancer of the small intestine and cancer of the esophagus.

Non-limiting examples of cancers that can be treated using the integrin-binding polypeptide-Fc fusions of the invention include, but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; multiple myeloma and post-transplant lymphoproliferative disorder (PTLD). In some embodiments, other cancers amenable for treatment by the present invention include, but are not limited to, carcinoma, lymphoma, blastoma, sarcoma, and leukemia or lymphoid malignancies. More particular examples of such cancers include colorectal, bladder, ovarian, melanoma, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. Preferably, the cancer is selected from the group consisting of colorectal cancer, breast cancer, rectal cancer, non-small cell lung cancer, non-Hodgkin's lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, and multiple myeloma. In an exemplary embodiment the cancer is an early or advanced (including metastatic) bladder, ovarian or melanoma. In another embodiment the cancer is colorectal cancer. In some embodiments, the methods of the present invention are useful for the treatment of vascularized tumors.

It will be appreciated by those skilled in the art that amounts for each of the IL-2, extended-PK IL-2, integrin-binding polypeptide-Fc fusion, and optionally an immune checkpoint modulator, including an inhibitor (or an antagonist of VEGF), that are sufficient to reduce tumor growth and size, or a therapeutically effective amount, will vary not only on the particular compounds or compositions selected, but also with the route of administration, the nature of the condition being treated, and the age and condition of the patient, and will ultimately be at the discretion of the patient's physician or pharmacist. The length of time during which the compounds used in the instant method will be given varies on an individual basis. As described herein, immune checkpoint inhibitors include anti-PD-1 antibodies and anti-PD-L1 antibodies.

It will be appreciated by those skilled in the art that the colon carcinoma model used herein in the examples (MC38 murine colon carcinoma) is a generalized model for solid tumors. That is, efficacy of treatments in this model is also predictive of efficacy of the treatments in other non-melanoma solid tumors. For example, as described in Baird et al. (J Immunology 2013; 190:469-78; Epub Dec. 7, 2012), efficacy of cps, a parasite strain that induces an adaptive immune response, in mediating anti-tumor immunity against B16F10 tumors was found to be generalizable to other solid tumors, including models of lung carcinoma and ovarian cancer. In another example, results from a line of research into VEGF targeting lymphocytes also shows that results in B16F10 tumors were generalizable to the other tumor types studied (Chinnasamy et al., JCI 2010; 120:3953-68; Chinnasamy et al, Clin Cancer Res 2012; 18: 1672-83). In yet another example, immunotherapy involving LAG-3 and PD-1 led to reduced tumor burden, with generalizable results in a fibrosarcoma and colon adenocarcinoma cell lines (Woo et al., Cancer Res 2012; 72:917-27).

In some embodiments, the integrin-binding polypeptide-Fc fusions are used to treat cancer. In some embodiments, the integrin-binding polypeptide-Fc fusions, and optional immune checkpoint inhibitor (or an antagonist of VEGF), are used to treat cancer. In some embodiments, the IL-2 or extended-PK IL-2, integrin-binding polypeptide-Fc fusions, and optional immune checkpoint inhibitor (or an antagonist of VEGF), are used to treat cancer. In some embodiments, the IL-2, integrin-binding polypeptide-Fc fusions, and optional immune checkpoint inhibitor (or an antagonist of VEGF), are used to treat cancer. In some embodiments, the extended-PK IL-2, integrin-binding polypeptide-Fc fusions, and optional immune checkpoint inhibitor (or an antagonist of VEGF), are used to treat cancer.

In some embodiments, the IL-2 or extended-PK IL-2, integrin-binding polypeptide-Fc fusions, and optional immune checkpoint inhibitor (or an antagonist of VEGF) are used to treat melanoma, leukemia, lung cancer, breast cancer, prostate cancer, ovarian cancer, colon cancer, renal carcinoma, and brain cancer.

In some embodiments, the IL-2 or extended-PK IL-2, integrin-binding polypeptide-Fc fusions and optional immune checkpoint inhibitor (or an antagonist of VEGF) inhibit growth and/or proliferation of tumor cells.

In some embodiments, the IL-2 or extended-PK IL-2, integrin-binding polypeptide-Fc fusions, and optional immune checkpoint inhibitor (or an antagonist of VEGF) reduce tumor size.

In some embodiments, the IL-2 extended-PK IL-2, integrin-binding polypeptide-Fc fusions, and optional immune checkpoint inhibitor (or an antagonist of VEGF) inhibit metastases of a primary tumor.

In some embodiments, an integrin-binding polypeptide-Fc fusions and an immune checkpoint inhibitor (or an antagonist of VEGF), with or without IL-2, inhibit growth and/or proliferation of tumor cells. In some embodiments, an integrin-binding polypeptide-Fc fusions and an immune checkpoint inhibitor (or an antagonist of VEGF), with or without IL-2, reduce tumor size. In certain embodiments, an integrin-binding polypeptide-Fc fusions and an immune checkpoint inhibitor, with or without IL-2, inhibit metastases of a primary tumor.

It will be appreciated by those skilled in the art that reference herein to treatment extends to prophylaxis as well as the treatment of the noted cancers and symptoms.

"Cancer therapy" herein refers to any method which prevents or treats cancer or ameliorates one or more of the symptoms of cancer. Typically, such therapies will comprise administration of integrin-binding polypeptide-Fc fusions either alone or in combination with chemotherapy or radiotherapy or other biologics and for enhancing the activity thereof. In some embodiments, cancer therapy can include or be measured by increased survival. In some embodiments, cancer therapy results in a reduction in tumor volume.

XVII. Therapy Efficacy Readouts

Efficacy readouts can include monitoring for changes in $\alpha\beta$ and/or $\gamma\delta$ T cells, cytotoxic T cell activity, changes in markers such as CD137, CD107a, changes in NK and/or NK/T activity, interferon-$\gamma$ production, changes in regulatory T-cell (including changes in Treg number), changes in macrophage number, changes in neutrophil pro-tumorigenic activity, T-cell activation, CTL activation, changes in activation markers such as CD45RA or CCR7, as well as cancer cell cytotoxicity assays.

XVIII. Kits

A kit can include an integrin-binding polypeptide-Fc fusion and optionally an immune checkpoint inhibitor (or an antagonist of VEGF), as disclosed herein, and instructions for use. Additionally, a kit can include IL-2 or extended-PK IL-2, an integrin-binding polypeptide-Fc fusion, and optionally an immune checkpoint inhibitor (or an antagonist of VEGF), as disclosed herein, and instructions for use. The kits may comprise, in a suitable container, IL-2 or extended-PK IL-2, an integrin-binding polypeptide-Fc fusion, an optional immune checkpoint inhibitor (or an antagonist of VEGF), one or more controls, and various buffers, reagents, enzymes and other standard ingredients well known in the art. Some embodiments include a kit with extended-PK IL-2, knottin-Fc, and optional immune checkpoint inhibitor (or an antagonist of VEGF) in the same vial. In certain embodiments, a kit includes extended-PK IL-2, knottin-Fc, and optional immune checkpoint inhibitor (or an antagonist of VEGF) in separate vials.

The container can include at least one vial, well, test tube, flask, bottle, syringe, or other container means, into which IL-2 or extended-PK IL-2, an integrin-binding polypeptide-Fc fusion, and optionally an immune checkpoint inhibitor (or an antagonist of VEGF) may be placed, and in some instances, suitably aliquoted. Where an additional component is provided, the kit can contain additional containers into which this component may be placed. The kits can also include a means for containing IL-2 or extended-PK IL-2, an integrin-binding polypeptide-Fc fusion, and optionally an immune checkpoint inhibitor (or an antagonist of VEGF) and any other reagent containers in close confinement for commercial sale. Such containers may include injection or blow-molded plastic containers into which the desired vials are retained. Containers and/or kits can include labeling with instructions for use and/or warnings.

The present disclosure is further illustrated by the following examples, which should not be construed as further limiting. The contents of all figures and all references, Genbank sequences, patents and published patent applications cited throughout this application are expressly incorporated herein by reference. In particular, the disclosures of PCT publication WO 13/177187, U.S. Pat. No. 8,536,301, and U.S. Patent Publication No. 2014/0073518 are expressly incorporated herein by reference.

EXAMPLES

Below are examples of specific embodiments for carrying out the methods described herein. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for. The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); A. L. Lehninger, Biochemistry (Worth Publishers, Inc., current addition); Sambrook, et al., Molecular Cloning: A Laboratory Manual ($2^{nd}$ Edition, 1989); Methods In Enzymology (S. Colowick and N. Kaplan eds., Academic Press, Inc.); Remington's Pharmaceutical Sciences, $18^{th}$ Edition (Easton, Pa.: Mack Publishing Company, 1990); Carey and Sundberg Advanced Organic Chemistry $3^{rd}$ Ed. (Plenum Press) Vols A and B(1992).

Moreover, while the examples below employ IL-2 of mouse origin and mouse Fc fused as part of the integrin-binding polypeptide-Fc fusion, it should be understood that corresponding human IL-2 or extended-PK IL-2 (i.e., human serum albumin (HSA) and human IL-2, and variants thereof) and integrin-binding polypeptide-Fc fusions comprising a human Fc (i.e., Fc from human IgG1 fused to the integrin-binding polypeptide) can be readily generated by those of ordinary skill in the art using methods described supra, and used in the methods disclosed herein.

Example 1

MC38-NODU-E202 Materials and Methods

Three potential therapeutic candidates were designed and tested. These variants comprised our tumor targeting peptide (2.5F) fused to an antibody Fc domain (human IgG1). NOD201: no linker, NOD203: a short [Gly4Ser] linker, and NOD204: a long [Gly4Ser3] linker. These three constructs were expressed with a signal peptide derived from the Azurocidin preproprotein (note: the signal peptide is a sequence that directs the protein expression within the cell). Genes encoding for the open reading frames of these constructs were codon optimized for mammalian cell expression, and protein constructs were produced by transient expression in human embryonic kidney cells. 100 mL cultures were purified by MabSelect SuRe resin, quantified by UV/Vis absorbance, and analyzed by SDS-PAGE and size exclusion chromatography. The proteins were >98% monomer (i.e. lack of aggregates) when analyzed by size exclusion chromatography.

Serum stability of the proteins was measured after incubation in mouse serum for 48 hours at 37° C. as compared to untreated sample. Protein integrity was measured by binding to $\alpha v\beta 3$ integrin by Biolayer Interferometry. All NOD fusion proteins were not compromised after incubation in mouse serum.

Melting temperature (Tm) was measured in two different buffers, PBS and citrate. Tm for all proteins was 68° C. in PBS and 66° C. in citrate.

NOD201X, which contains a scrambled integrin binding sequence, was also cloned and produced in in HEK cells as a negative control.

NOD201M contains the 2.5F peptide fused to a mouse Fc domain. This construct is necessary for experiments in syngeneic mouse experiments (mice with an intact immune system). NOD201M was produced in HEK cells for animal experiments.

NOD201 was found to be a "Universal" tumor targeting agent, capable of potentiating T cell directed cancer immunotherapies (e.g. checkpoint blockade, IL-2) as well as driving T cell infiltration of tumors through targeting innate effector functions to integrins.

While not being bound by theory, the proposed NOD201 mechanism of action is that ADCC drives cross priming of T cell response. This is believed to require: Fc effector functions, macrophages, CD8+ T cells, and CD8+ dendritic cells. Fc effector functions create inflammatory TME (tumor microenvironment), which results in increased intratumoral chemokines.

Example 2

MC38-NODU-E202 Materials and Methods

Mice

Female C57BL/6 mice (C57BL/6/NCrl, Charles River) were seven weeks old on D1 of the study and had a BW range of 15.5-21.8 g. The animals were fed ad libitum water (reverse osmosis, 1 ppm Cl) and NIH 31 Modified and Irradiated Lab Diet® consisting of 18.0% crude protein, 5.0% crude fat, and 5.0% crude fiber. The mice were housed on irradiated Enrich-o'Cobs™ bedding in static microisolators on a 12-hour light cycle at 20-22° C. (68-72° F.) and 40-60% humidity. CR Discovery Services specifically complies with the recommendations of the *Guide for Care and Use of Laboratory Animals* with respect to restraint, husbandry, surgical procedures, feed and fluid regulation, and veterinary care. The animal care and use program at CR Discovery Services is accredited by the Association for Assessment and Accreditation of Laboratory Animal Care International, which assures compliance with accepted standards for the care and use of laboratory animals.

Tumor Cell Culture

MC38 murine colon carcinoma cells provided by Nodus Therapeutics, Inc. were grown in Dulbecco's Modified Eagle Medium (DMEM) supplemented with 10% fetal bovine serum and 2 mM glutamine, 100 units/mL penicillin G sodium, 100 μg/mL streptomycin sulfate, and 25 μg/mL gentamicin. Cell cultures were maintained in tissue culture flasks in a humidified incubator at 37° C., in an atmosphere of 5% $CO_2$ and 95% air.

Tumor Implantation and Measurement

The MC38 colon cells used for implantation were harvested during log phase growth and resuspended in cold RPMI media. Mice were anesthetized with isoflurane prior to implantation. Each mouse was injected subcutaneously in the right flank with $1 \times 10^6$ tumor cells (0.1 mL cell suspension) and tumors were monitored as their volumes approached the target range of 60 to 180 mm³. Seven Days after tumor implantation, on D1 of the study, animals with individual tumor volumes ranging from 63 to 172 mm³ were sorted into eleven groups (n=10) with group mean tumor volumes ranging from 109-112 mm³. Tumors were measured with calipers twice weekly in two dimensions. Tumor size was calculated using the formula:

$$\text{Tumor Volume (mm}^3\text{)} = \frac{w^2 \times l}{2}$$

where w=width and l=length, in mm, of a tumor. Tumor weight may be estimated with the assumption that 1 mg is equivalent to 1 mm³ of tumor volume.

Test Articles

The integrin-binding polypeptide-Fc fusion NOD201M (code-named KW2, Lot. No. BP-046-016-2), Proleukin (Lot. No. 502519AA) and anti-PD-1 (Lot. No. 614616J2). NOD201M, Proleukin and anti-PD-1 were protected from light and stored at 4° C. All agents were prepared according to protocol instructions.

On each day of dosing, NOD201M was diluted in phosphate buffered saline (PBS) to yield a 2.08 mg/mL dosing solution. Dosing solutions were stored at 4° C.

On each day of dosing, Proleukin was dissolved in sterile water to yield a 0.04 mg/mL dosing solution. Dosing solutions were stored at 4° C.

On each day of dosing, anti-PD-1 was diluted in PBS to yield a 2 mg/mL dosing solution. Dosing solutions were stored at 4° C.

Treatment

Eleven groups of C57BL/6 mice (n=10) were dosed beginning on D1 according to the MC38-NODU-e202 protocol in Table 1. Vehicle (PBS) and NOD201M (dosed at 500 or 1000 μg/animal), were administered intravenously (i.v.) in a dosing volume of 0.24 mL/mouse. Proleukin (dosed at 4 or 40 μg/animal), was administered i.v. or subcutaneously (s.c.) in a dosing volume of 0.1 mL/mouse. Anti-PD-1 (dosed at 200 μg/animal), was administered i.v. in a dosing volume of 0.1 mL/mouse. All volumes were dosed not adjusted according to the body weights of the individual animals.

Group 1 animals served as controls and received vehicle, i.v on Days 1, 7, 13, 19.

Group 2 animals received NOD201M at 500 μg/animal i.v. on Days 1, 7, 13, 19.

Group 3 animals received Proleukin at 40 μg/animal i.v. on Days 2-4, 8-10, 14-16, 20-22.

Group 4 animals received Proleukin at 4 μg/animal s.c. on Days 2-4, 8-10, 14-16, 20-22.

Group 5 animals received NOD201M at 500 μg/animal i.v. on Days 1, 7, 13, 19 in combination with Proleukin at 40 μg/animal i.v. on Days 2-4, 8-10, 14-16, 20-22.

Group 6 animals received NOD201M at 500 μg/animal i.v. on Days 1, 7, 13, 19 in combination with Proleukin at 4 μg/animal s.c. on Days 2-4, 8-10, 14-16, 20-22.

Group 7 animals received anti-PD-1 at 200 μg/animal i.v. on Days 1, 7, 13, 19.

Group 8 animals received NOD201M at 500 μg/animal i.v. on Days 1, 7, 13, 19 in combination with anti-PD-1 at 200 μg/animal i.v. on Days 1, 7, 13, 19.

Group 9 animals received NOD201M at 500 μg/animal i.v. on Days 1, 7, 13, 19 in combination with anti-PD-1 at 200 μg/animal i.v. on Days 1, 7, 13, 19 and Proleukin at 4 μg/animal s.c. on Days 2-4, 8-10, 14-16, 20-22.

Group 10 animals received NOD201M at 1000 μg/animal i.v. on Days 1, 7, 13, 19 in combination with anti-PD-1 at 200 μg/animal i.v. on Days 1, 7, 13, 19 and Proleukin at 4 μg/animal s.c. on Days 2-4, 8-10, 14-16, 20-22.

Group 11 animals received NOD201M at 1000 μg/animal i.v. on Days 1, 7, 13, 19 in combination with Proleukin at 4 μg/animal s.c. on Days 2-4, 8-10, 14-16, 20-22.

Endpoint and Tumor Growth Delay (TGD) Analysis

Tumors were measured using calipers twice per week, and each animal was euthanized when its tumor reached the endpoint volume of 1000 mm³ or at the end of the study (Day 85), whichever came first. Animals that exited the study for tumor volume endpoint were documented as euthanized for tumor progression (TP), with the date of euthanasia. The time to endpoint (TTE) for analysis was calculated for each mouse by the following equation:

$$TTE = \frac{\log_{10}(\text{endpoint volume}) - b}{m}$$

where TTE is expressed in Days, endpoint volume is expressed in mm³, b is the intercept, and m is the slope of the line obtained by linear regression of a log-transformed tumor growth data set.

The data set consisted of the first observation that exceeded the endpoint volume used in analysis and the three consecutive observations that immediately preceded the attainment of this endpoint volume. The calculated TTE is usually less than the TP date, the day on which the animal was euthanized for tumor size. Animals with tumors that did not reach the endpoint volume were assigned a TTE value equal to the last day of the study (Day 85). In instances in which the log-transformed calculated TTE preceded the day prior to reaching endpoint or exceeded the day of reaching tumor volume endpoint, a linear interpolation was performed to approximate the TTE. Any animal classified as having died from NTR (non-treatment-related) causes due to accident (NTRa) or due to unknown etiology (NTRu) were excluded from TTE calculations (and all further analyses). Animals classified as TR (treatment-related) deaths or NTRm (non-treatment-related death due to metastasis) were assigned a TTE value equal to the day of death.

Treatment outcome was evaluated from tumor growth delay (TGD), which is defined as the increase in the median time to endpoint (TTE) in a treatment group compared to the control group:

TGD=$T-C$, expressed in Days, or as a percentage of the median TTE of the control group:

$$\% \ TGD = \frac{T - C}{C} \times 100$$

where:
T=median TTE for a treatment group, and
C=median TTE for the designated control group.

MTV and Criteria for Regression Responses

Treatment efficacy may be determined from the tumor volumes of animals remaining in the study on the last day. The MTV (n) was defined as the median tumor volume on the last day of the study in the number of animals remaining (n) whose tumors had not attained the endpoint volume.

Treatment efficacy may also be determined from the incidence and magnitude of regression responses observed during the study. Treatment may cause partial regression (PR) or complete regression (CR) of the tumor in an animal. In a PR response, the tumor volume was 50% or less of its Day 1 volume for three consecutive measurements during the course of the study, and equal to or greater than 13.5 mm$^3$ for one or more of these three measurements. In a CR response, the tumor volume was less than 13.5 mm$^3$ for three consecutive measurements during the course of the study. An animal with a CR response at the termination of a study was additionally classified as a tumor-free survivor (TFS). Animals were monitored for regression responses.

Toxicity

Animals were weighed daily for the first five Days of the study and twice weekly thereafter. The mice were observed frequently for health and overt signs of any adverse treatment related (TR) side effects, and noteworthy clinical observations were recorded. Individual body weight loss was monitored per protocol, and any animal with weight loss exceeding 30% for one measurement, or exceeding 25% for three measurements, was to be euthanized for health as a TR death. If group mean body weight recovered, dosing may resume in that group, but at a lower dose or less frequent dosing schedule. Acceptable toxicity was defined as a group mean BW loss of less than 20% during the study and not more than one TR death among ten treated animals, or 10%. Any dosing regimen resulting in greater toxicity is considered above the maximum tolerated dose (MTD). A death was to be classified as TR if it was attributable to treatment side effects as evidenced by clinical signs and/or necropsy, or may also be classified as TR if due to unknown causes during the dosing period or within 14 Days of the last dose. A death was classified as NTR if there was evidence that the death was related to the tumor model, rather than treatment-related. NTR deaths are further categorized as NTRa (due to accident or human error), NTRm (due to necropsy-confirmed tumor dissemination by invasion or metastasis), and NTRu (due to unknown causes).

Statistical and Graphical Analyses

Prism (GraphPad) for Windows 7.01 was used for graphical presentations and statistical analyses. Survival was analyzed by the Kaplan-Meier method. The logrank (Mantel-Cox) and Gehan-Breslow-Wilcoxon tests determined the significance of the difference between the overall survival experiences (survival curves) of two groups, based on TTE values. All test results are shown in Appendix B. Two-tailed statistical analyses were conducted at significance level $P=0.05$. The analyses were not corrected for multiple comparisons. Prism summarizes test results as not significant (ns) at $P>0.05$, significant (symbolized by "*") at $0.01<P\leq0.05$, very significant ("") at $0.001<P\leq0.01$, and extremely significant ("*") at $P\leq0.001$. Because tests of statistical significance do not provide an estimate of the magnitude of the difference between groups, all levels of significance were described as either significant or not significant within the text of this report. Groups with regimens that exceeded the limits for acceptable toxicity were not evaluated statistically.

Figure 2:
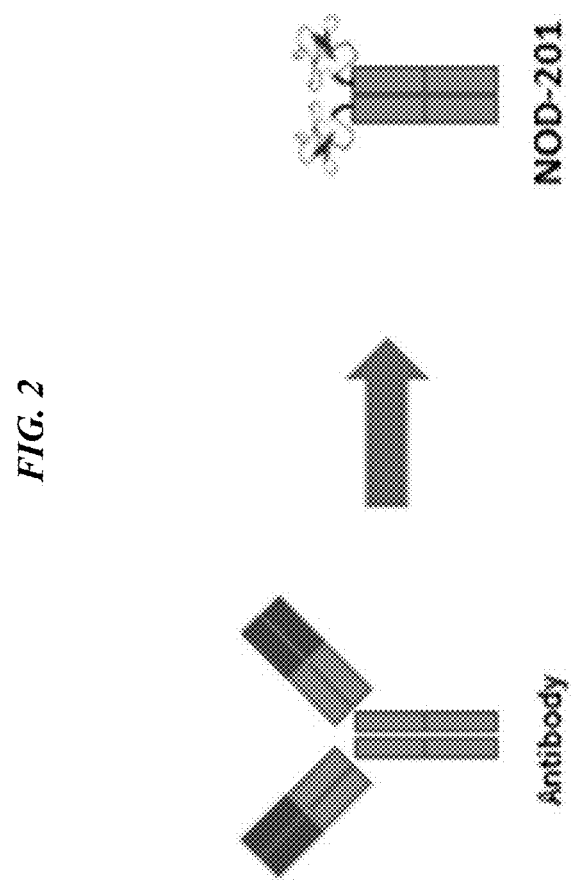
FIG. 2. NOD201, a "pseudo-mAb" created by fusing an engineered cystine knot (knottin) peptide to an Fc domain. This construct targets innate effector functions (ADCC and CDC) against $\alpha_v\beta_1$, $\alpha_v\beta_3$, $\alpha_v\beta_5$, $\alpha_v\beta_6$, and $\alpha_5\beta_1$ integrin.

A scatter plot was constructed to show TTE values for individual mice, by group (FIG. 1). Group median tumor volumes were plotted as functions of time (FIG. 2, upper panel). When an animal exited the study because of tumor size, the final tumor volume recorded for the animal was included with the data used to calculate the median volume at subsequent time points. A Kaplan-Meier plot was constructed to show the percentage of animals in each group remaining on study versus time (FIG. 17, lower panel).

Figures 3A, 3B:
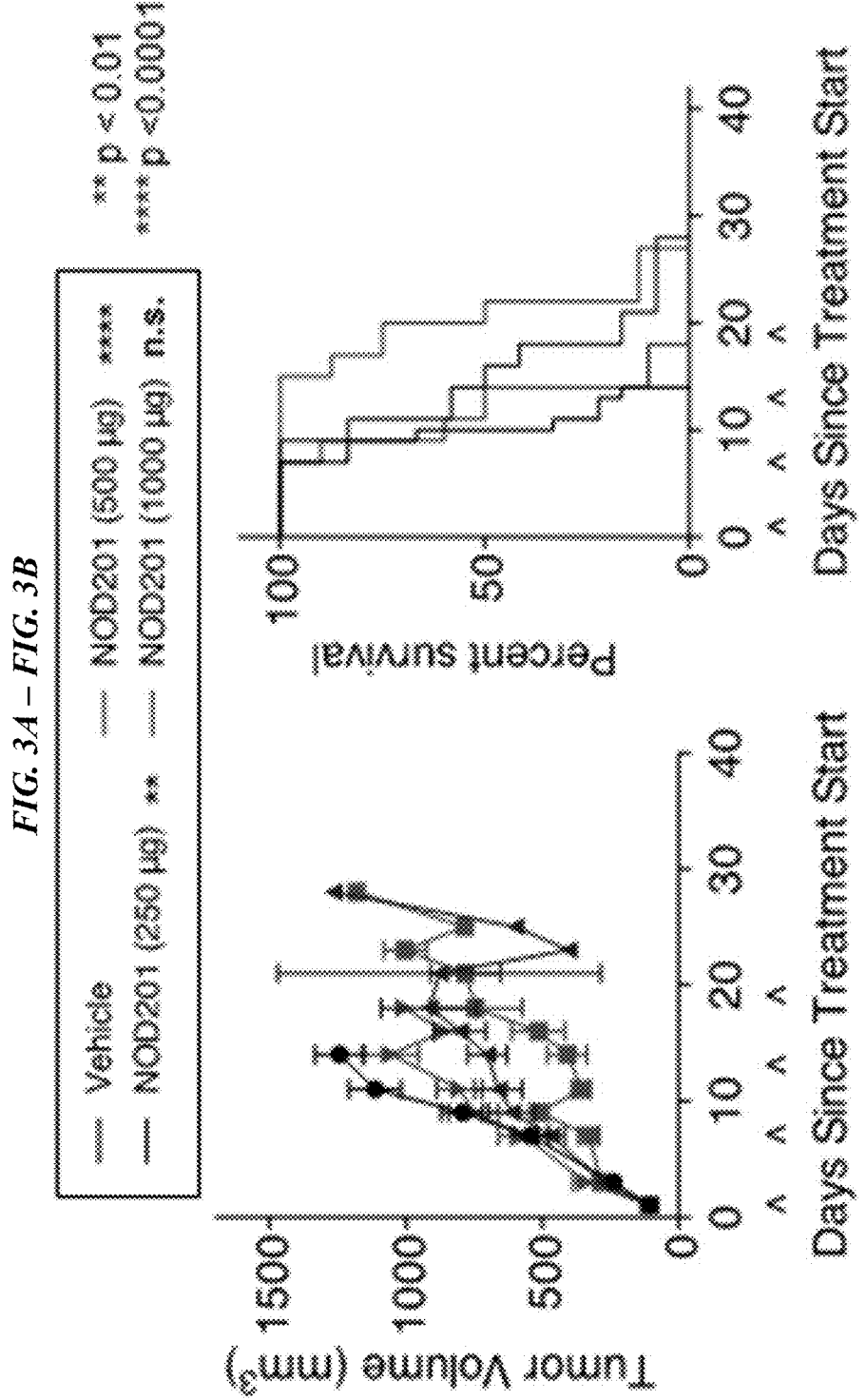
FIG. 3A-FIG. 3B. NOD201M has weak efficacy as a monotherapy. Left, Tumor volume curves Right, Kaplan-Meier curves. NOD201M was administered IV at doses of 250 µg, 500 µg, or 1000 µg on days 1, 7, 13, 19 (i.e., once per week) after inoculated tumors reached an average size of 60-180 mm³. Vehicle: phosphate buffered saline. MC38 colon tumor model.

Group median tumor volumes were plotted as a function of time, and were truncated after the second TR death in a group. Mean plots were also included for this study (FIG. 3). Group mean BW changes over the course of the study were graphed as percent change, ±SEM, from Day 1 (FIG. 19). Tumor growth and BW change curves excluded data for animals assessed as NTR deaths, and were truncated after more than half the mice in a group exited the study.

Example 3

B16F10 Experimental Description

Female C57BL/6 mice (C57BL/6/NCrl, Charles River) were 8-12 weeks old at the start of the study. Study start is the day of tumor cell implant (Day 1). Animals (n=10 per group) were randomized into treatment groups base on Day 1 bodyweight. B16F10 melanoma cells used for implantation were provided by Charles River Laboratories and were harvested during log phase growth and resuspended in media. Mice were anesthetized with isoflurane prior to implantation.

Each mouse was injected subcutaneously in the right flank with $1\times10^6$ tumor cells (0.1 mL cell suspension) with 0% Matrigel. Treatment started four days after implantation. Animal body weight was measured at least twice per week during the study. Tumors were measured with calipers at least twice weekly in two dimensions. Tumor size was calculated using the formula:

$$\text{Tumor Volume (mm}^3) = \frac{w^2 \times l}{2}$$

where w=width and l=length, in mm, of a tumor. Tumor weight may be estimated with the assumption that 1 mg is equivalent to 1 mm³ of tumor volume.

Group 1 animals served as controls and received vehicle (phosphate buffered saline), i.v on Days 4, 10, 16, 22.

Group 2 animals received NOD201M at 1000 µg/animal i.v. on Days 4, 10, 16, 22.

Group 3 animals received anti-PD1 antibody at 200 µg/animal i.v. on Days 4, 10, 16, 22. Anti-PD1 was clone RMP1-14 (rat IgG)—BioXcell cat #BP0146

Group 4 animals received Proleukin at 4 µg/animal s.c. on Days 5-7, 11-13, 17-19, 23-25.

Group 5 animals received NOD201M at 1000 µg/animal i.v. on Days 4, 10, 16, 22 in combination with anti-PD1 antibody at 200 µg/animal i.v. on Days 4, 10, 16, 22.

Group 6 animals received NOD201M at 1000 µg/animal i.v. on Days 4, 10, 16, 22 in combination with Proleukin at 4 µg/animal s.c. on Days 5-7, 11-13, 17-19, 23-25.

Group 7 animals received NOD201M at 500 µg/animal i.v. on Days 4, 10, 16, 22 in combination with anti-PD1 antibody at 200 µg/animal i.v. on Days 4, 10, 16, 22, and Proleukin at 4 µg/animal s.c. on Days 5-7, 11-13, 17-19, 23-25.

Measurement of Tumor Cell Infiltrates Following Treatment

Animals received NOD201M at 1000 µg/animal i.v. on Days 1, 7 alone or in combination with anti-PD-1 at 200 µg/animal i.v. on Days 1, 7, and/or Proleukin at 4 µg/animal s.c. on Days 2-4, 8-9. On day 9, 24 hours following the Proleukin injection, tumors were harvested, preserved, and processed to single cell suspensions. Cell suspensions were stained for cell surface markers using antibodies described below, and analyzed by flow cytometry. Data is represented as the % of CD45+ cells in the tumor.

Panel: CD4, CD8, Treg, Total MDSC, and NK

| Cell population | Phenotypic Markers | Antibody panel |
|---|---|---|
| CD4 | CD45⁺CD3⁺CD4⁺CD8⁻ | CD45, CD3, CD4, CD8, |
| CD8 | CD45⁺CD3⁺CD4⁻CD8⁺ | CD11b, CD25, Gr-1, |
| Tregs | CD45⁺CD3⁺CD4⁺CD25⁺FoxP3⁺ | FoxP3, CD49b(DX5), |
| MDSC | CD45⁺CD3⁻CD11b⁺Gr-1⁺ | LIVE/DEAD |
| NK | CD49b(DX5)+ and CD11b$^{low}$ | |

FoxP3, internal marker

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed is:

1. A method for treating cancer in a subject comprising administering to the subject an effective amount of (i) an integrin-binding polypeptide-Fc fusion wherein said integrin-binding polypeptide-Fc fusion is administered in a therapeutically effective amount, wherein said integrin-binding polypeptide comprises a sequence selected from the group consisting of SEQ ID NO:130 (GCPRPRGDNPPLTCSQDSDCLAGCVCGPNGFCG) and SEQ ID NO:131 (GCPRPRGDNPPLTCKQDSDCLAGCVCGPNGFCG), wherein said integrin-binding polypeptide is conjugated to an Fc domain, and wherein said integrin-binding polypeptide-Fc fusion binds to at least two integrins; and (ii) an interleukin-2 (IL-2), wherein said IL-2 is administered at a 12 MIU/m2 or lower daily dose, and
 wherein said IL-2 is administered at day 2, day 3, or day 4 after administration of said integrin-binding polypeptide-Fc fusion.

2. The method of claim 1, wherein said Fc domain is selected from the group consisting of IgG1, IgG2, IgG3, and IgG4.

3. The method of claim 2, wherein said Fc domain is a human Fc domain.

4. The method of claim 1, wherein said integrin-binding polypeptide is conjugated directly to said Fc domain.

5. The method of claim 1, wherein said integrin-binding polypeptide is conjugated to said Fc domain through a linker polypeptide.

6. The method of claim 5, wherein said linker polypeptide is selected from the group consisting of GGGGS (SEQ ID NO:136) and GGGGSGGGGSGGGGS (SEQ ID NO:137).

7. The method of claim 1, wherein said integrin-binding polypeptide-Fc fusion comprises an integrin-binding polypeptide sequence in the presence or absence of a linker, wherein said sequence is selected from the group consisting of GCPRPRGDNPPLTCSQDSDCLAGCVCGPNGFCG (SEQ ID NO:130), GCPRPRGDNPPLTCKQDSDCLAGCVCGPNGFCG (SEQ ID NO:131), GCPRPRGDNPPLTCSQDSDCLAGCVCGPNGFCGGGGS (SEQ ID NO:132), GCPRPRGDNPPLTCKQDSDCLAGCVCGPNGFCGGGGS (SEQ ID NO:133), GCPRPRGDNPPLTCSQDSDCLAGCVCGPNGFCGGGGGSGGGGSGGGGS (SEQ ID NO:134), and GCPRPRGDNPPLTCKQDSDCLAGCVCGPNGFCGGGGGSGGGGSGGGGS (SEQ ID NO:135), wherein said integrin-binding polypeptide sequence is directly linked to an Fc domain, wherein said Fc domain is selected from the group consisting of IgG1, IgG2, IgG3, and IgG4.

8. The method of claim 1, wherein said IL-2 is administered at a 10 MIU/m2 or lower daily dose.

9. The method of claim 1, wherein said IL-2 is Proleukin.

10. The method of claim 1, wherein said integrin-binding polypeptide is not conjugated to said Fc domain through a linker polypeptide.

11. The method of claim 1, wherein said integrin-binding polypeptide-Fc fusion binds to at least two integrins selected from the group consisting of $\alpha_v\beta_1$, $\alpha_v\beta_3$, $\alpha_v\beta_5$, $\alpha_v\beta_6$, and $\alpha_5\beta_1$.

12. The method of claim 1, wherein said IL-2 is administered simultaneously with administration of said integrin-binding polypeptide-Fc fusion.

13. The method of claim 1, wherein said method further comprises administering an immune checkpoint inhibitor.

14. The method of claim 13, wherein said immune checkpoint inhibitor is a PD-1 inhibitor.

15. The method of claim 14, wherein said PD-1 inhibitor is an anti-PD-1 antibody.

16. The method of claim 13, wherein said immune checkpoint inhibitor is an anti-PD-1 antibody, and wherein further administering both IL-2 and said immune checkpoint inhibitor induces:
 (i) increased tumor infiltration of CD8+ T-cells as compared to administration of an IL-2 and/or an anti-PD-1 antibody individually, and/or
 (ii) a greater decrease in myeloid-derived suppressor cells (MDSC) cells as compared to administration of an IL-2 and/or an anti-PD-1 antibody individually.

17. The method of claim 15, wherein administering said anti-PD-1 antibody induces:
 (i) increased tumor infiltration of CD8+ T-cells as compared to administration of an integrin-binding polypeptide-Fc fusion alone, and/or
 (ii) a greater decrease in myeloid-derived suppressor cells (MDSC) cells as compared to administration of an integrin-binding polypeptide-Fc fusion alone.

* * * * *